(12) United States Patent
Akama et al.

(10) Patent No.: US 10,562,921 B2
(45) Date of Patent: Feb. 18, 2020

(54) OXABOROLE ESTERS AND USES THEREOF

(71) Applicant: Anacor Pharmaceuticals, Inc., New York, NY (US)

(72) Inventors: Tsutomu Akama, Sunnyvale, CA (US); David Scott Carter, Sunnyvale, CA (US); Jason S. Halladay, Los Gatos, CA (US); Robert T. Jacobs, Wake Forest, NC (US); Yang Liu, Foster City, CA (US); Jacob J. Plattner, Berkeley, CA (US); Yong-Kang Zhang, San Jose, CA (US); Michael John Witty, Dover (GB)

(73) Assignee: Anacor Pharmaceuticals, Inc., New York, NY (US)

( * ) Notice: Subject to any disclaimer, the term of this patent is extended or adjusted under 35 U.S.C. 154(b) by 0 days.

(21) Appl. No.: 15/590,159

(22) Filed: May 9, 2017

(65) Prior Publication Data

US 2017/0327519 A1    Nov. 16, 2017

Related U.S. Application Data

(60) Provisional application No. 62/335,565, filed on May 12, 2016.

(51) Int. Cl.

| | |
|---|---|
| *A61K 31/166* | (2006.01) |
| *C07F 5/02* | (2006.01) |
| *A61K 31/443* | (2006.01) |
| *A61K 31/4525* | (2006.01) |
| *A61K 31/69* | (2006.01) |
| *A61K 31/4178* | (2006.01) |
| *A61K 31/431* | (2006.01) |
| *A61K 31/47* | (2006.01) |
| *A61K 31/5377* | (2006.01) |

(52) U.S. Cl.
CPC ............ *C07F 5/027* (2013.01); *A61K 31/166* (2013.01); *A61K 31/443* (2013.01); *A61K 31/4525* (2013.01); *A61K 31/69* (2013.01); *C07F 5/025* (2013.01); *A61K 31/4178* (2013.01); *A61K 31/431* (2013.01); *A61K 31/47* (2013.01); *A61K 31/5377* (2013.01); *Y02A 50/414* (2018.01)

(58) Field of Classification Search
CPC ....................................................... C07F 5/027
See application file for complete search history.

(56) References Cited

U.S. PATENT DOCUMENTS

| 4,861,760 A | 8/1989 | Mazuel et al. |
|---|---|---|
| 4,911,920 A | 3/1990 | Jani et al. |
| 5,212,162 A | 5/1993 | Missel et al. |
| 5,403,841 A | 4/1995 | Lang et al. |
| 2014/0213551 A1 | 7/2014 | Jacobson et al. |

FOREIGN PATENT DOCUMENTS

| WO | 96/05309 A2 | 2/1996 |
|---|---|---|
| WO | 2010/045503 A1 | 4/2010 |
| WO | 2010/045505 A1 | 4/2010 |
| WO | 2012/109164 A1 | 8/2012 |
| WO | 2015/013318 A1 | 1/2015 |
| WO | 2015/097276 A1 | 7/2015 |
| WO | 2017/029289 A1 | 2/2017 |

OTHER PUBLICATIONS

Wislicenus, J. "Adolph Strecker's Short Textbook of Organic Chemistry" 1881, Spottiswoode: London, pp. 38-39.*
Berge et al, "Pharmaceutical Salts", Journal of Pharmaceutical Sciences 66(1):1-19 (1977).
Carpino, "1-Hydroxy-7-azabenzotriazole. An Efficient Peptide Coupling Additive", J. Am. Chem. Soc. 115(10):4397-4398 (1993).
Carpino, "Tetramethylfluoroformamidinium Hexafluorophosphate: A Rapid-Acting Peptide Coupling Reagent for Solution and Solid Phase Peptide Synthesis", J. Am. Chem. Soc. 117(19):5401-5402 (1995).
Ding et al, "Discovery of Novel Benzoxaborole-Based Potent Antitrypanosomal Agents", ACS Medicinal Chemistry Letters 1(4):165-169 (2010).
Jones et al, "Antiestrogens. 2. Structure-Activity Studies in a Series of 3-Aroyl-2-arylbenzo[b]thiophene Derivatives Leading to [6-Hydroxy-2-(4-hydroxyphenyl)benzo[b]thien-3-yl][4-[2-(1-piperidinyl)ethoxy]-phenyl]methanone Hydrochloride (LY156758), a Remarkably Effective Estrogen Antagonist with Only Minimal Intrinsic Estrogenicity". J. Med. Chem. 27(8):1057-1066 (1984).
Li et al, "The development of highly efficient onium-type peptide coupling reagents based upon rational molecular design", J. Peptide Res. 58:129-139 (2001).
Moncayo et al, "An update on Chagas disease (human American trypanosomiasis", Annals of Tropical Medicine & Parasitology 100(8):663-677 (2006).
Schofield et al, "The future of Chagas disease control", Trends in Parasitology 22(12):583-588 (2006).
World Health Organization, "Control of Chagas Disease", WHO Technical Report Series 905 (2002).
PCT International Search Report and Written Opinion for International Patent Application No. PCT/IB2017/052522 dated Jun. 26, 2017.
Bellera et al, "Application of Computer-Aided Drug Repurposing in the Search of New Cruzipain Inhibitors: Discover of Amiodarone and Bromocriptine Inhibitory Effects", Journal of Chemical Information and Modeling 53:2402-2408 (2013).
Bosc et al, "Highly improved antiparasitic activity after introduction of an N-benzylimidazole moiety on protein farnesyltransferase inhibitors", European Journal of Medicinal Chemistry 109:173-186 (2016).

(Continued)

*Primary Examiner* — David K O'Dell
(74) *Attorney, Agent, or Firm* — A. David Joran

(57) ABSTRACT

The present invention provides oxaborole ester compounds and compositions thereof which are useful to treat diseases associated with parasites, such as Chagas Disease and African Animal Trypanosomosis.

22 Claims, No Drawings

(56) References Cited

OTHER PUBLICATIONS

Grewal et al, "Recent Updates on Development of Drug Molecules for Human African Trypanosomiasis", Current Topics in Medicinal Chemistry 16:2245-2265 (2016).

Lam et al, "Discovery and Evaluation of Thiazinoquinones as Anti-Protozoal Agents", Marine Drugs 11:3472-3499 (2013).

* cited by examiner

OXABOROLE ESTERS AND USES THEREOF

BACKGROUND OF THE INVENTION

Trypanosomatids are a group of kinetoplastid protozoa distinguished by having only a single flagellum. Trypanosomatids are responsible for diseases such as South American trypanosomiasis (Chagas Disease) and African Animal Trypanosomosis (AAT).

Chagas disease, caused by the protozoan parasite *Trypanosoma cruzi*, is endemic to many countries in Latin America. The World Health Organization has estimated that 16-18 million people are currently infected and 90 million are at risk of acquiring the infection (WHO 2002, Schofield et al, 2006). The estimated global burden of the disease is 649,000 disability adjusted life years (the number of healthy years of life lost due to premature death and disability). Causing about 14,000 deaths annually, Chagas disease kills more people in Latin America than any other parasitic disease, including malaria.

*T. cruzi* is transmitted by various insect vectors that belong to the Reduviidae family. Transmission to humans is dependent on living conditions as these insects inhabit houses of mud and thatch which are common in lower socioeconomic areas. Infection may also be acquired by consuming contaminated food, congenitally, or via blood transfusion or organ transplantation. The acute phase of *T. cruzi* infection is generally controlled by the emerging immune response and is mild or asymptomatic and thus often undetected. However, the vast majority of infected individuals fail to clear the infection and thus remain chronically infected; 30-40% of these will eventually develop life-threatening heart or gastrointestinal disease. Chronic Chagas remains an incurable disease that causes long term severe disability or death in approximately one-third of infected individuals. In addition, disability caused by chronic Chagas disease has a great social and economic impact, including unemployment and decreased earning ability. From a 2012 estimate by the World Health Organization, over 500,000 Disability-Adjusted Life Years (DALYs) were attributable to Chagas disease (Moncayo A, Ortiz Yanine M. Ann Trop Med Parasitol. 2006; 100:663-677). In addition to the loss in productivity, the medical costs to treat infected individuals who develop severe cardiac or chronic digestive problems are high.

It has long been established that *T. cruzi* can infect dogs, particularly those who are housed outdoors in the southern US, Central, and South America. A recent study in Texas suggested that shelter dogs serve as a good sentinel for all dogs, and found that ~9% of shelter dogs evaluated across Texas harbored *T. cruzi*. In Texas, *T. cruzi* infection in dogs is considered a "notifiable condition"—any dog found to be harboring the parasite must be reported to the Texas Department of State Health Services. As there is no approved treatment for Chagas disease in dogs, animals may be euthanized.

African animal trypanosomosis is endemic to 37 African countries, affecting livestock on 10 million km$^2$ of arable land and remains a major constraint to agricultural production, in particular livestock production in these areas. Trypanosomosis is also prevalent in Central and South America. The disease is caused primarily by three protozoan parasites: *Trypanosoma congolense* (*T. congolense*), *T. vivax* and *T. evansi*, and is vectored by the tsetse fly and, for *T. evansi*, also mechanically transferred from host to host by the *tabanus* spp. of biting fly. The disease is characterized by progressive anemia, loss of condition and lassitude with recurrent episodes of fever and parasitemia. The severity of the disease varies with *Trypanosoma* species, breed, age and health status of the infected animal. In cattle, this infection causes major mortality and morbidity with significant negative effects on growth, lactation, weaning age, and weight. In draught animals the power, speed and distance covered per day is also impacted. Trypanosomosis has a major economic impact on cattle production in Africa and, if untreated, generally results in chronic illness with high mortality. Trypanosomosis has been estimated to cost African livestock farmers US $2 to 5 billion per annum. In the absence of vaccines, control of this disease has for long been focused on chemotherapy and vector control. For many decades only three compounds, diminazene, isometamidium, and homidium, have been widely used as trypanocides, and consequently drug resistance in the target pathogens has become a major concern. Novel chemical entities with novel mechanisms of action are urgently needed to combat these diseases.

SUMMARY OF THE INVENTION

In certain embodiments, the present invention provides a compound of formula I:

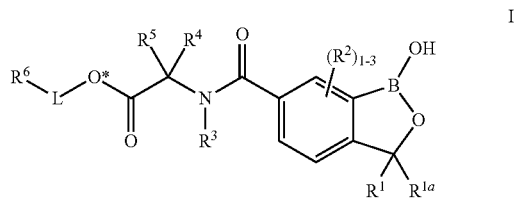

or a pharmaceutically acceptable salt thereof, wherein each of R$^1$, R$^{1a}$, R$^2$, R$^3$, R$^4$, R$^5$, R$^6$, and L is as defined and described in classes and subclasses herein.

DETAILED DESCRIPTION OF CERTAIN EMBODIMENTS

In some embodiments, the present invention provides a compound of formula I:

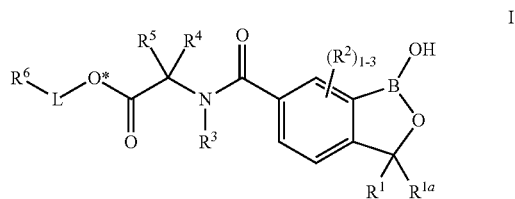

or a pharmaceutically acceptable salt thereof, wherein:
R$^1$ is hydrogen or C$_{1-6}$ aliphatic;
R$^{1a}$ is hydrogen or C$_{1-6}$ aliphatic; or
R$^1$ and R$^{1a}$ are taken together with the carbon atom to which they are attached to form an optionally substituted 3- to 6-membered spiro carbocyclic ring;
each R$^2$ is independently hydrogen, -halogen, —OR, —NO$_2$, —CN, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, or an optionally substituted group selected from the group consisting of $C_{1-6}$ aliphatic and 3- to 6-membered saturated or partially unsaturated monocyclic carbocyclyl;

$R^3$ is hydrogen or optionally substituted $C_{1-6}$ aliphatic;

$R^4$ is hydrogen, a natural or unnatural amino acid side-chain group, or an optionally substituted group selected from the group consisting of $C_{1-6}$ aliphatic, 3- to 7-membered saturated or partially unsaturated monocyclic carbocyclyl, and phenyl; or
- $R^3$ and $R^4$ are taken together with the carbon atom attached to $R^4$ and the nitrogen atom attached to $R^3$ to form an optionally substituted 3- to 6-membered heterocyclyl ring having 0-1 additional heteroatoms selected from oxygen, nitrogen, or sulfur;

$R^5$ is hydrogen or optionally substituted $C_{1-6}$ aliphatic; or
- $R^4$ and $R^5$ are taken together with the carbon atom to which they are attached to form an optionally substituted ring selected from a 3- to 6-membered spiro heterocyclic ring having 1-2 heteroatoms selected from oxygen, nitrogen, or sulfur, and a 3- to 6-membered saturated or partially unsaturated monocyclic spiro carbocyclic ring;

L is a covalent bond or an optionally substituted, bivalent $C_{1-10}$ saturated or unsaturated, straight or branched, hydrocarbon chain, wherein one, two, or three methylene units of L are optionally and independently replaced by -Cy-, —O—, —SO—, —SO$_2$—, —C(O)—, —C(O)N(R)—, —S—, —N(R)—, —C(O)O—, —OC(O)—, —N(R)C(O)—, —N(R)SO$_2$—, or —SO$_2$N(R)—;
- wherein each -Cy- is independently an optionally substituted bivalent ring selected from the group consisting of phenylene, 3- to 7-membered saturated or partially unsaturated monocyclic carbocyclylene, 3- to 7-membered saturated or partially unsaturated monocyclic heterocyclylene having 1-2 heteroatoms selected from oxygen, nitrogen, or sulfur, 5- to 6-membered heteroarylene having 1-4 heteroatoms selected from oxygen, nitrogen, or sulfur, 7- to 10-membered saturated or partially unsaturated bicyclic carbocyclylene, 8- to 10-membered bicyclic arylene, 7- to 10-membered saturated or partially unsaturated bicyclic heterocyclylene having 1-4 heteroatoms selected from oxygen, nitrogen, or sulfur, and 7- to 10-membered bicyclic heteroarylene having 1-4 heteroatoms selected from oxygen, nitrogen, or sulfur;

$R^6$ is hydrogen, -halogen, —OR, —NO$_2$, —CN, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, an optionally substituted group selected from the group consisting of $C_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 8- to 10-membered bicyclic aryl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, and bridged bicyclic;

each R is independently hydrogen or optionally substituted $C_{1-6}$ aliphatic;

wherein when L is a covalent bond $R^6$ is other than —OR, -halogen, —NO$_2$, —CN, —SR, —N(R)$_2$, —S(O)R, —S(O)$_2$R, —SO$_2$N(R)$_2$, —OC(O)R, —N(R)C(O)R, —N(R)C(O)OR, —N(R)SO$_2$R, or —OC(O)N(R)$_2$; and wherein when L is other than a covalent bond it includes a carbon atom bonded to the carboxyl oxygen denoted O*.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocyclyl," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocyclyl" or "cycloalkyl") refers to a monocyclic $C_3$-$C_7$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl, or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those where the group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-10}$ (or $C_{1-6}$, etc.) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In some embodiments, an 8-10 membered bicyclic aryl group is an optionally substituted naphthyl ring. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in this context in reference to a ring atom, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein, the phrase "natural amino acid side-chain group" refers to the side-chain group of any of the 20 amino acids naturally occurring in proteins. Such natural amino acids include the nonpolar, or hydrophobic amino acids, glycine, alanine, valine, leucine isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids may have charged side-chains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of a hydroxyl protecting group.

As used herein, the phrase "unnatural amino acid side-chain group" refers to the side-chain group of amino acids not included in the list of 20 amino acids naturally occurring in proteins, as described above. Such amino acids include the D-isomer of any of the 20 naturally occurring amino acids. Unnatural amino acids also include homoserine, ornithine, norleucine, and thyroxine. Other unnatural amino acids side-chains are well known to one of ordinary skill in the art and include unnatural aliphatic side chains. Other unnatural amino acids include modified amino acids, including those that are N-alkylated, cyclized, phosphorylated, acetylated, amidated, azidylated, labelled, and the like. In some embodiments, an unnatural amino acid is a D-isomer. In some embodiments, an unnatural amino acid is a L-isomer.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR^\circ$; $-SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)O$-N(R^\circ)_2$; or $-(C_{1-4}$ straight or branched alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-C(O)SR^\bullet$, $-(C_{1-4}$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*_2, =NNHC(O)R*, =NNHC(O)OR*, =NNHS(O)_2R*, =NR*, =NOR*, $-O(C(R^*_2))_{2-3}O-$, or $-S(C(R^*_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, —NHR*, —NR*$_2$, or —NO$_2$, wherein each R* is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

In certain embodiments, the neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The term "oxo," as used herein, means an oxygen that is double bonded to a carbon atom, thereby forming a carbonyl.

The symbol "⌇", except when used as a bond to depict unknown or mixed stereochemistry, denotes the point of attachment of a chemical moiety to the remainder of a molecule or chemical formula.

Compounds

As described above, in certain embodiments provided compounds are of formula I:

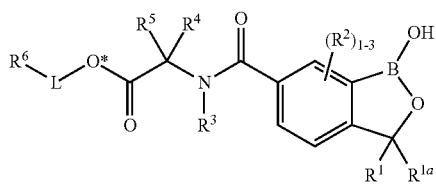

I or a pharmaceutically acceptable salt thereof, wherein each of R$^1$, R$^{1a}$, R$^2$, R$^3$, R$^4$, R$^5$, R$^6$, and L is as defined above and described in classes and subclasses herein, both singly and in combination.

As used herein, unless otherwise stated, references to formula I also include all subgenera of formula I defined and described herein (e.g., formulae II, III, III-a, IV, V, V-a, V-b, VI-a, VI-b, VI-c, VI-d, VI-e, VI-f, VII-a, VII-b, VII-c, VIII-a, VIII-b, VIII-c, IX-a, and IX-b).

It will be appreciated that the "O*" used in formula I is an oxygen atom, and the "*" is used herein to refer to connectivity with the L group.

In some embodiments, R$^1$ and R$^{1a}$ are hydrogen. In some embodiments, R$^1$ and R$^{1a}$ are methyl.

In some embodiments, R$^1$ and R$^{1a}$ are taken together with the carbon atom to which they are attached to form an optionally substituted 3- to 6-membered spiro carbocyclic ring. In some embodiments, R$^1$ and R$^{1a}$ are taken together with the carbon atom to which they are attached to form a 6-membered spiro carbocyclic ring. In some embodiments, R$^1$ and R$^{1a}$ are taken together with the carbon atom to which they are attached to form a 5-membered spiro carbocyclic ring. In some embodiments, R$^1$ and R$^{1a}$ are taken together with the carbon atom to which they are attached to form a 4-membered spiro carbocyclic ring. In some embodiments, R$^1$ and R$^{1a}$ are taken together with the carbon atom to which they are attached to form a 3-membered spiro carbocyclic ring.

In some embodiments, R$^2$ is hydrogen. In some embodiments, R$^2$ is optionally substituted $C_{1-6}$ aliphatic. In some embodiments, R$^2$ is $C_{1-6}$ aliphatic. In some embodiments, R$^2$ is methyl. In some embodiments, R$^2$ is ethyl, propyl, or isopropyl. In some embodiments, R$^2$ is methoxy or ethoxy.

In certain embodiments, one R$^2$ is present. In certain embodiments, two R$^2$ are present. In certain embodiments, three R$^2$ are present.

In some embodiments, R$^2$ is optionally substituted 3- to 6-membered saturated or partially unsaturated monocyclic carbocyclyl. In some embodiments, R$^2$ is 3- to 6-membered saturated monocyclic carbocyclyl. In some embodiments, R$^2$ is cyclopropyl.

In some embodiments, R$^2$ is halogen. In some embodiments, R$^2$ is fluorine.

In some embodiments, R$^2$ is $C_{1-6}$ aliphatic substituted with halogen. In some embodiments, R$^2$ is —CH$_2$F$_2$ or —CF$_3$. In some embodiments, R$^2$ is $C_{1-6}$ aliphatic substituted with hydrogen.

In some embodiments, R$^3$ is hydrogen. In some embodiments, R$^3$ is optionally substituted $C_{1-6}$ aliphatic. In some embodiments, R$^3$ is methyl.

In some embodiments, R$^4$ is hydrogen. In some embodiments, R$^4$ is a natural or unnatural amino acid side-chain group.

In some embodiments, R$^4$ is optionally substituted group selected from the group consisting of $C_{1-6}$ aliphatic. In some embodiments, R$^4$ is methyl, ethyl, isopropyl, t-butyl, —C(CH$_3$)$_2$OH, or —(CH$_2$)$_2$OH. In some embodiments, R$^4$ is methyl. In some embodiments, R$^4$ is isopropyl. In some embodiments, R$^4$ is t-butyl.

In some embodiments, R$^4$ is —(CH$_2$)$_m$SR, —(CH$_2$)$_m$OH, —(CH$_2$)$_m$F, —(CH$_2$)$_m$C(O)N(R)$_2$, or —C(O)OR, wherein m is 1, 2, 3, 4, 5, or 6. In some embodiments, R$^4$ is —(CH$_2$)$_2$SCH$_3$. In some embodiments, R$^4$ is —CH$_2$OH. In some embodiments, R$^4$ is —CH$_2$C(O)NH$_2$ or —(CH$_2$)$_2$C(O)NH$_2$.

In some embodiments, m is 0, 1, 2, or 3.

In some embodiments, R$^4$ is phenyl. In some embodiments, R$^4$ is phenyl optionally substituted with —OH.

In some embodiments, R$^4$ is optionally substituted 3- to 7-membered saturated or partially unsaturated monocyclic carbocyclyl. In some embodiments, R$^4$ is 3- to 7-membered saturated or partially unsaturated monocyclic carbocyclyl. In some embodiments, R$^4$ is cyclopropyl. In some embodiments, R$^4$ is cyclobutyl. In some embodiments, R$^4$ is cyclopentyl.

In some embodiments, R⁴ is

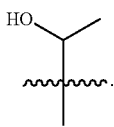

In some embodiments, R⁴ is

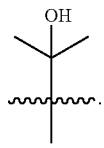

In some embodiments, R⁴ is

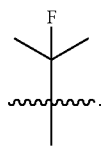

In some embodiments, R⁴ is

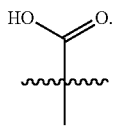

In some embodiments, R⁴ is

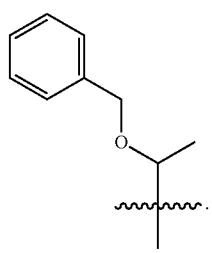 [SMILES: *C(C)OCc1ccccc1]

In some embodiments, R⁴ is

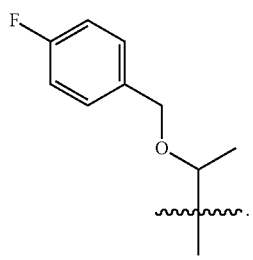

In some embodiments, R⁴ is —(CH$_2$)$_m$R⁷ or —CH(CH$_3$)OCH$_2$R⁷, wherein R⁷ is R⁷ is an optionally substituted ring selected from the group consisting of phenyl, 8- to 10-membered bicyclic aryl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, and 5- to 10-membered monocyclic or bicyclic heteroaryl having 1-4 heteroatoms independently selected from nitrogen, oxygen, or sulfur. In some embodiments, R⁴ is —CH$_2$R⁷, wherein R⁷ is optionally substituted phenyl. In some embodiments, R⁴ is —(CH$_2$)$_2$R⁷, wherein R⁷ is optionally substituted phenyl. In some embodiments, R⁴ is —(CH$_2$)$_3$R⁷, wherein R⁷ is optionally substituted phenyl.

In some embodiments, R⁷ is an optionally substituted ring selected from the group consisting an optionally substituted group selected from the group consisting of C$_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 8- to 10-membered bicyclic aryl, 7- to 10-membered saturated or partially unsaturated bicyclic heterocyclyl having 1-4 heteroatoms selected from oxygen, nitrogen, or sulfur, and 7- to 10-membered bicyclic heteroaryl having 1-4 heteroatoms selected from oxygen, nitrogen, or sulfur.

In some embodiments, R⁴ is —(CH$_2$)$_n$SR, —(CH$_2$)$_n$OH, —(CH$_2$)$_n$F, —(CH$_2$)$_n$C(O)N(R)$_2$, —C(O)OR, —(CH$_2$)$_n$R⁷, or —CH(CH$_3$)OCH$_2$R⁷, R⁷ is an optionally substituted ring selected from the group consisting an optionally substituted group selected from the group consisting of C$_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 8- to 10-membered bicyclic aryl, 7- to 10-membered saturated or partially unsaturated bicyclic heterocyclyl having 1-4 heteroatoms selected from oxygen, nitrogen, or sulfur, and 7- to 10-membered bicyclic heteroaryl having 1-4 heteroatoms selected from oxygen, nitrogen, or sulfur; and m is selected from 0, 1, 2, or 3.

In some embodiments, R⁷ is optionally substituted C$_{1-6}$ aliphatic. In some embodiments, R⁷ is isopropyl.

In some embodiments, R⁷ is optionally substituted phenyl. In some embodiments, R⁷ is phenyl substituted with one or more halogens. In some embodiments, R⁷ is phenyl substituted with one fluorine.

In some embodiments, R⁷ is optionally substituted 3- to 7-membered saturated or partially unsaturated monocyclic carbocyclyl. In some embodiments, R⁷ is optionally substituted 3- to 7-membered saturated or partially unsaturated monocyclic heterocyclyl having 1-2 heteroatoms selected from oxygen, nitrogen, or sulfur.

In some embodiments, R⁷ is optionally substituted 5- to 6-membered heteroaryl having 1-4 heteroatoms selected from oxygen, nitrogen, or sulfur. In some embodiments, R⁷ is a 6-membered heteroaryl having one nitrogen. In some embodiments, R⁷ is pyridyl.

In some embodiments, R⁷ is optionally substituted 7- to 10-membered bicyclic heteroaryl having 1-4 heteroatoms selected from oxygen, nitrogen, or sulfur. In some embodiments, R⁷ is optionally substituted 10-membered bicyclic heteroaryl having one heteroatom selected from nitrogen.

In certain embodiments, $R^3$ and $R^4$ are taken together with the carbon atom attached to $R^4$ and the nitrogen atom attached to $R^3$ form optionally substituted 3- to 6-membered heterocyclyl ring having 0-1 additional heteroatoms selected from oxygen, nitrogen, or sulfur. In some embodiments, $R^3$ and $R^4$ together with the carbon atom attached to $R^4$ and the nitrogen atom attached to $R^3$ form a 5-membered monocyclic heterocycle. For example, in the compound of Example 6-012, $R^3$ and $R^4$ form a 5-membered monocyclic heterocycle having one nitrogen:

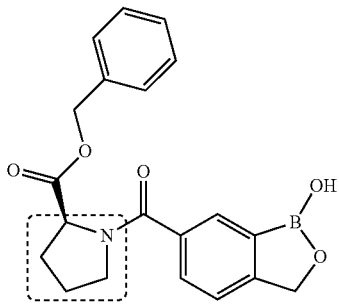

6-012

In some embodiments, $R^5$ is hydrogen. In some embodiments, $R^5$ is optionally substituted $C_{1-6}$ aliphatic. In some embodiments, $R^5$ is methyl.

In some embodiments, $R^4$ and $R^5$ are taken together with the carbon atom to which they are attached to form an optionally substituted 3- to 6-membered spiro heterocyclic ring having 1-2 heteroatoms selected from oxygen, nitrogen, or sulfur. In some embodiments, $R^4$ and $R^5$ are taken together with the carbon atom to which they are attached to form a 4-membered spiro heterocyclic ring having one oxygen. For example, in the compound of Example 6-224, $R^4$ and $R^5$ form a 4-membered spiro heterocyclic ring having one oxygen:

6-224

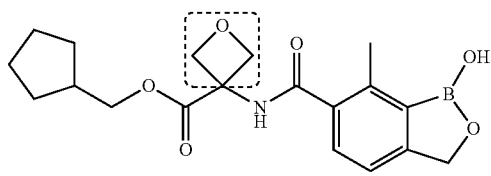

In some embodiments, $R^4$ and $R^5$ are taken together with the carbon atom to which they are attached to form optionally substituted 3- to 6-membered saturated or partially unsaturated monocyclic spiro carbocyclic ring. In some embodiments, $R^4$ and $R^5$ are taken together with the carbon atom to which they are attached to form a 3-membered saturated or partially unsaturated monocyclic spiro carbocyclic ring. In some embodiments, $R^4$ and $R^5$ are taken together with the carbon atom to which they are attached to form a 4-membered saturated or partially unsaturated monocyclic spiro carbocyclic ring.

In some embodiments, L is a covalent bond. In some embodiments, L is optionally substituted, bivalent $C_{1-10}$ saturated or unsaturated, straight or branched, hydrocarbon chain, wherein one, two, or three methylene units of L are optionally and independently replaced by —O—, —SO—, —S(O)$_2$—, —C(O)—, —C(O)N(R)—, —S—, —N(R)—, —C(O)O—, —OC(O)—, —N(R)C(O)—, —N(R)S(O)$_2$—, or —S(O)$_2$N(R)—. In some embodiments, L is an optionally substituted, bivalent $C_{1-10}$ saturated or unsaturated straight chain substituted with one or more halogen, —CF$_3$, or —OH. In some embodiments, L is optionally substituted —CH$_2$—. In some embodiments L is —CH$_2$—, wherein —CH$_2$— is substituted with one or two methyl groups. In some embodiments L is —CH$_2$—, wherein —CH$_2$— is substituted with two methyl groups. In some embodiments L is —CH$_2$—, wherein —CH$_2$— is substituted with methyl.

In some embodiments, L is optionally substituted —CH$_2$CH$_2$—. In some embodiments, L is —CH$_2$CH$_2$— substituted with one or more methyl groups. In some embodiments, L is —CH$_2$CH$_2$— substituted with methyl. In some embodiments, L is —CH$_2$CH$_2$— substituted with —OH. In some embodiments, L is —CH$_2$CH$_2$— substituted with halogen. In some embodiments, L is —CH$_2$CH$_2$— substituted with fluorine.

In some embodiments, L is optionally substituted —CH$_2$CH$_2$CH$_2$—. In some embodiments, L is —CH$_2$CH$_2$CH$_2$— substituted with —OH. In some embodiments, L is —CH$_2$CH$_2$CH$_2$— substituted with —CH$_2$OH.

In some embodiments, L is optionally substituted, bivalent $C_{1-10}$ saturated or unsaturated, straight or branched, hydrocarbon chain, wherein one, two, or three methylene units of L are optionally and independently replaced by -Cy-. In some embodiments, one or two methylene units of L are independently replaced by -Cy- wherein -Cy- is 4- to 7-membered saturated or partially unsaturated monocyclic heterocyclylene having 1-2 heteroatoms selected from oxygen, nitrogen, or sulfur. In some embodiments, L is

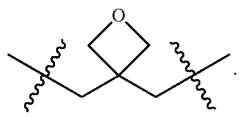 [SMILES: *CC1(C*)COC1]

In some embodiments, L is

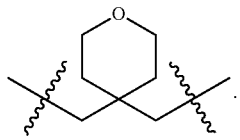 [SMILES: *CC1(C*)CCOCC1]

In some embodiments, L is optionally substituted, bivalent $C_{1-6}$ saturated or unsaturated, straight or branched, hydrocarbon chain, wherein one, two, or three methylene units of L are optionally and independently replaced by -Cy-, —O—, —SO—, —SO$_2$—, —C(O)—, —C(O)N(R)—, —S—, —N(R)—, —C(O)O—, —OC(O)—, —N(R)C(O)—, —N(R)SO$_2$—, or —SO$_2$N(R)—.

In some embodiments, L is optionally substituted, bivalent $C_{1-5}$ saturated or unsaturated, straight or branched, hydrocarbon chain, wherein one, two, or three methylene units of L are optionally and independently replaced by -Cy-, —O—, —SO—, —SO$_2$—, —C(O)—, —C(O)N(R)—, —S—, —N(R)—, —C(O)O—, —OC(O)—, —N(R)C(O)—, —N(R)SO$_2$—, or —SO$_2$N(R)—.

In some embodiments, L is optionally substituted, bivalent $C_{1-4}$ saturated or unsaturated, straight or branched, hydrocarbon chain, wherein one or two methylene units of L are optionally and independently replaced by -Cy-, —O—, —SO—, —SO$_2$—, —C(O)—, —C(O)N(R)—, —S—, —N(R)—, —C(O)O—, —OC(O)—, —N(R)C(O)—, —N(R)SO₂—, or —SO₂N(R)—.

In some embodiments, L is optionally substituted, bivalent $C_{1-3}$ saturated or unsaturated, straight or branched, hydrocarbon chain, wherein one or two methylene units of L are optionally and independently replaced by -Cy-, —O—, —SO—, —SO₂—, —C(O)—, —C(O)N(R)—, —S—, —N(R)—, —C(O)O—, —OC(O)—, —N(R)C(O)—, —N(R)SO₂—, or —SO₂N(R)—.

In some embodiments, L is optionally substituted, bivalent $C_{2-6}$ saturated or unsaturated, straight or branched, hydrocarbon chain, wherein one, two or three methylene units of L are optionally and independently replaced by -Cy-, —O—, —SO—, —SO₂—, —C(O)—, —C(O)N(R)—, —S—, —N(R)—, —C(O)O—, —OC(O)—, —N(R)C(O)—, —N(R)SO₂—, or —SO₂N(R)—.

In some embodiments, L is optionally substituted, bivalent $C_{2-4}$ saturated or unsaturated, straight or branched, hydrocarbon chain, wherein one or two methylene units of L are optionally and independently replaced by -Cy-, —O—, —SO—, —SO₂—, —C(O)—, —C(O)N(R)—, —S—, —N(R)—, —C(O)O—, —OC(O)—, —N(R)C(O)—, —N(R)SO₂—, or —SO₂N(R)—.

In some embodiments, one or two methylene units of L are replaced by -Cy-. In some embodiments, -Cy- is selected from:

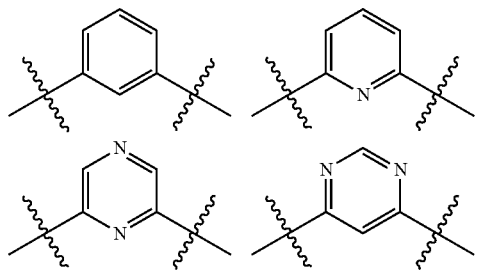

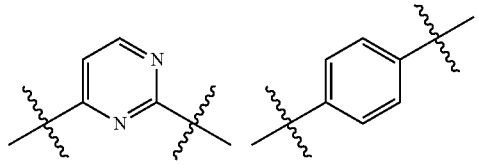

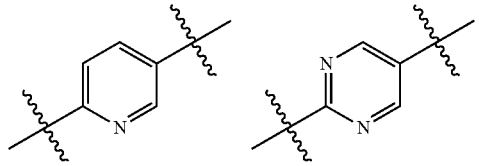

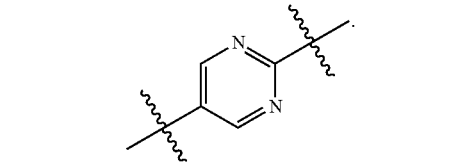

In some embodiments, L is selected from:

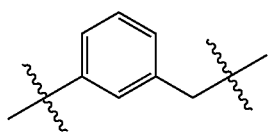

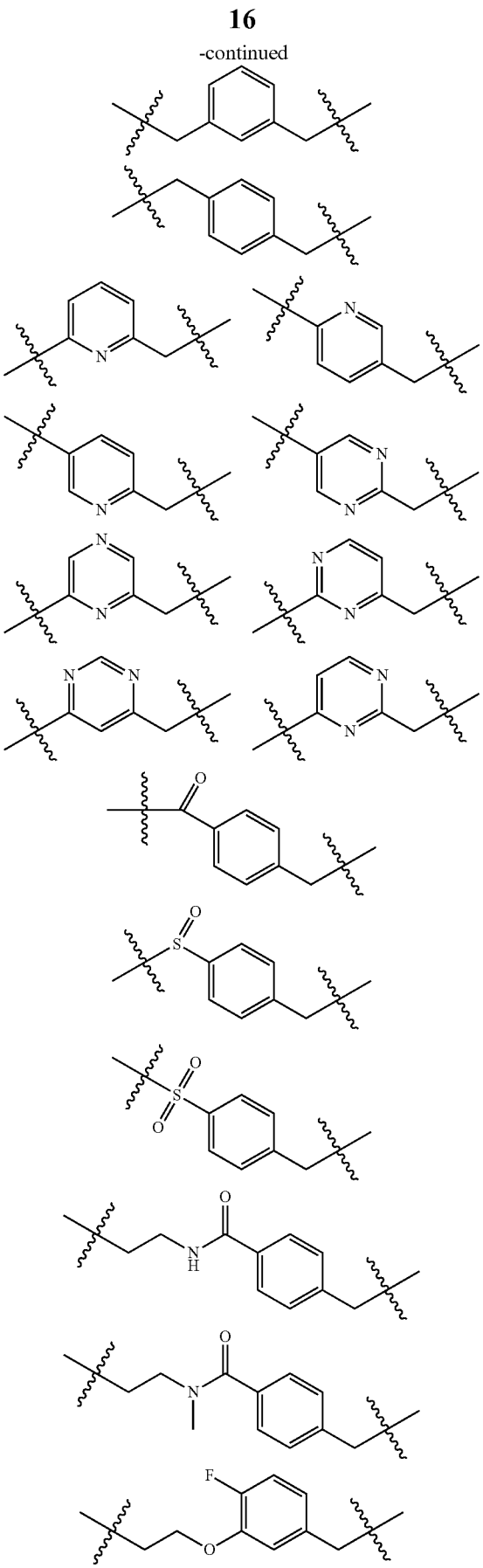

-continued

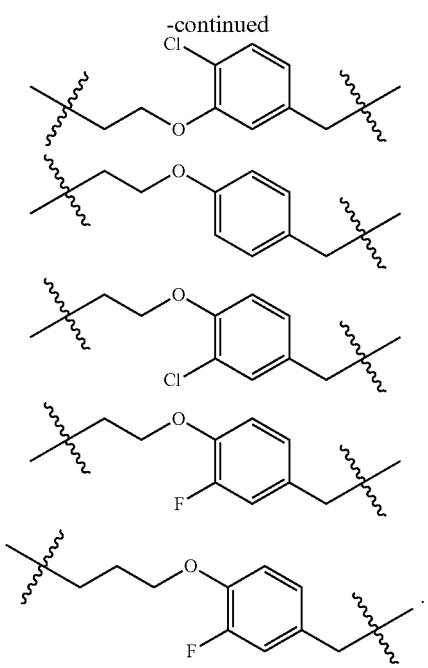

In some embodiments, R⁶ is optionally substituted phenyl. In some embodiments, R⁶ is phenyl. In some embodiments, R⁶ is phenyl substituted with one or more groups selected from —OR, —NO₂, —CN, —SR, —N(R)₂, —C(O)R, —C(O)OR, —S(O)R, —S(O)₂R, —C(O)N(R)₂, —S(O)₂N(R)₂, —OC(O)R, —N(R)C(O)R, —N(R)C(O)OR, —N(R)SO₂R, or —OC(O)N(R)₂. In some embodiments, R⁶ is phenyl substituted with —CN. In some embodiments, R⁶ is phenyl substituted with —OCF₃.

In some embodiments, R⁶ is phenyl substituted with —S(O)CH₃. In some embodiments, R⁶ is phenyl substituted with —S(O)CH₂CH₃. In some embodiments, R⁶ is phenyl substituted with —S(O)₂CH₃. In some embodiments, R⁶ is phenyl substituted with —S(O)₂CH₂CH₃. In some embodiments, R⁶ is phenyl substituted with —S(O)₂CH(CH₃)₂. In some embodiments, R⁶ is phenyl substituted with —S(O)₂CH₂CH₃. In some embodiments, R⁶ is phenyl substituted with —S(O)₂NH₂. In some embodiments, R⁶ is phenyl substituted with —NHS(O)₂CH₃. In some embodiments, R⁶ is phenyl substituted —CH₂NH(CH₃). In some embodiments, R⁶ is phenyl substituted with —S(O)₂CH₃ and —CH₂N(CH₃)₂.

In some embodiments, R⁶ is phenyl substituted with one or more halogen groups. In some embodiments, R⁶ is phenyl substituted with one or more fluorine groups. In some embodiments, R⁶ is phenyl substituted with one or more chlorine groups. In some embodiments, R⁶ is phenyl substituted with one fluorine. In some embodiments, R⁶ is phenyl substituted with one chlorine. In some embodiments, R⁶ is phenyl substituted with two fluorine groups. In some embodiments, R⁶ is phenyl substituted with three fluorine groups. In some embodiments, R⁶ is phenyl substituted with —CF₃. In some embodiments, R⁶ is phenyl substituted with —CF₃ and one fluorine. In some embodiments, R⁶ is phenyl substituted with one fluorine and one chlorine.

In some embodiments, R⁶ is phenyl substituted with one or more optionally substituted C₁₋₆ aliphatic. In some embodiments, R⁶ is phenyl substituted with one or more methyl groups.

In some embodiments, R⁶ is optionally substituted 5- to 6-membered heteroaryl having 1-4 heteroatoms selected from oxygen, nitrogen, or sulfur. In some embodiments, R⁶ is optionally substituted 6-membered heteroaryl having 1-2 heteroatoms selected from oxygen, nitrogen, or sulfur. In some embodiments, R⁶ is optionally substituted 6-membered heteroaryl having 1-2 heteroatoms selected from oxygen or nitrogen. In some embodiments, R⁶ is optionally substituted 6-membered heteroaryl having 1-2 heteroatoms selected from nitrogen. In some embodiments, R⁶ is

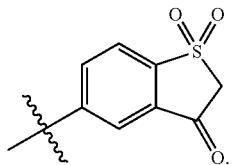 [SMILES: *c1ccc2c(c1)C(=O)CS2(=O)=O]

In some embodiments, R6 is optionally substituted pyridyl, pyrimidinyl, or pyrazinyl. In some embodiments, R⁶ is pyridyl. In some embodiments, R⁶ is pyridyl substituted with —CN or —CF₃. In some embodiments, R⁶ is pyridyl substituted with halogen. In some embodiments, R⁶ is pyridyl substituted with fluorine. In some embodiments, R⁶ is pyridyl substituted with fluorine and —CF₃. In some embodiments, R⁶ is

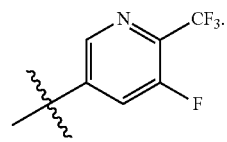

In some embodiments, R⁶ is pyridyl substituted with morpholinyl. In some embodiments, R⁶ is pyridyl substituted with piperazinyl.

In some embodiments, R⁶ is pyrimidinyl substituted with halogen. In some embodiments, R⁶ is pyrimidinyl substituted with fluorine. In some embodiments, R⁶ is pyrimidinyl substituted with —CF₃. In some embodiments, R⁶ is pyrimidinyl substituted with —NH₂.

In some embodiments, R⁶ is pyrazinyl substituted with morpholinyl. In some embodiments, R⁶ is pyrazinyl substituted with piperazinyl. In some embodiments, R⁶ is pyrazinyl substituted with

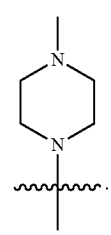

In some embodiments, R⁶ is optionally substituted 5-membered heteroaryl having 1-3 heteroatoms selected from oxygen, nitrogen, or sulfur. In some embodiments, R⁶ is optionally substituted 5-membered heteroaryl having 2 heteroatoms selected from oxygen, nitrogen, or sulfur. In some embodiments, R⁶ is optionally substituted thiazolyl or imidazolyl.

In some embodiments, R$^6$ is optionally substituted 7- to 10-membered bicyclic heteroaryl having 1-4 heteroatoms selected from oxygen, nitrogen, or sulfur. In some embodiments, R$^6$ is optionally substituted 10-membered bicyclic heteroaryl having 2 heteroatoms selected from nitrogen. In some embodiments, R$^6$ is optionally substituted 10-membered bicyclic heteroaryl having 1 heteroatom selected from nitrogen. In some embodiments, R$^6$ is optionally substituted 9-membered bicyclic heteroaryl having 1 heteroatom selected from nitrogen.

In some embodiments, R$^6$ is optionally substituted 7- to 10-membered saturated or partially unsaturated bicyclic heterocyclyl having 1-4 heteroatoms selected from oxygen, nitrogen, or sulfur. In some embodiments, R$^6$ is optionally substituted 9-membered saturated or partially unsaturated bicyclic heterocyclyl having one heteroatom selected from sulfur.

In some embodiments, R$^6$ is optionally substituted 3- to 7-membered saturated or partially unsaturated monocyclic heterocyclyl having 1-2 heteroatoms selected from oxygen, nitrogen, or sulfur. In some embodiments, R$^6$ is optionally substituted 6-membered saturated or partially unsaturated monocyclic heterocyclyl having 1-2 heteroatoms selected from oxygen, nitrogen, or sulfur. In some embodiments, R$^6$ is optionally substituted 6-membered saturated or partially unsaturated monocyclic heterocyclyl having 1-2 heteroatoms selected from oxygen or nitrogen. In some embodiments, R$^6$ is optionally substituted 6-membered saturated or partially unsaturated monocyclic heterocyclyl having one oxygen and one nitrogen. In some embodiments, R$^6$ is optionally substituted 6-membered saturated or partially unsaturated monocyclic heterocyclyl having two nitrogens. In some embodiments, R$^6$ is optionally substituted morpholinyl. In some embodiments, R$^6$ is optionally substituted piperazine. In some embodiments, R$^6$ is morpholinyl substituted with one or more methyl groups. In some embodiments, R$^6$ is optionally substituted 6-membered saturated or partially unsaturated monocyclic heterocyclyl having one heteroatom selected from oxygen. In some embodiments, R$^6$ is

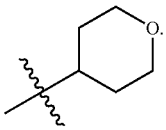

In some embodiments, R$^6$ is optionally substituted 5-membered saturated or partially unsaturated monocyclic heterocyclyl having 2 heteroatom selected from oxygen, nitrogen, or sulfur. In some embodiments, R$^6$ is optionally substituted 5-membered saturated or partially unsaturated monocyclic heterocyclyl having 2 heteroatom selected from oxygen or nitrogen. In some embodiments, R$^6$ is optionally substituted oxazolidinyl or dioxolanyl. In some embodiments, R$^6$ is dioxolanyl substituted with two methyl groups.

In some embodiments, R$^6$ is optionally substituted 5-membered saturated or partially unsaturated monocyclic heterocyclyl having one heteroatom selected from oxygen, nitrogen, or sulfur. In some embodiments, R$^6$ is optionally substituted 5-membered saturated or partially unsaturated monocyclic heterocyclyl having one heteroatom selected from oxygen. In some embodiments, R$^6$ is optionally substituted 5-membered saturated or partially unsaturated monocyclic heterocyclyl having one heteroatom selected from nitrogen. In some embodiments, R$^6$ is R$^6$ optionally substituted pyrrolidinyl or tetrahydrofuranyl. In some embodiments, is pyrrolidinyl or tetrahydrofuranyl.

In some embodiments, R$^6$ is optionally substituted 4-membered saturated or partially unsaturated monocyclic heterocyclyl having one heteroatom selected from oxygen, nitrogen, or sulfur. In some embodiments, R$^6$ is optionally substituted 4-membered saturated or partially unsaturated monocyclic heterocyclyl having one heteroatom selected from oxygen. In some embodiments, R$^6$ is optionally substituted oxetanyl. In some embodiments, R$^6$ is oxetanyl.

In some embodiments, R$^6$ is optionally substituted 3- to 7-membered saturated or partially unsaturated monocyclic carbocyclyl. In some embodiments, R$^6$ is optionally substituted 6-membered saturated or partially unsaturated monocyclic carbocyclyl. In some embodiments, R$^6$ is optionally substituted cyclohexyl. In some embodiments, R$^6$ is cyclohexyl. In some embodiments, R$^6$ is cyclohexyl substituted with one or more halogen groups. In some embodiments, R$^6$ is cyclohexyl substituted with two fluorine groups. In some embodiments, R$^6$ is

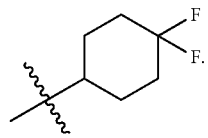 [SMILES: *C1CCC(F)(F)CC1]

In some embodiments, R$^6$ is optionally substituted 5-membered saturated or partially unsaturated monocyclic carbocyclyl. In some embodiments, R$^6$ is optionally substituted cyclopentyl. In some embodiments, R$^6$ is cyclopentyl.

In some embodiments, R$^6$ is optionally substituted 4-membered saturated or partially unsaturated monocyclic carbocyclyl. In some embodiments, R$^6$ is optionally substituted cyclobutyl. In some embodiments, R$^6$ is cyclobutyl.

In some embodiments, R$^6$ is —OR, —NO$_2$, —CN, —SR, —N(R)$_2$, —C(O)R, —C(O)OR, —S(O)R, —S(O)$_2$R, —C(O)N(R)$_2$, —S(O)$_2$N(R)$_2$, —OC(O)R, —N(R)C(O)R, —N(R)C(O)OR, —N(R)S(O)$_2$R, or —OC(O)N(R)$_2$. In some embodiments, R$^6$ is —OH. In some embodiments, R$^6$ is —CN. In some embodiments, R$^6$ is —OCF$_3$. In some embodiments, R$^6$ is —SOCH$_3$. In some embodiments, R$^6$ is —S(O)CH$_2$CH$_3$. In some embodiments, R$^6$ is —S(O)$_2$CH$_3$. In some embodiments, R$^6$ is —S(O)$_2$CH$_2$CH$_3$. In some embodiments, R$^6$ is —S(O)$_2$CH(CH$_3$)$_2$. In some embodiments, R$^6$ is —S(O)$_2$NH$_2$. In some embodiments, R$^6$ is —NHS(O)$_2$CH$_3$. In some embodiments, R$^6$ is —CH$_2$NH (CH$_3$).

In some embodiments, R$^6$ is halogen. In some embodiments, R$^6$ is fluorine. In some embodiments, R$^6$ is chlorine.

In some embodiments, R$^6$ is hydrogen.

In some embodiments, R$^6$ is optionally substituted group selected from:

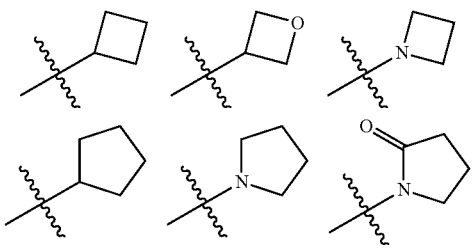

-continued

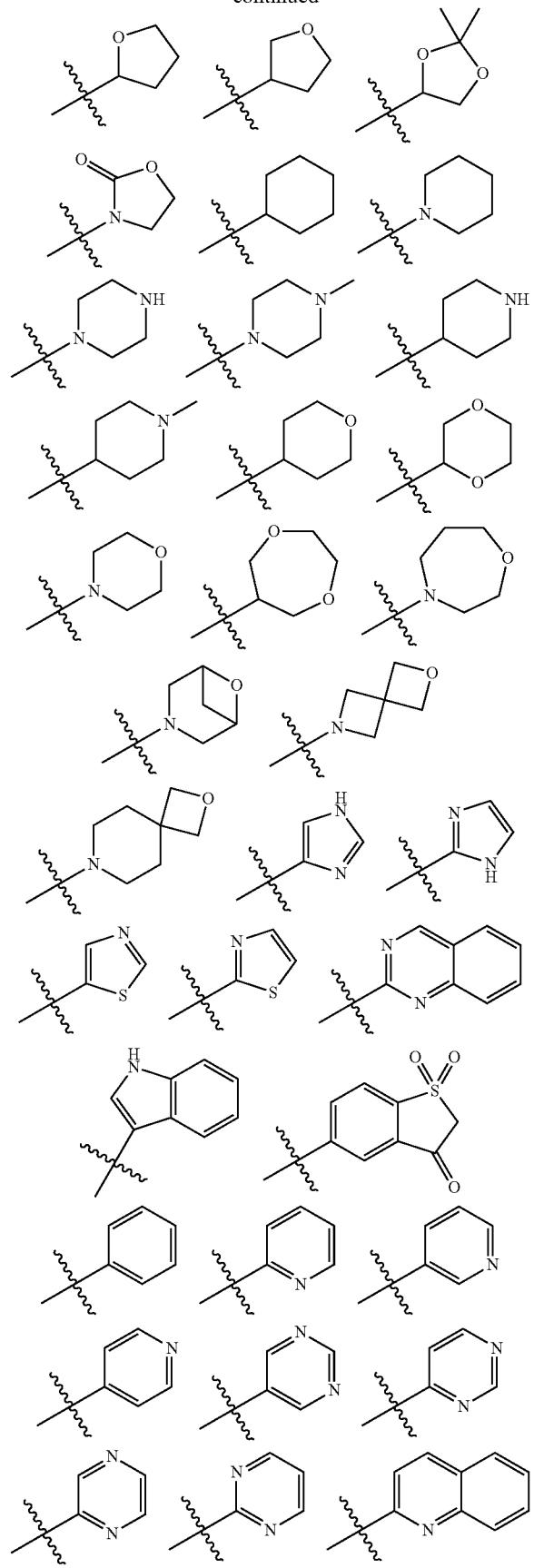

-continued

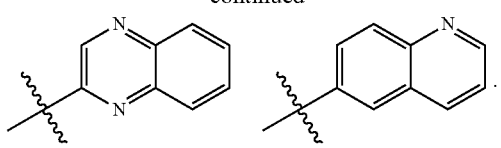

In some embodiments, $R^6$ is substituted with one or more groups selected from the group consisting of -halogen, —OR, —NO$_2$, —CN, —SR, —N(R)$_2$, —C(O)R, —C(O)OR, —S(O)R, —S(O)$_2$R, —C(O)N(R)$_2$, —S(O)$_2$N(R)$_2$, —OC(O)R, —N(R)C(O)R, —N(R)C(O)OR, —N(R)S(O)$_2$R, —OC(O)N(R)$_2$, and C$_{1-6}$ aliphatic optionally substituted with halogen. In some embodiments, $R^6$ is substituted with one or more groups selected from the group consisting of methyl, —F, —Cl, —OH, —OCH$_3$, —NH$_2$, —NHCH$_3$, —N(CH$_3$)CH$_3$, —CF$_3$, —CN, —OCF$_3$, —S(O)$_2$CH$_3$, and —NHS(O)$_2$CH$_3$.

In some embodiments, $R^6$ is optionally substituted C$_{1-6}$ aliphatic. In some embodiments, $R^6$ is C$_{1-6}$ aliphatic.

In some embodiments, $R^6$ is —CF$_3$.

In some embodiments, $R^6$ is selected from:

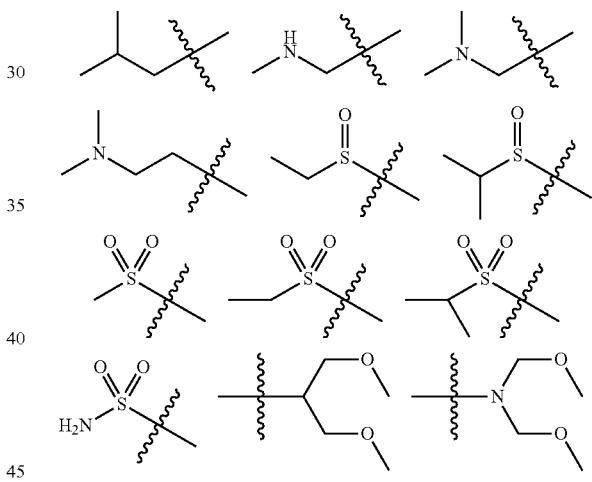

In some embodiments, L is a covalent bond and $R^6$ is hydrogen.

In some embodiments, L is a covalent bond and $R^6$ is phenyl. In some embodiments, L is a —CH$_2$— and $R^6$ is phenyl. In some embodiments, L is a —CH$_2$(CH$_3$)— and $R^6$ is phenyl.

In some embodiments, L is —CH$_2$— and $R^6$ is phenyl substituted with one fluorine. In some embodiments, L is —CH$_2$— and $R^6$ is phenyl substituted with two fluorine groups. In some embodiments, L is —CH$_2$— and $R^6$ is

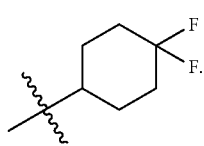 [SMILES: *C1CCC(F)(F)CC1]

In some embodiments, L is —CH$_2$— and R$^6$ is

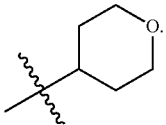 [SMILES: *C1CCOCC1]

In some embodiments, L is a covalent bond and R$^6$ is cyclohexyl. In some embodiments, L is a covalent bond and R$^6$ is cyclopentyl. In some embodiments, L is a covalent bond and R$^6$ is cyclobutyl. In some embodiments, L is a covalent bond and R$^6$ is

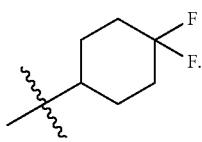 [SMILES: *C1CCC(F)(F)CC1]

In some embodiments, L is a covalent bond and R$^6$ is tetrahydropyranyl. In some embodiments, L is a covalent bond and R$^6$ is tetrahydrofuranyl. In some embodiments, L is a covalent bond and R$^6$ is oxetanyl.

In some embodiments, provided compounds are of formula II:

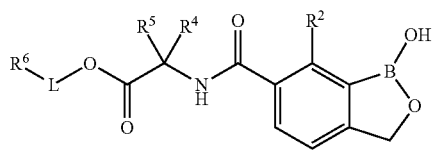

or a pharmaceutically acceptable salt thereof, wherein each of R$^2$, R$^4$, R$^5$, R$^6$ and L is as defined above and described in classes and subclasses herein, both singly and in combination.

In some embodiments, provided compounds are of formula III:

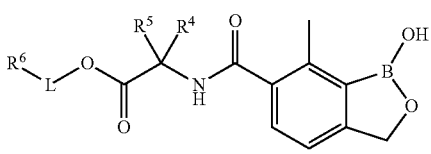

or a pharmaceutically acceptable salt thereof, wherein each of R$^4$, R$^5$, R$^6$ and L is as defined above and described in classes and subclasses herein, both singly and in combination.

In some embodiments, provided compounds are of formula III-a:

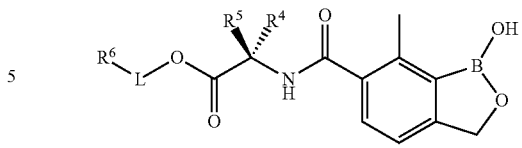

or a pharmaceutically acceptable salt thereof, wherein each of R$^4$, R$^5$, R$^6$ and L is as defined above and described in classes and subclasses herein, both singly and in combination. In some embodiments of compounds of formula III-a, L is a covalent bond and R$^6$ is

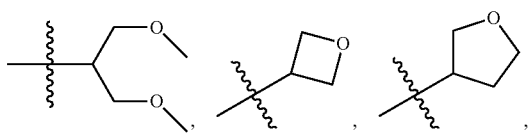

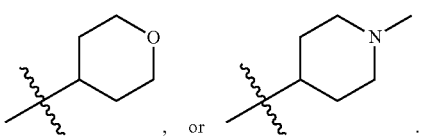

In some embodiments, provided compounds are of formula IV:

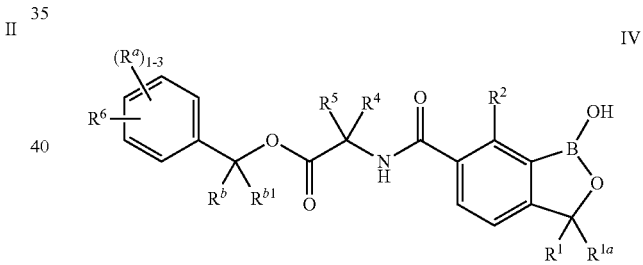

or a pharmaceutically acceptable salt thereof, wherein each of R$^1$, R$^{1a}$, R$^b$, R$^{b1}$, R$^a$, R$^4$, R$^5$, and R$^6$ is as defined above and described in classes and subclasses herein, both singly and in combination. In some embodiments, each R$^a$ is independently -hydrogen, -halogen, —OR, —NO$_2$, —CN, —SR, —N(R)$_2$, —C(O)R, —C(O)OR, —S(O)R, —S(O)$_2$R, —C(O)N(R)$_2$, —S(O)$_2$N(R)$_2$, —OC(O)R, —N(R)C(O)R, —N(R)C(O)OR, —N(R)S(O)$_2$R, or —OC(O)N(R)$_2$. In some embodiments, each R$^a$ is independently hydrogen, methyl, —F, —Cl, —CF$_3$, —CN, —OCF$_3$, or —S(O)$_2$CH$_3$. In some embodiments, R$^a$ is independently fluorine or chlorine.

In some embodiments, R$^b$ and R$^{b1}$ are hydrogen. In some embodiments, R$^b$ and R$^{b1}$ are methyl. In some embodiments, R$^b$ is methyl and R$^{b1}$ is hydrogen. In some embodiments of compounds of formula IV, R$^6$ is fluorine and one R$^a$ is fluorine. In some embodiments of compounds of formula IV, R$^6$ is fluorine and two R$^a$ are fluorine.

In some embodiments, provided compounds are of formula V:

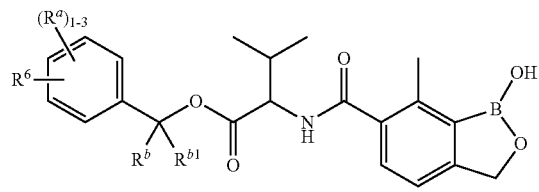

V or a pharmaceutically acceptable salt thereof, wherein each of $R^b$, $R^{b1}$, $R^a$, and $R^6$ is as defined above and described in classes and subclasses herein, both singly and in combination. In some embodiments of compounds of formula V, $R^6$ is —$S(O)_2CH_3$ and $R^a$ is —$CH_2N(CH_3)_2$.

In some embodiments, provided compounds are of formula V-a and V-b:

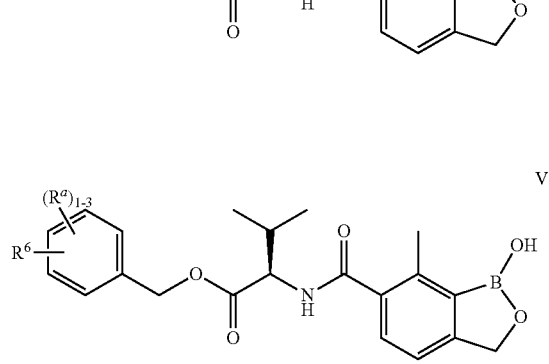

V-a

V-b or a pharmaceutically acceptable salt thereof, wherein each of $R^a$ and $R^6$ is as defined above and described in classes and subclasses herein, both singly and in combination.

In some embodiments, provided compounds are of formula VI-a, VI-b, VI-c, VI-d, VI-e, or VI-f:

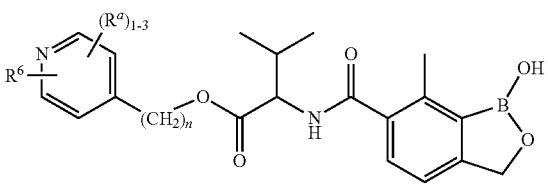

VI-a

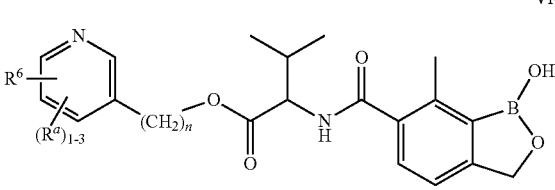

VI-b

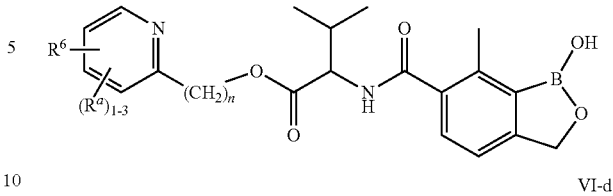

VI-c

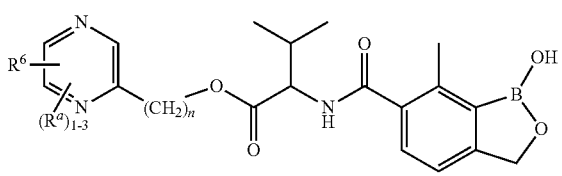

VI-d

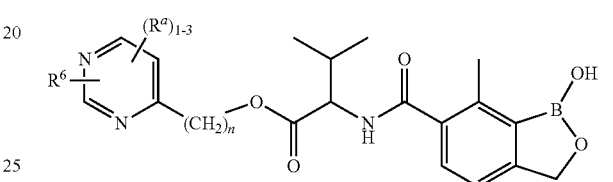

VI-e

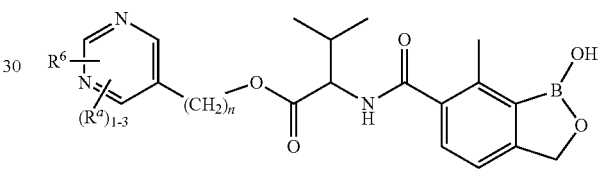

VI-f or a pharmaceutically acceptable salt thereof, wherein each of n, $R^a$ and $R^6$ is as defined above and described in classes and subclasses herein, both singly and in combination. In some embodiments of compounds of formula VI-a-f, n is 1, 2 and 3. In some embodiments of compounds of formula VI-a-f, $R^6$ is —F, —$CF_3$, —CN, —$N(CH_3)_2$, —$NH(CH_3)$ or —$NH_2$ and $R^a$ is hydrogen. In some embodiments of compounds of formula VI-a-f, $R^6$ is hydrogen and $R^a$ is hydrogen.

In some embodiments, provided compounds are of formula VII-a, VII-b or VII-c:

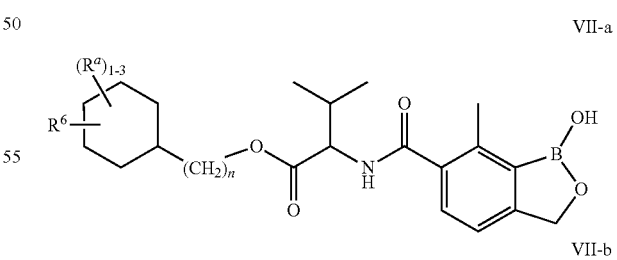

VII-a

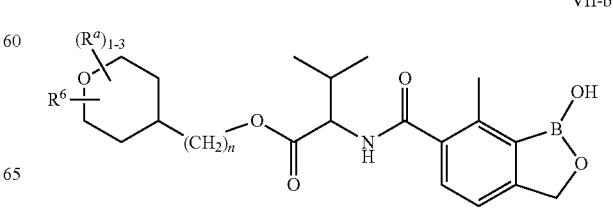

VII-b

VII-c

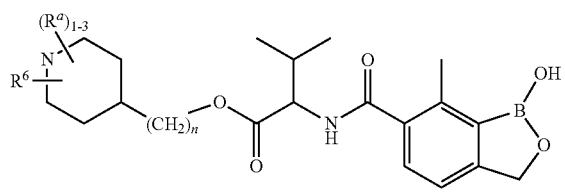

or a pharmaceutically acceptable salt thereof, wherein each of n, $R^a$ and $R^6$ is as defined above and described in classes and subclasses herein, both singly and in combination. In some embodiments of compounds of formula VII-a-c, n is 0, 1, 2 and 3.

In some embodiments, provided compounds are of formula VIII-a, VIII-b, or VIII-c:

VIII-a

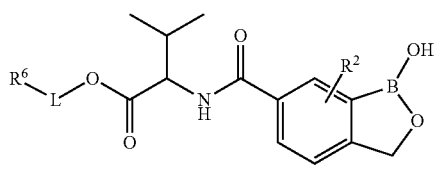

VIII-b

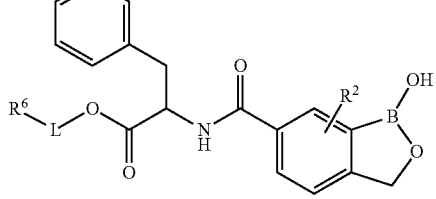

VIII-c

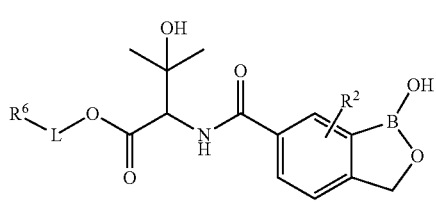

or a pharmaceutically acceptable salt thereof, wherein each of $R^2$, $R^6$ and L is as defined above and described in classes and subclasses herein, both singly and in combination.

In some embodiments, provided compounds are of formula IX-a or IX-b:

IX-a

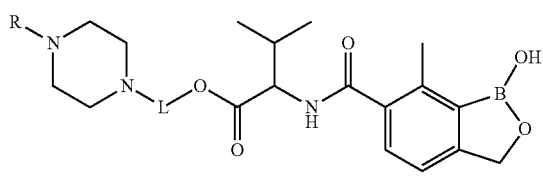

IX-b

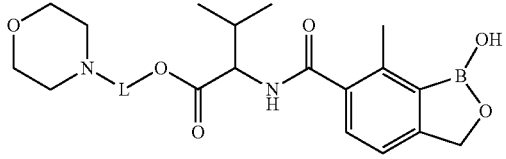

or a pharmaceutically acceptable salt thereof, wherein R is hydrogen or methyl and L is as defined above and described in classes and subclasses herein. In some embodiments, provided compounds are of formula IX-a or IX-b and L is selected from:

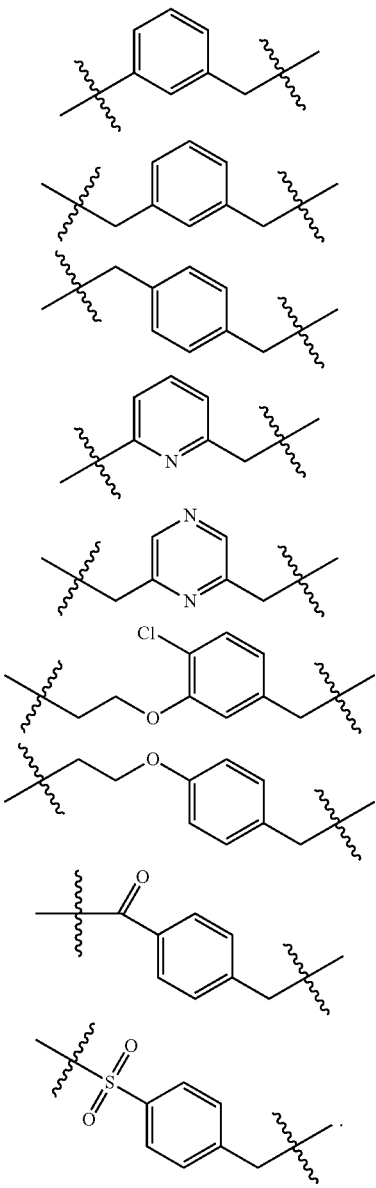

General Methods of Providing the Present Compounds

Compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

In certain embodiments, the present compounds are generally prepared according to Scheme A set forth below:

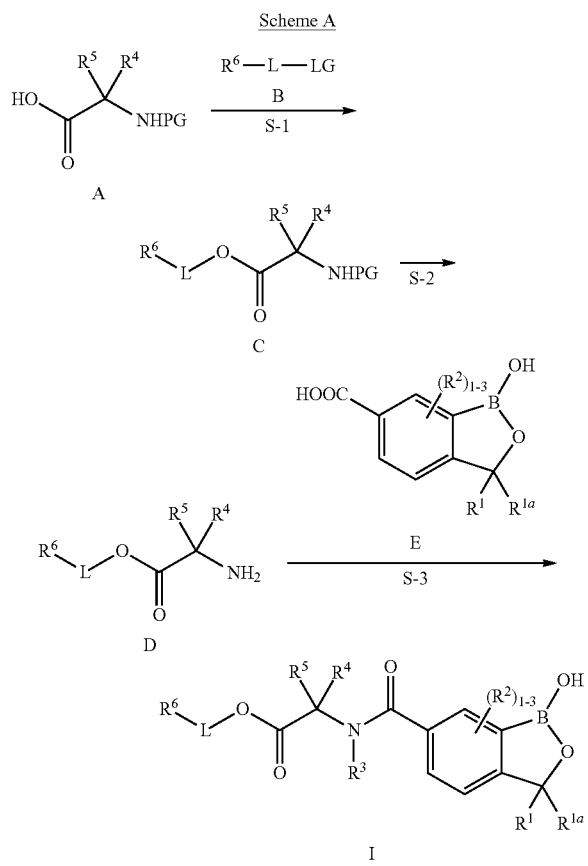

wherein each of $R^1$, $R^{1a}$, $R^2$, $R^3$, $R^4$, $R^5$, $R^6$, and L is as defined and described in classes and subclasses herein, and PG and LG are described below.

The group "LG" in Scheme A is a suitable leaving group, i.e., groups that are subject to nucleophilic displacement. A "suitable leaving group" is a chemical group that is readily displaced by a desired incoming chemical moiety such as an amine. Suitable leaving groups are well known in the art, e.g., see, "Advanced Organic Chemistry," Jerry March, 5$^{th}$ Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, acyl, and diazonium moieties. Examples of suitable leaving groups include chloro, iodo, bromo, fluoro, acetoxy, methoxy, methanesulfonyloxy (mesyloxy), tosyloxy, triflyloxy, nitro-phenylsulfonyloxy (nosyloxy), and bromo-phenylsulfonyloxy (brosyloxy).

The groups "PG" in Scheme A is a suitable protecting group, as defined above and described herein. One of ordinary skill will be familiar with a variety of protecting group and protecting group strategies that many be employed. Suitable hydroxyl and amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference.

At Step S-1, amino acid A is coupled under suitable conditions with compound B to form compound C. In some embodiments, Step S-1 employs a suitable base. Such suitable bases and suitable conditions are known in the art and can vary upon the choice of LG. In some embodiments, a suitable base is an inorganic base. In some embodiments, a suitable base is $K_2CO_3$.

One of ordinary skill in the art will appreciate that a variety of suitable leaving groups LG of compound B can be used to facilitate the reaction described in Step S-1, and all such suitable leaving groups are contemplated by the present invention. In some embodiments, LG is halogen. In some embodiments, LG is chloro. In some embodiments, LG is trichloroacetimidate.

Step S-1 may optionally employ a suitable solvent. Such suitable solvents include, for example, polar aprotic solvents (i.e., THF, DMF, dioxane, acetonitrile, and combinations thereof).

At Step S-2, compound C is deprotected under suitable conditions as described in Greene and Wuts (supra) to form amine D. Such suitable conditions are known in the art and can vary upon the choice of protecting group. In some embodiments, PG is a Boc group and suitable conditions comprise a suitable acid. In certain embodiments, a suitable acid is an inorganic acid or a Lewis acid. In some embodiments, the acid is HCl.

At Step S-3, amine D is coupled under suitable conditions with carboxylic acid E to form a compound of formula I. Step S-3 may employ peptide coupling reagents. In some embodiments, a peptide coupling reagent is selected from FDPP, PFPOH, BOP-Cl, EDC, EDCA, DCC, DIC, HOBt, HOAt, HBTU, HATU, HCTU, TBTU, PyBOP, or a combination thereof. In some embodiments, suitable conditions comprise a suitable coupling reagent selected from EDCI/HOBt, PyBOP, HATU, or BEM (Carpino, L. A. *J. Am. Chem. Soc.* 1993, 115, 4397. Carpino, L. A.; El-Faham, A. *J. Am. Chem. Soc.* 1995, 117, 5401. Li, P.; Xu, J. C. *J. Pept. Res.* 2001, 58, 129.) in the presence of a base familiar to one skilled in the art and in an appropriate solvent. In certain embodiments, a suitable base is an amine base. In some embodiments, an amine base is DIPEA. In some embodiments, suitable solvents for Step S-3 include, for example, polar aprotic solvents (i.e., THF, DMF, dioxane, acetonitrile, and combinations thereof).

An exemplary synthesis of useful intermediates such as carboxylic acid E is depicted in Scheme B. Additional syntheses are depicted in the ensuing Examples.

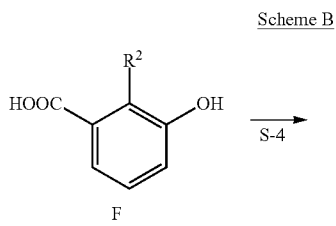

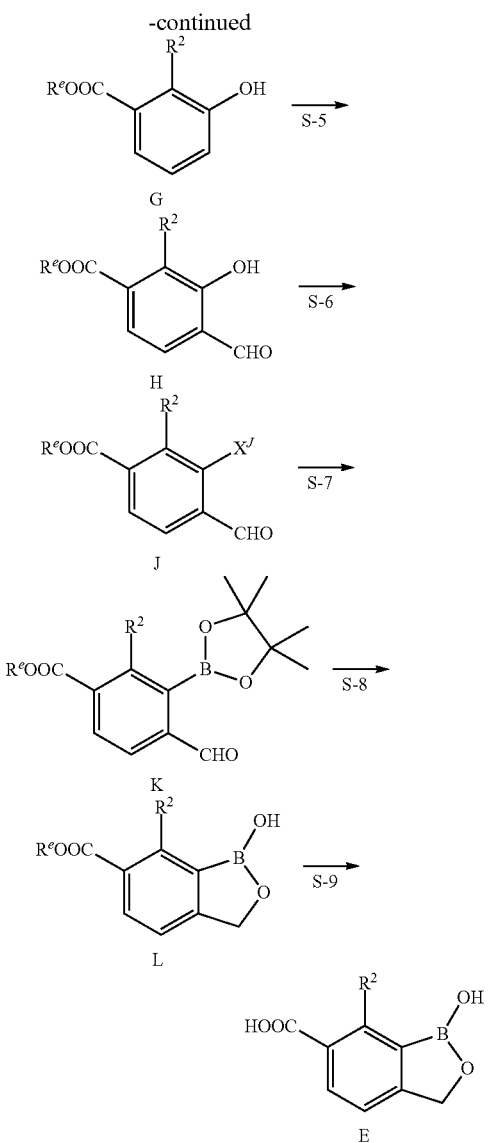

At Step S-4, acid F is esterified under suitable conditions to form ester G, wherein $R^e$ is a suitable group for forming a carboxylic ester. In some embodiments, $R^e$ is $C_{1-6}$ aliphatic. Suitable reagents for the esterification of acid F include alcohols. Step S-4 may employ a suitable acid. In certain embodiments, a suitable acid is an inorganic acid or a Lewis acid. In some embodiments, the acid is $H_2SO_4$.

At Step S-5, ester G undergoes formylation to form salicylaldehyde H. Suitable conditions for the ortho-formulation of phenols are known in the art. In some embodiments, suitable conditions comprise $MgCl_2$, an amine base, and paraformaldehyde. In some embodiments, an amine base is $Et_3N$. Step S-5 may optionally employ a suitable solvent. Suitable solvents for use in Step S-5 include polar aprotic solvents (i.e., THF, methyl-THF, dioxane, acetonitrile, and combinations thereof).

At Step S-6, salicylaldehyde H is reacted to form compound J. In some embodiments, $X^J$ is —OTf. Suitable conditions for the introduction of a triflate group are known in the art. In some embodiments, Step S-6 includes a base. In some embodiments, a base is an amine base. In certain embodiments, an amine base is pyridine, DMAP, or a combination thereof.

At Step S-7, compound J is borylated under suitable conditions to provide boronic ester K. Suitable conditions for the borylation of triflates are known in the art. In some embodiments, suitable conditions comprise bis(pinacolato) diboron, a base, and a palladium catalyst. In some embodiments, a base is potassium acetate. In some embodiments, a palladium catalyst is [1,1-bis(diphenylphosphino)ferrocene] dichloropalladium (II). Step S-7 may optionally employ a suitable solvent. Suitable solvents for use in Step S-7 include aprotic solvents (i.e., THF, methyl-THF, dioxane, acetonitrile, toluene, and combinations thereof).

It will be appreciated that groups other than triflate are suitable for compound J and borylation chemistry. For example, compound J may have a halogen (e.g., chloro, bromo, iodo) rather than a —OTf group. Suitable conditions for installing such a halogen group from compound H or other precursors are known in the art, as well as conditions for subsequent borylation. See, e.g., WO 2015013318 A1 as well as the ensuing Examples.

At Step S-8, boronic ester K is cyclized under suitable conditions to provide oxaborole L. In some embodiments, suitable conditions include a reducing agent. Suitable reducing agents include metal hydrides, for example borohydrides. In some embodiments, a reducing agent is sodium borohydride. Step S-8 optionally employs a suitable acid following the reduction. In certain embodiments, a suitable acid is an inorganic acid or a Lewis acid. In some embodiments, the acid is HCl. Step S-8 may optionally employ a suitable solvent. Suitable solvents for use in Step S-8 include, by way of non-limiting example, THF, dioxane, methanol, ethanol, and combinations thereof.

At Step S-9, oxaborole L is hydrolyzed to provide carboxylic acid E. Suitable conditions for ester hydrolysis are known in the art and include a base or acid-catalyzed reaction of an ester with water. Suitable bases include alkali hydroxides. In some embodiments, a suitable base is NaOH. In some embodiments, Step S-9 comprises an aqueous solution of NaOH.

In certain embodiments, each of the aforementioned synthetic steps may be performed sequentially with isolation of each intermediate performed after each step. Alternatively, each of steps S-1, S-2, S-3, S-4, S-5, S-6, S-7, S-8, and S-9 as depicted in Schemes A and B above, may be performed in a manner whereby no isolation of one or more intermediates is performed. Furthermore, it will be readily apparent to the skilled artisan that additional steps may be performed to accomplish particular protection group and/or deprotection strategies.

In certain embodiments, all the steps of the aforementioned synthesis may be performed to prepare the desired final product. In other embodiments, two, three, four, five, or more sequential steps may be performed to prepare an intermediate or the desired final product.

It will be appreciated by the skilled artisan that certain starting materials depicted in Schemes A and B may be readily interchanged with other starting materials or reagents to provide additional compounds of formula I. Such substitutions could be made with routine experimentation. For example, the amide nitrogen of the coupling product of amine D and carboxylic acid E may be modified to provide $R^3$ groups other than hydrogen. In addition, alkyl groups may be installed at the $R^1$ position via Grignard chemistry on intermediate aldehydes. Subsequent oxidation to the ketone followed by similar introduction of an $R^{1a}$ group may also be performed.

Methods of Use

In certain embodiments, compounds of the present invention are for use in medicine. In some embodiments, compounds of the present invention are useful in the treatment of parasitic infections. The term "parasitic infection" includes diseases or disorders involving parasites. In some embodiments, a "parasitic infection" includes diseases or disorders involving parasites such as *Trypanosoma cruzi, Trypanosoma congolense, Trypanosoma vivax*, and *Trypanosoma evansi*.

In some embodiments, compounds of the present invention are useful as therapeutics against Trypanosomatids. In some embodiments, parasites that can be treated by compounds of the present invention are *Trypanosoma cruzi, Trypanosoma congolense, Trypanosoma vivax*, and *Trypanosoma evansi*.

The term "subject," as used herein, refers to a mammal to whom a pharmaceutical composition is administered. Exemplary subjects include humans, as well as veterinary and laboratory animals such as horses, pigs, cattle, dogs, cats, rabbits, rats, mice, and aquatic mammals.

In certain embodiments, the present invention provides a method of treating a *T. congolense*-mediated disease or disorder in a subject comprising administering to a subject a provided compound. In some embodiments, the disease is trypanosomiasis. In some embodiments, the disease is African Animal Trypanosomosis (AAT).

In certain embodiments, the present invention provides a method of treating a *T. vivix*-mediated disease or disorder in a subject comprising administering to a subject a provided compound. In some embodiments, the disease is trypanosomiasis. In some embodiments, the disease is African Animal Trypanosomosis (AAT).

In some embodiments, the present invention provides a method of treating AAT comprising administering a provided compound to a subject suffering from AAT. In some embodiments, the subject suffering from AAT is a mammal. In some embodiments, the subject suffering from AAT is a cattle species. In some embodiments, the subject suffering from AAT a cow.

In certain embodiments, the present invention provides a method of treating a *T. cruzi*-mediated disease or disorder in a subject comprising administering to a subject a provided compound. In some embodiments, the disease is Chagas disease. In some embodiments, the present invention provides a method of treating Chagas disease comprising administering a provided compound to a subject suffering from Chagas disease. In some embodiments, the subject suffering from Chagas disease is a mammal. In some embodiments, the subject suffering from Chagas disease is a human. In some embodiments, the subject suffering from Chagas disease is a dog.

In some embodiments, the half maximal inhibitory concentration ($IC_{50}$) of the compound against a parasite is less than 1 uM. In some embodiments, the $IC_{50}$ of the compound against a parasite is less than 500 nM. In some embodiments, the $IC_{50}$ of the compound against a parasite is less than 100 nM. In some embodiments, the $IC_{50}$ of the compound against a parasite is less than 10 nM. In some embodiments, the $IC_{50}$ of the compound against a parasite is less than 1 nM. In some embodiments, the $IC_{50}$ of the compound against a parasite is less than 0.1 nM. In some embodiments, the $IC_{50}$ of the compound against a parasite is less than 0.01 nM. In some embodiments, the $IC_{50}$ of the compound against a parasite is less than 0.001 nM. In some embodiments, the $IC_{50}$ of the compound against a parasite is from 0.01 nM to 1 uM. In some embodiments, the $IC_{50}$ of the compound against a parasite is from 0.01 nM to 10 uM. In some embodiments, the $IC_{50}$ of the compound against a parasite is from 0.1 nM to 10 uM. In some embodiments, the $IC_{50}$ of the compound against a parasite is from 0.1 nM to 1 uM. In some embodiments, the $IC_{50}$ of compound against a parasite is from 0.1 nM to 100 nM. In some embodiments, the $IC_{50}$ of the compound against a parasite is from 0.1 nM to 10 nM.

The term "treatment" (also "treat" or "treating"), as used herein, refers to any administration of a substance (e.g., pharmaceutical composition) that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder, and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Approved more than four decades ago, the two drugs available to treat Chagas—benznidazole and nifurtimox—require a long duration of therapy (60-90 days), have serious safety concerns (20-30% side effects result in treatment discontinuation), have variable efficacy in chronic infection and Chagasic cardiomyopathy, are contraindicated in pregnancy, and have associated drug resistance. In some embodiments, provided methods are used to treat a subject previously treated for a parasitic infection. In some embodiments, provided methods are used to treat a subject previously treated with benznidazole and/or nifurtimox. In some embodiments, provided methods are used to treat a parasitic infection refractory to treatment with benznidazole and/or nifurtimox.

Pharmaceutical Compositions

In another aspect, the present invention provides pharmaceutical compositions comprising a compound of formula I or a compound of formula I in combination with a pharmaceutically acceptable excipient (e.g., carrier).

The pharmaceutical compositions include optical isomers, diastereomers, or pharmaceutically acceptable salts of the inhibitors disclosed herein. The compound of formula I included in the pharmaceutical composition may be covalently attached to a carrier moiety, as described above. Alternatively, the compound of formula I included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethylcellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be coadministered to the subject. Coadministration is meant to include simultaneous or sequential administration of the compounds individually or in combination (more than one compound). The preparations can also be combined, when desired, with other active substances (e.g. to reduce metabolic degradation).

Combinations

The compounds of the invention may also be used in combination with additional therapeutic agents. The invention thus provides, in a further aspect, a combination comprising a compound described herein or a pharmaceutically acceptable salt thereof together with at least one additional therapeutic agent. In an exemplary embodiment, the additional therapeutic agent is a compound of the invention. In an exemplary embodiment, the additional therapeutic agent includes a boron atom.

When a compound of the invention is used in combination with a second therapeutic agent active against the same disease state, the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian.

Formulations

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In some embodiments, suitable carriers for parenteral administration will be selected for human administration. In some embodiments, suitable carriers for parenteral administration will be selected for veterinary administration. In particular, carriers for parenteral administration include aqueous solutions of dextrose, saline, pure water, ethanol, glycerol, glycerol formal, polyethylene glycol, propylene glycol, peanut oil, sesame oil, polyoxyethylene-block polymers, pyrrolidine, N-methyl pyrrolidone, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

For administration to non-human animals, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also be formulated as a food or drink supplement for humans.

Effective Dosage

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to a parasitic infection, such compositions will contain an amount of active ingredient effective to achieve the desired result.

The dosage and frequency (single or multiple doses) of compound administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of killing parasites and/or controlling their growth or reproduction as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring kinase inhibition and adjusting the dosage upwards or downwards, as described above. Therapeutically effective amounts for use in animals (e.g., cattle) may be determined from animal models (e.g., mouse models).

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

EXAMPLES

The examples below are meant to illustrate certain embodiments of the invention, and not to limit the scope of the invention.

It will be appreciated that where an Example refers to another Example by referring to "Example I-XX", the reference is to the synthesis of the respective Compound 6-XX, or the relevant portion of the synthesis.

Example A-1: Preparation of Acid-04

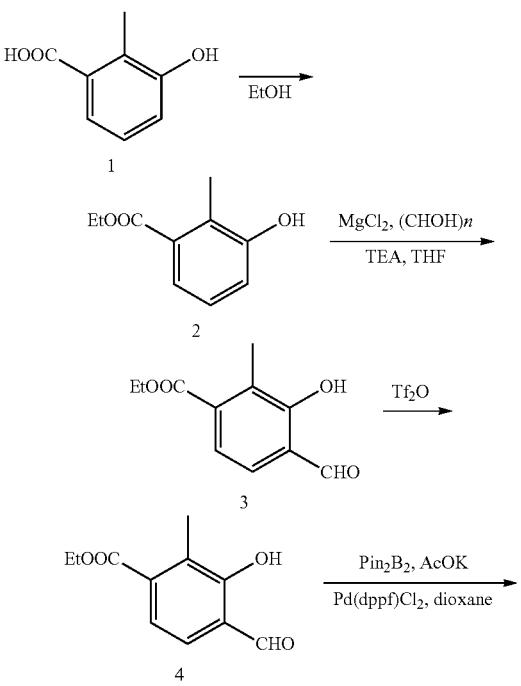

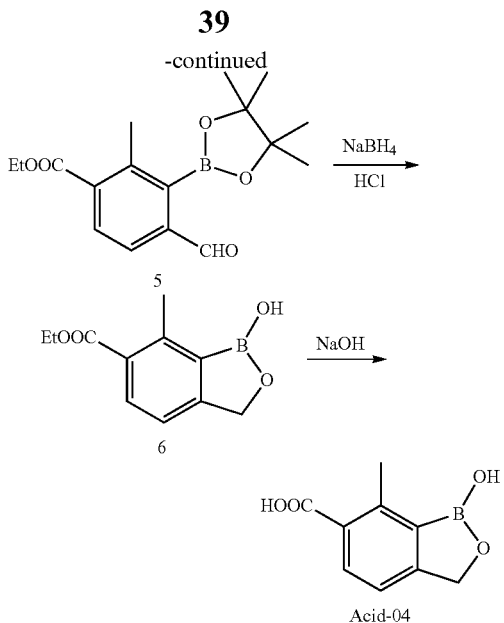

To a solution of 1 (1.65 kg, 10.8 mol) in EtOH (6.50 L) was added conc. H$_2$SO$_4$ (326 g, 3.25 mol). The reaction mixture was heated 105° C. for 24 h. TLC showed 1 was consumed completely. The mixture was cooled to 15° C. and concentrated to give the crude product. The residue was poured into 2 M NaHCO$_3$ (aq., 3 L) and the solid was filtered. The filtrate was concentrated to give 2 (1.75 kg, 90%) as brown solid. $^1$H NMR (400 MHz, CDCl$_3$) δ 7.41 (d, J=7.9 Hz, 1H), 7.11 (t, J=7.9 Hz, 1H), 6.94 (d, J=7.9 Hz, 1H), 4.58 (br s, 1H), 4.37 (q, J=7.4 Hz, 2H), 2.46 (s, 3H), 1.40 (t, J=7.1 Hz, 3H).

To a solution of 2 (800 g, 4.44 mol) in THF (6.50 L) were added MgCl$_2$ (634 g, 6.66 mol, 273 mL), TEA (1.80 kg, 17.8 mol) and (HCHO)n (600 g, 6.66 mol). The mixture was immediately heated to 90° C. for 14 h. TLC showed the 2 was completely consumed. The reaction mixture was cooled to 15° C., added ice H$_2$O (3 L) and slowly added 12 M HCl (1.5 L). The mixture was stirred for half an hour and then extracted with EtOAc (2 L). The combined organic layer was washed by sat. NaHCO$_3$ to neutral, dried over Na$_2$SO$_4$, filtered and concentrated under reduced pressure to give 3 (880 g, crude) as brown oil. $^1$H NMR (400 MHz, CDCl$_3$) δ 11.40 (s, 1H), 9.93 (s, 1H), 7.46 (d, J=7.6 Hz, 1H), 7.37 (d, J=8.0 Hz, 1H), 4.40 (q, J=7.4 Hz, 2H), 2.44 (s, 3H), 1.41 (t, J=7.1 Hz, 3H).

To a solution of 3 (900 g, 4.32 mol) in DCM (7.56 L) was added pyridine (1.02 kg, 12.9 mol) and DMAP (27 g, 221 mmol) respectively. The mixture was cooled to 0° C. and Tf$_2$O (1.60 kg, 5.66 mol) was added dropwise. The reaction mixture was warmed to 15° C. and stirred for 1 h. TLC showed 3 was completely consumed. The mixture was quenched with water (7.65 L) and then extracted with DCM (7.65 L×2). The combined organic layer was washed with water (2 L), dried over Na$_2$SO$_4$, filtered and concentrated under reduced pressure to give 4 (685 g, 47%) as a light yellow oil. $^1$H NMR (400 MHz, CDCl$_3$) δ 10.27 (s, 1H), 7.99 (d, J=8.0 Hz, 1H), 7.91-7.87 (m, 1H), 4.43 (q, J=7.0 Hz, 2H), 2.64 (s, 3H), 1.43 (t, J=7.3 Hz, 3H).

To a solution of 4 (1.00 kg, 2.94 mol), bis(pinacolato) diboron (1.12 kg, 4.41 mol) and KOAc (573 g, 5.84 mol) in 1,4-dioxane (6.50 L) was added Pd(dppf)Cl$_2$·CH$_2$Cl$_2$ (150 g, 184 mmol). The mixture was heated at 85° C. for 15 h under N$_2$ atmosphere. TLC showed 4 was consumed completely. The mixture was cooled to 15° C., filtered and concentrated to give the crude product. The residue was purified by column chromatography (SiO$_2$, petroleum ether/ethyl acetate=40/1 to 4:1) to give 5 (942 g, crude) as a yellow oil.

To a solution of 5 (1.20 kg, 3.77 mol) in MeOH (300 mL) and THF (6.00 L) was added NaBH$_4$ (80 g, 2.11 mol) in portions at 0° C. Then the reaction mixture was stirred at 15° C. for 1 h. HPLC showed 5 was consumed completely. The reaction solution was adjusted to pH=4 with 2 M HCl and then the organic layer removed in vacuo. The mixture was filtered. The cake was washed with petroleum ether (5 L) and dried in vacuum to give 6 (665 g, 80%) as a white solid. $^1$H NMR (400 MHz, DMSO-d$_6$) δ 9.18 (s, 1H), 7.89 (d, J=8.0 Hz, 1H), 7.32 (d, J=8.0 Hz, 1H), 5.00 (s, 2H), 4.30 (q, J=7.0 Hz, 2H), 2.68 (s, 3H), 1.33 (t, J=7.0 Hz, 3H).

To a mixture of 6 (867 g, 3.94 mol) in H$_2$O (5.00 L) was added NaOH (394 g, 9.85 mol) in one portion. The solution was heated at 40° C. for 3 hours. HPLC showed 6 was consumed completely. This batch was worked-up together with the other batches and acidified with 2 M HCl to pH=2. The solid was filtered and washed with H$_2$O (10 L). The cake was dried to give the Acid-04 (2.00 kg, 87%) as a white solid. $^1$H NMR (400 MHz, DMSO-d$_6$) δ 9.13 (br s, 1H), 7.89 (d, J=8.0 Hz, 1H), 7.28 (d, J=8.0 Hz, 1H), 4.98 (s, 2H), 2.68 (s, 3H).

Example A-2: Preparation of Acid-05

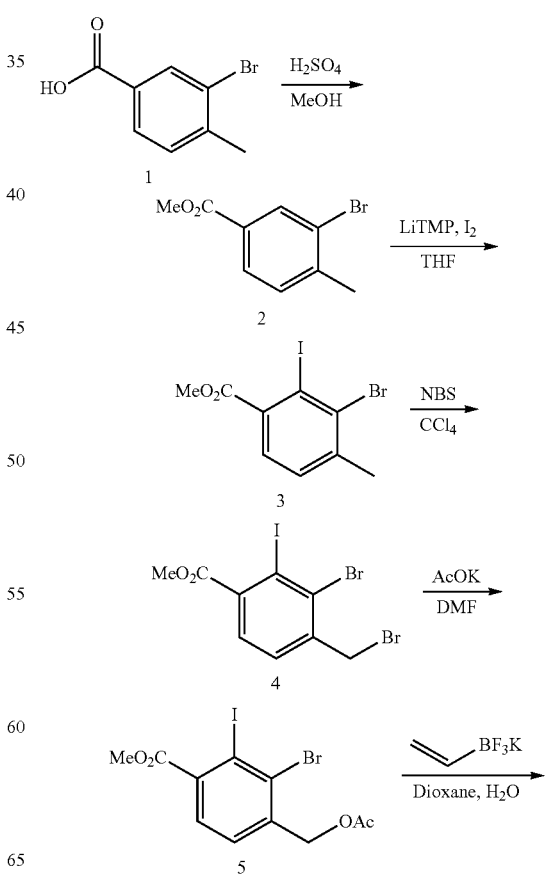

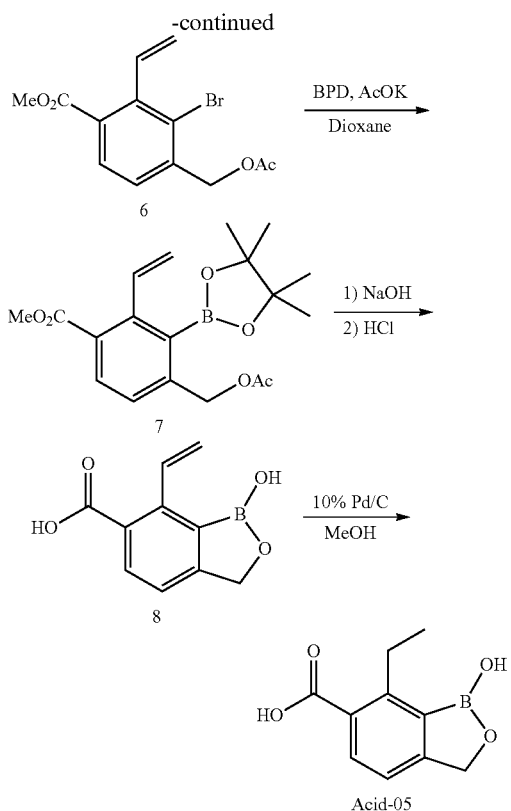

To a solution of 1 (100 g, 465 mmol) in MeOH (1 L) was added conc. H$_2$SO$_4$ (20 mL). The solution was heated at 80° C. for 16 h. The solvent was removed under reduced pressure and the residue was slowly poured into water (100 mL). The aqueous layer was extracted with EtOAc (200 mL×3). The combined organic layers were washed with aq. NaHCO$_3$ and brine, dried over Na$_2$SO$_4$ and concentrated under reduced pressure to afford crude 2 (102 g) as a yellow oil. $^1$H NMR (400 MHz, CDCl$_3$) δ 8.18 (d, J=1.2 Hz, 1H), 7.85 (d, J=6.0, 1.76 Hz, 1H), 7.28 (d, J=8.0 Hz, 1H), 3.90 (s, 3H), 2.44 (s, 3H).

To a solution of LiTMP (35.46 g, 251 mmol) in anhydrous THF (200 mL) was added n-BuLi (2.5 M, 100 mL, 251 mmol) dropwise at −10° C. under N$_2$. After cooling to −60° C., a solution of 2 (50.0 g, 218 mmol) in anhydrous THF (50 mL) was added dropwise under N$_2$ and the reaction mixture was stirred for another 30 min at −60° C. To the above mixture was added I$_2$ (166.2 g, 654.8 mmol) in one portion at −60° C. The resulting solution was warmed to 0° C. during an hour. The reaction mixture was quenched by sat. NH$_4$Cl aq. and the aqueous phase was extracted with DCM (100 mL×3). The combined organic phase was washed with sat. Na$_2$S$_2$O$_3$ aq. (100 mL×3), dried over anhydrous Na$_2$SO$_4$, filtered and concentrated in vacuum. The residue was purified via silica gel chromatography (petroleum ether/EtOAc=20/1) to give 3 (20 g, 26%) as a yellow oil. $^1$H NMR (400 MHz, CDCl$_3$) δ 7.45 (d, J=7.6 Hz, 1H), 7.27 (d, J=7.2 Hz, 1H), 3.96 (s, 3H), 2.59 (s, 3H).

A mixture of 3 (20.0 g, 56.3 mmol), NBS (10.0 g, 56.3 mmol) and BPO (1.36 g, 5.63 mmol) in CCl$_4$ (200 mL) was heated at 80° C. for 12 h under N$_2$ atmosphere. Then NBS (10.0 g, 56.3 mmol) and BPO (1.36 g, 5.63 mmol) were added again. After heating at 80° C. for another 6 h, the solvent was removed under reduced pressure to give crude 4, which was used to the next step without further purification.

A mixture of 4 (24.0 g, 55.3 mmol) and AcOK (10.86 g, 110.6 mmol) in DMF (250 mL) was heated at 80° C. for 4 h under N$_2$ atmosphere. The solvent was removed under reduced pressure. The residue was diluted with water (100 mL) and the aqueous layer was extracted with MTBE (100 mL×3). The combined organic layers were washed with brine (500 mL), dried over Na$_2$SO$_4$, filtered and concentrated under reduced pressure to give a residue which was purified via column chromatography (SiO$_2$, petroleum ether/EtOAc=20/1 to 5:1) to give 5 (7.00 g, 31%) as a yellow solid. $^1$H NMR (400 MHz, CDCl$_3$) δ 7.51 (d, J=8.0 Hz, 1H), 7.44 (d, J=8.0 Hz, 1H), 5.24 (s, 2H), 3.96 (s, 3H), 2.19 (s, 3H).

To a mixture of 5 (1.65 g, 4.00 mmol), trifluoro(vinyl)-X$^4$-borane potassium salt (696 mg, 5.20 mmol) and Cs$_2$CO$_3$ (2.61 g, 8.00 mmol) in 1,4-dioxane (30 mL) and water (0.4 mL) was added Pd(dppf)Cl$_2$·CH$_2$Cl$_2$ (326 mg, 0.400 mmol). The reaction mixture was heated at 100° C. for 18 h under N$_2$ atmosphere. The solvent was removed under reduced pressure. The crude was purified by prep. TLC with petroleum ether:EtOAc=10:1 as the eluent to obtain 6 (0.60 g, 48%) as a yellow oil. $^1$H NMR (400 MHz, CDCl$_3$) δ 7.61 (d, J=8.4 Hz, 1H), 7.36 (d, J=8.0 Hz, 1H), 6.93 (q, J=10.8 Hz, J=6.8 Hz, 1H), 5.49 (d, J=10.0 Hz, 1H), 5.27 (m, 1H), 5.23 (s, 2H), 3.84 (s, 3H), 2.17 (s, 3H).

To a mixture of 6 (0.63 g, 2.0 mmol), AcOK (395 mg, 4.00 mmol) and BPD (1.0 g, 4.0 mmol) in dioxane (12 mL) was added Pd(dppf)Cl$_2$·CH$_2$Cl$_2$ (164 mg, 0.2 mmol). The reaction mixture was stirred at 100° C. for 14 h under N$_2$ atmosphere. The solvent was removed under reduced pressure. The crude was purified by prep. TLC (SiO$_2$, petroleum ether/EtOAc=10/1) to give 7 (0.40 g, 55.2%) as a pale yellow oil. $^1$H NMR (400 MHz, CDCl$_3$) δ 7.87 (d, J=7.6 Hz, 1H), 7.44 (d, J=11.2 Hz, 1H), 7.36 (d, J=8.0 Hz, 1H), 5.36 (d, J=11.2 Hz, 1H), 5.30 (d, J=17.6 Hz, 1H), 5.19 (s, 2H), 3.85 (s, 3H), 2.09 (s, 3H), 1.36 (s, 12H).

To a solution of 7 (0.40 g, 1.1 mmol) in MeOH (10 mL) and water (0.3 mL) was added NaOH (133 mg, 3.33 mmol). The solution was stirred at 50° C. for 14 h. The solvent was removed under reduced pressure. The residue was diluted with water (5 mL) and adjusted to pH=2 with 2 M HCl. After filtration, 8 (160 mg, 71%) was obtained as a yellow solid. $^1$H NMR (400 MHz, CDCl$_3$) δ 8.98 (s, 1H), 7.77 (d, J=8.0 Hz, 1H), 7.36 (d, J=8.0 Hz, 1H), 7.22 (t, J=6.8 Hz, 1H), 5.70 (d, J=12 Hz, 1H), 5.42 (d, J=11.6 Hz, 1H), 5.00 (s, 1H).

A mixture of 8 (160 mg, 0.73 mmol) and 10% Pd/C (0.2 g) in MeOH (80 mL) was stirred at 20° C. for 14 h under H$_2$ (14 psi). After filtration, the filtrate was concentrated under reduced pressure to afford Acid-05 (150 mg, 99%) as a white solid. MS (ESI): mass calcd. for C$_{10}$H$_{11}$BO$_4$ 206.00, m/z found 205.2 [M−H]$^-$. $^1$H NMR (400 MHz, DMSO-d$_6$) δ 12.74 (s, 1H), 9.06 (s, 1H), 7.83 (d, J=8.0 Hz, 1H), 7.26 (d, J=8.0 Hz, 1H), 4.97 (s, 2H), 3.12 (m, 2H), 1.12 (t, J=7.6 Hz, 1H).

Example A-3: Preparation of Acid-06

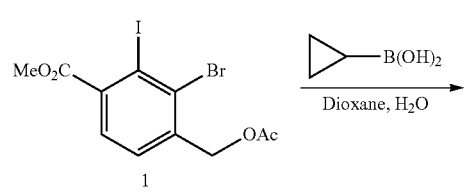

Example A-4: Preparation of Acid-07

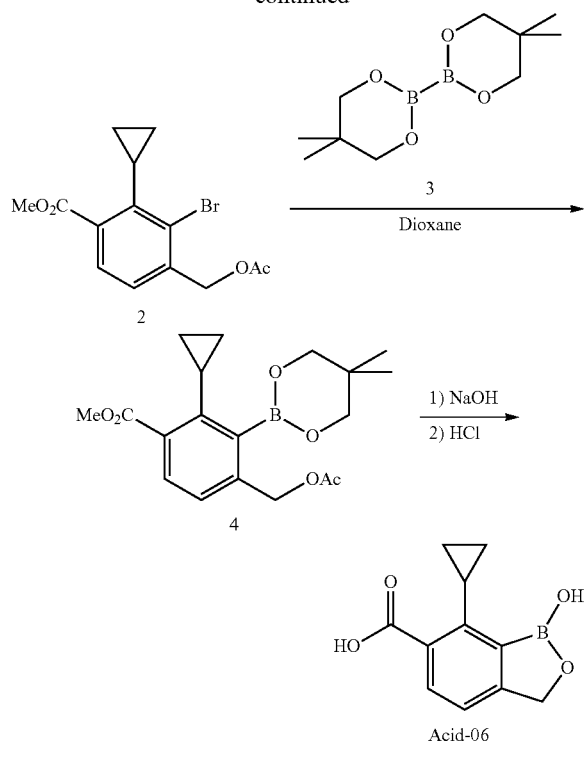

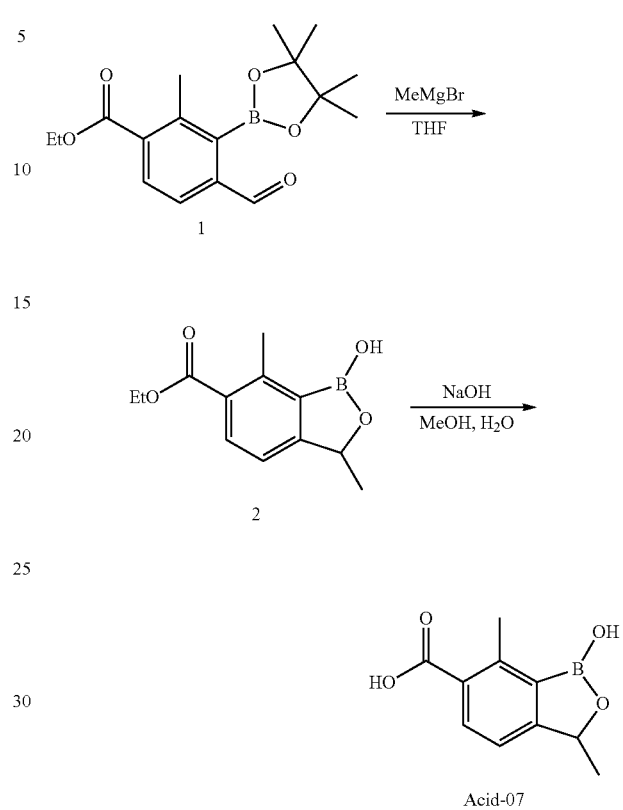

To a mixture of 1 (obtained in Reference Example 2; 1.65 g, 4.00 mmol), cyclopropylboronic acid (446 mg, 5.20 mmol) and Cs₂CO₃ (2.61 g, 8 mmol) in 1,4-dioxane (30 mL) and water (3 mL) was added Pd(dppf)Cl₂·CH₂Cl₂ (326 mg, 0.40 mmol). The reaction mixture was heated at 100° C. for 18 h under N₂ atmosphere. The solvent was removed under reduced pressure. The crude mixture was purified via prep. TLC with PE:EtOAc=10:1 as the eluent to obtain 2 (0.55 g, 43%) as a yellow oil. $^1$H NMR (400 MHz, CDCl₃) δ 7.47 (d, J=8.0 Hz, 1H), 7.29 (d, J=8.0 Hz, 1H), 5.22 (s, 2H), 3.92 (s, 1H), 5.27 (m, 3H), 2.16 (s, 3H), 2.03-1.99 (m, 1H), 1.09 (q, J=5.6 Hz, J=8.4 Hz, 1H), 0.49 (q, J=5.2 Hz, J=5.6 Hz, 1H).

To a mixture of 2 (0.50 g, 1.5 mmol), AcOK (300 mg, 3 mmol) and 3 (1.38 g, 6.10 mmol) in dioxane (8 mL) was added Pd(dppf)Cl₂·CH₂Cl₂ (500 mg, 0.60 mmol). The reaction mixture was stirred at 110° C. for 14 h under N₂ atmosphere. The solvent was removed under reduced pressure. The crude mixture was purified by prep. TLC (SiO₂, PE/EA=20/1) to give 4 (0.35 g, 64%) as colorless oil. $^1$H NMR (400 MHz, CDCl₃) δ 7.54 (d, J=7.6 Hz, 1H), 7.25 (d, J=7.2 Hz, 1H), 5.18 (s, 2H), 3.88 (s, 3H), 3.79 (s, 4H), 2.40 (m, 1H), 2.07 (s, 3H), 1.26 (s, 6H), 0.88 (s, 2H), 0.50 (t, J=4.4 Hz, 2H).

To a solution of 4 (0.32 g, 0.90 mmol) in MeOH (12 mL) and water (4 mL) was added NaOH (106 mg, 2.67 mmol). The solution was stirred at 80° C. for 14 h. The solvent was removed under reduced pressure. The residue was diluted with water (5 mL) and adjusted to pH=2 with 2 M HCl. After filtration, Acid-06 (170 mg, 88%) was obtained as a pale yellow solid. MS (ESI): mass calcd. for C₁₁H₁₁BO₄ 218.01, m/z found 219.1 [M+H]⁺. $^1$H NMR (400 MHz, DMSO-d₆) δ 12.82 (s, 1H), 8.93 (s, 1H), 7.59 (d, J=7.6 Hz, 1H), 7.26 (d, J=8.0 Hz, 1H), 4.97 (s, 2H), 2.27 (m, 1H), 0.89 (d, J=7.2 Hz, 2H), 0.70 (d, J=8.4 Hz, 2H).

To a solution of 1 (obtained in Reference Example 1; 50 mg, 157 umol) in THF (4 mL) was added MeMgBr (21 mg, 172 umol) at −78° C. The mixture was stirred at −78° C. for 1 h. The reaction mixture was quenched by saturated NH₄Cl solution (20 mL) at 15° C. and then extracted with EtOAc (5 mL×2). The combined organic layers were washed with saturated saline (5 mL×2), dried over anhydrous Na₂SO₄, filtered and concentrated under reduced pressure to give a residue. The residue was dissolved in DCM (5 mL), and then washed with 1 M HCl. The organic layer was washed with saturated saline (5 mL), dried over anhydrous Na₂SO₄, filtered and concentrated under reduced pressure to give a residue. The residue was purified by prep. TLC (PE/EtOAc=5/1) to give 2 (20 mg, 54%) was obtained as a yellow solid.

$^1$H NMR (400 MHz, CDCl₃) δ 8.01 (d, J=8.0 Hz, 1H), 7.16 (d, J=8.0 Hz, 1H), 5.30 (q, J=6.4 Hz, 1H), 4.38 (q, J=7.2 Hz, 2H), 2.80 (s, 3H), 1.52 (d, J=6.4 Hz, 3H), 1.41 (t, J=7.2 Hz, 3H).

A mixture of 2 (160 mg, 683 umol) and NaOH (82 mg, 2.0 mmol) in MeOH (10 mL) and water (10 mL) was degassed and purged with N₂ for 3 times. The mixture was stirred at 50° C. for 4 h under N₂ atmosphere. The solvent was removed under reduced pressure. The solution was adjusted with 1 M HCl to pH=2-3. Then white solid precipitated and filtered to give Acid-07 (100 mg, 71%) as a white solid. MS (ESI): mass calcd. for C₁₀H₁₁BO₄ 206.00, m/z found 207.1 [M+H]⁺. $^1$H NMR (400 MHz, DMSO-d₆) δ 12.74 (s, 1H), 9.04 (s, 1H), 7.89 (d, J=8.0 Hz, 1H), 7.27 (d, J=8.0 Hz, 1H), 5.22-5.17 (m, 1H), 2.67 (s, 3H), 1.40 (d, J=6.8 Hz, 3H).

Example A-5: Preparation of Acid-08

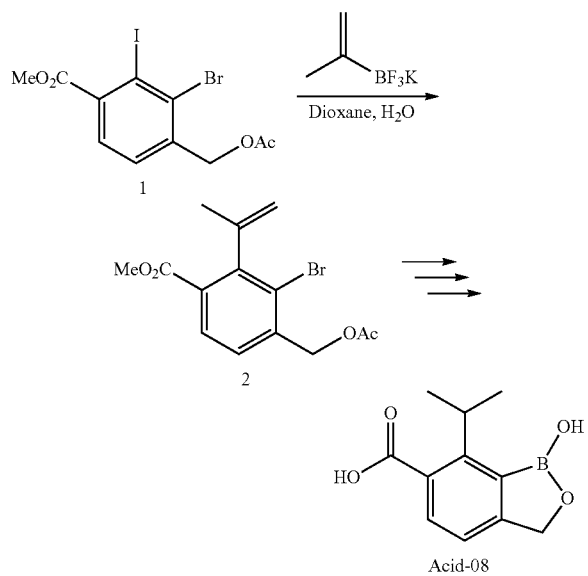

This compound was prepared from compound 1 obtained in Example A-2 and trifluoro(2-propenyl)-λ⁴-borane potassium salt in a similar manner to Example A-2. $^1$H NMR (400 MHz, DMSO-$d_6$) δ 12.90 (s, 1H), 9.26 (s, 1H), 7.56 (d, J=8.0 Hz, 1H), 7.25 (d, J=8.0 Hz, 1H), 4.99 (s, 2H), 3.58 (t, J=7.2 Hz, 1H), 1.35 (d, J=6.8 Hz, 6H).

Example A-6: Preparation of Acid-09

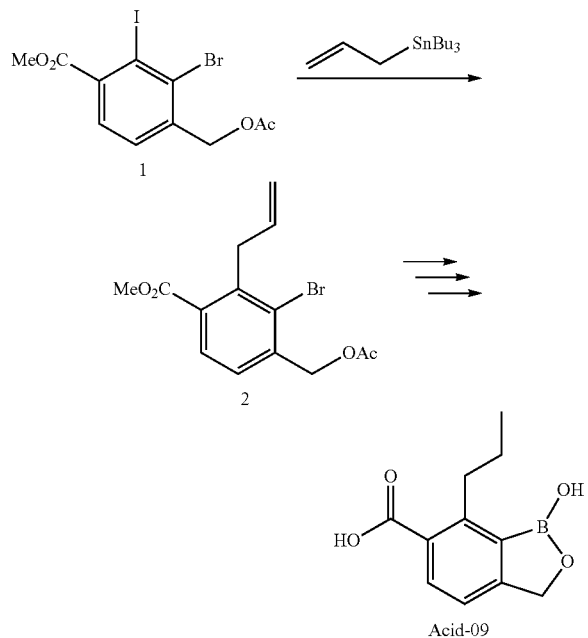

A mixture of 1 (obtained in Reference Example 2, 200 mg, 484 umol), allyl(tributyl)stannane (160 mg, 0.484 mmol), Pd(PPh$_3$)$_4$ (56 mg, 48 umol) in dioxane (5 mL) was degassed and purged with N$_2$ for 3 times, and then the mixture was stirred at 80° C. for 12 h under N$_2$ atmosphere. The solvent was removed under reduced pressure. The residue was purified by prep. TLC (PE/EtOAc=5/1) to give 2 (80 mg, 50%) as a yellow liquid. $^1$H NMR (400 MHz, CDCl$_3$) δ 7.78 (d, J=8.0 Hz, 1H), 7.33 (d, J=8.0 Hz, 1H), 6.00-5.91 (m, 1H), 5.24 (s, 2H), 5.08-4.99 (m, 2H), 3.98 (d, J=6.0 Hz, 2H), 3.90 (s, 3H), 2.19 (s, 3H). Acid-09 was obtained in a similar manner to Example A-2. MS (ESI): mass calcd. for C$_{11}$H$_{13}$BO$_4$ 220.03, m/z found 221 [M+H]$^+$.

Example A-7: Preparation of Acid-10

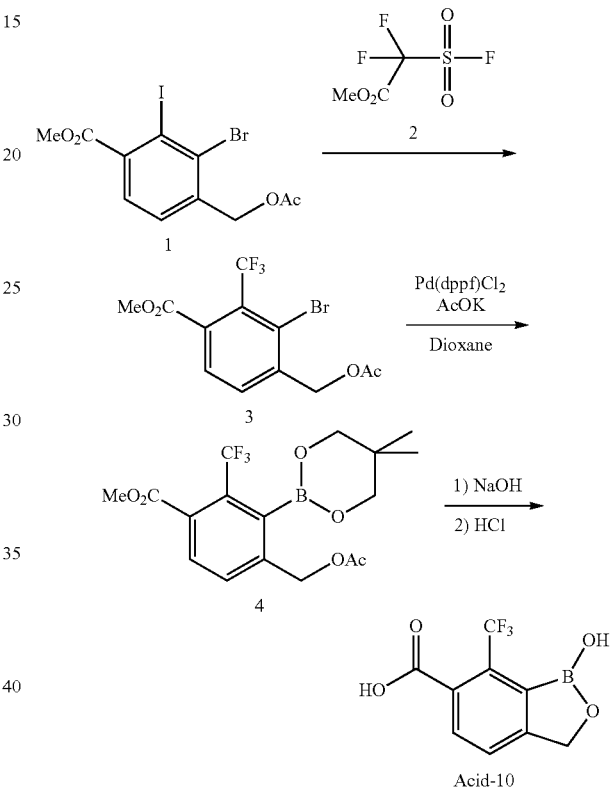

A mixture of 1 (obtained in Reference Example 2, 300 mg, 726 umol), CuI (276 mg, 1.5 mmol), 2 (139 mg, 726 umol) and HMPA (651 mg, 4 mmol) in DMF (5 mL) was stirred at 80° C. for 12 h under N$_2$ atmosphere. The solvent was removed under reduced pressure. The residue was purified via prep. HPLC (TFA condition) to give 3 (30 mg, 12%) as a white solid. $^1$H NMR (400 MHz, CDCl$_3$) δ 7.62 (d, J=7.6 Hz, 1H), 7.45 (d, J=8.0 Hz, 1H), 5.28 (s, 2H), 3.93 (s, 3H), 2.19 (s, 3H).

A mixture of 3 (100 mg, 281 umol), Pd(dppf)Cl$_2$ (82 mg, 0.11 mmol) and 2-(5,5-dimethyl-1,3,2-dioxaborinan-2-yl)-5,5-dimethyl-1,3,2-dioxaborinane (127 mg, 0.563 mmol) and AcOK (55 mg, 0.56 mmol) in dioxane (5 mL) was stirred at 100° C. for 12 h under N$_2$ atmosphere. The mixture was purified via prep. TLC (petroleum ether/EtOAc=5/1) to give crude 4 (35 mg) as a yellow solid. $^1$H NMR (400 MHz, CDCl$_3$) δ 7.80 (d, J=6.4 Hz, 1H), 7.60 (d, J=7.2 Hz, 1H), 5.25 (s, 2H), 3.92 (s, 3H), 3.80 (s, 4H), 2.11 (s, 3H), 1.18 (s, 6H).

To a mixture of 4 (900 mg, 2.00 mmol) in MeOH (9 mL) and H$_2$O (10 mL) was added NaOH (371 mg, 9.00 mmol). The mixture was stirred at 50° C. for 12 h. The organic solvent was removed under reduced pressure and the aqueous layer was adjusted to pH=2-3 by 1 M HCl. The solid was collected after filtered. The crude material was initially purified via prep. TLC (petroleum ether/EtOAc=1/1) then purified via prep. HPLC (TFA condition) to give the mixture of Acid-10 (150 mg) as a white solid. MS (ESI): mass calcd. for $C_9H_6BF_3O_4$ 245.95, m/z found 247 $[M+H]^+$.

Example A-8: Preparation of Acid-11

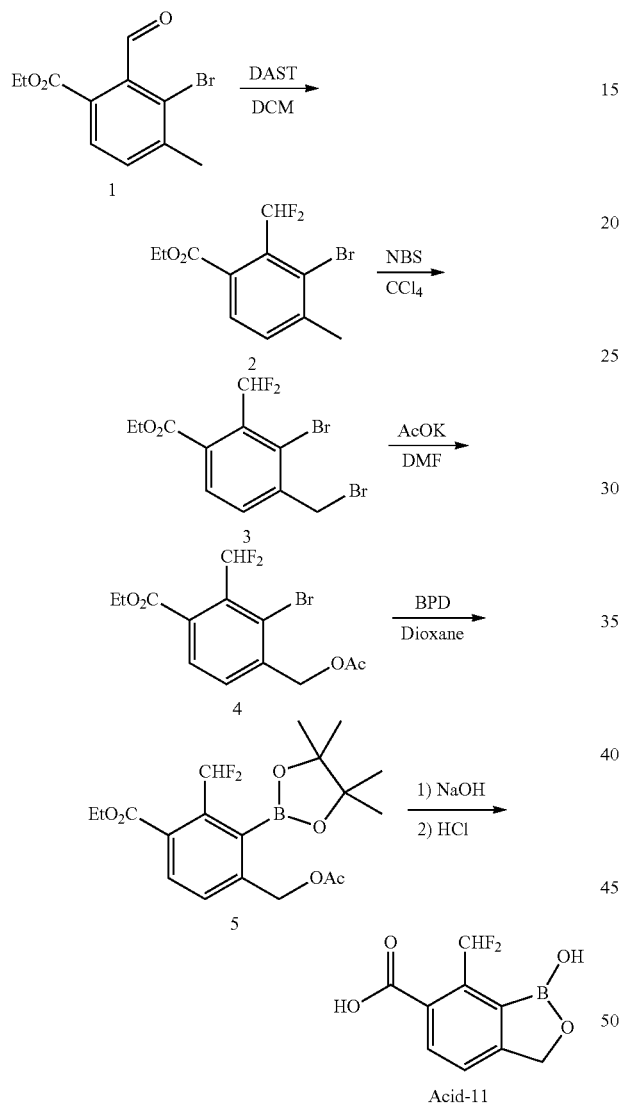

To a solution of 1 (15 g, 55 mmol) in DCM (100 mL) was added DAST (89.0 g, 553 mmol) dropwise at 0° C. The mixture was stirred at 0° C. for 16 h. The reaction mixture was poured into saturated $NaHCO_3$ (200 mL) slowly at 0° C., and then extracted with DCM (100 mL×2). The combined organic layers were washed with brine (50 mL×2), dried over $Na_2SO_4$, filtered and concentrated under reduced pressure to give 2 (11 g, yield 68%) as a pale yellow oil. $^1$H NMR (400 MHz, $CDCl_3$) δ 7.53 (d, J=8.0 Hz, 1H), 7.39 (d, J=8.0 Hz, 1H), 7.26 (t, J=35.6 Hz, 1H), 4.38 (q, J=8.0 Hz, 6.0 Hz, 2H), 2.49 (s, 3H), 1.38 (t, J=7.2 Hz, 3H).

A mixture of 2 (9.0 g, 31 mmol), NBS (6.0 g, 34 mmol) and BPO (744 mg, 3.00 mmol) in $CCl_4$ (100 mL) was degassed and purged with $N_2$ for 3 times. The reaction mixture was stirred at 80° C. for 16 h under $N_2$ atmosphere. The solvent was removed under reduced pressure to give 3 (11 g, crude) as a pale yellow solid which was used into the next step without further purification.

A mixture of 3 (11 g, crude) and AcOK (3.0 g, 33 mmol) in DMF (30 mL) was stirred at 60° C. for 2 h under $N_2$ atmosphere. The reaction mixture was diluted with $H_2O$ (100 mL) and then extracted with MTBE (100 mL×2). The combined organic layers were washed with brine 100 mL (50 mL×2), dried over $Na_2SO_4$, filtered and concentrated under reduced pressure. The residue was purified via column chromatography (petroleum ether/EtOAc=10/1) to give 4 (4.0 g, 39%) as a pale yellow oil. $^1$H NMR (400 MHz, $CDCl_3$) δ 7.65 (d, J=8.0 Hz, 1H), 7.57 (d, J=8.0 Hz, 1H), 7.26 (t, J=54 Hz, 1H), 5.25 (s, 2H), 4.40 (q, J=7.2 Hz, 2.8 Hz, 2H), 2.18 (s, 3H), 1.39 (t, J=7.2 Hz, 3H).

A mixture of 4 (50.0 mg, 142 umol), BPD (145 mg, 0.569 mmol), AcOK (56.0 mg, 0.569 mmol) and $Pd(dppf)Cl_2$ (21 mg, 0.028 mmol) in dioxane (2 mL) was degassed and purged with $N_2$ for 3 times. The mixture was stirred at 90° C. for 12 h under $N_2$ atmosphere. The reaction mixture was directly purified via prep. TLC (petroleum ether/EtOAc=5/1) to give 5 (5.0 mg, yield 8.8%) as a white solid. $^1$H NMR (400 MHz, $CDCl_3$) δ 7.96 (d, J=8.0 Hz, 1H), 7.72-7.37 (m, 2H), 5.23 (s, 2H), 4.39 (d, J=7.2 Hz, 2H), 2.12 (s, 3H), 1.42 (s, 12H).

A mixture of 5 (240 mg, 0.603 mmol) and NaOH (96 mg, 2.0 mmol) in MeOH (2 mL) and $H_2O$ (2 mL) was stirred at 50° C. for 12 h under $N_2$ atmosphere. The reaction mixture was concentrated under reduced pressure. The mixture was adjusted to pH=4 with 1 M HCl. The mixture was concentrated under reduced pressure to give Acid-11 (100 mg) as a white solid. MS (ESI): mass calcd. for $C_9H_7BF_2O_4$ 227.96, m/z found 229 $[M+H]^+$.

Example A-9: Preparation of Acid-12

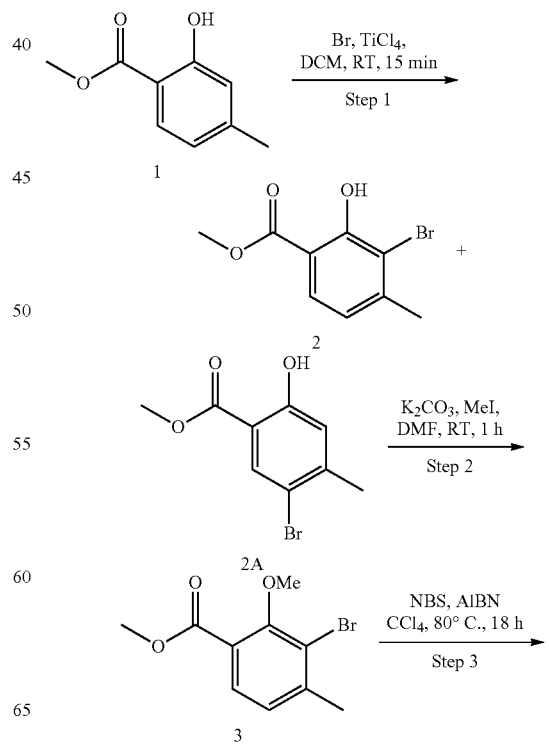

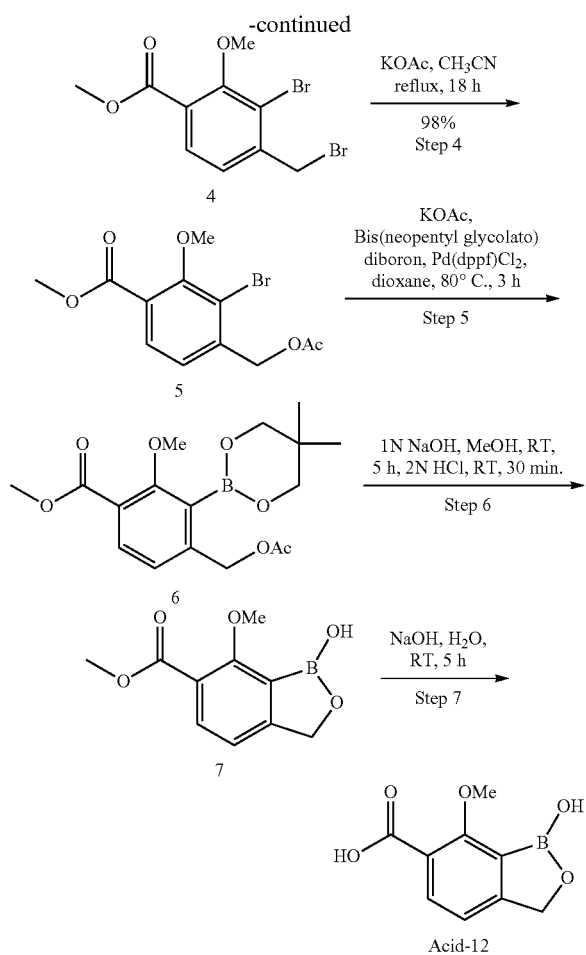

Step-1: To a stirred solution of compound-1 (10 g, 60.2 mmol) in DCM (100 ml) was added TiCl$_4$ (1 M solution in DCM, 150 mL, 150 mmol) dropwise at room temperature (RT). Then Br$_2$ (3.09 mL, 60.2 mmol) was added to the reaction mixture at RT. The reaction mixture was stirred at RT for 15 min. The progress of the reaction was monitored by TLC. TLC showed formation of two close polar spots with complete consumption of compound 1. The reaction was quenched with ice cold water and was extracted into petroleum ether (3×500 mL). The combined organic layers were washed with water, brine, and dried over Na$_2$SO$_4$. The solvent was removed under reduced pressure to afford the crude material. The crude compound was purified via column chromatography on silica gel (100-200 mesh, 100% petroleum ether) and 2.5 g of compound 2 (2.5 g, 12%), 8 g of compound 2A, and 5.4 g of a mixture of compound 2 and compound 2A was isolated.

Step 2: To a stirred solution of compound 2 (2.4 g, 9.836 mmol) in DMF (48 mL) was added K$_2$CO$_3$ (2.0 g, 14.75 mmol) at RT and was stirred at RT for 30 min. Then MeI (0.735 mL, 11.8 mmol) was added at rt and stirred at the same temperature for 2 h. The progress of the reaction was monitored by TLC. TLC showed formation of a non-polar spot with complete consumption of compound 2. The reaction mixture was quenched with ice cold water and was extracted into EtOAc (2×200 mL). The combined organic layers were washed with water, brine, and dried over Na$_2$SO$_4$. The solvent was removed under reduced pressure to afford the crude material. The crude compound was purified via column chromatography on silica gel (100-200 mesh, 2% EtOAc in petroleum ether) to afford compound 3 (2.5 g, 99%).

Step 3: To a stirred solution of compound 3 (2.5 g, 9.689 mmol) in CCl$_4$ (25 mL) was added AIBN (317 mg, 1.937 mmol) and NBS (2.06 g, 11.627 mmol) at RT. The reaction mixture was refluxed for 18 h. The reaction mixture was concentrated under reduced pressure to afford a crude residue. The residue was diluted with water and EtOAc. The organic layer was separated, washed with water, brine, and dried over Na$_2$SO$_4$. The solvent was removed under reduced pressure to get the crude material. The crude compound was purified by column chromatography (normal phase, 3% EtOAc:pet ether) to obtain compound 4 (1.5 g, 46%) as yellow syrup.

Step 4: To a stirred solution of compound 4 (1.3 g, 3.869 mmol) in CH$_3$CN (26 ml) was added KOAc (1.13 g, 11.607 mmol) at RT. The reaction mixture was stirred at reflux temperature for 18 h. The progress of reaction monitored by TLC and TLC showed formation of a polar spot with complete consumption of starting material. The reaction mixture was concentrated under reduced pressure to afford a crude residue. The crude residue was diluted with water and EtOAc. The organic layer was separated, washed with water, brine, and dried over Na$_2$SO$_4$. The solvent was removed under reduced pressure to get the compound 5 (1.2 g, 98%) as an off-white solid.

Step 5: To a stirred solution of compound 5 (1.7 g, 5.379 mmol) in 1,4-dioxane (20 vol) was added KOAc (1.58 g, 16.13 mmol) and bis-(neopentylglycolato) diborane (2.43 g, 10.759 mmol) at RT. The reaction mixture was degassed and filled with argon for 20 min. Then Pd (dppf)Cl$_2$. DCM (0.219 g, 0.268 mmol) was added at rt. The reaction mixture was heated at 80° C. for 3 h. The progress of the reaction was monitored by TLC. The reaction mixture was cooled to rt and was filtered through a pad of celite. The filtrate was concentrated under reduced pressure to afford a crude material. The crude compound was purified by column chromatography on silica gel (100-200 mesh, 15%-20% EtOAc: petroleum ether) to afford compound-6 (1.5 g, 80%) as a yellow syrup.

Step 6: To a stirred solution of compound 6 (1.5 g, semi-pure, 4.285 mmol) in MeOH (10 vol) was added 1N NaOH (0.514 g, 12.857 mmol) at 0° C. The reaction mixture was stirred at RT for 5 h. The progress of the reaction was monitored by TLC and TLC showed formation of polar spot with complete consumption of starting material. The reaction mixture was acidified with 2 N HCl to pH 3.0 and continued stirring at RT for 30 min. The reaction mixture was diluted with water and was extracted with EtOAc (2×200 ml). The combined organic layers were washed with brine solution and dried over Na$_2$SO$_4$. The solvent was removed under reduced pressure to afford the crude compound. The crude compound was purified by reverse phase HPLC to get compound 7 (400 mg, 42%) as pale yellow solid.

Step 7: To a stirred solution of compound 7 (400 mg, 1.8 mmol) in H$_2$O (20 vol) was added NaOH (216 mg, 5.404 mmol) at 0° C. The reaction mixture was allowed to RT for 5 h. The progress of reaction was monitored by TLC and TLC showed formation of a polar spot with complete consumption of starting material. The reaction mixture was acidified with 2 N HCl to pH 4.0 at 0° C. and was extracted with EtOAc (2×100 ml). The combined organic layers were washed with brine and dried over Na$_2$SO$_4$. The solvent was removed under reduced pressure to afford compound 8 (303 mg, 80%) as a white solid. $^1$H NMR (300 MHz, DMSO-d$_6$):

δ 12.6 (s, 1H), 9.34 (s, 1H), 7.76 (d, 1H), 7.10 (d, 1H), 5.02 (s, 2H), 4.0 (s, 3H); LC-MS: m/z 209.01 [M+H]$^+$.

Example A-10: Preparation of Acid-13

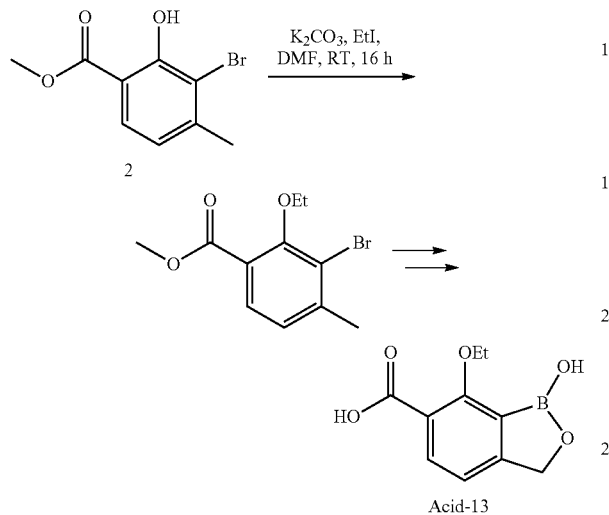

Acid-13

Acid-13 was prepared from iodoethane with compound 2 followed by the same method as the synthesis of Acid-12.

Step 1: To a stirred solution of compound 2 (3 g, 12.3 mmol) in DMF (30 mL) was added K$_2$CO$_3$ (2.54 g, 18.4 mmol) at RT and was stirred for 30 min. Then EtI (2.92 mL, 36.9 mmol) was added at RT and the reaction mixture was stirred at RT for 16 h. The progress of the reaction was monitored by TLC. TLC showed formation of a non-polar spot with complete consumption of starting material. The reaction mixture was quenched with ice cold water and was extracted with EtOAc (2×100 mL). The combined organic layers were washed with water, brine, and dried over Na$_2$SO$_4$. The solvent was removed under reduced pressure to afford a crude material. The crude compound was purified via column chromatography on silica-gel (100-200 mesh: 2-4% EtOAc in pet ether) to afford compound 3 (2.2 g, 66%) as a colorless liquid. $^1$H NMR (300 MHz, DMSO-d$_6$): δ 12.6 (s, 1H), 9.25 (s, 1H), 7.72 (d, 1H), 7.10 (d, 1H), 5.02 (s, 2H), 4.32 (qt, 2H), 1.28 (t, 3H); LC-MS: m/z 223.33 [M+H]$^+$.

Example A-11: Preparation of Acid-14

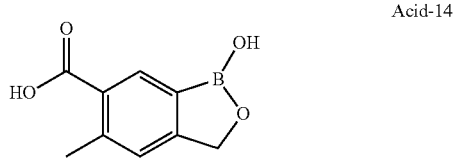

Acid-14

This compound was prepared from 5-hydroxy-2-methylbenzoic acid in a similar manner to Example A-1. $^1$H NMR (400 MHz, DMSO-d$_6$) δ 8.22 (s, 1H), 7.29 (s, 1H), 4.96 (s, 2H), 2.54 (s, 3H).

Example B-1: Preparation of 4-Fluorobenzyl-L-valinate

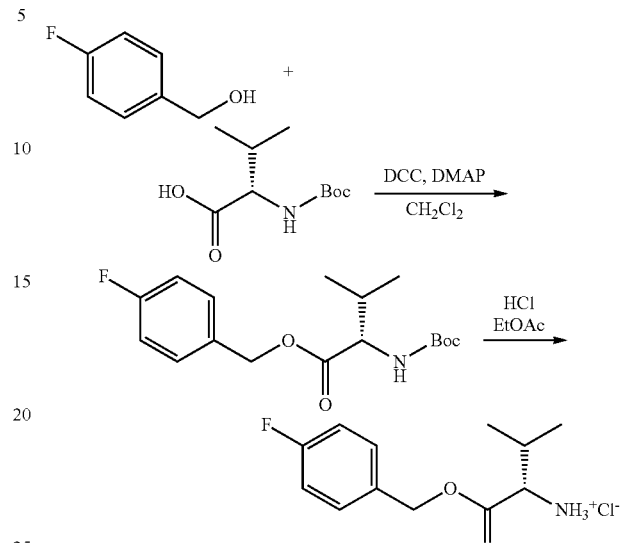

To a solution of N-BOC-(S)-valine (500.00 g, 2.30 mol, 1.00 eq) and 4-fluorobenzylalcohol (290 g, 2.30 mol, 248.10 mL) in dry DCM (6.0 L) was added DCC (854 g, 4.14 mol, 838 mL) and DMAP (39.36 g, 322.19 mmol). The reaction mixture was stirred at 25° C. for 15 h. The mixture was filtered and washed with DCM (2 L) and concentrated to give the crude product. The residue was purified via column chromatography (SiO$_2$, Petroleum ether/Ethyl acetate=50/1 to 10:1) to give 4-fluorobenzyl (tert-butoxycarbonyl)-L-valinate (708 g, 95% yield) as a white solid. $^1$H NMR (400 MHz CDCl$_3$) δ 7.35 (dd, J=8.2, 5.5, Hz, 2H), 7.05 (t, J=8.6 Hz, 2H), 5.19-5.08 (m, 2H), 5.01 (d, J=8.4 Hz, 1H), 4.25 (dd, J=8.4, 4.4, Hz, 1H), 2.13 (dd, J=6.2, 11.9 Hz, 1H), 1.44 (s, 9H), 0.93 (d, J=7.1 Hz, 3H), 0.84 (d, J=7.1 Hz, 3H).

The mixture of 4-fluorobenzyl (tert-butoxycarbonyl)-L-valinate (1.06 kg, 3.26 mol) in EtOAc/HCl (6.0 L) was stirred at 25° C. for 14 h. The solvent was removed under reduced pressure to give 4-fluorobenzyl L-valinate hydrochloride (780 g, 91%) was obtained as a white solid. $^1$H NMR (400 MHz CDCl$_3$) δ 8.90 (br s, 3H), 7.37 (dd, J=8.2, 5.5, Hz, 2H), 7.03 (t, J=8.4 Hz, 2H), 5.29-5.10 (m, 2H), 3.95 (br s, 1H), 2.44 (dd, J=11.0, 6.6 Hz, 1H), 1.08 (dd, J=10.1, 7.1 Hz, 6H).

Example 1. 2,6-Dimethylphenyl (1-hydroxy-1,3-dihydrobenzo[c][1,2]oxaborole-6-carbonyl)-L-alaninate (6-001)

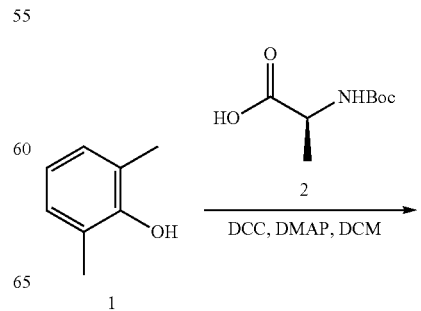

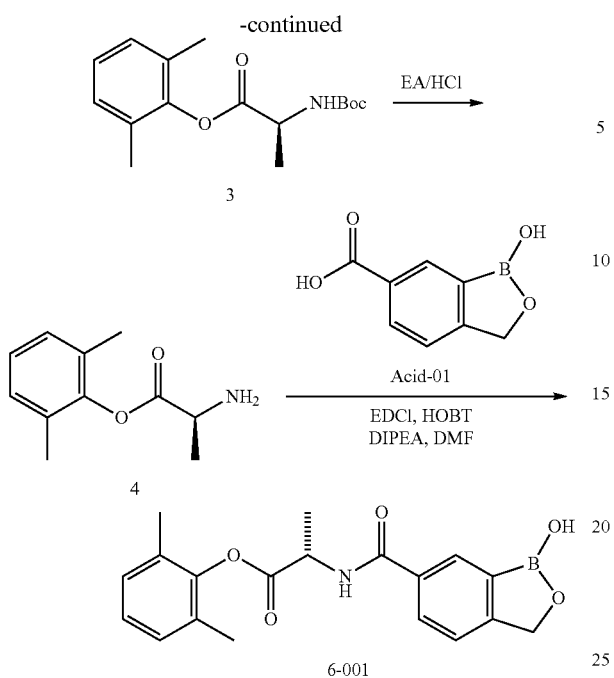

To a solution of compound 1 (1.22 g, 10.0 mmol), compound 2 (1.98 g, 10.5 mmol) and DMAP (122 mg, 1.00 mmol) in dichloromethane (50 mL) was slowly added DCC (2.26 g, 11.0 mmol) at 0° C. The mixture was stirred at 10° C. for overnight. The reaction mixture was concentrated and purified by silica gel column chromatography (PE:EA=10:1 to 5:1) to give compound 3 (2.0 g, yield 68%) as a white solid, which was used for following steps and confirmed at final stage.

To a solution of compound 3 (1.0 g, 3.4 mmol) in ethyl acetate (20 mL) was slowly added a solution of HCl in ethyl acetate (4 M, 20 mL) at 0° C. The mixture was stirred at 10° C. for 1 hour. TLC (PE:EA=10:1) showed starting material was completely consumed. The reaction mixture was concentrated to dryness to give compound 4 (750 mg, yield 95%) as a white solid.

To a solution of Acid-01 (*ACS Med. Chem. Lett.*, 2010, 1(4), 165-169, 178 mg, 1.00 mmol), compound 4 (230 mg, 1.00 mmol), EDC (384 mg, 2.00 mmol) and HOBt (270 mg, 2.00 mmol) in DMF (5 mL) was added DIPEA (387 mg, 3.00 mmol). The reaction mixture was stirred at 10° C. overnight, and then concentrated and purified by prep. HPLC to give 6-001 (270 mg, yield 76%) as a white solid. $^1$H NMR (400 MHz, DMSO-d$_6$) δ 9.31 (s, 1H), 9.02 (d, J=6.62 Hz, 1H), 8.30 (s, 1H), 8.00 (dd, J=7.94 Hz, 1.32 Hz, 1H), 7.51 (d, J=8.38 Hz, 1H), 7.13-6.99 (m, 3H), 5.04 (s, 2H), 4.74 (t, J=6.84 Hz, 1H), 2.10 (s, 6H), 1.63 (d, J=7.06 Hz, 3H); ESI-MS: m/z 354 [M+H]$^+$; HPLC purity: 100% (220 nm), 100% (254 nm).

Example 2. tert-butyl (1-hydroxy-1,3-dihydrobenzo[c][1,2]oxaborole-6-carbonyl)-L-alaninate (6-002)

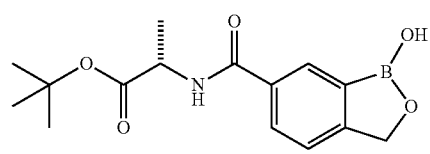

This compound was prepared from (S)-alanine tert-butyl ester and Acid-01 in a similar manner to the last step of Example 1. $^1$H NMR (400 MHz, DMSO-d$_6$) δ 9.30 (s, 1H), 8.68 (t, J 6.2 Hz, 1H), 8.22 (s, 1H), 7.96-7.92 (m, 2H), 5.01 (s, 2H), 4.30 (quint., J=6.1 Hz, 1H), 1.37 (s, 9H), 1.35 (d, J=6.1 Hz, 3H); ESI-MS: m/z 364 [M+OAc]$^-$; HPLC purity: 100% (220 nm), 100% (254 nm).

Example 3. (1-Hydroxy-7-methyl-1,3-dihydrobenzo[c][1,2]oxaborole-6-carbonyl)-L-valine (6-003)

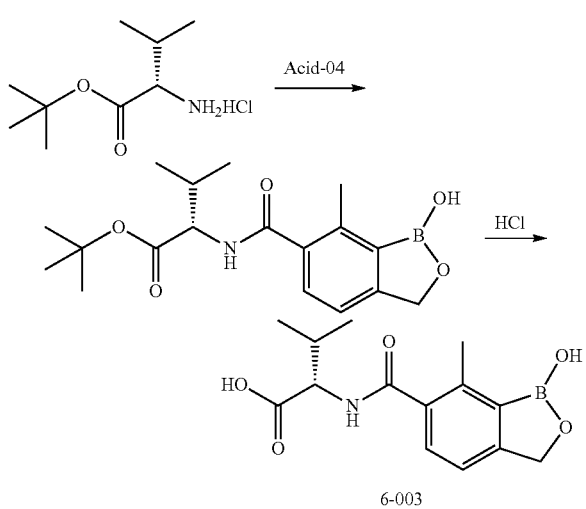

Compound 6-003 was prepared from Acid-04 and tert-Butyl L-valinate in a similar manner to the last step of Example 1 followed by the addition of HCl and purification by prep. HPLC (column: Luna C8 100×30 mm; liquid phase: 0.1% TFA-ACN; B %: 10%-35%, 12 min). $^1$H NMR (400 MHz, DMSO-d$_6$) δ 12.53 (s, 1H), 9.00 (s, 1H), 8.34 (d, J=8.4 Hz, 1H), 7.43-7.13 (m, 2H), 4.95 (s, 2H), 4.27 (dd, J=8.2 Hz, 6.4 Hz, 1H), 2.46 (s, 3H), 2.22-1.99 (m, 1H), 0.94 (t, J=6.8 Hz, 6H); ESI-MS: m/z 292 [M+H]$^+$; HPLC purity: 99.18% (220 nm), 100% (254 nm).

Example 4. Benzyl (1-hydroxy-1,3-dihydrobenzo[c][1,2]oxaborole-6-carbonyl)glycinate (6-004)

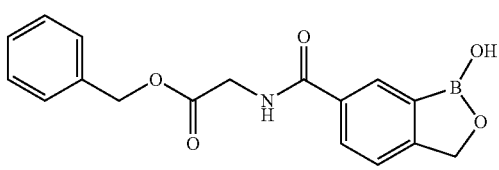

This compound was prepared from glycine benzyl ester and Acid-01 in a similar manner to Example 1. $^1$H NMR (400 MHz, DMSO-d$_6$) δ 9.32 (s, 1H), 8.99 (t, J=6.0 Hz, 1H), 8.23 (s, 1H), 7.93 (dd, J=7.9, 1.32 Hz, 1H), 7.49 (d, J=7.94 Hz, 1H), 7.41-7.21 (m, 5H), 5.14 (s, 2H), 5.03 (s, 2H), 4.06 (d, J=5.7 Hz, 2H); ESI-MS: m/z 326 [M+H]$^+$; HPLC purity: 100% (220 nm), 100% (254 nm).

Example 5. Benzyl (1-hydroxy-1,3-dihydrobenzo[c][1,2]oxaborole-6-carbonyl)-L-valinate (6-005)

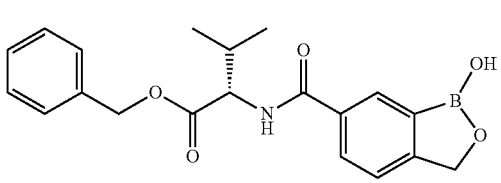

This compound was prepared from (S)-valine benzyl ester and Acid-01 in a similar manner to the last step of Example 1. $^1$H NMR (400 MHz, DMSO-d$_6$) δ 9.31 (br s, 1H), 8.66 (d, J=7.5 Hz, 1H), 8.23 (s, 1H), 7.95 (dd, J=7.9, 1.76 Hz, 1H), 7.49 (d, J=8.4 Hz, 1H), 7.38-7.31 (m, 4H), 5.24-5.09 (m, 2H), 5.04 (s, 2H), 4.33 (t, J=7.5 Hz, 1H), 2.29-2.11 (m, 1H), 0.95 (dd, J=18.96, 6.62 Hz, 6H). ESI-MS: m/z 368 [M+H]$^+$; HPLC purity: 98.3% (220 nm), 100% (254 nm).

Example 6. Benzyl (1-hydroxy-1,3-dihydrobenzo[c][1,2]oxaborole-6-carbonyl)-L-leucinate (6-006)

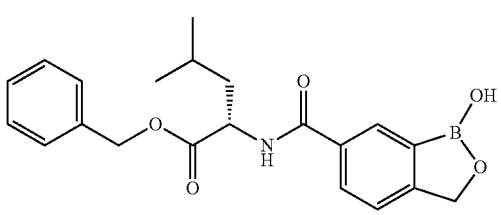

This compound was prepared from (S)-leucine benzyl ester and Acid-01 in a similar manner to the last step of Example 1. $^1$H NMR (400 MHz, DMSO-d$_6$) δ 9.32 (s, 1H), 8.79 (d, J=7.94 Hz, 1H), 8.23 (s, 1H), 7.93 (d, J=7.9 Hz, 1H), 7.48 (d, J=7.9 Hz, 1H), 7.38-7.25 (m, 5H), 5.12 (s, 2H), 5.03 (s, 2H), 4.52 (dd, J=6.8, 3.31 Hz, 1H), 1.90-1.42 (m, 3H), 0.90 (d, J=6.4 Hz, 3H), 0.87 (d, J=6.4 Hz, 3H), 6.39 Hz, 6H); ESI-MS: m/z 382 [M+H]$^+$; HPLC purity: 100% (220 nm), 100% (254 nm).

Example 7. Benzyl (1-hydroxy-1,3-dihydrobenzo[c][1,2]oxaborole-6-carbonyl)-L-serinate (6-007)

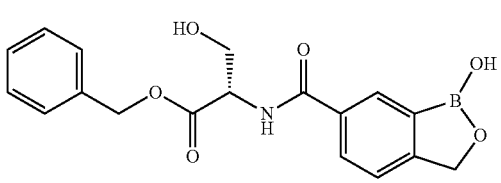

This compound was prepared from (S)-serine benzyl ester and Acid-01 in a similar manner to the last step of Example 1. $^1$H NMR (400 MHz, DMSO-d$_6$) δ 9.34 (s, 1H), 8.67 (d, 1H), 7.87 (s, 1H), 7.80 (d, 2H), 7.41-7.26 (m, 4H), 5.14 (s, 2H), 5.03 (s, 2H), 4.58 (m, 1H), 3.88-3.77 (m, 2H); ESI-MS: m/z 356 [M+H]$^+$; HPLC purity: 100% (220 nm), 100% (254 nm).

Example 8. Benzyl (1-hydroxy-1,3-dihydrobenzo[c][1,2]oxaborole-6-carbonyl)-L-methioninate (6-008)

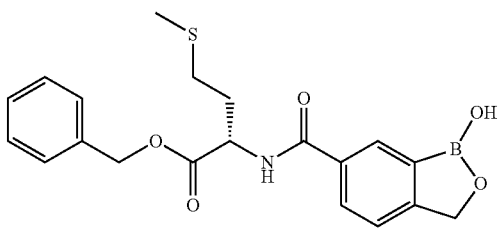

This compound was prepared from (S)-methionine benzyl ester and Acid-01 in a similar manner to the last step of Example 1. $^1$H NMR (400 MHz, DMSO-d$_6$) δ 9.32 (br s, 1H) 8.84 (d, J=7.5 Hz, 1H), 8.23 (s, 1H), 7.94 (d, J=7.9 Hz, 1H), 7.49 (d, J=7.9 Hz, 1H), 7.38-7.22 (m, 5H), 5.14 (d, J=4.0 Hz, 2H), 5.03 (s, 2H), 4.68-4.51 (m, 1H), 2.68-2.51 (m, 2H), 2.12-2.04 (m, 2H), 2.01 (s, 3H); ESI-MS: m/z 400 [M+H]$^+$; HPLC purity: 100% (220 nm), 100% (254 nm).

Example 9. Benzyl (1-hydroxy-1,3-dihydrobenzo[c][1,2]oxaborole-6-carbonyl)-L-phenylalaninate (6-009)

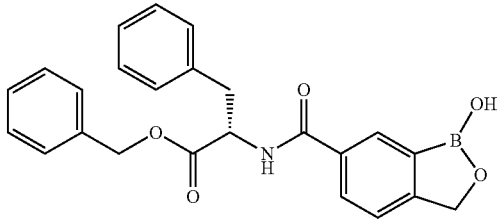

This compound was prepared from (S)-phenylalanine benzyl ester and Acid-01 in a similar manner to the last step of Example 1. $^1$H NMR (400 MHz, DMSO-d$_6$) δ 9.31 (s, 1H), 8.92 (d, J=8.0 Hz, 1H), 8.17 (s, 1H), 7.86 (d, J=8.0 Hz, 1H), 7.47 (d, J=8.0 Hz, 1H), 7.36-7.14 (m, 9H), 5.11 (d, J=4.41 Hz, 2H), 5.02 (s, 2H), 4.65-4.77 (m, 1H), 3.22-3.07 (m, 2H); ESI-MS m/z 416 [M+H]$^+$; HPLC purity: 100% (220 nm), 100% (254 nm).

Example 10. Benzyl (1-hydroxy-1,3-dihydrobenzo[c][1,2]oxaborole-6-carbonyl)-L-asparaginate (6-010)

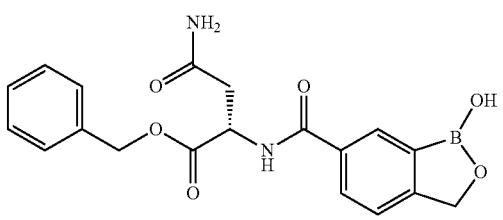

This compound was prepared from (S)-glutamine benzyl ester and Acid-01 in a similar manner to the last step of Example 1. $^1$H NMR (400 MHz, DMSO-d$_6$) δ 8.90 (d, J=7.06 Hz, 1H) 8.25 (s, 1H), 7.96 (dd, J=8.0, 1.76 Hz, 1H), 7.50 (d, J=8.4 Hz, 1H), 7.36-7.31 (m, 5H), 6.82 (br s, 1H), 5.19-5.10 (m, 2H), 5.04 (s, 2H), 4.47 (br s, 1H), 2.28-2.19 (m, 2H), 2.16-2.04 (m, 1H), 2.03-1.90 (m, 1H); ESI-MS m/z 397 [M+H]$^+$; HPLC purity: 99.39% (220 nm), 100% (254 nm).

Example 11. Benzyl (1-hydroxy-1,3-dihydrobenzo[c][1,2]oxaborole-6-carbonyl)-L-glutaminate (6-011)

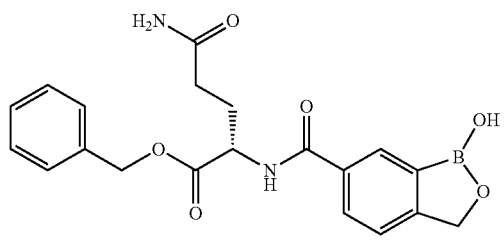

6-011

This compound was prepared from (S)-glutamine benzyl ester and Acid-01 in a similar manner to the last step of Example 1. $^1$H NMR (400 MHz, DMSO-d$_6$) δ 8.82 (d, J=7.5 Hz, 1H), 8.21 (s, 1H), 7.91 (dd, J=8.2, 1.54 Hz, 1H), 7.49 (d, J=7.9 Hz, 1H), 7.42 (br s, 1H), 7.38-7.23 (m, 5H), 6.97 (br s, 1H), 5.13 (s, 2H), 5.04 (s, 2H), 4.78-4.90 (m, 1H), 2.58-2.81 (m, 2H); ESI-MS m/z 383 [M+H]; HPLC purity: 98.69% (220 nm), 97.33% (254 nm).

Example 12. Benzyl (1-hydroxy-1,3-dihydrobenzo[c][1,2]oxaborole-6-carbonyl)-L-prolinate (6-012)

6-012

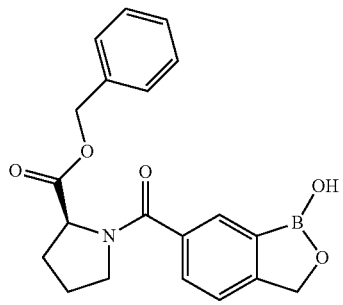

This compound was prepared from (S)-proline benzyl ester and Acid-01 in a similar manner to the last step of Example 1. $^1$H NMR (400 MHz, DMSO-d$_6$) δ 7.92 (s, 1H), 7.66-7.53 (m, 1H), 7.47 (d, J=7.9 Hz, 1H), 7.41-7.13 (m, 5H), 5.16 (s, 2H), 5.05-4.95 (m, 2H), 4.55 (dd, J=7.9, 4.41 Hz, 1H), 3.61-3.47 (m, 2H), 2.36-2.24 (m, 1H), 1.99-1.76 (m, 3H); ESI-MS: m/z 366 [M+H]; HPLC purity: 100% (220 nm), 100% (254 nm).

Example 13. Benzyl 2-(1-hydroxy-1,3-dihydrobenzo[c][1,2]oxaborole-6-carboxamido)-2-methylpropanoate (6-013)

6-013

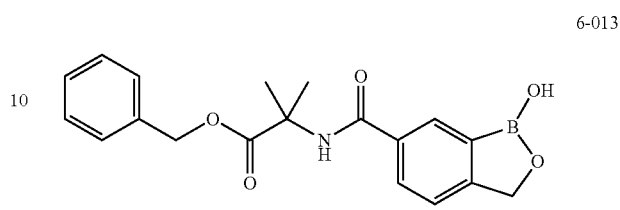

This compound was prepared from benzyl 2-amino-2-methylpropanoate and Acid-01 in a similar manner to the last step of Example 1. $^1$H NMR (400 MHz, DMSO-d$_6$) δ 9.31 (s, 1H), 8.71 (s, 1H), 8.20 (s, 1H), 7.90 (dd, J=7.94, 1.32 Hz, 1H), 7.47 (d, J=7.94 Hz, 1H), 7.34-7.18 (m, 5H), 5.04 (d, J=13.67 Hz, 4H), 1.48 (s, 6H); ESI-MS m/z 354 [M+H]; HPLC purity: 99.78% (220 nm), 100% (254 nm).

Example 14. 2,6-Dimethylbenzyl (1-hydroxy-1,3-dihydrobenzo[c][1,2]oxaborole-6-carbonyl)-L-alaninate (6-014)

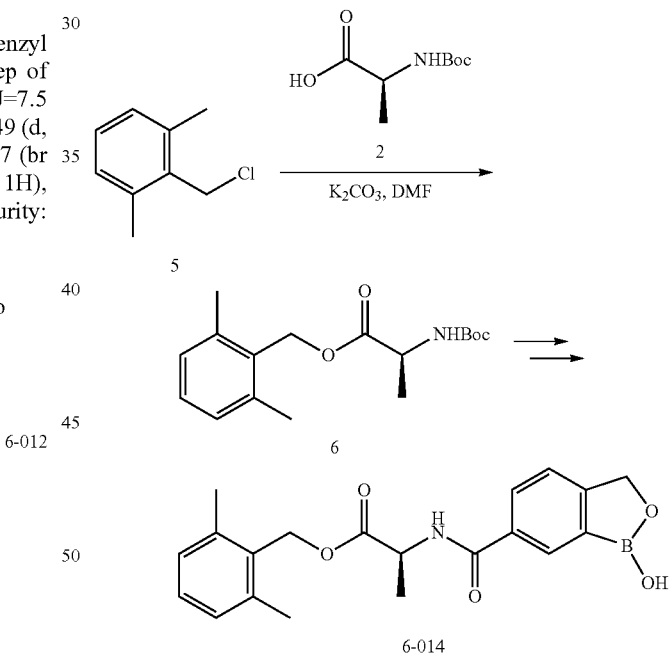

6-014

A mixture of compound 5 (775 mg, 5.00 mmol), compound 2 (1.00 g, 5.25 mmol) and K$_2$CO$_3$ (1.38 g, 10.0 mmol) in DMF (20 mL) was stirred at 10° C. for overnight. The reaction mixture was concentrated in vacuo and purified by silica gel column chromatography (PE:EA=10:1 to 5:1) to give compound 6 (1.3 g, yield 89%) as a white solid. In a similar manner to the last step of Example 1, 6-014 was obtained in two more steps from compound 6. $^1$H NMR (400 MHz, DMSO-d$_6$) δ 9.30 (s, 1H), 8.82 (d, J=6.6 Hz, 1H), 8.21 (s, 1H), 7.91 (d, J=7.9 Hz, 1H), 7.47 (d, J=7.9 Hz, 1H), 7.15-7.07 (m, 1H), 7.01 (d, J=7.5 Hz, 2H), 5.21-5.08 (m, 2H), 5.05-4.96 (m, 2H), 4.43 (q, J=7.2 Hz, 1H), 2.29 (s, 6H), 1.37 (d, J=7.1 Hz, 3H); ESI-MS: m/z 390 [M+Na]+; HPLC purity: 98.83% (220 nm), 100% (254 nm).

Example 15. 2-Phenylpropan-2-yl (1-hydroxy-1,3-dihydrobenzo[c][1,2]oxaborole-6-carbonyl)-L-alaninate (6-015)

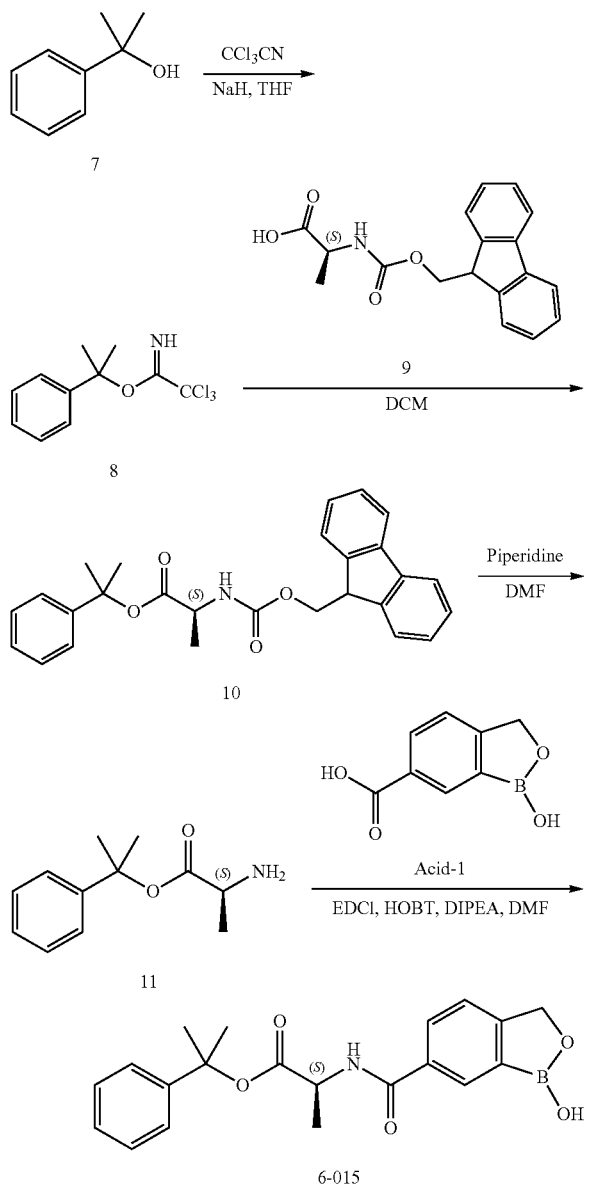

To a solution of compound 7 (1.36 g, 10 mmol) in dry THF (20 mL) was slowly added NaH (60% in mineral oil, 240 mg, 10 mmol) at 0° C. The mixture was stirred at 10° C. for 0.5 hour. Then CCl₃CN (1.43 g, 10 mmol) was added dropwise at 0° C., the resulting mixture was stirred at 10° C. for 1 hour. Organic solvent was removed under vacuum and the residue was suspended in hexane (20 mL) and MeOH (1 mL). Solid was removed by filtration and washed with hexane (3×5 mL). The filtrate was concentrated to dryness to give compound 8 (2.4 g, yield 86%) as a yellow oil.

A solution of compound 8 (837 mg, 3 mmol) and compound 9 (622 mg, 2 mmol) in DCM (30 mL) was stirred at 10° C. for 1 hour. TLC (PE:EA=5:1) indicated that starting material was completely consumed. The suspension was filtered. The filtrate was concentrated in vacuo and purified by silica gel column chromatography (PE:EA=10:1 to 5:1) to give compound 10 (850 mg, yield 98%) as a yellow oil.

To a solution of compound 10 (429 mg, 1 mmol) in DMF (5 mL) was slowly added piperidine (85 mg, 1 mmol), the reaction mixture was stirred at 10° C. for 1 hour. TLC (PE:EA=5:1) indicated that starting material was completely consumed. The suspension was filtered. The filtrate was concentrated to dryness in vacuo to give compound 11 (200 mg, yield 97%) as a yellow oil.

To a solution of Acid-1 (178 mg, 1 mmol), compound 11 (207 mg, 1 mmol), EDCI (384 mg, 2 mmol) and HOBT (270 mg, 2 mmol) in DMF (5 mL) was added DIPEA (387 mg, 3 mmol). The mixture was stirred at 10° C. for overnight and then purified by prep. HPLC to give 6-015 (50 mg, yield 14%) as a white solid. ¹H NMR (400 MHz, DMSO-d₆) δ 9.28 (s, 1H), 8.73 (d, J=7.1 Hz, 1H), 8.24 (s, 1H), 7.95 (d, J=8.8 Hz, 1H), 7.48 (d, J=7.9 Hz, 1H), 7.39-7.34 (m, 2H), 7.29 (t, J=7.5 Hz, 2H), 7.24-7.18 (m, 1H), 5.03 (s, 2H), 4.46 (q, J=7.3 Hz, 1H), 1.69 (d, J=8.4 Hz, 6H), 1.42 (d, J=7.50 Hz, 3H). ESI-MS m/z 390 [M+Na]+; HPLC purity: 98.55% (220 nm), 98.90% (254 nm).

Example 16. Methyl (1-hydroxy-1,3-dihydrobenzo[c][1,2]oxaborole-6-carbonyl)-L-alaninate (6-016)

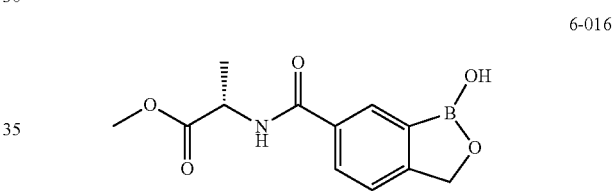

6-016

This compound was prepared from (S)-alanine methyl ester and Acid-01 in a similar manner to the last step of Example 1. ¹H NMR (400 MHz, DMSO-d₆) δ 9.30 (s, 1H), 8.80 (d, J=6.8 Hz, 1H), 8.22 (s, 1H), 7.93 (d, J=8.0 Hz, 1H), 7.47 (d, J=8.0 Hz, 1H), 5.01 (s, 2H), 4.45 (quint., J=7.2 Hz, 1H), 3.61 (s, 3H), 1.37 (d, J=7.2 Hz, 3H); ESI-MS m/z 264 [M+H]+; HPLC purity: 100% (220 nm), 100% (254 nm).

Example 17. Benzyl (S)-2-(1-hydroxy-1,3-dihydrobenzo[c][1,2]oxaboramido)-3,3-dimethylbutanoate (6-017)

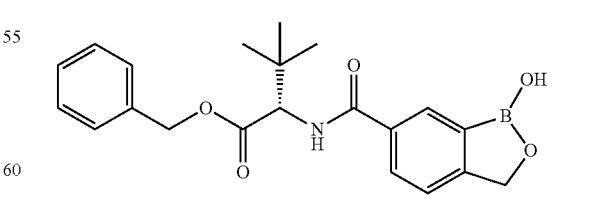

6-017

This compound was prepared from benzyl (S)-2-amino-3,3-dimethylbutanoate and Acid-01 in a similar manner to the last step of Example 1. ¹H NMR (400 MHz, DMSO-d₆) δ 9.34 (s, 1H), 8.44 (d, J=8.4 Hz, 1H), 7.83 (s, 1H), 7.79 (d, J=7.6 Hz, 1H), 7.76 (d, J=8.0 Hz, 1H), 7.40-7.29 (m, 5H), 5.18 (d, J=12.5 Hz, 1H), 5.11 (d, J=12.5 Hz, 1H), 5.03 (s, 2H), 4.44 (d, J=8.4 Hz, 1H), 1.02 (s, 9H); ESI-MS m/z 382 [M+H]⁺; HPLC purity: 100% (220 nm), 100% (254 nm).

Example 18. Methyl (1-hydroxy-1,3-dihydrobenzo[c][1,2]oxaborole-6-carbonyl)-D-phenylalaninate (6-018)

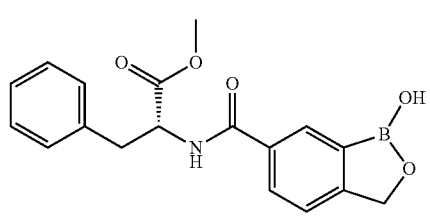

6-018

This compound was prepared from benzyl (S)-phenylalanine methyl ester and Acid-01 in a similar manner to the last step of Example 1. ¹H NMR (400 MHz, DMSO-d₆) δ 9.31 (s, 1H), 8.87 (d, J=7.9 Hz, 1H), 8.18 (s, 1H), 7.89 (dd, J=7.9, 1.32 Hz, 1H), 7.48 (d, J=7.9 Hz, 1H), 7.25-7.32 (m, 4H), 7.16-7.22 (m, 1H), 5.03 (s, 2H), 4.68 (ddd, J=9.7, 7.7, 5.5 Hz, 1H), 3.64 (s, 3H), 3.05-3.22 (m, 2H); ESI-MS m/z 340 [M+H]⁺; HPLC purity: 96.83% (220 nm), 95.71% (254 nm).

Example 19. (R)-1-Phenylethyl (1-hydroxy-1,3-dihydrobenzo[c][1,2]oxaborole-6-carbonyl)-L-alaninate (6-019)

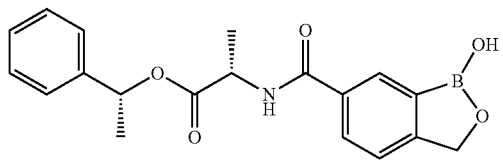

6-019

This compound was prepared from (R)-1-phenylethan-1-ol, compound 2 and Acid-01 in a similar manner to Example 1. ¹H NMR (400 MHz, DMSO-d₆) δ 9.28 (s 1H), 8.80 (d, J=6.4 Hz, 1H), 8.22 (s, 1H), 7.92 (d, J=7.6 Hz, 1H), 7.46 (d, J=7.6 Hz, 1H), 7.37-7.30 (m, 5H), 5.80 (m, 1H), 5.02 (s, 2H), 4.48 (t, J=6.8 Hz, 1H), 1.43-1.41 (m, 6H); ESI-MS m/z 376 [M+Na]⁺; HPLC purity: 99.63% (220 nm), 100% (254 nm).

Example 20. (R)-1-Phenylethyl (1-hydroxy-1,3-dihydrobenzo[c][1,2]oxaborole-6-carbonyl)-L-valinate (6-020)

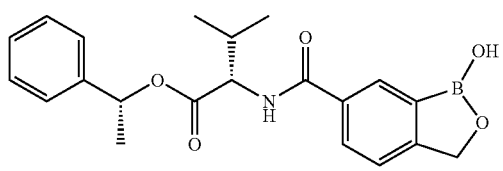

6-020

This compound was prepared from (R)-1-phenylethan-1-ol, N-BOC-(S)-valine and Acid-01 in a similar manner to Example 1. ¹H NMR (400 MHz, DMSO-d₆) δ 9.28 (s, 1H), 8.60 (d, J=7.6 Hz, 1H), 8.20 (s, 1H), 7.91 (d, J=7.6 Hz, 1H), 7.46 (d, J=8.0 Hz, 1H), 7.38-7.26 (m, 5H), 5.83 (m, 1H), 5.01 (s, 2H), 4.29 (t, J=8.0 Hz, 1H), 2.23-2.18 (m, 3H), 0.98 (d, J=7.2 Hz, 3H), 0.93 (d, J=6.4 Hz, 3H); ESI-MS m/z 404 [M+Na]⁺; HPLC purity: 99.80% (220 nm), 100% (254 nm).

Example 21. (R)-1-phenylethyl (1-hydroxy-1,3-dihydrobenzo[c][1,2]oxaborole-6-carbonyl)-L-phenylalaninate (6-021)

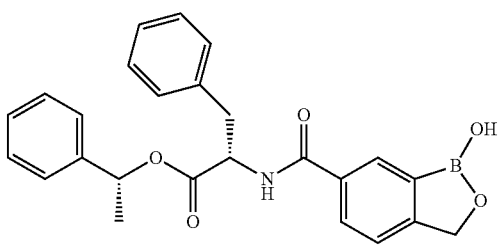

6-021

This compound was prepared from (R)-1-phenylethan-1-ol, N-BOC-(S)-phenylalanine and Acid-01 in a similar manner to Example 1. ¹H NMR (400 MHz, DMSO-d₆) δ 9.28 (s, 1H), 8.86 (d, J=7.6 Hz, 1H), 8.16 (s, 1H), 7.85 (d, J=8.0 Hz, 1H), 7.45 (d, J=8.0 Hz, 1H), 7.31-7.24 (m, 10H), 5.75 (m, 1H), 5.00 (s, 2H), 4.68 (m, 1H), 3.14 (d, J=7.6 Hz, 3H), 1.30 (d, J=6.8 Hz, 3H); ESI-MS m/z 452 [M+Na]⁺; HPLC purity: 99.22% (220 nm), 98.01% (254 nm).

Example 22. (S)-1-phenylethyl (1-hydroxy-1,3-dihydrobenzo[c][1,2]oxaborole-6-carbonyl)-L-alaninate (6-022)

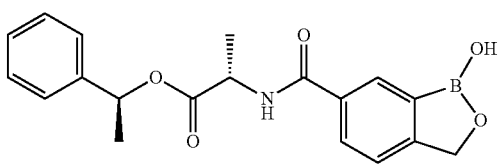

6-022

This compound was prepared from (S)-1-phenylethan-1-ol, N-BOC-(S)-alanine and Acid-01 in a similar manner to Example 1. ¹H NMR (400 MHz, DMSO-d₆) δ 9.28 (s, 1H), 8.78 (d, J=6.8 Hz, 1H), 8.22 (s, 1H), 7.93 (m, 1H), 7.47 (d, J=8.4 Hz, 1H), 7.32-7.26 (m, 5H), 5.79 (m, 1H), 5.02 (s, 2H), 4.49 (t, J=6.8 Hz, 1H), 1.45 (d, J=6.8 Hz, 3H), 1.36 (d, J=7.6 Hz, 3H);

ESI-MS m/z 376 [M+Na]⁺; HPLC purity: 94.63% (220 nm), 91.44% (254 nm).

Example 23. (S)-1-Phenylethyl (1-hydroxy-1,3-dihydrobenzo[c][1,2]oxaborole-6-carbonyl)-L-valinate (6-023)

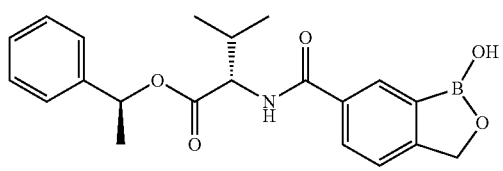
6-023

This compound was prepared from (S)-1-phenylethan-1-ol, N-BOC-(S)-valine and Acid-01 in a similar manner to Example 1. ¹H NMR (400 MHz, DMSO-d₆) δ 9.33 (s, 1H), 8.60 (d, J=8.0 Hz, 1H), 8.25 (s, 1H), 7.96 (d, J=8.4 Hz, 1H), 7.50 (d, J=8.0 Hz, 1H), 7.40-7.30 (m, 5H), 5.87 (m, 1H), 5.06 (s, 2H), 4.35 (m, 1H), 2.21 (m, 1H), 1.51 (d, J=6.8 Hz, 3H), 0.91-0.89 (m, 6H); ESI-MS m/z 404 [M+Na]⁺; HPLC purity: 98.86% (220 nm), 98.19% (254 nm).

Example 24. (S)-1-phenylethyl (1-hydroxy-1,3-dihydrobenzo[c][1,2]oxaborole-6-carbonyl)-L-phenylalaninate (6-024)

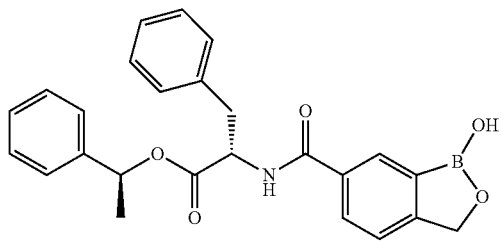
6-024

This compound was prepared from (S)-1-phenylethan-1-ol, N-BOC-(S)-phenylalanine and Acid-01 in a similar manner to Example 1. ¹H NMR (400 MHz, DMSO-d₆) δ 9.02 (s, 1H), 8.54 (d, J=8.0 Hz, 1H), 8.17 (s, 1H), 7.85 (d, J=7.6 Hz, 1H), 7.46 (d, J=8.0 Hz, 1H), 7.31-7.17 (m, 10H), 5.85 (m, 1H), 5.02 (s, 2H), 4.76 (m, 1H), 3.18 (m, 1H), 3.17 (m, 1H), 1.49 (d, J=6.8 Hz, 3H); ESI-MS m/z 452 [M+Na]⁺; HPLC purity: 98.92% (220 nm), 98.77% (254 nm).

Example 25. Methyl (R)-2-(1-hydroxy-1,3-dihydrobenzo[c][1,2]oxaborole-6-carboxamido)-4-phenylbutanoate (6-025)

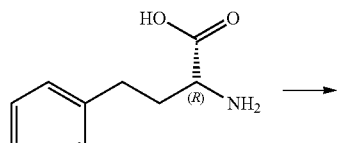
12

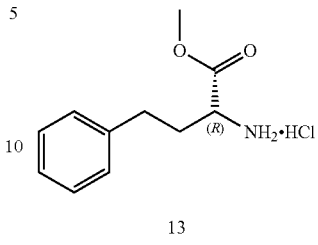
13

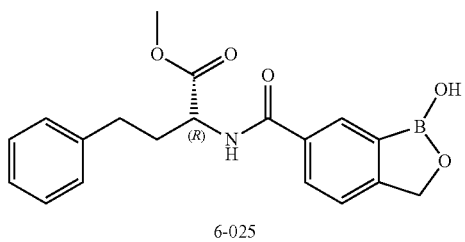
6-025

To a solution of compound 12 (1 g, 5.6 mmol) in MeOH (40 mL) was bubbled HCl gas at 0° C. for 30 min. Then the mixture was concentrated to dryness at 35° C. The residue was washed with MTBE and filtered to give compound 13 (0.80 g, 73%) which was used in the next step without further purification.

Compound 6-025 was prepared from 13 and Acid-01 in a similar manner to the last step of Example 1. ¹H NMR (400 MHz, DMSO-d₆) δ 9.33 (br s, 1H), 8.86 (d, J=7.5 Hz, 1H), 8.28 (s, 1H), 7.99 (dd, J=7.9, 1.76 Hz, 1H), 7.52 (d, J=7.9 Hz, 1H), 7.26-7.33 (m, 2H), 7.16-7.25 (m, 3H), 5.06 (s, 2H), 4.36-4.47 (m, 1H), 3.64 (s, 3H), 2.62-2.83 (m, 2H), 2.03-2.18 (m, 2H); ESI-MS m/z 354 [M+H]; HPLC purity: 99.62% (220 nm), 100% (254 nm).

Example 26. Methyl (1-hydroxy-1,3-dihydrobenzo[c][1,2]oxaborole-6-carbonyl)-L-phenylalaninate (6-026)

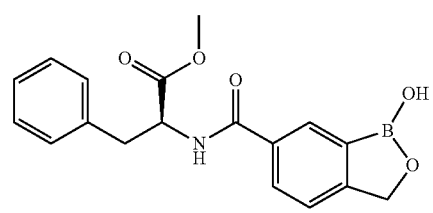
6-026

This compound was prepared from (S)-phenylalanine methyl ester and Acid-01 in a similar manner to the last step of Example 1. ¹H NMR (400 MHz, DMSO-d₆) δ 9.31 (s, 1H), 8.87 (d, J=7.8 Hz, 1H), 8.18 (s, 1H), 7.84-7.92 (m, 1H), 7.48 (d, J=8.0 Hz, 1H), 7.25-7.31 (m, 4H), 7.16-7.22 (m, 1H), 5.03 (s, 2H), 4.62-4.74 (m, 1H), 3.64 (s, 3H), 3.05-3.22 (m, 2H); ESI-MS m/z 340 [M+H]⁺; HPLC purity: 99.08% (220 nm), 99.48% (254 nm).

Example 27. Methyl (S)-2-(1-hydroxy-1,3-dihydrobenzo[c][1,2]oxaborole-6-carboxamido)-4-phenylbutanoate (6-027)

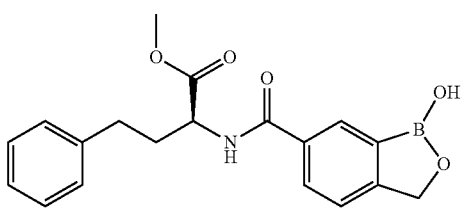

6-027

This compound was prepared from (S)-2-amino-4-phenylbutanoic acid and Acid-01 in a similar manner to Example 25. $^1$H NMR (400 MHz, DMSO-$d_6$) δ 9.33 (s, 1H), 8.86 (d, J=7.3 Hz, 1H), 8.28 (s, 1H), 7.99 (d, J=7.8 Hz, 1H), 7.52 (d, J=7.78 Hz, 1H), 7.26-7.32 (m, 2H), 7.17-7.25 (m, 3H), 5.06 (s, 2H), 4.35-4.47 (m, 1H), 3.64 (s, 3H), 2.61-2.83 (m, 2H), 2.03-2.17 (m, 2H); ESI-MS m/z 354 [M+H]$^+$; HPLC purity: 99.39% (220 nm).

Example 28. Methyl (S)-2-(1-hydroxy-1,3-dihydrobenzo[c][1,2]oxaborole-6-carboxamido)-5-phenylpentanoate (6-028)

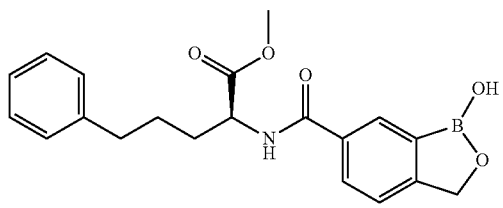

6-028

This compound was prepared from (S)-2-amino-5-phenylpentanoic acid and Acid-01 in a similar manner to Example 25 followed by chiral separation by chiral HPLC. $^1$H NMR (400 MHz, DMSO-$d_6$) δ 9.32 (s, 1H), 8.78 (d, J=7.3 Hz, 1H), 8.25 (s, 1H), 7.96 (dd, J=7.9, 1.13 Hz, 1H), 7.50 (d, J=8.0 Hz, 1H), 7.24-7.31 (m, 2H), 7.13-7.22 (m, 3H), 5.05 (s, 2H), 4.48 (q, J=7.3 Hz, 1H), 3.64 (s, 3H), 2.61 (t, J=6.65 Hz, 2H), 1.83 (q, J=7.53 Hz, 2H), 1.60-1.75 (m, 2H); ESI-MS m/z 389 [M+Na]$^+$; HPLC purity: 98.89% (220 nm), 98.87% (254 nm).

Example 29. Methyl (R)-2-(1-hydroxy-1,3-dihydrobenzo[c][1,2]oxaborole-6-carboxamido)-5-phenylpentanoate (6-029)

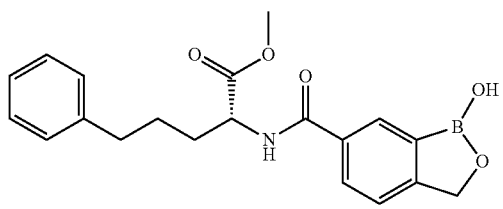

6-029

This compound was prepared from (R)-2-amino-5-phenylpentanoic acid and Acid-01 in a similar manner to Example 25 followed by chiral separation by chiral HPLC. $^1$H NMR (400 MHz, DMSO-$d_6$) δ 9.31 (s, 1H), 8.78 (d, J=7.3 Hz, 1H), 8.24 (s, 1H), 7.96 (dd, J=7.9, 1.38 Hz, 1H), 7.50 (d, J=7.8 Hz, 1H), 7.24-7.30 (m, 2H), 7.14-7.21 (m, 3H), 5.05 (s, 2H), 4.48 (q, J=7.2 Hz, 1H), 3.64 (s, 3H), 2.61 (t, J=6.7 Hz, 2H), 1.82 (q, J=7.7 Hz, 2H), 1.60-1.76 (m, 2H); ESI-MS m/z 368 [M+H]$^+$; HPLC purity: 98.74% (220 nm), 98.50% (254 nm).

Example 30. 4-Fluorobenzyl (1-hydroxy-1,3-dihydrobenzo[c][1,2]oxaborole-6-carbonyl)-L-valinate (6-030)

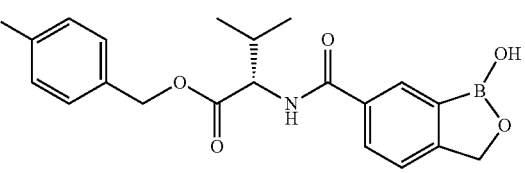

6-030

This compound was prepared from 4-fluorobenzylalcohol, N-BOC-(S)-valine and Acid-01 in a similar manner to Example 1. $^1$H NMR (400 MHz, DMSO-$d_6$) δ 9.34 (s, 1H), 8.67 (d, J=7.6 Hz, 1H), 8.24 (s, 1H), 7.96 (d, J=8.0 Hz, 1H), 7.51 (d, J=8.0 Hz, 1H), 7.45 (dd, J=8.4, 5.6 Hz, 2H), 7.21 (t, J=9.6 Hz, 2H), 5.19 (d, J=12.4 Hz, 1H), 5.13 (d, J=12.4 Hz, 1H), 5.06 (s, 2H), 4.33 (t, J=7.7 Hz, 1H), 2.21 (m, 1H), 0.98 (d, J=6.8 Hz, 3H), 0.96 (d, J=6.8 Hz, 3H); ESI-MS m/z 386 [M+H]$^+$; HPLC purity: 99.85% (220 nm), 100% (254 nm).

Example 31. 2,4-Difluorobenzyl (1-hydroxy-1,3-dihydrobenzo[c][1,2]oxaborole-6-carbonyl)-L-valinate (6-031)

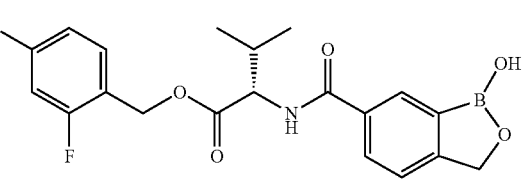

6-031

This compound was prepared from 2,4-difluorobenzylalcohol, N-BOC-(S)-valine and Acid-01 in a similar manner to Example 1. $^1$H NMR (400 MHz, DMSO-$d_6$) δ 9.34 (s, 1H), 8.63 (d, J=7.6 Hz, 1H), 8.20 (s, 1H), 7.91 (d, J=8.0 Hz, 1H), 7.55-7.46 (m, 4H), 5.18 (d, J=12.4 Hz, 1H), 5.11 (d, J=12.4 Hz, 1H), 5.02 (s, 2H), 4.28 (t, J=7.7 Hz, 1H), 2.15 (m, 1H), 0.93 (d, J=6.8 Hz, 3H), 0.88 (d, J=6.8 Hz, 3H); ESI-MS m/z 404 [M+H]$^+$; HPLC purity: 99.32% (220 nm), 100% (254 nm).

Example 32. Benzyl (1-hydroxy-3,3-dimethyl-1,3-dihydrobenzo[c][1,2]oxaborole-6-carbonyl)-L-valinate (6-032)

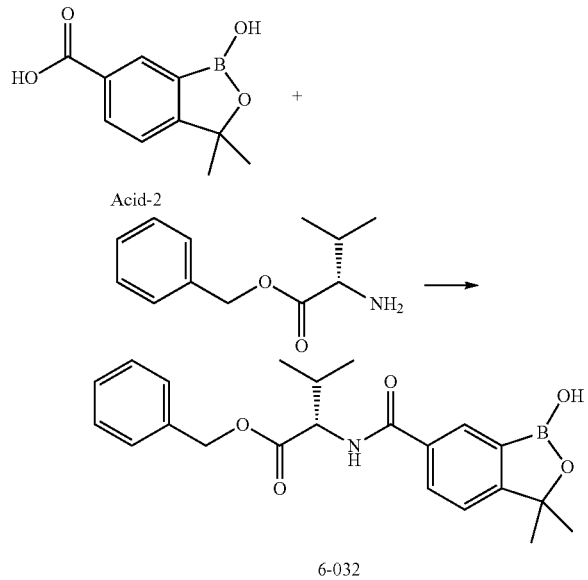

This compound was prepared from Acid-02 (WO 2012109164 A1) and (S)-valine benzyl ester in a similar manner to the last step of Example 1. $^1$H NMR (400 MHz, DMSO-d$_6$) δ 8.62 (d, J=7.6 Hz, 1H), 8.17 (s, 1H), 7.94 (d, J=8.0 Hz, 1H), 7.52 (d, J=8.0 Hz, 1H), 7.53-7.30 (m, 5H), 5.19 (d, J=12.4 Hz, 1H), 5.15 (d, J=12.4 Hz, 1H), 2.22 (m, 1H), 0.98 (d, J=6.8 Hz, 3H), 0.94 (d, J=6.8 Hz, 3H); ESI-MS m/z 396 [M+H]; HPLC purity: 98.56% (220 nm), 100% (254 nm).

Example 33. 4-Fluorobenzyl (1-hydroxy-3,3-dimethyl-1,3-dihydrobenzo[c][1,2]oxaborole-6-carbonyl)-L-valinate (6-033)

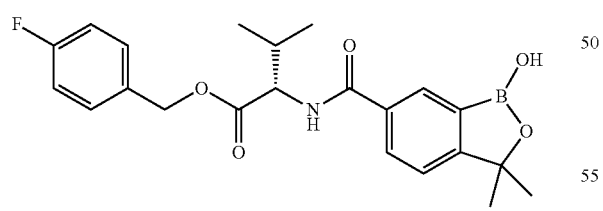

This compound was prepared from 4-fluorobenzylalcohol, N-BOC-(S)-valine and Acid-02 in a similar manner to Example 1. $^1$H NMR (400 MHz, DMSO-d$_6$) δ 8.62 (d, J=7.6 Hz, 1H), 8.16 (s, 1H), 7.93 (d, J=8.0 Hz, 1H), 7.52 (d, J=8.0 Hz, 1H), 7.45 (m, 2H), 7.20 (t, J=8.8 Hz, 2H), 5.20 (d, J=12.4 Hz, 1H), 5.10 (d, J=12.4 Hz, 1H) 4.34 (t, J=7.6 Hz, 1H), 2.20 (t, J=5.6 Hz, 1H), 1.47 (s, 6H), 0.99 (d, J=5.6 Hz, 3H), 0.90 (d, J=5.6 Hz, 3H); ESI-MS m/z 414 [M+H]$^+$; HPLC purity: 97.59% (220 nm), 100% (254 nm).

Example 34. 2,4-Difluorobenzyl (1-hydroxy-3,3-dimethyl-1,3-dihydrobenzo[c][1,2]oxaborole-6-carbonyl)-L-valinate (6-034)

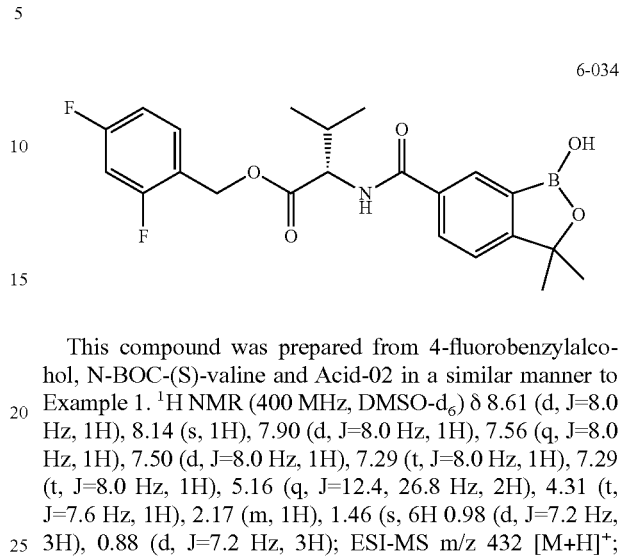

This compound was prepared from 4-fluorobenzylalcohol, N-BOC-(S)-valine and Acid-02 in a similar manner to Example 1. $^1$H NMR (400 MHz, DMSO-d$_6$) δ 8.61 (d, J=8.0 Hz, 1H), 8.14 (s, 1H), 7.90 (d, J=8.0 Hz, 1H), 7.56 (q, J=8.0 Hz, 1H), 7.50 (d, J=8.0 Hz, 1H), 7.29 (t, J=8.0 Hz, 1H), 7.29 (t, J=8.0 Hz, 1H), 5.16 (q, J=12.4, 26.8 Hz, 2H), 4.31 (t, J=7.6 Hz, 1H), 2.17 (m, 1H), 1.46 (s, 6H 0.98 (d, J=7.2 Hz, 3H), 0.88 (d, J=7.2 Hz, 3H); ESI-MS m/z 432 [M+H]$^+$; HPLC purity: 98.84% (220 nm), 100% (254 nm).

Example 35. Benzyl (7-fluoro-1-hydroxy-1,3-dihydrobenzo[c][1,2]oxaborole-6-carbonyl)-L-valinate (6-035)

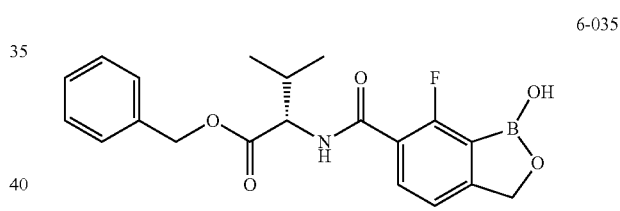

This compound was prepared from benzylalcohol, N-BOC-(S)-valine and Acid-03 in a similar manner to Example 1. ESI-MS m/z 386 [M+H]$^+$; HPLC purity: 100% (220 nm), 100% (254 nm).

Example 36. 4-Fluorobenzyl (7-fluoro-1-hydroxy-1,3-dihydrobenzo[c][1,2]oxaborole-6-carbonyl)-L-valinate (6-036)

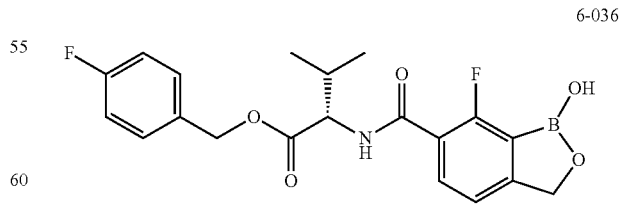

This compound was prepared from 4-fluorobenzylalcohol, N-BOC-(S)-valine and Acid-03 in a similar manner to Example 1. $^1$H NMR (400 MHz, DMSO-d$_6$) δ 9.38 (s, 1H), 8.58 (d, J=7.6 Hz, 1H), 7.65-7.47 (m, 1H), 7.45-7.43 (m, 2H), 7.30 (d, J=7.6 Hz, 1H), 7.23-7.19 (m, 2H), 5.20-5.11

(m, 2H), 5.04 (s, 2H), 4.38-4.35 (m, 1H), 2.19-2.12 (m, 1H), 0.94-0.91 (m, 6H); ESI-MS m/z 404 [M+H]⁺; HPLC purity: 100% (220 nm), 100% (254 nm).

Example 37. 2,4-Difluorobenzyl (7-fluoro-1-hydroxy-1,3-dihydrobenzo[c][1,2]oxaborole-6-carbonyl)-L-valinate (6-037)

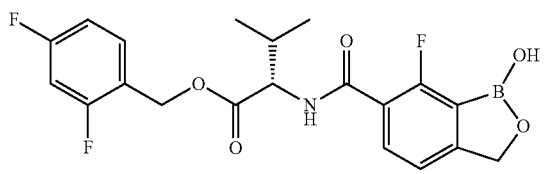

6-037

This compound was prepared from 2,4-difluorobenzylalcohol, N-BOC-(S)-valine and Acid-03 in a similar manner to Example 1. ¹H NMR (400 MHz, DMSO-d₆) δ 8.57 (d, J=7.6 Hz, 1H), 7.66-7.57 (m, 2H), 7.32-7.29 (m, 2H), 7.28-7.12 (m, 1H), 5.24-5.13 (m, 2H), 5.04 (s, 2H), 4.36-4.32 (m, 1H), 2.18-2.09 (m, 1H), 0.93-0.90 (m, 6H); ESI-MS m/z 422 [M+H]⁺; HPLC purity: 95.88% (220 nm), 97.81% (254 nm).

Example 38. Benzyl (1-hydroxy-7-methyl-1,3-dihydrobenzo[c][1,2]oxaborole-6-carbonyl)-L-valinate (6-038)

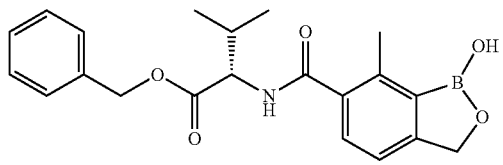

6-038

This compound was prepared from Acid-04 and (S)-valine benzyl ester in a similar manner to the last step of Example 1. ¹H NMR (400 MHz, DMSO-d₆) δ 9.03 (s, 1H), 8.57 (d, J=8.0 Hz, 1H), 7.41-7.23 (m, 7H), 5.16 (dd, J=12.4 Hz, J=20.0 Hz, 2H), 4.96 (s, 2H), 4.35 (t, J=7.2 Hz, 1H), 2.43 (s, 3H), 2.18-2.13 (m, 1H), 0.94 (d, J=5.6 Hz, 6H); ESI-MS m/z 382 [M+H]; HPLC purity: 100% (220 nm), 100% (254 nm).

Example 39. 2,4-Difluorobenzyl (1-hydroxy-7-methyl-1,3-dihydrobenzo[c][1,2]oxaborole-6-carbonyl)-L-valinate (6-039)

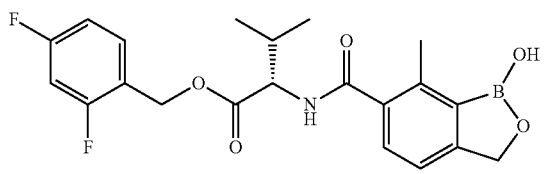

6-039

This compound was prepared from 2,4-difluorobenzylalcohol, N-BOC-(S)-valine and Acid-04 in a similar manner to Example 1. ¹H NMR (400 MHz, DMSO-d₆) δ 8.57 (d, J=7.6 Hz, 1H), 7.66-7.57 (m, 2H), 7.32-7.29 (m, 2H), 7.28-7.12 (m, 1H), 5.24-5.13 (m, 2H), 5.04 (s, 2H), 4.36-4.32 (m, 1H), 2.18-2.09 (m, 1H), 0.93-0.90 (m, 6H); ESI-MS m/z 418 [M+H]⁺; HPLC purity: 95.88% (220 nm), 97.81% (254 nm).

Example 40. 4-Chlorobenzyl (1-hydroxy-7-methyl-1,3-dihydrobenzo[c][1,2]oxaborole-6-carbonyl)-L-valinate (6-040)

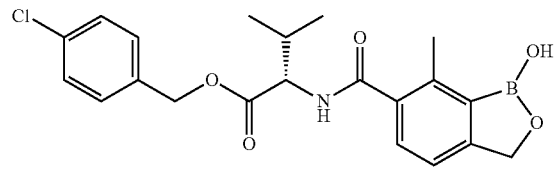

6-040

This compound was prepared from 4-chlorobenzylalcohol, N-BOC-(S)-valine and Acid-04 in a similar manner to Example 1. ¹H NMR (400 MHz, DMSO-d₆) δ 9.01 (s, 1H), 8.56 (d, J=7.5 Hz, 1H), 7.43 (s, 4H), 7.32 (d, J=7.9 Hz, 1H), 7.22 (d, J=7.9 Hz, 1H), 5.15 (d, J=4.0 Hz, 2H), 4.95 (s, 2H), 4.33 (t, J=7.3 Hz, 1H), 2.42 (s, 3H), 2.19-1.99 (m, 1H), 0.92 (d, J=6.6 Hz, 6H) ESI-MS m/z 416 [M+H]⁺; HPLC purity: 97.85% (220 nm), 98.66% (254 nm).

Example 41. 4-Trifluoromethylbenzyl (1-hydroxy-7-methyl-1,3-dihydrobenzo[c][1,2]oxaborole-6-carbonyl)-L-valinate (6-041)

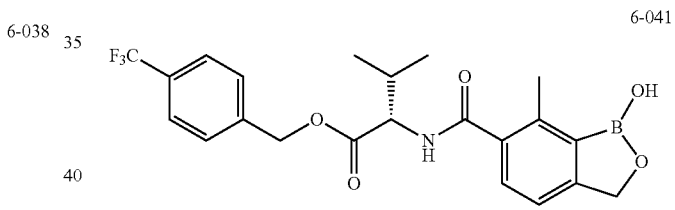

6-041

This compound was prepared from 4-trifluoromethylbenzylalcohol, N-BOC-(S)-valine and Acid-04 in a similar manner to Example 1. ¹H NMR (400 MHz, DMSO-d₆) δ 9.01 (s, 1H), 8.59 (d, J=7.5 Hz, 1H), 7.74 (d, J=7.9 Hz, 2H), 7.62 (d, J=8.4 Hz, 2H), 7.33 (d, J=7.5 Hz, 1H), 7.21 (d, J=7.5 Hz, 1H), 5.27 (s, 2H), 4.95 (s, 2H) 4.36 (t, J=7.3 Hz, 1H), 2.41 (s, 3H), 2.16 (dq, J=13.56, 6.65 Hz, 1H), 1.00-0.88 (m, 6H); ESI-MS m/z 450 [M+H]⁺; HPLC purity: 98.98% (220 nm), 100% (254 nm).

Example 42. 3-Fluorobenzyl (1-hydroxy-7-methyl-1,3-dihydrobenzo[c][1,2]oxaborole-6-carbonyl)-L-valinate (6-042)

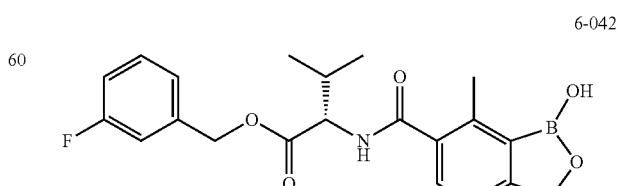

6-042

This compound was prepared from 3-fluorobenzylalcohol, N-BOC-(S)-valine and Acid-04 in a similar manner to Example 1. ¹H NMR (400 MHz, DMSO-d$_6$) δ 9.06 (s, 1H), 8.63 (d, J=7.8 Hz, 1H), 7.44 (q, J=7.36 Hz, 1H), 7.35 (d, J=7.8 Hz, 1H), 7.26 (d, J=6.8 Hz, 3H), 7.21-7.13 (m, 1H), 5.21 (s, 2H), 4.98 (s, 2H), 4.37 (t, J=7.2 Hz, 1H), 2.44 (s, 3H), 2.23-2.13 (m, 1H), 0.97-0.94 (m, 6H); ESI-MS m/z 400 [M+H]⁺; HPLC purity: 96.98% (220 nm), 100% (254 nm).

Example 43. 3-Chlorobenzyl (1-hydroxy-7-methyl-1,3-dihydrobenzo[c][1,2]oxaborole-6-carbonyl)-L-valinate (6-043)

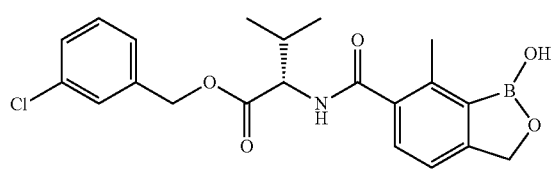

6-043

This compound was prepared from 3-chlorobenzylalcohol, N-BOC-(S)-valine and Acid-04 in a similar manner to Example 1. ¹H NMR (400 MHz, DMSO-d$_6$) δ 9.01 (s, 1H), 8.59 (d, J=7.50 Hz, 1H), 7.47 (s, 1H), 7.43-7.30 (m, 4H), 7.22 (d, J=7.5 Hz, 1H), 5.17 (d, J=1.8 Hz, 2H), 4.95 (s, 2H), 4.35 (t, J=7.3 Hz, 1H), 2.42 (s, 3H), 2.21-2.09 (m, 1H), 0.93 (d, J=6.62); ESI-MS m/z 416 [M+H]⁺; HPLC purity: 99.67% (220 nm), 100% (254 nm).

Example 44. 4-Cyanobenzyl (1-hydroxy-7-methyl-1,3-dihydrobenzo[c][1,2]oxaborole-6-carbonyl)-L-valinate (6-044)

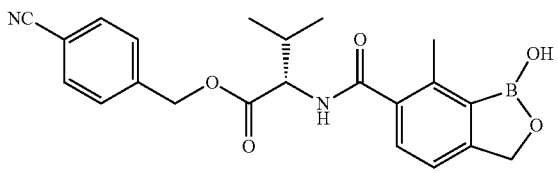

6-044

This compound was prepared from 4-cyanobenzylalcohol, N-BOC-(S)-valine and Acid-04 in a similar manner to Example 1. ¹H NMR (400 MHz, DMSO-d$_6$) δ 9.06 (s, 1H), 8.65 (d, J=7.5 Hz, 1H), 7.88 (d, J=8.28 Hz, 2H), 7.62 (d, J=8.0 Hz, 2H), 7.36 (d, J=7.8 Hz, 1H), 7.25 (d, J=7.8 Hz, 1H), 5.29 (s, 2H), 4.98 (s, 2H), 4.38 (t, J=7.2 Hz, 1H), 2.44 (s, 3H), 2.24-2.12 (m, 1H), 0.96 (dd, J=6.7, 1.63 Hz, 6H); ESI-MS m/z 407 [M+H]⁺; HPLC purity: 97.14% (220 nm), 98.60% (254 nm).

Example 45. 4-Fluorobenzyl (S)-2-(1-hydroxy-7-methyl-1,3-dihydrobenzo[c][1,2]oxaborole-6-carboxamido)-2-phenylacetate (6-045)

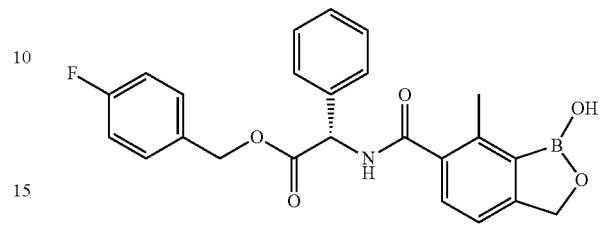

6-045

This compound was prepared from 4-fluorobenzylalcohol, N-BOC-(S)-phenylglycine and Acid-04 in a similar manner to Example 1. ¹H NMR (400 MHz, DMSO-d$_6$) δ 9.13 (d, J=7.1 Hz, 1H), 9.01 (s, 1H), 7.45 (d, J=6.2 Hz, 2H), 7.39-7.29 (m, 6H), 7.20 (d, J=7.9 Hz, 1H), 7.14 (t, J=8.8 Hz, 2H), 5.67 (d, J=7.5 Hz, 1H), 5.15 (s, 2H), 4.95 (s, 2H), 2.43 (s, 3H); ESI-MS m/z 434 [M+H]⁺; HPLC purity: 99.70% (220 nm), 100% (254 nm).

Example 46. 3-Trifluoromethylbenzyl (1-hydroxy-7-methyl-1,3-dihydrobenzo[c][1,2]oxaborole-6-carbonyl)-L-valinate (6-046)

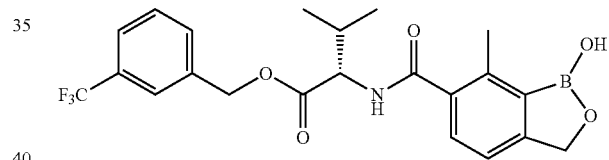

6-046

This compound was prepared from 3-trifluoromethylbenzylalcohol, N-BOC-(S)-valine and Acid-04 in a similar manner to Example 1. ¹H NMR (400 MHz, DMSO-d$_6$) δ 9.01 (s, 1H), 8.59 (d, J=7.5 Hz, 1H), 7.56-7.83 (m, 4H), 7.15-7.39 (m, 2H), 5.27 (d, J=1.8 Hz, 2H), 4.95 (s, 2H), 4.35 (t, J=7.1 Hz, 1H), 2.41 (s, 3H), 2.15 (dd, J=13.5, 6.8 Hz, 1H), 0.93 (d, J=6.17 Hz, 6H); ESI-MS m/z 450 [M+H]⁺; HPLC purity: 99.75% (220 nm), 100% (254 nm).

Example 47. 3-Cyanobenzyl (1-hydroxy-7-methyl-1,3-dihydrobenzo[c][1,2]oxaborole-6-carbonyl)-L-valinate (6-047)

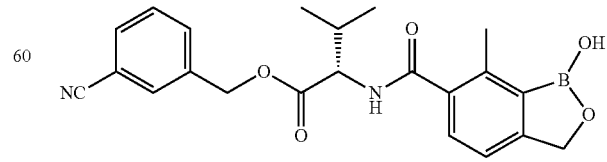

6-047

This compound was prepared from 3-cyanobenzylalcohol, N-BOC-(S)-valine and Acid-04 in a similar manner to Example 1. ¹H NMR (400 MHz, DMSO-d₆) δ 9.01 (s, 1H), 8.60 (d, J=7.9 Hz, 1H), 7.87 (s, 1H), 7.82-7.70 (m, 2H), 7.63-7.56 (m, 1H), 7.33 (d, J=7.9 Hz, 1H), 7.22 (d, J=7.9 Hz, 1H), 5.22 (s, 2H), 4.95 (s, 2H), 4.35 (t, J=7.3 Hz, 1H), 2.41 (s, 3H), 2.16 (dq, J=13.45, 6.69 Hz, 1H), 0.94 (d, J=6.6 Hz, 6H); ESI-MS m/z 407 [M+H]⁺; HPLC purity: 96.71% (220 nm), 94.02% (254 nm).

Example 48. 2,4-Difluorobenzyl (1-hydroxy-7-methyl-1,3-dihydrobenzo[c][1,2]oxaborole-6-carbonyl)-L-valinate (6-048)

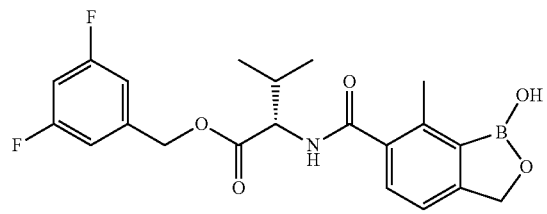

6-048

This compound was prepared from 2,4-difluorobenzylalcohol, N-BOC-(S)-valine and Acid-04 in a similar manner to Example 1. ¹H NMR (400 MHz, DMSO-d₆) δ 9.02 (s, 1H), 8.62 (d, J=7.9 Hz, 1H), 7.34 (d, J=7.9 Hz, 1H), 7.27-7.03 (m, 4H), 5.19 (s, 2H), 4.95 (s, 2H), 4.36 (t, J=7.3 Hz, 1H), 2.42 (s, 3H), 2.16 (d, J=6.6 Hz, 1H), 0.95 (dd, J=6.84, 2.4 Hz, 6H); ESI-MS m/z 418 [M+H]⁺; HPLC purity: 99.91% (220 nm), 100% (254 nm).

Example 49. 4-Fluoro-3-(trifluoromethyl)benzyl (1-hydroxy-7-methyl-1,3-dihydrobenzo[c][1,2]oxaborole-6-carbonyl)-L-valinate (6-049)

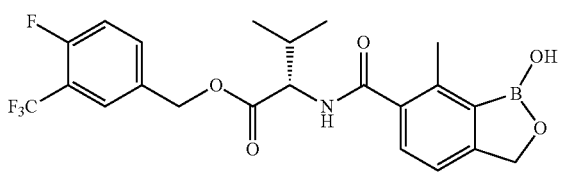

6-049

This compound was prepared from 4-fluoro-3-trifluoromethylbenzylalcohol, N-BOC-(S)-valine and Acid-04 in a similar manner to Example 1. ¹H NMR (400 MHz, DMSO-d₆) δ 9.01 (s, 1H), 8.58 (d, J=7.5 Hz, 1H), 7.93-7.76 (m, 2H), 7.68-7.49 (m, 1H), 7.38-7.16 (m, 2H), 5.24 (s, 2H), 4.95 (s, 2H), 4.33 (t, J=7.3 Hz, 1H), 2.40 (s, 3H), 2.14 (d, J=6.6 Hz, 1H), 0.93 (d, J=7.1 Hz, 6H); ESI-MS m/z 468 [M+H]⁺; HPLC purity: 96.57% (220 nm), 97.23% (254 nm).

Example 50. 4-Fluorobenzyl (S)-2-(1-hydroxy-7-methyl-1,3-dihydrobenzo[c][1,2]oxaborole-6-carboxamido)-2-phenylacetate (6-050)

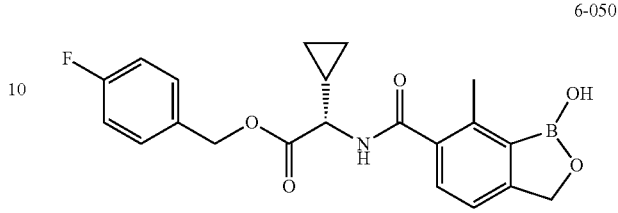

6-050

This compound was prepared from 4-fluorobenzylalcohol, N-BOC-(S)-cyclopropylglycine and Acid-04 in a similar manner to Example 1. ¹H NMR (400 MHz, DMSO-d₆) δ 9.03 (d, J=5.3 Hz, 1H), 8.83 (s., 1H), 7.45 (s., 2H), 7.36 (d, J=7.1 Hz, 1H), 7.28-7.14 (m, 3H), 5.24-5.09 (m, 2H), 4.97 (d, J=4.4 Hz, 2H), 3.79 (s, 1H), 2.44 (d, J=4.9 Hz, 3H), 1.19 (s, 1H), 0.60-0.35 (m, 4H); ESI-MS m/z 398 [M+H]⁺; HPLC purity: 99.52% (220 nm), 100% (254 nm).

Example 51. 3-Chloro-4-fluorobenzyl (1-hydroxy-7-methyl-1,3-dihydrobenzo[c][1,2]oxaborole-6-carbonyl)-L-valinate (6-051)

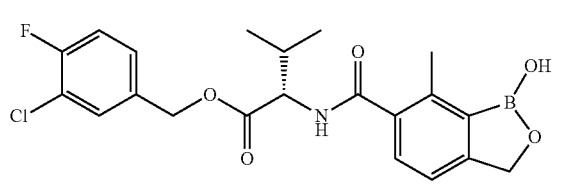

6-051

This compound was prepared from 3-chloro-4-fluorobenzylalcohol, N-BOC-(S)-valine and Acid-04 in a similar manner to Example 1. ¹H NMR (400 MHz, DMSO-d₆) δ 9.02 (s, 1H), 8.58 (d, J=7.5 Hz, 1H), 7.64 (d, J=7.5 Hz, 1H), 7.43 (d, J=7.5 Hz, 2H), 7.33 (d, J=7.9 Hz, 1H), 7.22 (d, J=7.9 Hz, 1H), 5.16 (s, 2H), 4.96 (s, 2H), 4.33 (t, J=7.3 Hz, 1H), 2.42 (s, 3H), 2.23-2.07 (m, 1H), 0.97-0.86 (m, 6H); ESI-MS m/z 434 [M+H]⁺; HPLC purity: 95.56% (220 nm), 98.25% (254 nm).

Example 52. 4-Fluorobenzyl (7-ethyl-1-hydroxy-1,3-dihydrobenzo[c][1,2]oxaborole-6-carbonyl)-L-valinate (6-052)

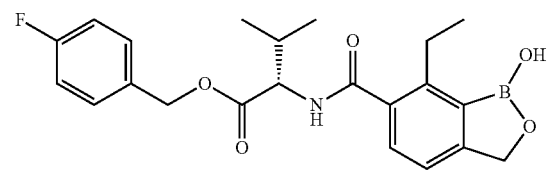

6-052

This compound was prepared from 4-fluorobenzylalcohol, N-BOC-(S)-valine and Acid-05 in a similar manner to Example 1. $^1$H NMR (400 MHz, DMSO-d$_6$) δ 8.98 (s, 1H), 8.58 (d, J=8.0 Hz, 1H), 7.47-7.43 (m, 2H), 7.29 (d, J=8.0 Hz, 1H), 7.23-7.18 (m, 3H), 5.14 (s, 2H), 4.96 (s, 2H), 4.34 (t, J=7.6 Hz, 1H), 2.86-2.80 (m, 2H), 2.13 (t, J=6.8 Hz, 1H), 1.06 (t, J=6.8 Hz, 3H), 0.92 (d, J=4.4 Hz, 6H); ESI-MS m/z 414 [M+H]$^+$; HPLC purity: 96.93% (220 nm), 95.38% (254 nm).

Example 53. Benzyl (7-ethyl-1-hydroxy-1,3-dihydrobenzo[c][1,2]oxaborole-6-carbonyl)-L-valinate (6-053)

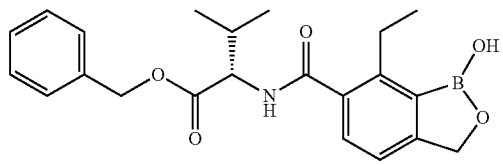

6-053

This compound was prepared from (S)-valine benzyl ester and Acid-05 in a similar manner to the last step of Example 1. $^1$H NMR (400 MHz, DMSO-d$_6$) δ 8.98 (s, 1H), 8.58 (d, J=8.0 Hz, 1H), 7.40-7.30 (m, 5H), 7.21 (d, J=7.6 Hz, 1H), 5.16 (s, 2H), 4.96 (s, 2H), 4.36 (t, J=7.6 Hz, 1H), 2.84 (q, J=7.2 Hz, J=7.6 Hz, 2H), 2.16 (t, J=6.8 Hz, 1H), 1.07 (t, J=7.2 Hz, 3H), 0.92 (d, J=6.8 Hz, 6H); ESI-MS m/z 396 [M+H]$^+$; HPLC purity: 97.21% (220 nm), 95.72% (254 nm).

Example 54. 4-Trifluoromethoxybenzyl (1-hydroxy-7-methyl-1,3-dihydrobenzo[c][1,2]oxaborole-6-carbonyl)-L-valinate (6-054)

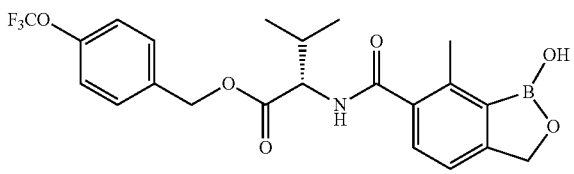

6-054

This compound was prepared from 4-trifluoromethoxybenzylalcohol, N-BOC-(S)-valine and Acid-04 in a similar manner to Example 1. $^1$H NMR (400 MHz, DMSO-d$_6$) δ 9.01 (s, 1H), 8.57 (d, J=7.9 Hz, 1H), 7.53 (d, J=8.4 Hz, 2H), 7.44-7.30 (m, 3H), 7.21 (d, J=7.5 Hz, 1H), 5.36-5.08 (m, 2H), 4.96 (s, 2H), 4.34 (t, J=7.3 Hz, 1H), 2.41 (s, 3H), 2.22-2.07 (m, 1H), 0.93 (d, J=6.17 Hz, 6H); ESI-MS m/z 466 [M+H]$^+$; HPLC purity: 99.63% (220 nm), 95.53% (254 nm).

Example 55. 3-Trifluoromethoxybenzyl (1-hydroxy-7-methyl-1,3-dihydrobenzo[c][1,2]oxaborole-6-carbonyl)-L-valinate (6-055)

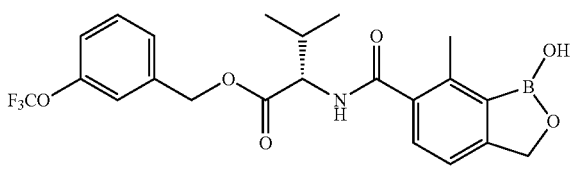

6-055

This compound was prepared from 3-trifluoromethoxybenzylalcohol, N-BOC-(S)-valine and Acid-04 in a similar manner to Example 1. $^1$H NMR (400 MHz, DMSO-d$_6$) δ 9.01 (s, 1H), 8.59 (d, J=7.50 Hz, 1H), 7.54-7.49 (m, 1H), 7.46-7.38 (m, 2H) 7.36-7.31 (m, 2H) 7.33 (d, J=7.50 Hz, 2H) 7.21 (d, J=7.9 Hz, 1H) 5.29-5.17 (m, 2H) 4.96 (s, 2H) 4.35 (t, J=7.3 Hz, 1H) 2.42 (s, 3H) 2.15 (dq, J=13.51, 6.82 Hz, 1H) 0.94 (d, J=6.6 Hz, 3H), 0.92 (d, J=6.6 Hz, 3H); ESI-MS m/z 466 [M+H]$^+$; HPLC purity: 100% (220 nm), 100% (254 nm).

Example 56. 4-(Methylsulfonyl)benzyl (1-hydroxy-7-methyl-1,3-dihydrobenzo[c][1,2]oxaborole-6-carbonyl)-L-valinate (6-056)

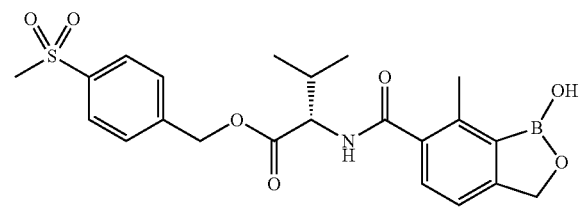

6-056

This compound was prepared from 4-(methyl sulfonyl) benzylalcohol, N-BOC-(S)-valine and Acid-04 in a similar manner to Example 1. $^1$H NMR (400 MHz, DMSO-d$_6$) δ 9.03 (s, 1H), 8.61 (d, J=7.5 Hz, 1H), 7.93 (d, J=7.9 Hz, 2H), 7.67 (d, J=7.5 Hz, 2H), 7.43-7.19 (m, 2H), 5.29 (s, 2H), 4.96 (s, 2H), 4.38 (t, J=7.1 Hz, 1H), 3.21 (s, 3H), 2.43 (s, 3H), 2.25-2.09 (m, 1H), 0.96 (d, J=6.2 Hz, 6H); ESI-MS m/z 460 [M+H]$^+$; HPLC purity: 100% (220 nm), 100% (254 nm).

Example 57. 4-Fluorobenzyl (7-ethyl-1-hydroxy-1,3-dihydrobenzo[c][1,2]oxaborole-6-carbonyl)-L-valinate (6-057)

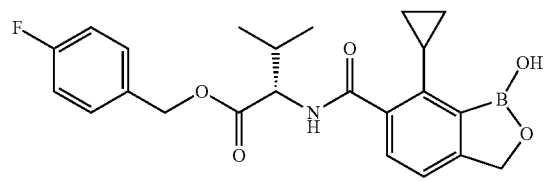

6-057

This compound was prepared from 4-fluorobenzylalcohol, N-BOC-(S)-valine and Acid-06 in a similar manner to Example 1. $^1$H NMR (400 MHz, DMSO-d$_6$) δ 8.90 (s, 1H), 8.62 (d, J=7.2 Hz, 1H), 7.47 (t, J=6.0 Hz, 2H), 7.23 (d, J=8.0 Hz, 4H), 5.19 (s, 2H), 4.96 (s, 2H), 4.34 (t, J=7.2 Hz, 1H), 2.15-2.13 (m, 2H), 0.94 (d, J=4.4 Hz, 6H), 0.77 (d, J=5.2 Hz, 4H); ESI-MS m/z 426 [M+H]$^+$; HPLC purity: 98.89% (220 nm), 99.55% (254 nm).

Example 58. Benzyl (7-ethyl-1-hydroxy-1,3-dihydrobenzo[c][1,2]oxaborole-6-carbonyl)-L-valinate (6-058)

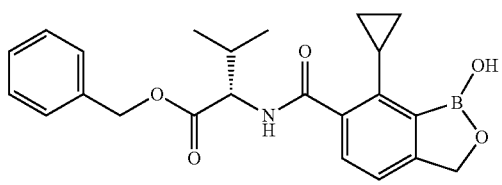

6-058

This compound was prepared from (S)-valine benzyl ester and Acid-06 in a similar manner to the last step of Example 1. ¹H NMR (400 MHz, DMSO-d₆) δ 8.90 (s, 1H), 8.62 (d, J=7.6 Hz, 1H), 7.41-7.35 (m, 5H), 7.22 (t, J=5.2 Hz, 2H), 5.21-5.14 (m, 2H), 4.96 (s, 2H), 4.35 (t, J=7.2 Hz, 1H), 2.16-2.14 (m, 2H), 0.96-0.94 (m, 6H), 0.79-0.76 (m, 4H); ESI-MS m/z 408 [M+H]⁺; HPLC purity: 99.97% (220 nm), 100% (254 nm).

Example 59. 4-Fluorobenzyl (S)-2-cyclobutyl-2-(1-hydroxy-7-methyl-1,3-dihydrobenzo[c][1,2]oxaborole-6-carboxamido)acetate (6-059)

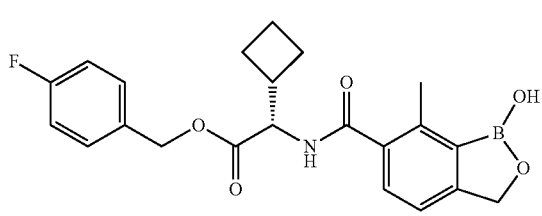

6-059

This compound was prepared from 4-fluorobenzylalcohol, (S)-2-((tert-butoxycarbonyl)amino)-2-cyclobutylacetic acid and Acid-04 in a similar manner to Example 1. ¹H NMR (400 MHz, DMSO-d₆) δ 9.02 (s, 1H), 8.55 (d, J=7.5 Hz, 1H), 7.42 (dd, J=8.38, 5.7 Hz, 2H), 7.32 (d, J=7.9 Hz, 1H), 7.26-7.14 (m, 3H), 5.23-5.02 (m, 2H), 4.95 (s, 2H), 4.39 (dd, J=9.3, 7.5 Hz, 1H), 2.73-2.61 (m, 1H), 2.42 (s, 3H), 2.04-1.71 (m, 6H); ESI-MS m/z 412 [M+H]⁺; HPLC purity: 98.85% (220 nm), 94.70% (254 nm).

Example 60. 4-Fluorobenzyl (S)-2-cyclopentyl-2-(1-hydroxy-7-methyl-1,3-dihydrobenzo[c][1,2]oxaborole-6-carboxamido)acetate (6-060)

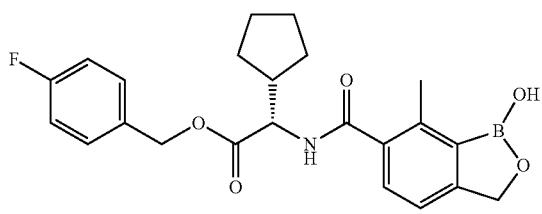

6-060

This compound was prepared from 4-fluorobenzylalcohol, (S)-2-((tert-butoxycarbonyl)amino)-2-cyclopentylacetic acid and Acid-04 in a similar manner to Example 1. ¹H NMR (400 MHz, DMSO-d₆) δ 9.01 (s, 1H), 8.64 (d, J=7.5 Hz, 1H), 7.44 (dd, J=8.6, 5.51 Hz, 2H), 7.31 (d, J=7.9 Hz, 1H), 7.24-7.15 (m, 3H), 5.19-5.07 (m, 2H), 4.95 (s, 2H), 4.29 (t, J=8.2 Hz, 1H), 2.41 (s, 3H), 2.29-2.19 (m, 1H), 1.80-1.38 (m, 8H); ESI-MS m/z 426 [M+H]⁺; HPLC purity: 98.85% (220 nm), 94.70% (254 nm).

Example 61. 4-Fluorobenzyl (3,7-dimethyl-1-hydroxy-1,3-dihydrobenzo[c][1,2]oxaborole-6-carbonyl)-L-valinate (6-061)

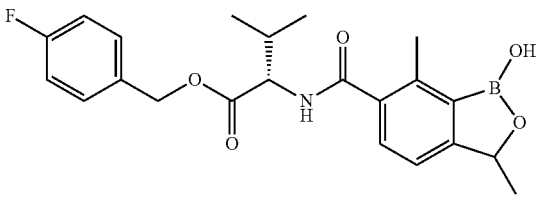

6-061

This compound was prepared from 4-fluorobenzylalcohol, N-BOC-(S)-valine and Acid-07 in a similar manner to Example 1. ¹H NMR (400 MHz, DMSO-d₆) δ 8.98 (s, 1H), 8.60 (d, J=8.0 Hz, 1H), 7.48-7.44 (m, 2H), 7.33 (d, J=6.0 Hz, 1H), 7.23-7.20 (m, 3H), 5.20-5.11 (m, 3H), 4.32 (s, 1H), 2.50 (s, 3H), 2.16-2.11 (m, 1H), 1.39 (d, J=6.0 Hz, 3H), 0.93 (d, J=6.4 Hz, 6H); ESI-MS m/z 414 [M+H]⁺; HPLC purity: 99.31% (220 nm), 99.01% (254 nm).

Example 62. 4-Fluorobenzyl (1-hydroxy-7-isopropyl-1,3-dihydrobenzo[c][1,2]oxaborole-6-carbonyl)-L-valinate (6-062)

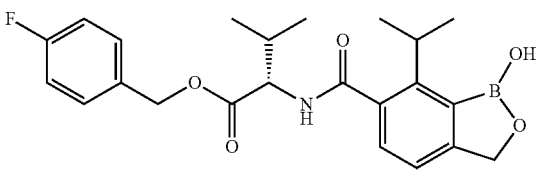

6-062

This compound was prepared from 4-fluorobenzylalcohol, N-BOC-(S)-valine and Acid-08 in a similar manner to Example 1. ¹H NMR (400 MHz, DMSO-d₆) δ 9.15 (s, 1H), 8.58 (d, J=8.0 Hz, 1H), 7.46-7.43 (m, 2H), 7.22-7.16 (m, 4H), 5.17-5.10 (m, 2H), 4.96 (s, 2H), 4.34 (t, J=7.2 Hz, 1H), 3.19 (t, J=6.4 Hz, 1H), 2.15-2.10 (m, 1H), 1.29-1.24 (m, 6H), 0.87 (t, J=3.2 Hz, 6H); ESI-MS m/z 428 [M+H]⁺; HPLC purity: 99.85% (220 nm), 100% (254 nm).

Example 63. Benzyl (1-hydroxy-7-isopropyl-1,3-dihydrobenzo[c][1,2]oxaborole-6-carbonyl)-L-valinate (6-063)

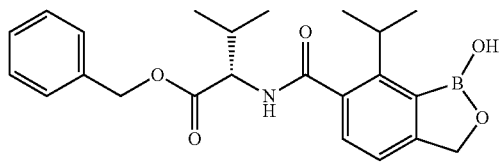

6-063

This compound was prepared from (S)-valine benzyl ester and Acid-08 in a similar manner to the last step of Example 1. ¹H NMR (400 MHz, DMSO-d₆) δ 9.15 (s, 1H), 8.58 (d, J=7.6 Hz, 1H), 7.40-7.34 (m, 5H), 7.19 (t, J=1.6 Hz, 2H), 5.12 (d, J=2.4 Hz, 1H); 4.96 (s, 2H), 4.35 (t, J=6.8 Hz, 1H), 3.24-3.17 (m, 1H), 2.17-2.12 (m, 1H), 1.29-1.23 (m, 6H), 0.91 (d, J=6.8 Hz, 6H); ESI-MS m/z 410 [M+H]⁺; HPLC purity: 99.91% (220 nm), 100% (254 nm).

Example 64. 4-fluorobenzyl (1-hydroxy-7-propyl-1, 3-dihydrobenzo[c][1,2]oxaborole-6-carbonyl)-L-valinate (6-064)

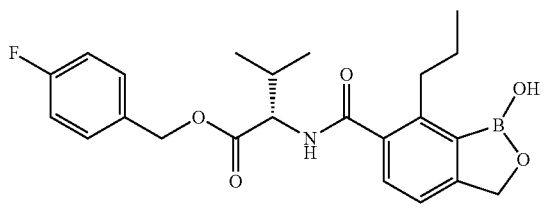

6-064

This compound was prepared from 4-fluorobenzylalcohol, N-BOC-(S)-valine and Acid-09 in a similar manner to Example 1. ¹H NMR (400 MHz, DMSO-d₆) δ 8.97 (s, 1H), 8.59 (d, J=8.0 Hz, 1H), 7.48-7.45 (m, 2H), 7.31 (d, J=8.0 Hz, 1H), 7.24-7.21 (m, 3H), 5.12 (s, 2H), 4.97 (s, 2H), 4.35 (t, J=7.2 Hz, 1H), 2.86-2.80 (m, 2H), 2.18-2.12 (m, 1H), 1.50 (s, 2H), 0.93 (d, J=3.2 Hz, 6H), 0.81 (t, J=7.2 Hz, 3H); ESI-MS m/z 428 [M+H]⁺; HPLC purity: 96.59% (220 nm), 93.52% (254 nm).

Example 65. Benzyl (1-hydroxy-7-isopropyl-1,3-dihydrobenzo[c][1,2]oxaborole-6-carbonyl)-L-valinate (6-065)

6-065

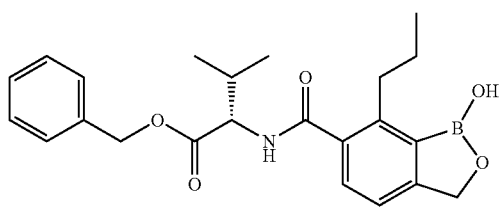

This compound was prepared from (S)-valine benzyl ester and Acid-09 in a similar manner to the last step of Example 1. ¹H NMR (400 MHz, DMSO-d₆) δ 8.97 (s, 1H), 8.59 (d, J=7.6 Hz, 1H), 7.41-7.24 (m, 7H), 5.17 (s, 2H), 4.97 (s, 2H), 4.36 (t, J=6.8 Hz, 1H), 2.85 (t, J=8.0 Hz, 2H), 2.18-2.13 (m, 1H), 1.50 (s, 2H), 0.93 (d, J=3.2 Hz, 6H), 0.81 (t, J=7.6 Hz, 3H); ESI-MS m/z 410 [M+H]⁺; HPLC purity: 96.53% (220 nm), 94.89% (254 nm).

Example 66. 4-Fluorobenzyl 1-(1-hydroxy-7-methyl-1,3-dihydrobenzo[c][1,2]oxaborole-6-carboxamido)cyclobutane-1-carboxylate (6-066)

6-066

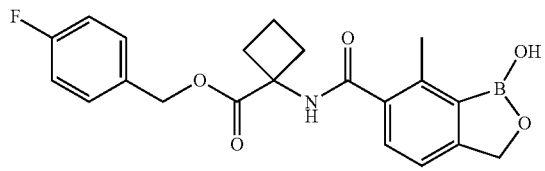

This compound was prepared from 4-fluorobenzylalcohol, 1-((tert-butoxycarbonyl)amino)cyclobutane-1-carboxylic acid and Acid-04 in a similar manner to Example 1. ¹H NMR (400 MHz, DMSO-d₆) δ 9.02 (d, J=5.7 Hz, 2H), 7.43 (dd, J=8.4, 5.7 Hz, 2H), 7.33 (d, J=7.5 Hz, 1H), 7.26-7.14 (m, 3H), 5.14 (s, 2H), 4.96 (s, 2H), 2.60-2.54 (m, 2H), 2.40 (s, 3H), 2.35-2.22 (m, 2H), 2.04-1.78 (m, 2H); ESI-MS m/z 398 [M+H]⁺; HPLC purity: 98.46% (220 nm), 97.78% (254 nm).

Example 67. (5-Fluoropyridin-2-yl)methyl (1-hydroxy-7-methyl-1,3-dihydrobenzo[c][1,2]oxaborole-6-carbonyl)-L-valinate (6-067)

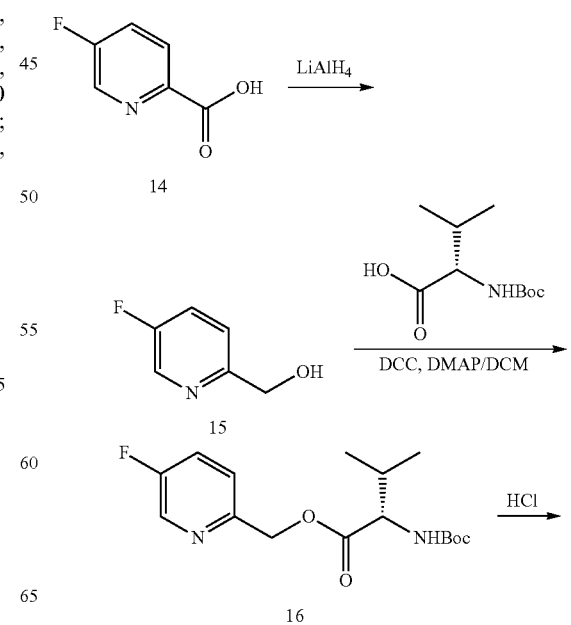

81
-continued

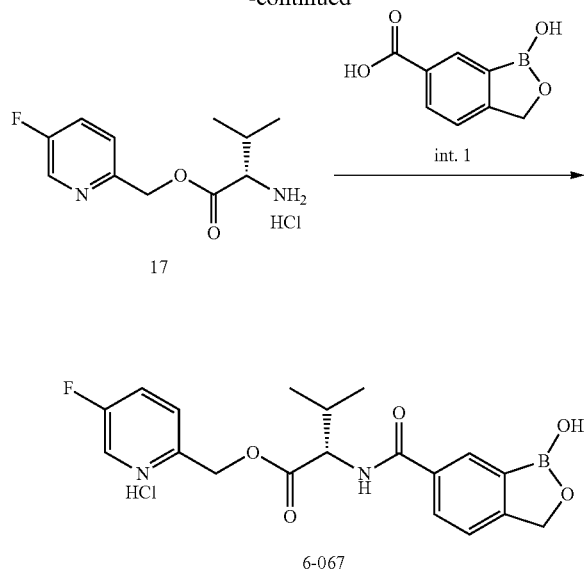

A mixture of 14 (500 mg, 4 mmol) and LiAlH₄ (202 mg, 5 mmol) in THF (10 mL) was degassed and purged with N₂ for 3 times, and then the mixture was stirred at 0° C. for 12 h under N₂ atmosphere. The reaction mixture was quenched by saturated sodium potassium tartrate (0.8 mL) at 15° C., and then filtered. The mixture was diluted with H₂O (5 mL) and extracted with EtOAc (5 mL×3). The combined organic layer was washed with brine (5 mL×2), dried over Na₂SO₄, filtered and concentrated under reduced pressure to give 15 (236 mg, 52%) as a yellow solid. $^1$H NMR (400 MHz, DMSO-d₆) δ 8.43 (d, J=2.8 Hz, 1H), 7.45-7.41 (m, 1H), 7.31-7.27 (m, 1H), 4.76 (s, 2H). A mixture of 15 (1 g, 8 mmol), DCC (3 g, 16 mmol), DMAP (96 mg, 786 umol) and N-BOC-(S)-valine (2 g, 9 mmol) in DCM (5 mL) was degassed and purged with N₂ for 3 times, and then the mixture was stirred at 25° C. for 12 h under N₂ atmosphere. The reaction mixture was filtered and concentrated under reduced pressure. The residue was purified by column chromatography (SiO₂, PE/EtOAc=5:1) to give 16 (1.3 g, 51%) as a yellow liquid. $^1$H NMR (400 MHz, DMSO-d₆) δ 8.55 (s, 1H), 7.71-7.83 (m, 1H), 7.54-7.51 (m, 1H), 7.25 (d, J=8.0 Hz, 1H), 5.22-5.13 (m, 2H), 3.91 (t, J=7.2 Hz, 1H), 2.06-2.02 (m, 1H), 1.38 (s, 9H), 0.87 (d, J=6.4 Hz, 6H).

To a mixture of 16 (1.3 g, 4 mmol) in EtOAc (20 mL) was added HCl/EtOAc (6 M, 10 mL). The mixture was stirred at 15° C. for 2 h under N₂ atmosphere. The reaction mixture was concentrated under reduced pressure to give 17 (800 mg, 77%) as a yellow solid.

$^1$H NMR (400 MHz, DMSO-d₆) δ 8.58 (d, J=2.4 Hz, 1H), 8.51 (s, 2H), 7.84-7.80 (m, 1H), 7.65-7.61 (m, 1H), 5.36-5.27 (m, 2H), 4.04-4.00 (m, 1H), 2.23-2.19 (m, 1H), 0.99-0.94 (m, 6H).

The compound 6-067 was prepared from 17 and Acid-04 in a similar manner to the last step of Example 1. $^1$H NMR (400 MHz, DMSO-d₆) δ 8.96 (s, 1H), 8.60 (d, J=7.6 Hz, 1H), 8.55 (d, J=2.4 Hz, 1H) 7.78 (td, J=8.8, 3.6 Hz, 1H) 7.56 (dd, J=8.4, 4.0 Hz, 1H), 7.34 (d, J=7.6 Hz, 1H), 7.22 (d, J=8.0 Hz, 1H), 5.22 (s, 2H), 4.95 (s, 2H), 4.37 (t, J=7.2 Hz, 1H), 2.42 (s, 3H), 2.21-2.12 (m, 1H), 0.96 (dd, J=6.8, 2.4 Hz, 6H); ESI-MS m/z 401 [M+H]⁺; HPLC purity: 100% (220 nm), 100% (254 nm).

82

Example 68. 4-Fluorobenzyl 1-(1-hydroxy-7-methyl-1,3-dihydrobenzo[c][1,2]oxaborole-6-carboxamido)cyclopropane-1-carboxylate (6-068)

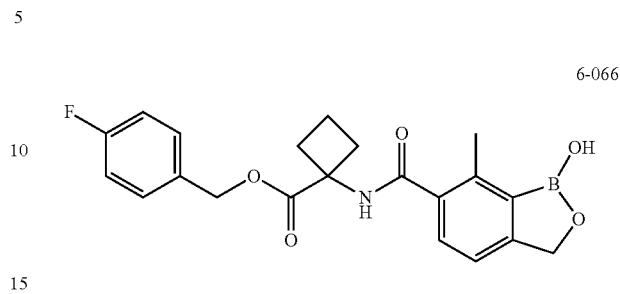

This compound was prepared from 4-fluorobenzylalcohol, 1-((tert-butoxycarbonyl)amino)cyclopropane-1-carboxylic acid and Acid-04 in a similar manner to Example 1. $^1$H NMR (400 MHz, DMSO-d₆) δ 9.02 (s, 1H), 8.83 (s, 1H), 7.47-7.38 (m, 2H), 7.31 (d, J=7.5 Hz, 1H), 7.20 (t, J=7.7 Hz, 3H), 5.12 (s, 2H), 4.95 (s, 2H), 2.39 (s, 3H), 1.45 (s, 2H), 1.17 (s, 2H); ESI-MS m/z 384 [M+H]⁺; HPLC purity: 97.30% (220 nm), 98.64% (254 nm).

Example 69. Methyl (1-hydroxy-7-methyl-1,3-dihydrobenzo[c][1,2]oxaborole-6-carbonyl)-L-valinate (6-069)

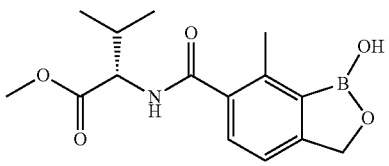

This compound was prepared from (S)-valine methyl ester and Acid-04 in a similar manner to the last step of Example 1. $^1$H NMR (400 MHz, DMSO-d₆) δ 9.01 (s, 1H), 8.52 (d, J=7.5 Hz, 1H), 7.35 (d, J=7.5 Hz, 1H), 7.23 (d, J=7.5 Hz, 1H), 4.96 (s, 2H), 4.29 (t, J=7.3 Hz, 1H), 3.66 (s, 3H), 2.45 (s, 3H), 2.11 (d, J=7.1 Hz, 1H), 0.94 (d, J=4.2 Hz, 3H), 0.92 (d, J=4.2 Hz, 3H); ESI-MS m/z 306 [M+H]⁺; HPLC purity: 99.96% (220 nm), 100% (254 nm).

Example 70. 4-Fluorobenzyl (1-hydroxy-7-(trifluoromethyl)-1,3-dihydrobenzo[c][1,2]oxaborole-6-carbonyl)-L-valinate (6-070)

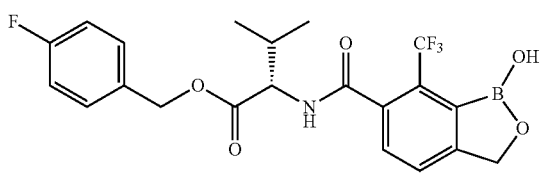

This compound was prepared from 4-fluorobenzylalcohol, N-BOC-(S)-valine and Acid-10 in a similar manner to Example 1. $^1$H NMR (400 MHz, DMSO-d₆) δ 9.23 (s, 1H), 8.88 (d, J=8.0 Hz, 1H), 7.70 (d, J=8.0 Hz, 1H), 7.47 (dd, J=8.4, 6.4 Hz, 2H), 7.41 (d, J=8.0 Hz, 1H), 7.22 (t, J=8.8 Hz, 2H), 5.23-5.21 (m, 2H), 5.08 (s, 2H), 4.35 (t, J=7.2 Hz, 1H), 2.18-2.09 (m, 1H), 0.98-0.81 (m, 6H); ESI-MS m/z 454 [M+H]$^+$; HPLC purity: 98.51% (220 nm), 98.43% (254 nm).

Example 71. Benzyl (1-hydroxy-7-(trifluoromethyl)-1,3-dihydrobenzo[c][1,2]oxaborole-6-carbonyl)-L-valinate (6-071)

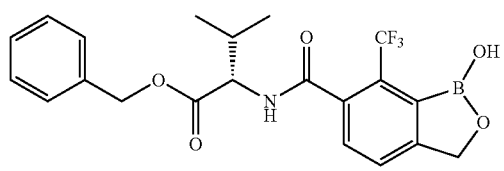

6-071

This compound was prepared from (S)-valine benzyl ester and Acid-10 in a similar manner to the last step of Example 1. $^1$H NMR (400 MHz, DMSO-d$_6$) δ 9.21 (br s, 1H), 8.87 (d, J=7.6 Hz, 1H), 7.69 (d, J=7.6 Hz, 1H), 7.40 (s, 6H), 525-5.13 (m, 2H), 5.08 (s, 2H), 4.37 (t, J=6.8 Hz, 1H), 2.16-2.14 (m, 1H), 0.92 (d, J=3.6 Hz, 6H); ESI-MS m/z 436 [M+H]$^+$; HPLC purity: 98.07% (220 nm), 93.03% (254 nm).

Example 72. 3-(4-Methylpiperazin-1-yl)benzyl (1-hydroxy-7-methyl-1,3-dihydrobenzo[c][1,2]oxaborole-6-carbonyl)-L-valinate (6-072)

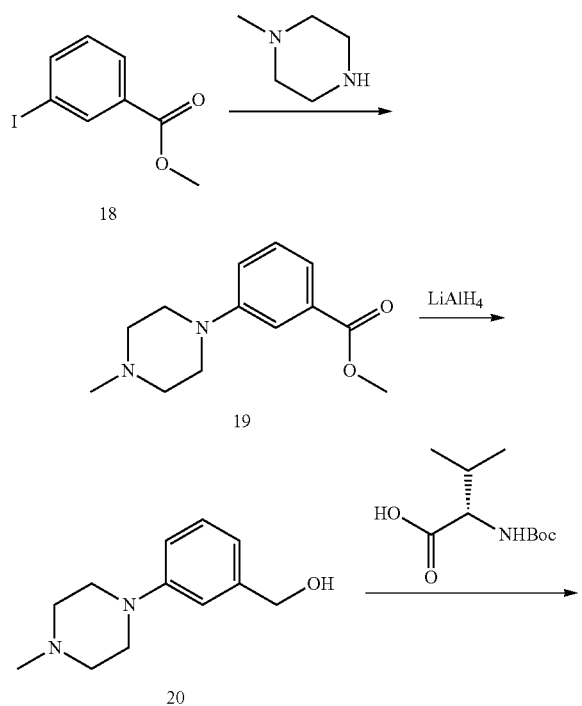

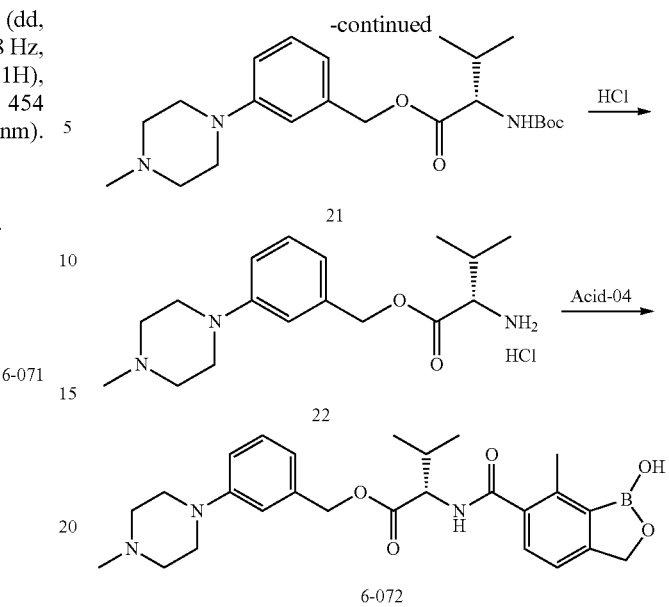

A mixture of 18 (5.00 g, 19.1 mmol), N-methylpiperazine (5.73 g, 57.2 mmol), Pd$_2$(dba)$_3$ (3.49 g, 3.82 mmol), Cs$_2$CO$_3$ (12.4 g, 38.2 mmol) and 2,2'-bis(diphenylphosphino)-1,1'-binaphthalene (3.56 g, 5.72 mmol) in 1,4-dioxane (5 mL) was degassed and purged with N$_2$ for 3 times, and then the mixture was stirred at 80° C. for 18 h under N$_2$ atmosphere. Then the mixture was cooled to 15° C., filtered and concentrated in vacuum. The residue was purified via column chromatography (DCM/MeOH=20:1) to give 19 (1.40 g, 31%) as brown oil. $^1$H NMR (400 MHz, DMSO-d$_6$) δ 7.60 (s, 1H), 7.52 (d, J=7.5 Hz, 1H), 7.34-7.30 (m, 1H), 7.12 (dd, J=7.7, 2.4 Hz, 1H), 3.91 (s, 3H), 3.29-3.25 (m, 4H), 2.62-2.65 (m, 4H), 2.37 (s, 3H). To a solution of 19 (1.40 g, 5.98 mmol) in THF (10 mL) was added LiAlH$_4$ (454 mg, 12.0 mmol) at 0° C. The mixture was stirred at 70° C. for 2 h. The mixture was cooled to 0° C. and quenched by saturated solution of potassium sodium tartrate (3 mL), the precipitate formed was collected, filtered to remove the precipitate. The organic phase was concentrated in vacuum. The residue was purified via column chromatography (DCM/MeOH=20:1) to give 20 (530 mg, 43%) as brown solid. $^1$H NMR (400 MHz, DMSO-d$_6$) δ 7.26 (s, 1H), 6.96 (s, 1H), 6.91-6.80 (m, 2H), 4.66 (s, 2H), 3.32-3.05 (m, 4H), 2.66-2.48 (m, 4H), 2.36 (s, 3H). To a solution of 20 (530 mg, 2.57 mmol) in DCM (10 mL) was added N-Boc-(S)-valine (670 mg, 3.08 mmol), DCC (795 mg, 3.86 mmol) and DMAP (62.8 mg, 0.514 mmol). The mixture was stirred at 15° C. for 24 h. The mixture was filtered and concentrated in vacuum. The residue was purified by column chromatography (DCM/MeOH=20:1) to give 21 (600 mg, 58%) as a brown solid. To a solution of 21 (200 mg, 0.493 mmol) in EtOAc (5 mL) was added HCl/EtOAc (4 M, 2 mL). The mixture was stirred at 15° C. for 15 h. Then the mixture was concentrated in vacuum, the precipitate formed was collected by filtration to give 22 (120 mg, 71%) as a yellow solid.

Compound 6-072 was prepared from 22 and Acid-04 in a similar manner to the last step of Example 1. $^1$H NMR (400 MHz, DMSO-d$_6$) δ 9.05 (s, 1H), 8.59 (d, J=7.8 Hz, 1H), 7.36 (d, J=7.8 Hz, 1H), 7.27-7.15 (m, 2H), 6.94 (s, 1H), 6.90 (d, J=8.3 Hz, 1H), 6.79 (d, J=7.3 Hz, 1H), 5.11 (d, J=7.3 Hz, 2H), 4.98 (s, 2H), 4.35 (t, J=7.3 Hz, 1H), 3.16-3.07 (m, 4H), 2.45 (s, 3H), 2.43-2.38 (m, 4H), 2.21 (s, 3H) 2.17 (br s, 1H), 1.00-0.92 (m, 6H); ESI-MS m/z 480 [M+H]; HPLC purity: 98.26% (220 nm), 99.95% (254 nm).

Example 73. 4-Fluorobenzyl (7-(difluoromethyl)-1-hydroxy-1,3-dihydrobenzo[c][1,2]oxaborole-6-carbonyl)-L-valinate (6-073)

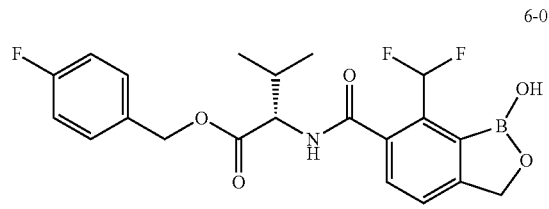

6-073

This compound was prepared from 4-fluorobenzylalcohol, N-BOC-(S)-valine and Acid-11 in a similar manner to Example 1. $^1$H NMR (400 MHz, DMSO-d$_6$) δ 9.18 (s, 1H), 8.83 (d, J=7.6 Hz, 1H), 7.62 (d, J=7.6 Hz, 1H), 7.54-7.39 (m, 3H), 7.22 (t, J=8.8 Hz, 2H), 7.04 (t, J=54.8 Hz, 1H), 5.22-5.12 (m, 2H), 5.07 (s, 2H), 4.39-4.31 (m, 1H), 2.15 (td, J=13.6, 6.4 Hz, 1H), 0.97-0.83 (m, 6H); ESI-MS m/z 436 [M+H]$^+$; HPLC purity: 98.74% (220 nm), 100% (254 nm).

Example 74. 4-Fluorobenzyl (1-hydroxy-7-methyl-1,3-dihydrobenzo[c][1,2]oxaborole-6-carbonyl)-L-threoninate (6-074)

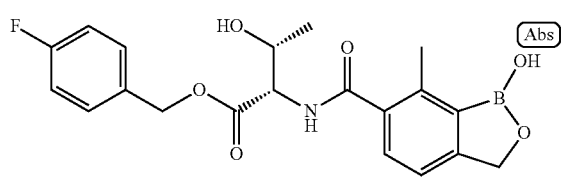

6-074

This compound was prepared from 4-fluorobenzylalcohol, N-BOC-(L)-threonine and Acid-04 in a similar manner to Example 1. $^1$H NMR (400 MHz, DMSO-d$_6$) δ 9.06 (s, 1H), 8.16 (d, J=8.3 Hz, 1H), 7.52-7.38 (m, 3H), 7.30-7.15 (m, 3H), 5.25-5.10 (m, 2H), 4.98 (s, 2H), 4.84 (d, J=6.5 Hz, 1H), 4.52 (dd, J=3.6, 8.2 Hz, 1H), 4.20 (br s, 1H), 2.46 (s, 3H), 1.16 (d, J=6.3 Hz, 3H); ESI-MS m/z 402 [M+H]$^+$; HPLC purity: 98.36% (220 nm), 97.90% (254 nm).

Example 75. 4-(Methyl sulfonamido)benzyl (1-hydroxy-7-methyl-1,3-dihydrobenzo[c][1,2]oxaborole-6-carbonyl)-L-valinate (6-074)

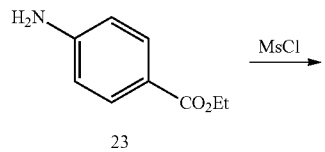

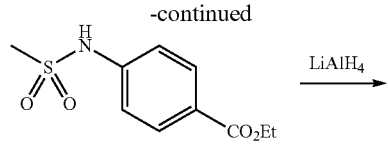

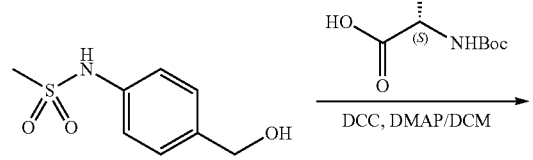

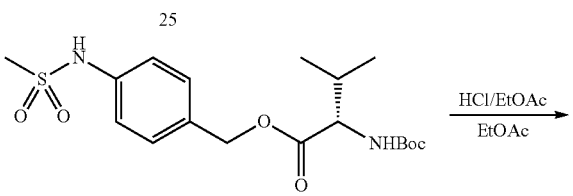

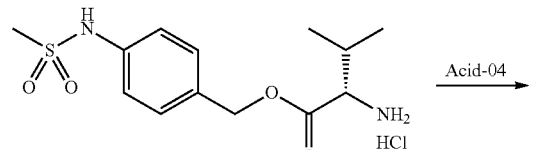

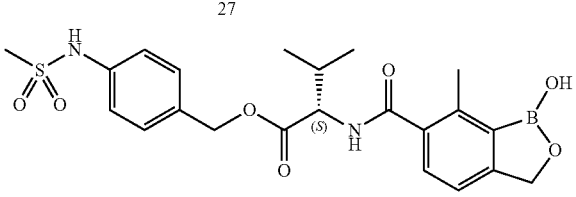

To a solution of 23 (5.0 g, 30 mmol) and pyridine (7.0 g, 91 mmol) in DCM (20 mL) was added MsCl (4.0 g, 36 mmol) dropwise at 0° C. under N$_2$ atmosphere. The reaction mixture was stirred at 0° C. for 0.4 h. The reaction mixture was quenched by H$_2$O (50 mL) at 0° C., and then extracted with DCM (50 mL×2). The combined organic layers were washed with brine (50 mL×2), dried over Na$_2$SO$_4$, filtered and concentrated under reduced pressure to give 24 (7.0 g, 95%) as a red solid. $^1$H NMR (400 MHz, DMSO-d$_6$) δ 8.03 (d, J=8.4 Hz, 2H), 7.28 (d, J=6.0 Hz, 2H), 4.37 (m, 2H), 3.08 (s, 3H), 1.39 (t, J=6.4 Hz, 3H). To a mixture of 24 (2.0 g, 8.0 mmol) in THF (30 mL) was added LiAlH$_4$ (468 mg, 12.0 mmol) slowly at 0° C. and then the reaction mixture was stirred at 15° C. for 12 h under N$_2$ atmosphere. The reaction mixture was quenched by 0.5 mL of saturated sodium potassium. After filtered, the filtrate was concentrated under reduced pressure to give 25 (300 mg, 18%) as a white solid. $^1$H NMR (400 MHz, DMSO-d$_6$) δ 9.62 (s, 1H), 7.27 (d, J=8.0 Hz, 2H), 7.16 (d, J=8.0 Hz, 2H), 5.12 (s, 1H), 4.44 (d, J=4.4 Hz, 2H), 2.94 (s, 3H). A mixture of 25 (500 mg, 2.50 mmol), N-Boc-(S)-valine (1.2 g, 5.5 mmol), DCC (1 g, 5 mmol) and DMAP (30 mg, 0.25 mmol) in DCM (10 mL) was stirred at 15° C. for 12 h under N$_2$ atmosphere. After filtered, the filtrate was concentrated under reduced pressure. The crude was purified via column chromatography (petroleum ether/EtOAC=2:1) to give 26 (600 mg, crude) as a white solid. To a solution of 26 (600 mg) in EtOAc (100 mL) was added HCl/EtOAc (6 M, 2 mL) dropwise and then the mixture was stirred at 15° C. for 2 h under N₂ atmosphere. The reaction mixture was concentrated under reduced pressure to give 27 (400 mg, crude) as a white solid.

Compound 6-075 was prepared from 27 and Acid-04 in a similar manner to the last step of Example 1. $^1$H NMR (400 MHz, DMSO-d$_6$) δ 9.80 (s, 1H), 9.03 (s, 1H), 8.55 (d, J=8.0 Hz, 1H), 7.41-7.30 (m, 3H), 7.26-7.14 (m, 3H), 5.19-5.05 (m, 2H), 4.97 (s, 2H), 4.33 (t, J=7.2 Hz, 1H), 3.01-2.94 (m, 3H), 2.43 (s, 3H) 2.14 (q, J=13.6, 6.8 Hz, 1H), 1.00-0.89 (m, 6H); ESI-MS m/z 475 [M+H]; HPLC purity: 97.85% (220 nm), 92.14% (254 nm).

Example 76. 4-(Methylsulfonyl)benzyl (7-ethyl-1-hydroxy-1,3-dihydrobenzo[c][1,2]oxaborole-6-carbonyl)-L-valinate (6-076)

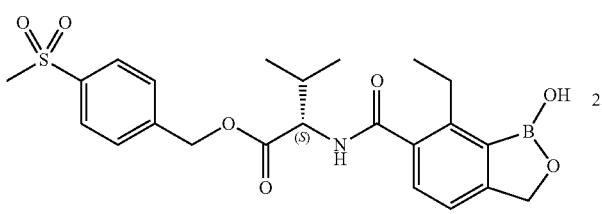

6-076

This compound was prepared from 4-fluorobenzylalcohol, N-BOC-(S)-valine and Acid-05 in a similar manner to Example 1. $^1$H NMR (400 MHz, DMSO-d$_6$) δ 8.99 (s, 1H), 8.64 (d, J=8.0 Hz, 1H), 7.91 (d, J=8.0 Hz, 2H), 7.65 (d, J=8.4 Hz, 2H), 7.31 (d, J=8.0 Hz, 1H), 7.22 (d, J=8.0 Hz, 1H), 5.32-5.25 (m, 2H), 4.96 (s, 2H), 4.38 (t, J=7.2 Hz, 1H), 3.20 (s, 3H), 2.86-2.81 (m, 2H), 2.20-2.15 (s, 1H), 1.06 (t, J=7.2 Hz, 3H), 1.00 (d, J=7.2 Hz, 3H), 0.95 (d, J=7.0 Hz, 3H); ESI-MS m/z 474 [M+H]$^+$; HPLC purity: 98.27% (220 nm), 98.06% (254 nm).

Example 77. 4-Fluorobenzyl O-benzyl-N-(1-hydroxy-7-methyl-1,3-dihydrobenzo[c][1,2]oxaborole-6-carbonyl)-L-threoninate (6-077)

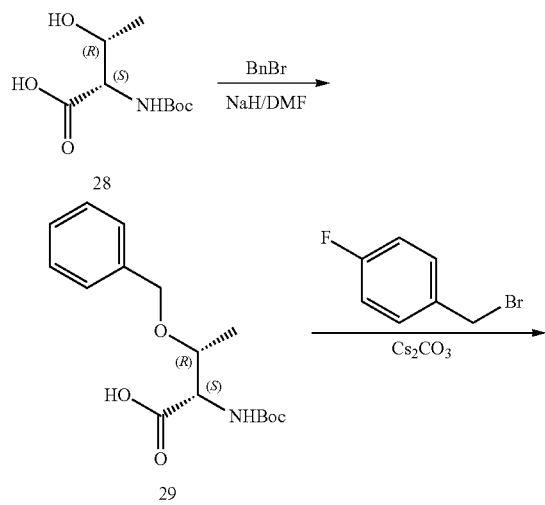

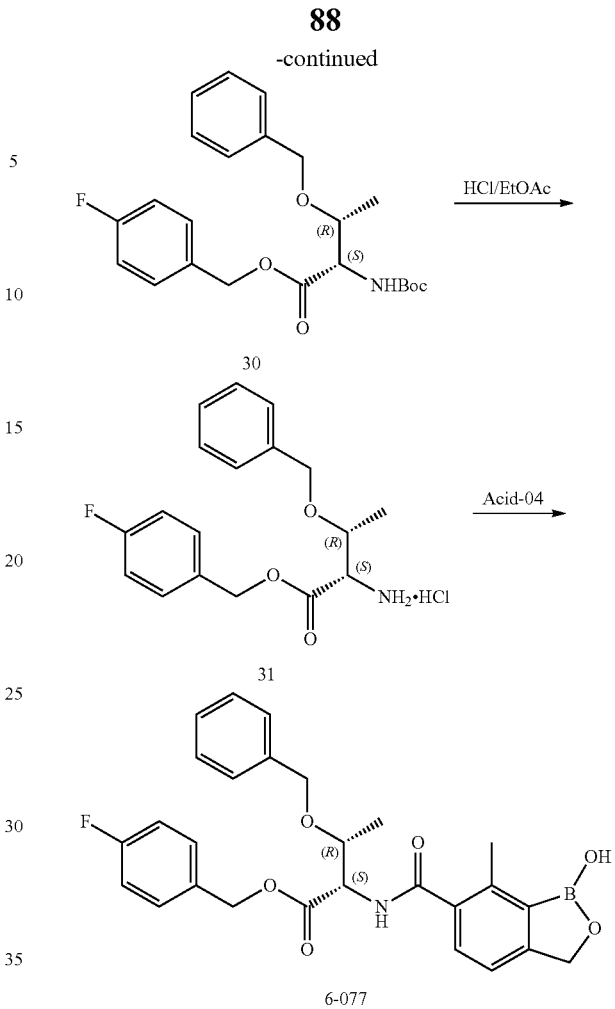

To a solution of (tert-butoxycarbonyl)-L-threonine (1.00 g, 4.56 mmol) in DMF (15 mL) was added NaH (401 mg, 10.0 mmol) at −15° C. Then bromoethylbenzene (858 mg, 5.02 mmol) was added. The mixture was stirred at 15° C. for 10 h. LCMS showed desired mass was detected. The reaction mixture was quenched by addition aq. 1 M HCl to pH=4 and extracted with EtOAc 15 mL (5 mL×3). The combined organic layers were washed with brine 5 mL, dried over Na₂SO₄, filtered and concentrated under reduced pressure to give a residue. The residue was purified by prep. HPLC (column: Luna C8 100×30 5 u; liquid phase: [A-TFA/H₂O=0.075% v/v; B-ACN] B %: 35%-55%, 12 min]). After prep. HPLC purification, the eluent was concentrated to remove organic solvent. The residual aqueous solution was lyophilized to give 29 (1.00 g, 71%) as a white solid. To a solution of 29 (1.00 g, 3.23 mmol) in DMF (15 mL) was added Cs₂CO₃ (1.16 g, 3.55 mmol) at 0° C. Then 1-(bromomethyl)-4-fluorobenzene (672 mg, 3.55 mmol) was added. The mixture was stirred at 15° C. for 8 h. HPLC indicated the reaction was complete and desired mass was detected according to LCMS. The reaction mixture was quenched by addition water 15 mL and extracted with EtOAc 45 mL (15 mL×3). The combined organic layers were washed with brine 20 mL, dried over Na₂SO₄, filtered and concentrated under reduced pressure to give a residue. The residue was purified by prep. HPLC (column: Waters Xbridge 150×25 5 u; liquid phase: [A-10 mM NH₄HCO₃ in H₂O; B-ACN] B %: 45%-75%, 20 min]). After prep. HPLC purification, the eluent was concentrated to remove organic solvent. The residual aqueous solution was lyophilized to give 30 (610 mg, 45%) as a yellow oil. $^1$H NMR (400 MHz, DMSO-d$_6$) δ 7.32-7.25 (m, 5H), 7.18 (d, J=7.5 Hz, 2H), 6.97 (t, J=8.6 Hz, 2H), 5.30 (d, J=9.7 Hz, 1H), 5.08 (s, 2H), 4.50 (d, J=11.9 Hz, 1H), 4.34 (dd, J=1.8, 9.7 Hz, 1H), 4.26 (d, J=11.9 Hz, 1H), 4.18-4.10 (m, 1H), 1.45 (s, 9H), 1.26 (d, J=6.2 Hz, 3H). A mixture of 30 (501 mg, 1.20 mmol) and HCl/EtOAc (4 M, 3.00 mL) was stirred at 15° C. for 5 h. TLC showed the reaction was completed. The reaction mixture was concentrated under reduced pressure to give 31 (410 mg, 97% yield) as a yellow solid.

Compound 6-077 was prepared from 31 and Acid-04 in a similar manner to the last step of Example 1. $^1$H NMR (400 MHz, DMSO-d$_6$) δ 9.02 (s, 1H), 8.52 (d, J=8.4 Hz, 1H), 7.45-7.35 (m, 3H), 7.32-7.20 (m, 6H), 7.13 (t, J=8.8 Hz, 2H), 5.16 (s, 2H), 4.97 (s, 2H), 4.75 (dd, J=7.09, 4.0 Hz, 1H), 4.53 (d, J=11.9 Hz, 1H), 4.37 (d, J=11.9 Hz, 1H), 4.17-4.09 (m, 1H), 2.45 (s, 3H), 1.23 (d, J=6.2 Hz, 3H); ESI-MS m/z 492 [M+H]; HPLC purity: 100% (220 nm), 100% (254 nm).

Example 78. Methyl O-benzyl-N-(1-hydroxy-7-methyl-1,3-dihydrobenzo[c][1,2]oxaborole-6-carbonyl)-L-threoninate (6-078)

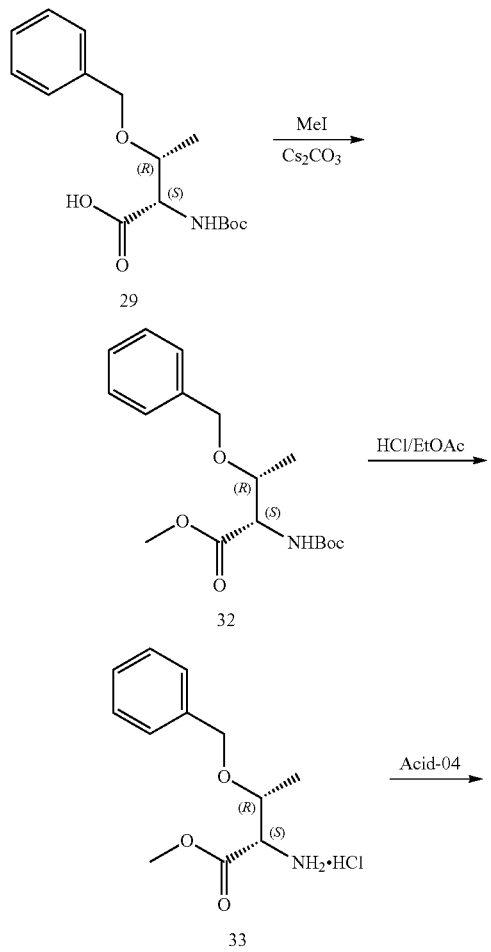

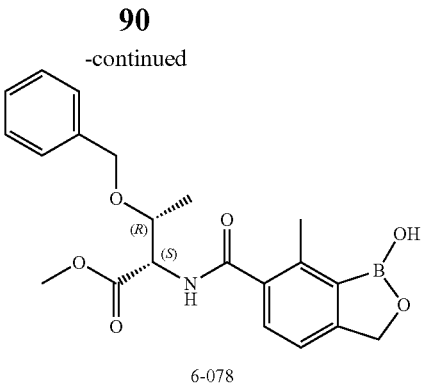

6-078

To a solution of 29 (600 mg, 1.94 mmol) in DMF (3 mL) was added Cs$_2$CO$_3$ (695 mg, 2.13 mmol) at 0° C. Then iodomethane (303 mg, 2.13 mmol) was added. The mixture was stirred at 15° C. for 10 h. HPLC indicated the reaction was complete and desired mass was detected according to LCMS. The reaction mixture was quenched by addition water 15 mL and extracted with EtOAc (15 mL×3). The combined organic layers were washed with brine 15 mL, dried over Na$_2$SO$_4$, filtered and concentrated under reduced pressure to give a residue. The residue was purified by prep. HPLC (column: Waters Xbridge 150×25 5 u; liquid phase: [A-10 mM NH$_4$HCO$_3$ in H$_2$O; B-ACN] B %: 30%-60%, 20 min]). After prep. HPLC purification, the eluent was concentrated to remove organic solvent. The residual aqueous solution was lyophilized to give 32 (520 mg, 83%) as a yellow oil. $^1$H NMR (400 MHz, DMSO-d$_6$) δ 7.36-7.24 (m, 5H), 5.31 (d, J=9.3 Hz, 1H), 4.57 (d, J=11.9 Hz, 1H), 4.41-4.28 (m, 2H), 4.16-4.09 (m, 1H), 3.68 (s, 3H), 1.46 (s, 9H), 1.27 (d, J=6.2 Hz, 3H).

Compound 6-078 was prepared from 32 and Acid-04 in a similar manner to the last two steps of Example 77. $^1$H NMR (400 MHz, DMSO-d$_6$) δ 9.03 (br s, 1H), 8.47 (d, J=8.4 Hz, 1H), 7.39 (d, J=7.9 Hz, 1H), 7.36-7.18 (m, 6H), 4.97 (s, 2H), 4.69 (dd, J=4.2, 8.2 Hz, 1H), 4.59-4.53 (m, 1H), 4.43 (d, J=11.9 Hz, 1H), 4.09 (dd, J=4.4, 6.2 Hz, 1H), 3.66 (s, 3H), 2.48 (br s, 3H), 1.23 (d, J=6.2 Hz, 3H); ESI-MS m/z 398 [M+H]; HPLC purity: 99.60% (220 nm), 97.96% (254 nm).

Example 79. Benzyl (7-(difluoromethyl)-1-hydroxy-1,3-dihydrobenzo[c][1,2]oxaborole-6-carbonyl)-L-valinate (6-079)

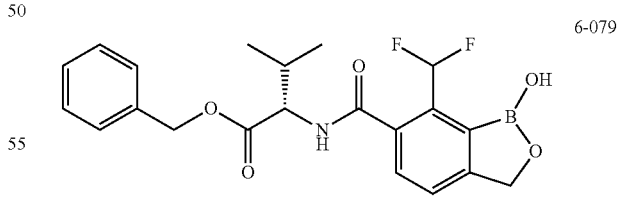

6-079

This compound was prepared from (S)-valine benzyl ester and Acid-11 in a similar manner to the last step of Example 1. $^1$H NMR (400 MHz, DMSO-d$_6$) δ 9.18 (s, 1H), 8.84 (d, J=8.0 Hz, 1H), 7.62 (d, J=8.0 Hz, 1H), 7.50 (d, J=8.0 Hz, 1H), 7.44-7.31 (m, 5H), 7.05 (t, J=54.8 Hz, 1H), 5.23-5.14 (m, 2H), 5.07 (s, 2H), 4.37 (t, J=7.2 Hz, 1H), 2.17 (dq, J=13.6, 6.6 Hz, 1H), 0.94 (d, J=6.4 Hz, 6H); ESI-MS m/z 418 [M+H]$^+$; HPLC purity: 99.93% (220 nm), 100% (254 nm).

Example 80. 3-(Methylsulfonyl)benzyl (1-hydroxy-7-methyl-1,3-dihydrobenzo[c][1,2]oxaborole-6-carbonyl)-L-valinate (6-080)

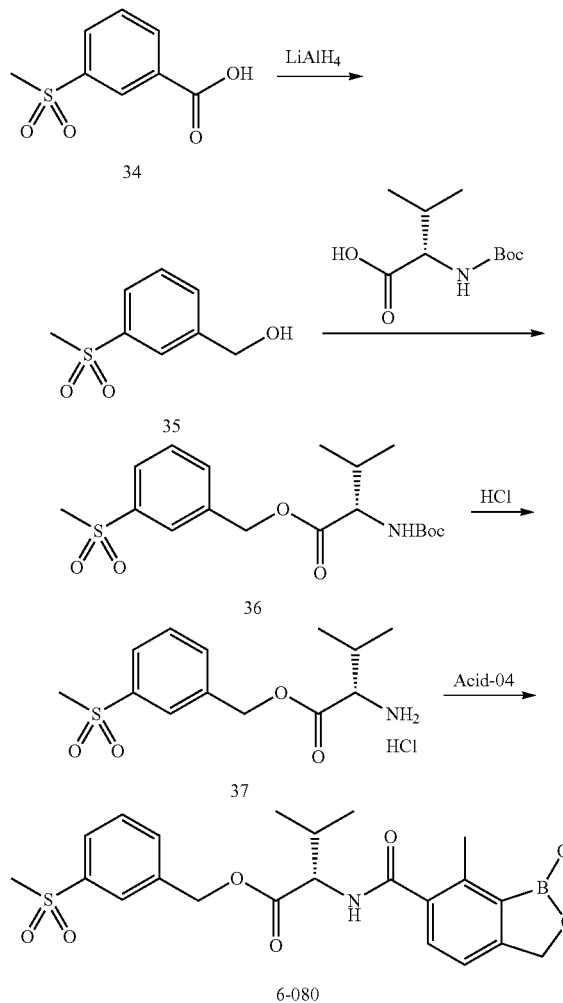

To a solution of 34 (2.00 g, 9.99 mmol) in THF (10 mL) was added LiAlH$_4$ (758 mg, 20.0 mmol) at 0° C. The mixture was stirred at 15° C. for 14 h. The mixture was cooled to 0° C. and quenched by saturated solution of potassium sodium tartrate (2 mL), the precipitate formed was collected, filtered to remove the precipitate. The organic phase was concentrated in vacuo to give 35 (1.40 g, 63%). $^1$H NMR (400 MHz, CDCl$_3$) δ 7.97 (s, 1H), 7.87 (d, J=7.5 Hz, 1H), 7.67 (d, J=7.9 Hz, 1H), 7.63-7.53 (m, 1H), 4.82 (d, J=5.7 Hz, 2H), 3.07 (s, 3H).

To a solution of 35 (1.03 g, 5.52 mmol) in DCM (10 mL) were added N-Boc-(S)-valine (1.00 g, 4.60 mmol), DCC (1.42 g, 6.90 mmol) and DMAP (56.2 mg, 0.460 mmol). The mixture was stirred at 15° C. for 14 h. The reaction mixture was filtered and concentrated under reduced pressure (40° C.) to give a residue. The residue was purified via column chromatography (SiO$_2$, petroleum ether/ethyl acetate=2:1) to give 36 (1.20 g, 68%) was obtained as a yellow oil.

To a solution of 36 (400 mg, 1.04 mmol) in EtOAc (10 mL) was added HCl/EtOAc (4 M, 5.2 mL). The mixture was stirred at 15° C. for 1.5 h. Then the reaction mixture was concentrated under reduced pressure (40° C.) to remove the solvent. Then the precipitate formed was collected, filtered to give 37 (280 mg, 84%) was obtained as a white solid. $^1$H NMR (400 MHz, DMSO-d$_6$) δ 8.64 (s, 3H), 8.00 (s, 1H), 7.91 (d, J=7.9 Hz, 1H), 7.80 (d, J=7.9 Hz, 1H), 7.72-7.65 (m, 1H), 5.35 (s, 2H), 3.94 (d, J=4.4 Hz, 1H), 3.22 (s, 3H), 2.20 (m, 1H), 0.97 (d, J=7.2 Hz, 3H), 0.93 (d, J=7.2 Hz, 3H).

Compound 6-080 was prepared from 37 and Acid-04 in a similar manner to the last step of Example 1. $^1$H NMR (400 MHz, DMSO-d$_6$) δ 9.04 (s, 1H), 8.61 (d, J=7.5 Hz, 1H), 7.98 (s, 1H), 7.90 (d, J=7.9 Hz, 1H), 7.77 (d, J=7.9 Hz, 1H), 7.71-7.65 (m, 1H), 7.34 (d, J=7.5 Hz, 1H), 7.23 (d, J=7.9 Hz, 1H), 5.30 (s, 2H), 4.97 (s, 2H), 4.37 (t, J=7.1 Hz, 1H), 3.21 (s, 3H), 2.43 (s, 3H), 2.17 (dd, J=13.5, 6.84 Hz, 1H), 0.95 (d, J=6.6 Hz, 6H); ESI-MS m/z 460 [M+H]$^+$; HPLC purity: 100% (220 nm), 100% (254 nm).

Example 81. 3-((Dimethylamino)methyl)benzyl (1-hydroxy-7-methyl-1,3-dihydrobenzo[c][1,2]oxaborole-6-carbonyl)-L-valinate (6-081)

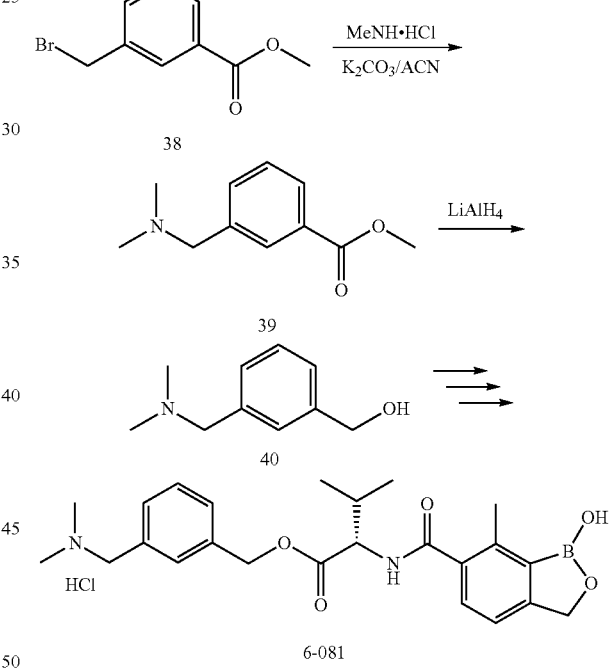

To a solution of 38 (4.58 g, 20.0 mmol) and Me$_2$NH.HCl (2.45 g, 30.0 mmol) in CH$_3$CN (50 mL) was added K$_2$CO$_3$ (11.1 g, 80.0 mmol). The mixture was stirred at 60° C. for 12 h. The reaction mixture was filtered, the residue was washed with EtOAc (20 mL) and then the filtrate concentrated under reduced pressure. The crude product was purified by silica gel column chromatography (DCM:MeOH=10:1) to give 39 (1.6 g, 41%) as a yellow oil. $^1$H NMR (400 MHz, CDCl$_3$) δ 7.96 (s, 1H), 7.92 (d, J=8.0 Hz, 1H), 7.51 (d, J=7.6 Hz, 1H), 7.38 (t, J=7.2 Hz, 1H), 3.90 (s, 3H), 3.45 (s, 2H), 2.23 (s, 6H). To a solution of 39 (1.60 g, 8.28 mmol) in THF (30 mL) was added LiAlH$_4$ (471 mg, 12.0 mmol) in portions at 0° C. The mixture was stirred at 15° C. for 12 h. The reaction mixture was quenched by saturated sodium potassium tartrate (1.8 mL) at 0° C., and then filtered. The filtrate was concentrated under reduced pressure to give 40 (1.32 g, 96%) as a yellow oil.

Compound 6-081 was prepared from 40 and Acid-04 in a similar manner to Example 1. $^1$H NMR (400 MHz, DMSO-$d_6$) δ 9.81 (s, 1H), 9.02 (s, 1H), 8.56 (d, J=7.6 Hz, 1H), 7.52 (s, 1H), 7.48 (s, 2H), 7.32 (d, J=7.2 Hz, 1H), 7.21 (d, J=8.0 Hz, 1H), 5.20 (s, 2H), 4.95 (s, 2H), 4.33 (t, J=7.6 Hz, 1H), 4.25 (d, J=4.0 Hz, 3H), 2.69 (s, 6H), 2.41 (s, 3H), 2.18-2.12 (m, 1H), 0.94-0.92 (m, 6H); ESI-MS m/z 439 [M+H]$^+$; HPLC purity: 97.97% (220 nm), 98.89% (254 nm).

Example 82. 3-((4-Methylpiperazin-1-yl)methyl) benzyl (1-hydroxy-7-methyl-1,3-dihydrobenzo[c][1,2]oxaborole-6-carbonyl)-L-valinate (6-082)

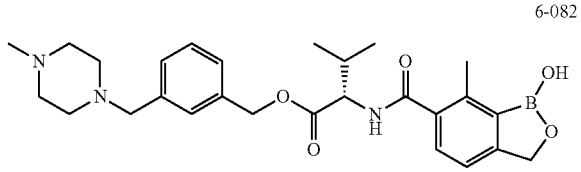 [SMILES: Cc1c(C(=O)N[C@H](C(=O)OCc2cccc(CN3CCN(C)CC3)c2)C(C)C)ccc2c1B(O)OC2]

6-082

This compound was prepared from 38, 1-methylpiperazine, and Acid-04 in a similar manner to Example 81. $^1$H NMR (400 MHz, DMSO-$d_6$) δ 9.01 (s, 1H), 8.57 (d, J=8.0 Hz, 1H), 7.44 (s, 2H), 7.49 (s, 2H), 7.32 (d, J=8.0 Hz, 1H), 7.22 (d, J=7.6 Hz, 1H), 5.18 (s, 2H), 4.95 (s, 2H), 4.33 (t, J=7.2 Hz, 1H), 3.16 (d, J=8.8 Hz, 2H), 2.78 (s, 3H), 2.31 (s, 3H), 2.18-2.12 (m, 1H), 0.95-0.92 (m, 6H); ESI-MS m/z 494 [M+H]$^+$; HPLC purity: 98.25% (220 nm), 100% (254 nm).

Example 83. 3-(Morpholinomethyl)benzyl (1-hydroxy-7-methyl-1,3-dihydrobenzo[c][1,2]oxaborole-6-carbonyl)-L-valinate (6-083)

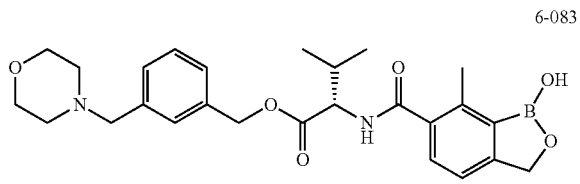 [SMILES: Cc1c(C(=O)N[C@H](C(=O)OCc2cccc(CN3CCOCC3)c2)C(C)C)ccc2c1B(O)OC2]

6-083

This compound was prepared from 38, 1-methylpiperazine, and Acid-04 in a similar manner to Example 81. $^1$H NMR (400 MHz, DMSO-$d_6$) δ 9.01 (s, 1H), 8.57 (d, J=7.2 Hz, 1H), 7.56 (s, 2H), 7.49 (s, 2H), 7.31 (d, J=7.2 Hz, 1H) 7.21 (d, J=7.6 Hz, 1H), 5.19 (s, 2H), 4.95 (s, 2H), 4.35-4.31 (m, 3H), 3.88 (d, J=12.8 Hz, 2H), 3.66 (s, 2H), 3.18 (s, 2H), 3.04 (s, 2H), 2.31 (s, 3H), 2.18-2.13 (m, 1H), 0.93-0.92 (m, 6H); ESI-MS m/z 481 [M+H]$^+$; HPLC purity: 96.43% (220 nm), 94.91% (254 nm).

Example 84. 4-(Methylsulfonyl)benzyl (1-hydroxy-7-isopropyl-1,3-dihydrobenzo[c][1,2]oxaborole-6-carbonyl)-L-valinate (6-084)

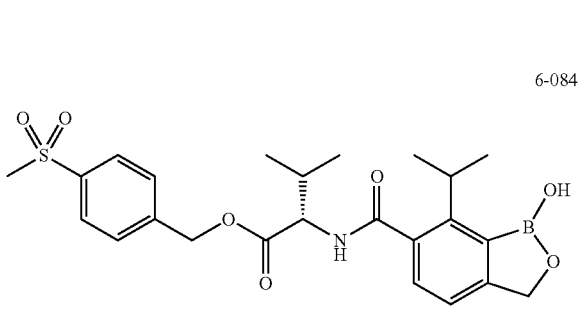 [SMILES: CC(C)c1c(C(=O)N[C@H](C(=O)OCc2ccc(S(C)(=O)=O)cc2)C(C)C)ccc2c1B(O)OC2]

6-084

This compound was prepared from 4-(methyl sulfonyl) benzylalcohol, N-BOC-(S)-valine and Acid-08 in a similar manner to Example 1. $^1$H NMR (400 MHz, DMSO-$d_6$) δ 9.15 (s, 1H), 8.64 (d, J=8.0 Hz, 1H), 7.92 (d, J=8.4 Hz, 2H), 7.66 (d, J=8.0 Hz, 2H), 7.21-7.18 (m, 2H), 5.28 (s, 2H), 4.96 (s, 2H), 4.38 (t, J=7.6 Hz, 1H), 3.20-3.18 (m, 4H), 2.19-2.14 (m, 1H), 1.27 (t, J=6.4 Hz, 6H), 0.94 (d, J=6.8 Hz, 6H); ESI-MS m/z 488 [M+H]$^+$; HPLC purity: 98.60% (220 nm), 97.23% (254 nm).

Example 85. 4-((4-Methylpiperazin-1-yl)sulfonyl) benzyl (1-hydroxy-7-methyl-1,3-dihydrobenzo[c][1,2]oxaborole-6-carbonyl)-L-valinate (6-085)

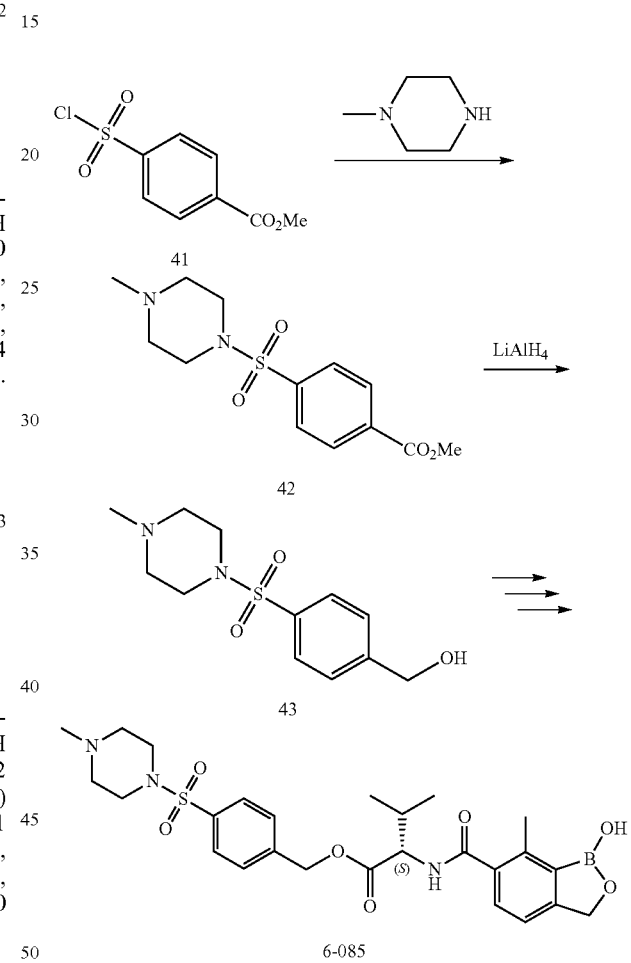

To a solution of 41 (1.0 g, 4.0 mmol) and Et$_3$N (1.3 g, 13 mmol) in DCM (10 mL) was added 1-methylpiperazine (1.1 g, 11 mmol) at 0° C. The reaction mixture was stirred for an hour and then washed with H$_2$O (10 mL×4), dried over Na$_2$SO$_4$, filtered and concentrated under reduced pressure to give 42 (700 mg, 55%) as a white solid. $^1$H NMR (400 MHz, CDCl$_3$) δ 8.19 (d, J=8.4 Hz, 2H), 7.83 (d, J=8.4 Hz, 2H), 3.97 (s, 3H), 3.07 (br s, 4H), 2.48 (t, J=4.8 Hz, 4H), 2.27 (s, 3H). To a solution of 42 (700 mg, 2.40 mmol) in THF (20 mL) was added LiAlH$_4$ (134 mg, 3.60 mmol). The mixture was stirred at 0° C. for 12 h. 0.5 mL of saturated sodium potassium tartrate was added to the reaction mixture and stirred for 10 min. Then the mixture filtered and concentrated under reduced pressure to give 43 (300 mg, 48%) as a white solid. $^1$H NMR (400 MHz, CDCl$_3$) δ 7.74 (d, J=8.0

Hz, 2H), 7.52 (d, J=8.4 Hz, 2H), 4.78 (s, 2H), 3.04 (br s, 4H), 2.48 (t, J=4.4 Hz, 4H), 2.27 (s, 3H).

Compound 6-085 was prepared from 43 and Acid-04 in a similar manner to Example 1. $^1$H NMR (400 MHz, DMSO-$d_6$) δ 9.05 (s, 1H), 8.65 (d, J=7.6 Hz, 1H), 7.81 (d, J=8.4 Hz, 2H), 7.72 (d, J=8.4 Hz, 2H), 7.36 (d, J=8.0 Hz, 1H), 7.25 (d, J=7.6 Hz, 1H), 5.39-5.27 (m, 2H), 4.98 (s, 2H), 4.38 (t, J=7.2 Hz, 1H), 3.79 (d, J=12.4 Hz, 4H), 3.15 (d, J=9.2 Hz, 4H), 2.76 (s, 3H), 2.45 (s, 1H), 2.22-2.15 (m, 1H), 0.98 (d, J=6.4, 3.6 Hz, 6H); ESI-MS m/z 544 [M+H]$^+$; HPLC purity: 92.93% (220 nm), 88.77% (254 nm).

Example 86. 4-(Morpholinosulfonyl)benzyl (1-hydroxy-7-methyl-1,3-dihydrobenzo[c][1,2]oxaborole-6-carbonyl)-L-valinate (6-086)

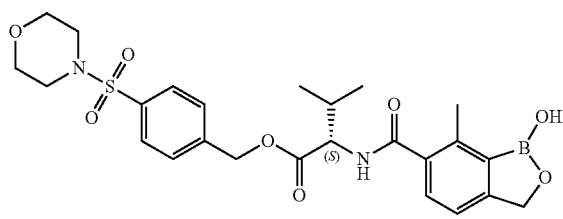

6-086

Compound 6-086 was prepared in a similar manner to Example 85 using morpholine instead of 1-methylpiperazine. $^1$H NMR (400 MHz, DMSO-$d_6$) δ 9.01 (s, 1H), 8.60 (d, J=7.6 Hz, 1H), 7.73 (d, J=7.6 Hz, 2H), 7.67 (d, J=8.0 Hz, 2H), 7.32 (d, J=7.6 Hz, 1H), 7.21 (d, J=8.0 Hz, 1H), 5.29 (s, 2H), 4.95 (s, 2H), 4.36 (t, J=7.2 Hz, 1H), 3.60 (s, 4H), 2.83 (s, 4H), 2.42 (s, 3H), 2.19-2.14 (m, 1H), 0.93 (d, J=6.4 Hz, 6H); ESI-MS m/z 531 [M+H]$^+$; HPLC purity: 99.94% (220 nm), 100% (254 nm).

Example 87. 4-Fluorobenzyl (1-hydroxy-7-methyl-1,3-dihydrobenzo[c][1,2]oxaborole-6-carbonyl)-D-valinate (6-087)

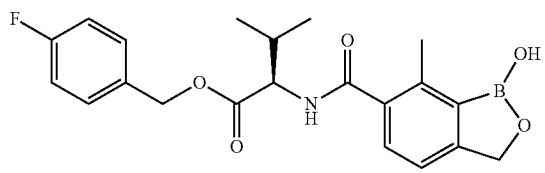

6-087

This compound was prepared from 4-fluorobenzylalcohol, N-BOC-(R)-valine and Acid-04 in a similar manner to Example 1. $^1$H NMR (400 MHz, DMSO-$d_6$) δ 9.03 (s, 1H), 8.56 (d, J=7.5 Hz, 1H), 7.46 (dd, J=8.4, 5.73 Hz, 2H), 7.33 (d, J=7.5 Hz, 1H), 7.27-7.15 (m, 3H), 5.16 (d, J=7.5 Hz, 2H), 4.97 (s, 2H), 4.34 (t, J=7.1 Hz, 1H), 2.45-2.41 (m, 3H), 2.14 (dd, J=13.5, 6.8 Hz, 1H), 1.02-0.82 (m, 6H); ESI-MS m/z 400 [M+H]$^+$; HPLC purity: 98.94% (220 nm), 99.52% (254 nm).

Example 88. 4-Fluorobenzyl (1-hydroxy-7-methyl-1,3-dihydrobenzo[c][1,2]oxaborole-6-carbonyl)-L-allothreoninate (6-088)

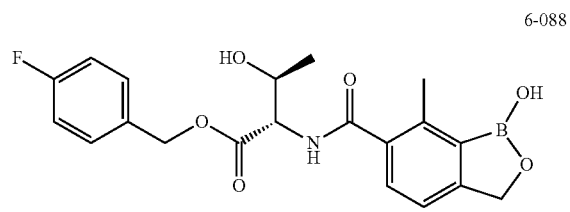 [SMILES: Cc1c(C(=O)N[C@H](C(=O)OCc2ccc(F)cc2)[C@H](C)O)ccc2c1B(O)OC2]

6-088

This compound was prepared from 4-fluorobenzylalcohol, N-BOC-(L)-allothreonine and Acid-04 in a similar manner to Example 1. $^1$H NMR (400 MHz, DMSO-$d_6$) δ 9.02 (s, 1H), 8.46 (d, J=7.6 Hz, 1H), 7.44 (t, J=6.0 Hz, 2H), 7.33 (d, J=8.0 Hz, 1H), 7.23-7.16 (m, 3H), 5.13 (d, J=3.2 Hz, 2H), 5.04 (d, J=5.6 Hz, 1H), 4.95 (s, 2H), 4.38 (t, J=6.8 Hz, 1H), 4.00 (t, J=6.0 Hz, 1H), 2.41 (s, 3H), 1.16 (d, J=6.0 Hz, 3H); ESI-MS m/z 402 [M+H]$^+$; HPLC purity: 96.86% (220 nm), 95.47% (254 nm).

Example 89. 4-(Isopropyl sulfinyl)benzyl (1-hydroxy-7-methyl-1,3-dihydrobenzo[c][1,2]oxaborole-6-carbonyl)-L-valinate (6-089)

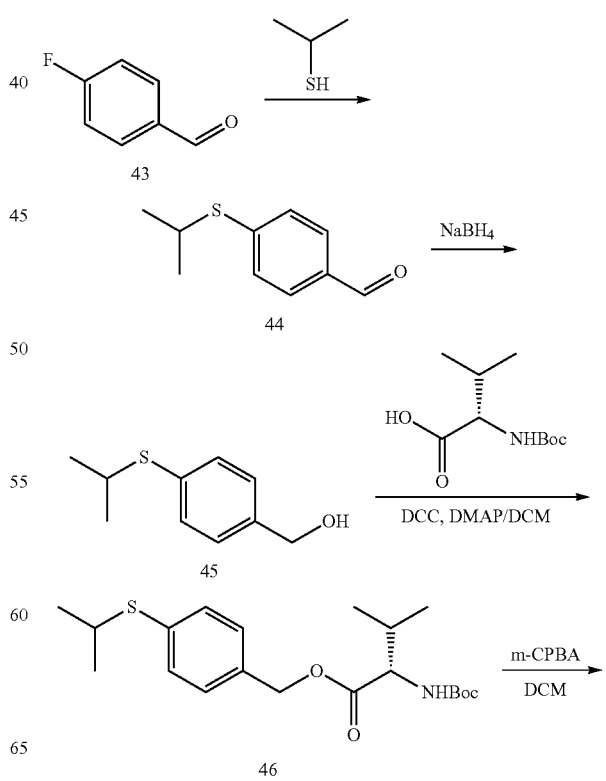

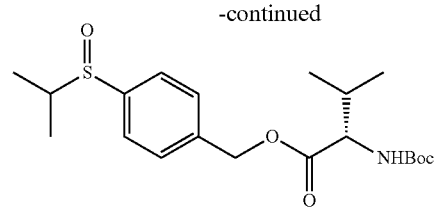

47

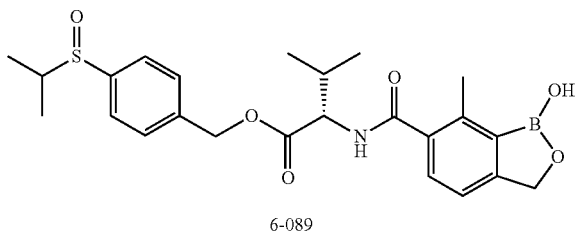

6-089

To a solution of 43 (5.00 g, 40.3 mmol) in DMSO (25 mL) was added propane-2-thiol (3.38 g, 44.3 mmol) and $K_2CO_3$ (11.1 g, 80.6 mmol). The mixture was stirred at 100° C. for 16 h. The mixture was cooled to 15° C. and poured into ice-water (30 mL) and stirred for 20 mins. The aqueous phase was extracted with EtOAc (20 mL×3). The combined organic phase was washed with brine (15 mL×2), dried over $Na_2SO_4$, filtered and concentrated in vacuum to give 44 (6.3 g, 87%) as a colorless oil. $^1$H NMR (400 MHz, DMSO-$d_6$) δ 9.93 (s, 1H), 7.82 (d, J=8.4 Hz, 2H), 7.49 (d, J=8.4 Hz, 2H), 3.79-3.72 (s, 1H), 1.31 (d, J=7.6 Hz, 6H). To a solution of 44 (3.00 g, 16.6 mmol) in THF (20 mL) and MeOH (4 mL) was added $NaBH_4$ (755 mg, 20.0 mmol) in portions at 0° C., and then the mixture was stirred at 15° C. for 2 h. The reaction mixture was quenched by water (20 mL) at 0° C., and then extracted with DCM (20 mL×3). The combined organic layers were dried over $Na_2SO_4$, filtered and concentrated under reduced pressure to give 45 (2.99 g, 99%) as a colorless oil. $^1$H NMR (400 MHz, $CDCl_3$) δ 7.38 (d, J=8.0 Hz, 2H), 7.295 (d, J=8.0 Hz, 2H), 4.66 (s, 2H), 3.39-3.32 (m, 1H), 1.28 (d, J=6.4 Hz, 6H).

A mixture of 45 (2.9 g, 15.9 mmol), DCC (5.91 g, 28.6 mmol), DMAP (194 mg, 1.6 umol) and N-Boc-(S)-valine (3.46 g, 15.9 mmol) in DCM (20 mL) was stirred at 15° C. for 10 h. The reaction mixture was filtered and the filtrate was concentrated under reduced pressure. The residue was purified by silica gel column chromatography (petroleum ether:EtOAc=5:1) to give 46 (4.73 g, 78%) as a white solid. $^1$H NMR (400 MHz, $CDCl_3$) δ 7.36 (d, J=8.4 Hz, 2H), 7.27 (d, J=8.4 Hz, 2H), 5.13 (q, J=17.2, 12.0, Hz, 2H), 4.25 (dd, J=4.0 Hz, 1H), 3.43-3.35 (m, 1H), 2.16-2.11 (m, 1H), 1.43 (s, 9H), 1.29 (d, J=6.8 Hz, 6H), 0.93 (d, J=7.2 Hz, 3H), 0.84 (d, J=6.4 Hz, 3H). To a solution of 46 (1.00 g, 2.62 mmol) in DCM (20 mL) was added mCPBA (1.13 g, 6.55 mmol) in portions, and then the mixture was stirred at 15° C. for 10 h. The reaction mixture was filtered and the filtrate was concentrated under reduced pressure. The residue was purified via prep. TLC (petroleum ether:EtOAc=2:1) to give 47 (0.82 g, yield 78.73%) as a colorless oil.

Compound 6-089 was prepared from 47 and Acid-04 in a similar manner to the last two steps of Example 1. $^1$H NMR (400 MHz, DMSO-$d_6$) δ 9.06 (s, 1H), 8.62 (d, J=7.2 Hz, 1H), 7.62 (s, 4H), 7.34 (d, J=7.6 Hz, 1H), 7.23 (d, J=7.2 Hz, 1H), 5.26 (d, J=7.2 Hz, 2H), 4.98 (s, 2H), 4.36 (t, J=6.8 Hz, 1H), 2.98-2.92 (m, 1H), 2.42 (s, 3H), 2.20-2.15 (m, 1H), 1.17 (d, J=6.8 Hz, 3H), 0.95-0.91 (m, 9H); ESI-MS m/z 472 [M+H]$^+$; HPLC purity: 99.29% (220 nm), 99.18% (254 nm).

Example 90. 4-(Methyl sulfinyl)benzyl (1-hydroxy-7-methyl-1,3-dihydrobenzo[c][1,2]oxaborole-6-carbonyl)-L-valinate (6-090)

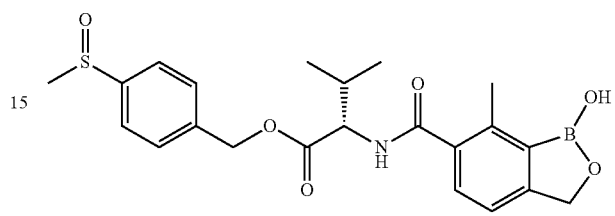

6-090

Compound 6-090 was prepared from 4-(methylthio)benzylalcohol and Acid-04 in a similar manner to the last two steps of Example 89. $^1$H NMR (400 MHz, DMSO-$d_6$) δ 9.01 (s, 1H), 8.58 (d, J=7.5 Hz, 1H), 7.68 (d, J=8.4 Hz, 2H), 7.62-7.55 (m, 2H), 7.32 (d, J=7.5 Hz, 1H), 7.21 (d, J=7.9-Hz, 1H), 5.23 (s, 2H), 4.95 (s, 2H), 4.35 (s, 1H), 2.72 (s, 3H), 2.41 (s, 3H), 2.19-2.12 (m, 1H), 0.94 (d, J=6.6-Hz, 6H); ESI-MS m/z 444 [M+H]$^+$; HPLC purity: 99.44% (220 nm), 100% (254 nm).

Example 91. 4-Fluorobenzyl 3-fluoro-2-(1-hydroxy-7-methyl-1,3-dihydrobenzo[c][1,2]oxaborole-6-carboxamido)-3-methylbutanoate (6-091)

6-091

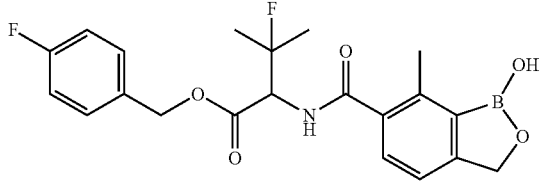

This compound was prepared from 2-((tert-butoxycarbonyl)amino)-3-fluoro-3-methylbutanoic acid, 4-fluorobenzyl alcohol and Acid-04 in a similar manner to Example 1. $^1$H NMR (400 MHz, DMSO-$d_6$) δ 9.03 (s, 1H), 8.82 (d, J=7.9 Hz, 1H), 7.46 (dd, J=8.2, 6.0 Hz, 2H), 7.33 (d, J=7.9 Hz, 1H), 7.26-7.16 (m, 3H), 5.20 (d, J=6.2 Hz, 2H), 4.97 (s, 2H), 4.76 (dd, J=16.1, 8.2 Hz, 1H), 2.42 (s, 3H), 1.54-1.38 (m, 6H); ESI-MS m/z 418[M+H]$^+$; HPLC purity: 98.90% (220 nm), 95.67% (254 nm).

Example 92. 4-(Isopropyl sulfinyl)benzyl (1-hydroxy-7-methyl-1,3-dihydrobenzo[c][1,2]oxaborole-6-carbonyl)-L-valinate (6-092)

46 $\xrightarrow{\text{m-CPBA}}$ DCM

-continued

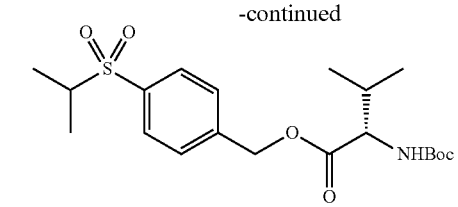

48

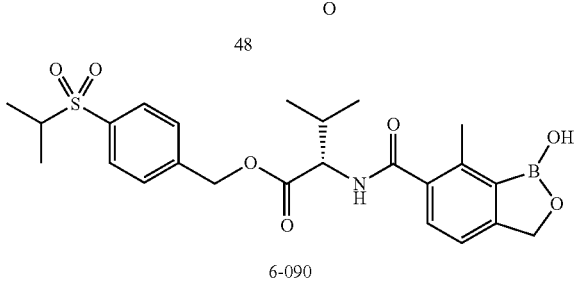

6-090

To a solution of 46 (1.00 g, 2.62 mmol) in DCM (20 mL) was added mCPBA (2.13 g, 10.5 mmol) in portions, and then the mixture was stirred at 15° C. for 10 h. The reaction mixture was filtered and the filtrate was concentrated under reduced pressure. The residue was purified via prep. TLC (petroleum ether:EtOAc=5:1) to give 48 (0.95 g, 88%) as a colorless oil. $^1$H NMR (400 MHz, CDCl$_3$) δ 7.87 (d, J=8.4 Hz, 2H), 7.54 (d, J=8.0 Hz, 2H), 5.29 (s, 2H), 4.14-4.09 (m, 1H), 3.22-3.13 (m, 1H), 2.20-2.13 (m, 1H), 1.43 (s, 9H), 1.28 (d, J=6.4 Hz, 6H), 0.96 (d, J=6.8 Hz, 3H), 0.87 (d, J=6.4 Hz, 3H).

Compound 6-090 was prepared from 48 and Acid-04 in a similar manner to the last two steps of Example 1. $^1$H NMR (400 MHz, DMSO-d$_6$) δ 9.01 (s, 1H), 8.60 (d, J=6.8 Hz, 1H), 7.84 (d, J=6.4 Hz, 2H), 7.67 (d, J=6.4 Hz, 2H), 7.32 (d, J=6.4 Hz, 1H), 7.21 (d, J=7.2 Hz, 1H), 5.29 (s, 2H), 4.95 (s, 2H), 4.38-4.35 (m, 1H), 3.43-3.37 (m, 1H), 2.40 (s, 3H), 2.19-2.14 (m, 1H), 1.12 (d, J=5.6 Hz, 6H), 0.93 (d, J=6.4 Hz, 6H); ESI-MS m/z 488 [M+H]$^+$; HPLC purity: 99.98% (220 nm), 100% (254 nm).

Example 93. 4-(Isopropyl sulfinyl)benzyl (1-hydroxy-7-methyl-1,3-dihydrobenzo[c][1,2]oxaborole-6-carbonyl)-L-valinate (6-093)

6-093

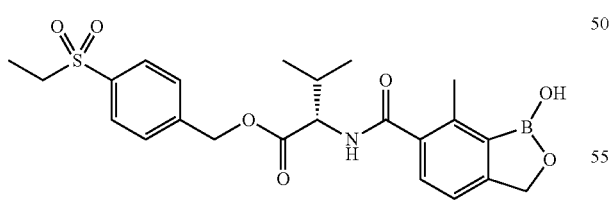

Compound 6-093 was prepared in a similar manner to Examples 89 and 92 using ethanethiol instead of 2-propanethiol. $^1$H NMR (400 MHz, DMSO-d$_6$) δ 9.03 (s, 1H), 8.62 (d, J=7.2 Hz, 1H), 7.89 (d, J=7.2 Hz, 2H), 7.68 (d, J=7.6 Hz, 2H), 7.35 (d, J=7.6 Hz, 1H), 7.23 (d, J=7.2 Hz, 1H), 5.30 (s, 2H), 4.97 (s, 2H), 4.38 (m, 1H), 3.30 (t, J=6.8 Hz, 2H), 2.42 (s, 3H), 2.19-2.07 (m, 1H), 1.08 (t, J=6.4 Hz, 3H), 0.96 (d, J=6.0 Hz, 6H); ESI-MS m/z 474 [M+H]$^+$; HPLC purity: 99.86% (220 nm), 100% (254 nm).

Example 94. 4-(Ethylsulfinyl)benzyl (1-hydroxy-7-methyl-1,3-dihydrobenzo[c][1,2]oxaborole-6-carbonyl)-L-valinate (6-094)

6-094

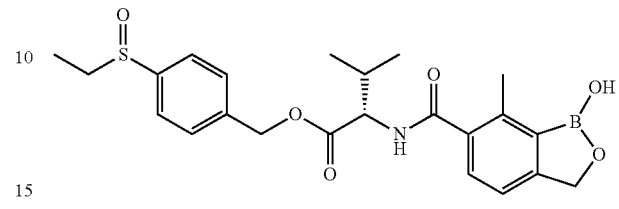

Compound 6-093 was prepared in a similar manner to Example 89 using ethanethiol instead of 2-propanethiol. $^1$H NMR (400 MHz, DMSO-d$_6$) δ 9.04 (s, 1H), 8.60 (d, J=8.0 Hz, 1H), 7.68-7.59 (m, 4H), 7.33 (d, J=7.2 Hz, 1H), 7.22 (d, J=7.6 Hz, 1H), 5.28-5.21 (m, 2H), 4.97 (s, 2H), 4.38-4.34 (m, 1H), 3.04-2.99 (m, 1H), 2.78-2.74 (m, 1H), 2.42 (s, 3H), 2.18-2.16 (m, 1H), 1.05 (t, J=7.6 Hz, 3H), 0.95-0.93 (m, 6H); ESI-MS m/z 458 [M+H]$^+$; HPLC purity: 99.56% (220 nm), 100% (254 nm).

Example 95. 2-(Pyrrolidin-1-yl)ethyl (1-hydroxy-7-methyl-1,3-dihydrobenzo[c][1,2]oxaborole-6-carbonyl)-L-valinate (6-095)

6-095

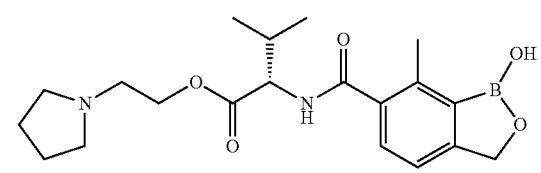

This compound was prepared from 2-pyrrolidinoethanol, N-BOC-(S)-valine and Acid-04 in a similar manner to Example 1. $^1$H NMR (400 MHz, DMSO-d$_6$) δ 9.07 (s, 1H), 8.67 (br s, 1, H), 7.40 (br s, 1H), 7.26 (br s, 1H), 4.97 (s, 2H), 4.48 (m, 1H), 4.40 (m, 2H), 3.65-3.52 (m, 4H), 3.07 (m, 2H), 2.47 (s, 3H), 2.21 (m, 1H), 2.02-1.81 (m, 4H), 0.97 (s, 6H); ESI-MS m/z 389 [M+H]$^+$; HPLC purity: 94.65% (220 nm), 94.92% (254 nm).

Example 96. 2-(4-Methylpiperazin-1-yl)ethyl (1-hydroxy-7-methyl-1,3-dihydrobenzo[c][1,2]oxaborole-6-carbonyl)-L-valinate (6-096)

6-095

This compound was prepared from 2-(4-methylpiperazin-1-yl)ethan-1-ol, N-BOC-(S)-valine and Acid-04 in a similar manner to Example 1. $^1$H NMR (400 MHz, DMSO-d$_6$) δ 9.09 (s, 1H), 8.64 (d, J=7.2 Hz, 1H), 7.40 (d, J=7.2 Hz, 1H), 7.26 (d, J=7.2 Hz, 1H), 4.97 (s, 2H), 4.48 (s, 1H), 4.41 (d, J=7.2 Hz, 2H), 3.37 (s, 8H), 2.80 (s, 3H), 2.47 (s, 3H), 2.22-2.18 (m, 1H), 0.97 (d, J=6.0 Hz, 6H); ESI-MS m/z 418 [M+H]$^+$; HPLC purity: 99.13% (220 nm), 99.60% (254 nm).

Example 97. 4-Fluorobenzyl O-(4-fluorobenzyl)-N-(1-hydroxy-7-methyl-1,3-dihydrobenzo[c][1,2]oxaborole-6-carbonyl)-L-allothreoninate (6-097)

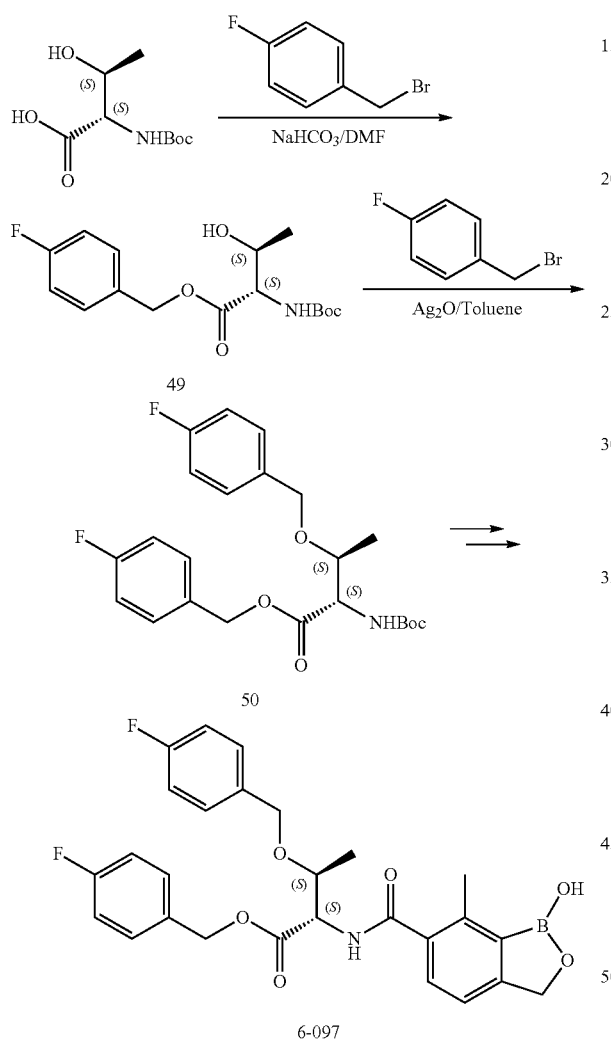

6-097

To a solution of N-BOC-(L)-allothreonine (300 mg, 1.37 mmol) in DMF (5 mL) was added NaHCO$_3$ (345 mg, 4.10 mmol) at 0° C. Then 4-fluorobenzyl bromide (310 mg, 1.64 mmol) was added dropwise and the reaction mixture was stirred at 15° C. for 12 h. The reaction mixture was diluted with water (20 mL) and then extracted with MTBE (15 mL×2). The combined organic layers were washed with brine (10 mL×2), dried over Na$_2$SO$_4$, filtered and concentrated under reduced pressure to give 49 (400 mg, 89%) as a colorless oil. $^1$H NMR (400 MHz, CDCl$_3$) δ 7.34 (t, J=4.8 Hz, 2H), 7.04 (t, J=8.8 Hz, 2H), 5.45 (s, 1H), 5.20-5.12 (m, 2H), 4.39 (s, 1H), 4.13 (s, 1H), 1.43 (s, 9H), 1.14 (s, 3H). To a solution of 49 (600 mg, 1.83 mmol) in toluene (15 mL) was added Ag$_2$O (1.27 g, 5.50 mmol) and 4-fluorobenzyl bromide (415 mg, 2.20 mmol). The mixture was stirred at 120° C. for 12 h. After filtered, the filtrate was concentrated under reduced pressure. The residue was purified by prep. HPLC (TFA condition) to give 50 (50 mg, 5.2%) as a yellow oil.

Compound 6-097 was prepared from 50 and Acid-04 in a similar manner to the last two steps of Example 1. $^1$H NMR (400 MHz, DMSO-d$_6$) δ 9.02 (s, 1H), 8.66 (d, J=8.4 Hz, 1H), 7.40 (d, J=7.6 Hz, 2H), 7.32-7.29 (m, 3H), 7.22 (d, J=7.6 Hz, 1H), 7.17-7.12 (m, 4H), 5.14 (d, J=2.8 Hz, 2H), 4.95 (s, 2H), 4.74 (t, J=7.6 Hz, 1H), 4.53-4.43 (m, 2H), 3.95 (t, J=6.0 Hz, 1H), 2.40 (s, 3H), 1.19 (d, J=6.4 Hz, 3H); ESI-MS m/z 510 [M+H]$^+$; HPLC purity: 99.37% (220 nm), 100% (254 nm).

Example 98. 3,4-Difluorobenzyl (S)-3-hydroxy-2-(1-hydroxy-7-methyl-1,3-dihydrobenzo[c][1,2]oxaborole-6-carboxamido)-3-methylbutanoate (6-098)

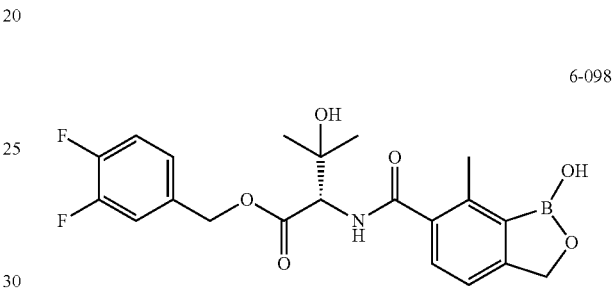

6-098

This compound was prepared from 3,4-difluorobenzylalcohol, (S)-2-((tert-butoxycarbonyl)amino)-3-hydroxy-3-methylbutanoic acid and Acid-04 in a similar manner to Example 1. $^1$H NMR (400 MHz, DMSO-d$_6$) δ 9.07 (s, 1H), 8.29 (d, J=8.0 Hz, 1H), 7.56-7.41 (m, 2H), 7.37 (d, J=7.2 Hz, 1H), 7.29 (s, 1H), 7.25 (d, J=7.2 Hz, 1H), 5.17 (s, 2H), 4.97 (s, 2H), 4.87 (s, 1H), 4.47 (d, J=8.0 Hz, 1H), 2.43 (s, 3H), 1.25 (s, 3H), 1.24 (s, 3H); ESI-MS m/z 434 [M+H]$^+$; HPLC purity: 96.90% (220 nm), 95.33% (254 nm).

Example 99. 3,5-Difluorobenzyl (S)-3-hydroxy-2-(1-hydroxy-7-methyl-1,3-dihydrobenzo[c][1,2]oxaborole-6-carboxamido)-3-methylbutanoate (6-099)

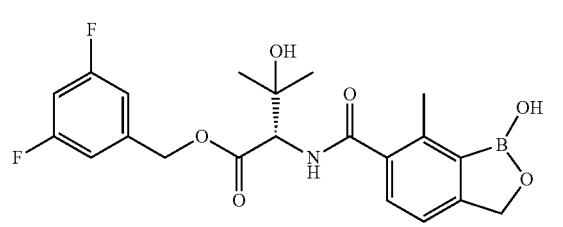

6-099

This compound was prepared from 3,5-difluorobenzylalcohol, (S)-2-((tert-butoxycarbonyl)amino)-3-hydroxy-3-methylbutanoic acid and Acid-04 in a similar manner to Example 1. $^1$H NMR (400 MHz, DMSO-d$_6$) δ 9.07 (s, 1H), 8.34 (d, J=8.0 Hz, 1H), 7.39 (d, J=7.2 Hz, 1H), 7.26 (d, J=8.0 Hz, 1H), 7.18 (d, J=8.0 Hz, 3H), 5.23 (s, 2H), 5.00 (s, 2H), 4.92 (s, 1H), 4.51 (d, J=8.0 Hz, 1H), 2.45 (s, 3H), 1.27 (d, J=5.6 Hz, 6H); ESI-MS m/z 434 [M+H]$^+$; HPLC purity: 100% (220 nm), 100% (254 nm).

Example 100. 3,4,5-Trifluorobenzyl (S)-3-hydroxy-2-(1-hydroxy-7-methyl-1,3-dihydrobenzo[c][1,2]oxaborole-6-carboxamido)-3-methylbutanoate (6-100)

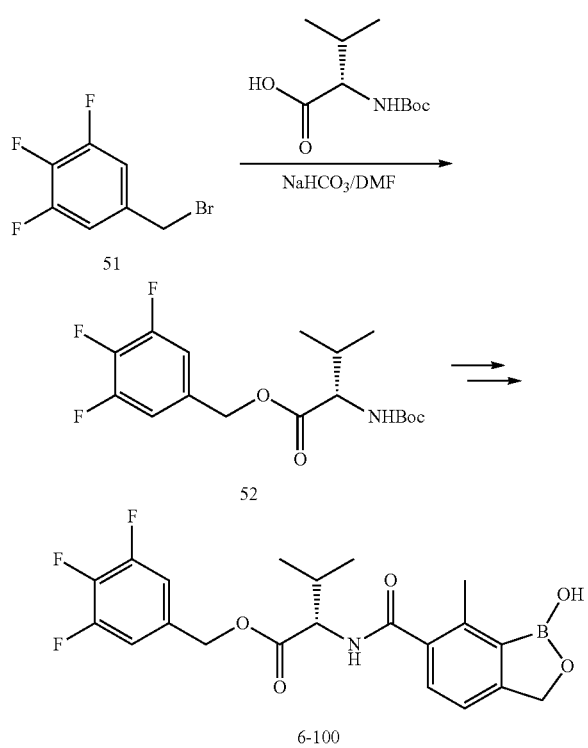

To a mixture of N-Boc-(S)-valine (300 mg, 1.38 mmol) and NaHCO₃ (347 mg, 4.14 mmol) in DMF (3 mL) was added 51 (341 mg, 1.52 mmol) at 0° C. The mixture was stirred at 15° C. for 14 h. Then water (5 mL) was added, the mixture was extracted with MTBE (5 mL×3). The combined organic phase was washed with brine (2 mL×3), dried over Na₂SO₄, filtered and concentrated in vacuum to give crude 52 (1.4 g) as a brown oil.

Compound 6-100 was prepared from 52 and Acid-04 in a similar manner to the last two steps of Example 1. ¹H NMR (400 MHz, DMSO-d₆) δ 9.04 (s, 1H), 8.64-8.63 (m, 1H), 7.42-7.36 (m, 3H), 7.34-7.23 (m, 1H), 5.21-5.14 (m, 2H), 4.97 (s, 2H), 4.38-4.36 (m, 1H), 2.20-2.15 (m, 1H), 2.43 (s, 3H), 0.97 (s, 3H), 0.95 (s, 3H); ESI-MS m/z 436 [M+H]⁺; HPLC purity: 99.52% (220 nm), 100% (254 nm).

Example 101. 3,4,5-Difluorobenzyl (S)-3-hydroxy-2-(1-hydroxy-7-methyl-1,3-dihydrobenzo[c][1,2]oxaborole-6-carboxamido)-3-methylbutanoate (6-101)

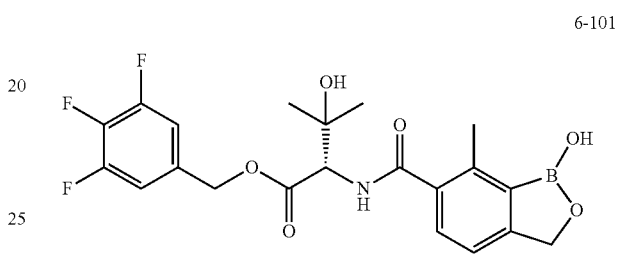

This compound was prepared from 3,4,5-trifluorobenzylalcohol, (S)-2-((tert-butoxycarbonyl)amino)-3-hydroxy-3-methylbutanoic acid and Acid-04 in a similar manner to Example 100. ¹H NMR (400 MHz, DMSO-d₆) δ 9.05 (s, 1H), 8.32-8.30 (m, 1H), 7.43-7.37 (m, 3H), 7.26-7.24 (m, 1H), 5.19 (s, 2H), 4.98 (s, 2H), 4.90 (s, 1H), 4.50-4.48 (m, 1H), 2.33 (s, 3H), 1.26 (s, 3H), 1.21 (s, 3H); ESI-MS m/z 434 [M+H]⁺; HPLC purity: 96.90% (220 nm), 95.33% (254 nm).

Example 102. 4-(Piperazine-1-carbonyl)benzyl (1-hydroxy-7-methyl-1,3-dihydrobenzo[c][1,2]oxaborole-6-carbonyl)-L-valinate (6-102)

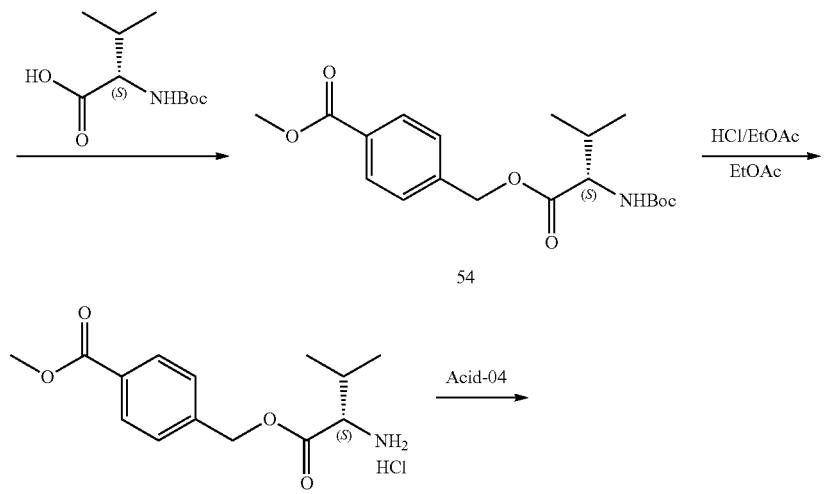

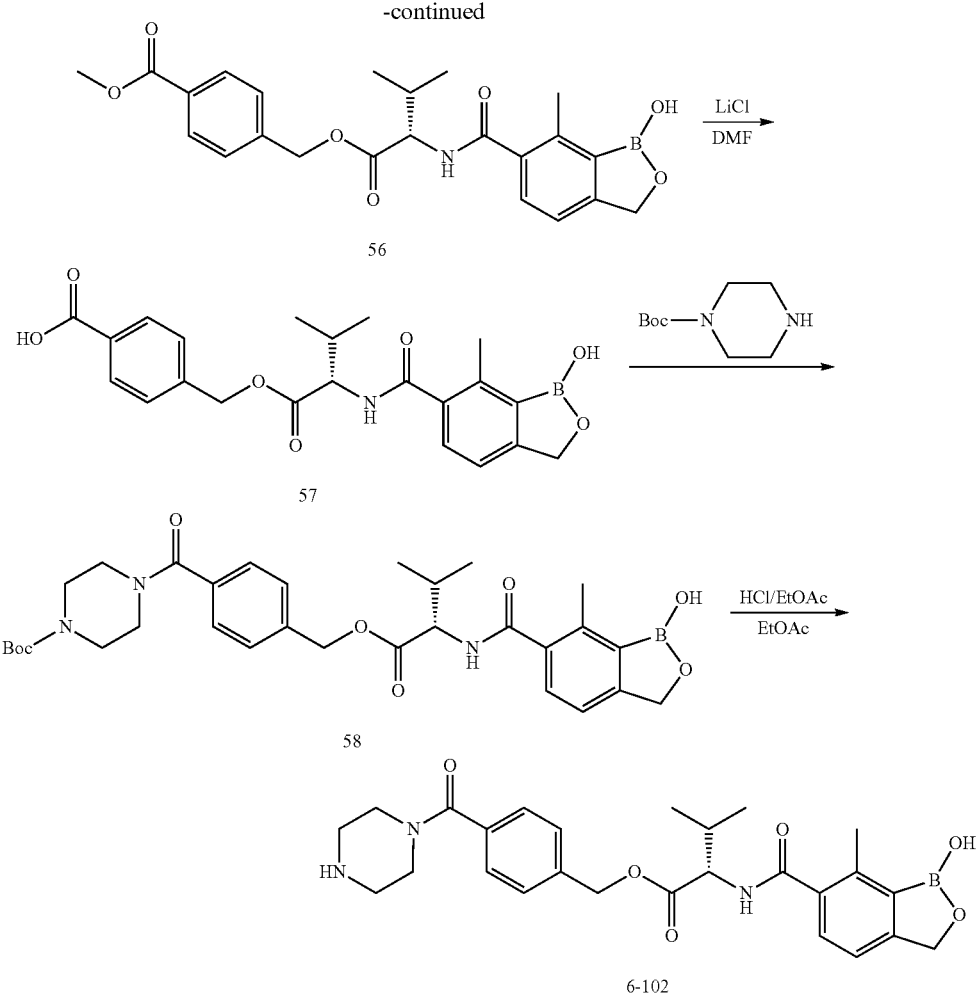

To a solution of N-Boc-(S)-valine (5.0 g, 23 mmol) in DMF (100 mL) was added NaHCO$_3$ (5.8 g, 69 mmol) at 0° C. Then 53 (5.27 g, 23 mmol) was added dropwise at 0° C. and then the reaction mixture was stirred at 15° C. for 12 h. The reaction mixture was diluted with water (200 mL) and then extracted with MTBE (100 mL×3). The combined organic layers were washed with water (100 mL×2), dried over Na$_2$SO$_4$, filtered and concentrated under reduced pressure to give 54 (7.5 g, yield 88.7%) as a colorless oil. $^1$H NMR (400 MHz, CDCl$_3$) δ 8.02 (d, J=7.6 Hz, 2H), 7.41 (d, J=8.0 Hz, 2H), 5.26-5.16 (m, 2H), 5.01-4.99 (m, 1H), 4.28-4.26 (m, 1H), 3.92 (s, 3H), 2.16-2.14 (m, 1H), 1.43 (s, 9H), 0.94 (d, J=6.4 Hz, 3H), 0.85 (d, J=6.8 Hz, 3H). To a solution of 54 (1.83 g, 5.00 mmol) in EtOAc (25 mL) was added HCl/EtOAc (4 M, 12.5 mL). The reaction solution was stirred at 15° C. for 12 h. The solvent was removed under reduced pressure to give 55 (1.4 g, 93%) as a white solid which was used in the next step without further purification. $^1$H NMR (400 MHz, CDCl$_3$) δ 8.97 (s, 2H), 8.00 (d, J=8.0 Hz, 2H), 7.43 (d, J=8.4 Hz, 2H), 5.31-5.21 (m, 2H), 3.95 (s, 1H), 3.90 (s, 3H), 2.45-2.44 (m, 1H), 1.11 (s, J=7.2 Hz, 3H), 1.07 (d, J=6.8 Hz, 3H). To a solution of 55 (0.50 g, 2.6 mmol) in DMF (1 mL) was added HATU (1.49 g, 3.9 mmol), TEA (1 g, 10.4 mmol) and Acid-04 (0.78 g, 2.6 mmol). The reaction mixture was stirred at 15° C. for 2 h. The mixture was poured into water (30 mL) and extracted with EtOAc (30 mL×3). The combined organic layer was washed with brine (30 mL×2), dried over Na$_2$SO$_4$ and concentrated under reduced pressure to give 56 (1.14 g, 79%) as a white solid. $^1$H NMR (400 MHz, DMSO-d$_6$) δ 9.02 (s, 1H), 8.59 (d, J=8.0 Hz, 1H), 7.94 (d, J=8.4 Hz, 2H), 7.52 (d, J=8.4 Hz, 2H), 7.33 (d, J=7.6 Hz, 1H), 7.21 (d, J=8.0 Hz, 1H), 5.25-5.22 (m, 2H), 4.95 (s, 2H), 3.84 (s, 4H), 2.42 (s, 3H), 2.16-2.15 (m, 1H), 0.94 (d, J=6.4 Hz, 6H).

To a solution of 56 (440 mg, 1.00 mmol) in DMF (10 mL) was added LiCl (424 mg, 10.0 mmol). The mixture was stirred at 140° C. for 12 h. The solvent was removed under reduced pressure and the residue was dissolved in water (20 mL), made pH=5 with 3 M HCl. The aqueous layer was extracted with EtOAc (20 mL×3). The combined organic layer was dried and concentrated under reduced pressure. The residue was purified by prep. HPLC under acid condition to give 57 (30 mg, 7.1%) as a white solid. To a solution of 57 (30 mg, 0.07 mmol) in DMF (1 mL) was added HATU (40 mg, 0.10 mmol), TEA (21 mg, 0.21 mmol) and N-Boc-piperazine (14 mg, 0.077 mmol) and the reaction mixture was stirred at 15° C. for two hours. The mixture was poured into water (5 mL) and extracted with EtOAc (5 mL×3). The combined organic layer was dried over Na$_2$SO$_4$ and concentrated under reduced pressure to give 88 (40 mg, 96%) as a white solid. MS (ESI): mass calcd. for $C_{31}H_{40}BN_3O_8$ 593.29, m/z found 594.4 [M+H]$^+$. A solution of 58 (40 mg, 0.067 mmol) and HCl/EtOAc (4 M, 0.84 mL) in EtOAc (1 mL) was stirred at 15° C. for 30 min. After filtered, the residue was purified by prep. HPLC under acid condition to give 6-102 (11 mg, 29%) as a white solid. ¹H NMR (400 MHz, DMSO-d₆) δ 9.02 (s, 1H), 8.95 (s, 2H), 8.58 (d, J=7.6 Hz, 1H), 7.47 (s, 4H), 7.33 (d, J=7.6 Hz, 1H), 7.22 (d, J=7.6 Hz, 1H), 5.22 (s, 2H), 4.96 (s, 2H), 4.35 (t, J=7.2 Hz, 1H), 3.62 (s, 4H), 3.14 (s, 4H), 2.43 (s, 3H), 2.17-2.13 (m, 1H), 0.95 (d, J=6.4 Hz, 3H), 0.94 (d, J=6.8 Hz, 3H); ESI-MS m/z 494 [M+H]⁺; HPLC purity: 95.40% (220 nm), 96.27% (254 nm).

Example 103. 4-((2-(Dimethylamino)ethyl)carbamoyl)benzyl (1-hydroxy-7-methyl-1,3-dihydrobenzo[c][1,2]oxaborole-6-carbonyl)-L-valinate (6-103)

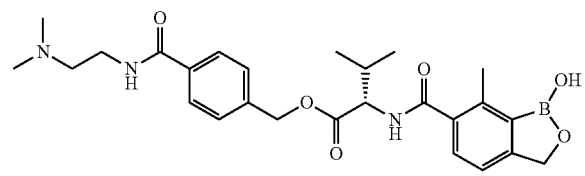

6-103

Compound 6-103 was prepared in a similar manner to the 5ᵗʰ step of Example 102 using N¹,N¹-dimethylethane-1,2-diamine instead of N-Boc-piperazine. ¹H NMR (400 MHz, DMSO-d₆) δ 9.02 (s, 1H), 8.56 (d, J=7.6 Hz, 1H), 8.37 (t, J=5.6 Hz, 1H), 7.80 (d, J=8.0 Hz, 2H), 7.44 (d, J=8.4 Hz, 2H), 7.31 (d, J=7.6 Hz, 1H), 7.20 (d, J=7.6 Hz, 1H), 5.23-5.16 (m, 2H), 4.94 (s, 2H), 4.34 (t, J=7.2 Hz, 1H), 3.35-3.30 (m, 2H), 2.46-2.38 (m, 5H), 2.19 (s, 6H), 2.17-2.13 (m, 1H), 0.94-0.88 (m, 6H); ESI-MS m/z 496 [M+H]⁺; HPLC purity: 96.95% (220 nm), 98.33% (254 nm).

Example 104. (1,1-Dioxido-3-oxo-2,3-dihydrobenzo[b]thiophen-5-yl)methyl (1-hydroxy-7-methyl-1,3-dihydrobenzo[c][1,2]oxaborole-6-carbonyl)-L-valinate (6-104)

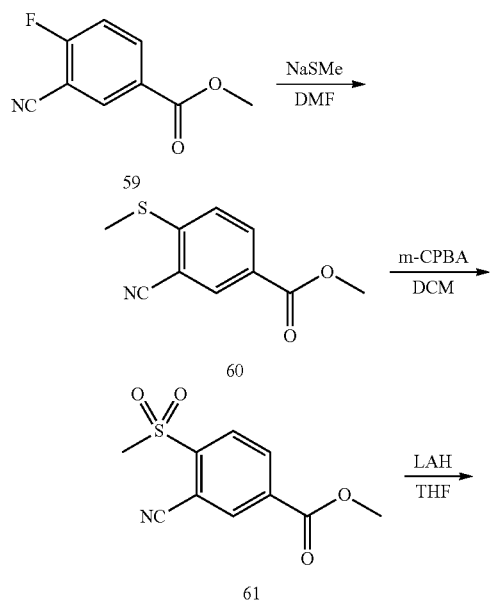

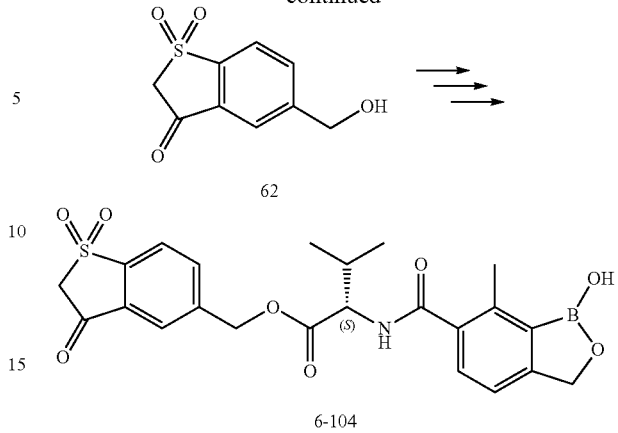

To a solution of 59 (5.0 g, 28 mmol) in DMF (20 mL) was added MeSNa (13 g, 36 mmol). The mixture was stirred at 80° C. for 14 h. The mixture was cooled to 15° C., poured into ice-water (50 mL) and stirred for 30 min. There was precipitate formed which was collected after filtered to give 60 (3.6 g, 62%) as an off white solid. ¹H NMR (400 MHz, CDCl₃) δ 8.24 (s, 1H), 8.17-8.14 (m, 1H), 7.33-7.30 (m, 1H), 3.94 (s, 3H) 2.61 (s, 3H). To a solution of 60 (3.00 g, 14.5 mmol) in DCM (20 mL) was added mCPBA (7.4 g, 36 mmol). The mixture was stirred at 15° C. for 24 h. Water (40 mL) was added into the mixture and stirred for 20 min. The organic phase was separated and was washed with 5% NaOH (20 mL). The combined organic phase was washed with sat. Na₂SO₃ (20 mL×3) and brine (20 mL×2), dried over Na₂SO₄, filtered and concentrated in vacuum to give 61 (2.9 g, 84%) as a white solid. ¹H NMR (400 MHz, DMSO-d₆) δ 8.58 (s, 1H), 8.46 (d, J=8.0 Hz, 1H), 8.28 (d, J=8.0 Hz, 1H), 3.94 (s, 3H), 3.46 (s, 3H). To a solution of 61 (2.00 g, 8.36 mmol) in THF (20 mL) was added LiAlH₄ (634 mg, 16.7 mmol) at 0° C. The mixture was stirred at 15° C. for 14 h. The mixture was quenched by saturated solution of potassium sodium tartrate (2 mL) and filtered. The filtrate was concentrated in vacuum to give crude 62 (1.2 g) as a yellow oil. ¹H NMR (400 MHz, DMSO-d₆) δ 8.10 (d, J=8.0 Hz, 1H), 7.98 (d, J=8.0 Hz, 1H), 7.3 (s, 1H), 5.64 (s, 1H), 4.65 (s, 2H), 4.58 (s, 2H).

Compound 6-104 was prepared from 62, N-Boc-(S)-valine and Acid-04 in a similar manner to Example 1. ¹H NMR (400 MHz, DMSO-d₆) δ 9.03 (s, 1H), 8.64 (d, J=7.6 Hz, 1H), 8.19 (d, J=8.0 Hz, 1H), 8.08 (d, J=8.0 Hz, 1H), 8.04 (s, 1H), 7.35 (d, J=8.0 Hz, 1H), 7.23 (d, J=8.0 Hz, 1H), 5.39 (s, 2H), 4.97 (s, 2H), 4.63 (s, 2H), 4.44-4.38 (m, 1H), 2.44 (s, 3H), 2.21-2.16 (m, 1H), 0.96 (d, J=6.8 Hz, 6H); ESI-MS m/z 484 [M+H]⁺; HPLC purity: 98.53% (220 nm), 99.73% (254 nm).

Example 105. 4-(4-Methylpiperazine-1-carbonyl)benzyl (1-hydroxy-7-methyl-1,3-dihydrobenzo[c][1,2]oxaborole-6-carbonyl)-L-valinate (6-105)

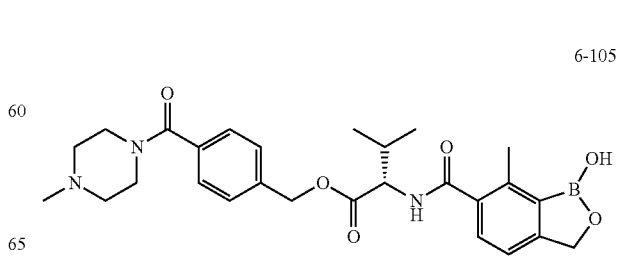

6-105

Compound 6-105 was prepared in a similar manner to Example 103 using N-methylpiperazine instead of N-Boc-piperazine. $^1$H NMR (400 MHz, DMSO-d$_6$) δ 9.03 (s, 1H), 8.57 (d, J=7.2 Hz, 1H), 7.48-7.43 (m, 4H), 7.31 (d, J=7.6 Hz, 1H), 7.20 (d, J=8.0 Hz, 1H), 5.20 (s, 2H), 4.94 (s, 2H), 4.33 (t, J=6.8 Hz, 1H), 3.52 (s, 4H), 3.05 (m, 4H), 2.74 (d, J=4.0 Hz, 3H), 2.29 (s, 3H), 2.13 (m, 1H), 0.94-0.92 (m, 6H); ESI-MS m/z 508[M+H]$^+$; HPLC purity: 95.08% (220 nm), 95.49% (254 nm).

Example 106. 4-((2-(Dimethylamino)ethyl)(methyl)carbamoyl)benzyl (1-hydroxy-7-methyl-1,3-dihydrobenzo[c][1,2]oxaborole-6-carbonyl)-L-valinate (6-106)

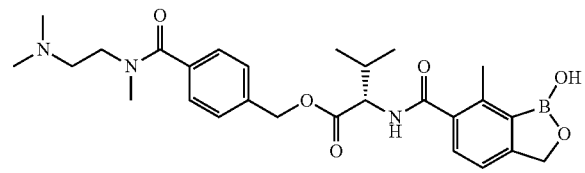

6-106

Compound 6-106 was prepared in a similar manner to Example 103 using N$^1$,N$^1$,N$^2$-trimethylethane-1,2-diamine instead of N-Boc-piperazine. $^1$H NMR (400 MHz, DMSO-d$_6$) δ 9.00 (s, 1H), 8.55 (d, J=8.0 Hz, 1H), 7.42 (d, J=8.0 Hz, 2H), 7.33 (d, J=8.0 Hz, 2H), 7.30 (d, J=8.0 Hz, 1H), 7.19 (d, J=8.0 Hz, 1H), 5.22-5.13 (m, 2H), 4.93 (s, 2H), 4.33 (t, J=7.2 Hz, 1H), 3.49 (s, 1H), 3.22 (s, 1H), 2.92-2.86 (m, 3H), 2.62 (s, 1H), 2.42 (s, 3H), 2.29 (s, 1H), 2.17-2.14 (m, 4H), 1.92 (s, 3H), 0.90 (d, J=6.0 Hz, 6H); ESI-MS m/z 510[M+H]$^+$; HPLC purity: 97.33% (220 nm), 97.78% (254 nm).

Example 107. 4-((2-(Dimethylamino)ethyl)(methyl)carbamoyl)benzyl (1-hydroxy-7-methyl-1,3-dihydrobenzo[c][1,2]oxaborole-6-carbonyl)-L-valinate (6-107)

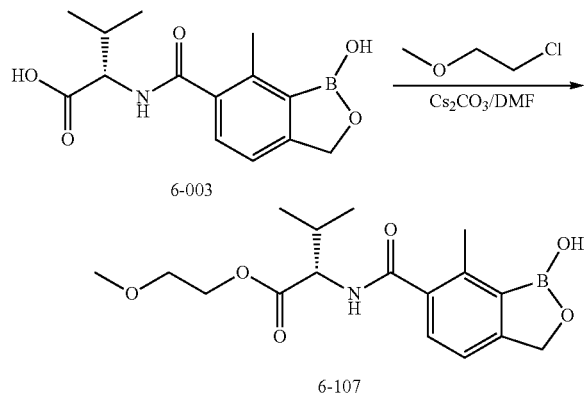

To a solution of 6-003 (300 mg, 1.03 mmol) in DMF (4 mL) was added 2-chloroethyl methyl ether (116 mg, 1.24 mmol) and Cs$_2$CO$_3$ (671 mg, 2.06 mmol). The mixture was stirred at 15° C. for 6 h. The mixture was purified by prep. HPLC (TFA condition) to give 6-107 (32 mg, 8.8%) as a white solid. $^1$H NMR (400 MHz, DMSO-d$_6$) δ 9.04 (s, 1H), 8.53-8.51 (m, 1H), 7.37 (d, J=8.0 Hz, 1H), 7.24 (d, J=8.0 Hz, 1H), 4.97 (s, 2H), 4.33-4.26 (m, 1H), 4.25-4.14 (m, 2H) 3.54 (s, 2H), 3.28 (s, 3H), 2.47 (s, 3H), 2.16-2.11 (m, 1H), 0.96 (d, J=8.0 Hz, 6H); ESI-MS m/z 350[M+H]$^+$; HPLC purity: 98.34% (220 nm), 96.76% (254 nm).

Example 108. 4-Sulfamoylbenzyl (1-hydroxy-7-methyl-1,3-dihydrobenzo[c][1,2]oxaborole-6-carbonyl)-L-valinate (6-108)

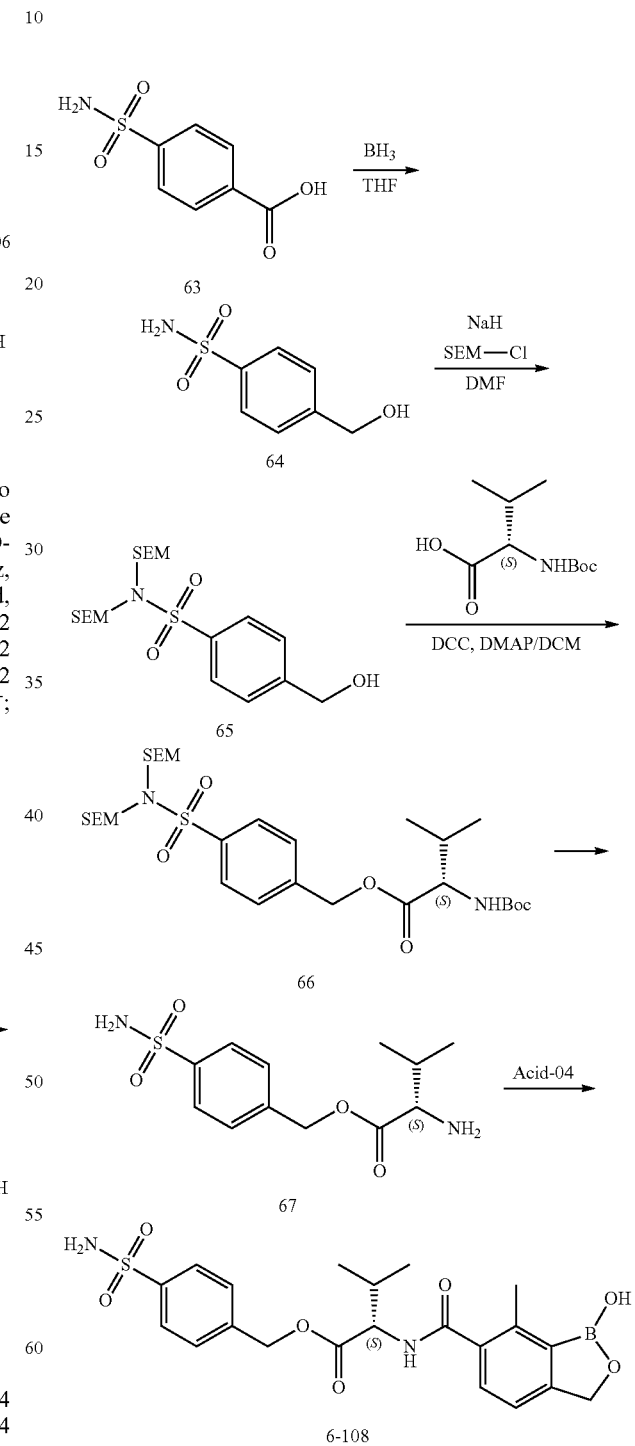

To a solution of 63 (5.0 g, 25 mmol) in THF (100 mL) was added BH$_3$-Me$_2$S (7.55 g, 100 mmol) dropwise at 0° C. over 10 min. After addition, the mixture was stirred at 10° C. for 12 h. The mixture was quenched by MeOH (100 mL) dropwise at 0° C. and then concentrated under reduced pressure to give 64 (3 g, yield 64.47%) as a white solid. $^1$H NMR (400 MHz, DMSO-$d_6$) δ 7.78 (d, J=8.0 Hz, 2H), 7.49 (d, J=8.4 Hz, 2H), 7.29 (s, 2H), 5.37 (s, 1H), 4.57 (s, 2H). To a mixture of 64 (1.5 g, 8.0 mmol) and NaH (705 mg, 32 mmol) in DMF (7 mL) was degassed and purged with $N_2$ for 3 times and stirred for 12 min, and then SEM-Cl (2.54 g, 15 mmol) was added to the mixture and stirred at 20° C. for 1 h under $N_2$ atmosphere. After quenched by addition NH$_4$Cl 50 mL at 10° C., the mixture was extracted with MTBE (50 mL×2), the combined organic layers were washed with brine (50 mL×2), dried over Na$_2$SO$_4$, filtered and concentrated under reduced pressure. The residue was purified by silica gel column chromatography (petroleum ether/EtOAc=2:1) to give 65 (2.2 g, 61%) as a white solid. $^1$H NMR (400 MHz, DMSO-$d_6$) δ 7.80 (d, J=8.0 Hz, 2H), 7.49 (d, J=8.0 Hz, 2H), 5.43 (t, J=5.2 Hz, 1H), 4.71 (s, 4H), 4.57 (d, J=4.8 Hz, 2H), 3.34 (t, J=8.4 Hz, 4H), 0.74 (t, J=8.0 Hz, 4H), −0.07 (s, 18H).

A mixture of 65 (1 g, 2.23 mmol), N-Boc-(S)-valine (533 mg, 2.45 mmol), DCC (920 mg, 4.46 mmol) and DMAP (27 mg, 223 umol) in DCM (20 mL) was degassed and purged with $N_2$ for 3 times, and then the mixture was stirred at 15° C. for 12 h under $N_2$ atmosphere. After filtered and concentrated under reduced pressure, the resulting residue was purified by silica gel column chromatography (petroleum ether/EtOAc=10:1) to give 66 (1.2 g, 83%) as a pale yellow oil. $^1$H NMR (400 MHz, CDCl$_3$) δ 8.24 (s, 1H), 7.90 (d, J=8.0 Hz, 2H), 7.46 (d, J=8.4 Hz, 2H), 5.26 (d, J=7.6 Hz, 1H), 5.15 (d, J=7.6 Hz, 1H), 4.77 (s, 4H), 4.29 (dd, J=8.4, 4.4 Hz, 1H), 3.48 (t, J=8.4 Hz, 4H), 2.18-2.14 (m, 1H), 1.45 (s, 9H), 0.88-0.83 (m, 10H), −0.02 (s, 18H). To a mixture of 66 (200 mg, 0.301 mmol) in MeOH (10 mL) was added AcCl (49 mg, 0.62 mmol) dropwise, and then the mixture was stirred at 0° C. for 1 h under $N_2$ atmosphere. The reaction mixture was concentrated under reduced pressure to give 67 (30 mg, 34%) as a colorless oil which was used in the next step without further purification. $^1$H NMR (400 MHz, DMSO-$d_6$) δ 8.52 (s, 2H), 7.89-7.82 (m, 2H), 7.62 (d, J=7.6 Hz, 2H), 5.34 (s, 2H), 3.99 (s, 1H), 2.21 (s, 1H), 0.97 (d, J=6.0 Hz, 3H), 0.94 (d, J=6.0 Hz, 3H).

Compound 6-108 was prepared from 67 and Acid-04 in a similar manner to the last step of Example 1. $^1$H NMR (400 MHz, DMSO-$d_6$) δ 9.06 (br s, 1H), 8.62 (d, J=6.8 Hz, 1H), 7.84 (d, J=7.6 Hz, 2H), 7.60 (d, J=7.6 Hz, 2H), 7.38-7.26 (m, 3H), 7.25 (d, J=6.8 Hz, 1H), 5.27 (s, 2H), 4.99 (s, 2H), 4.41-4.40 (m, 1H), 2.48 (s, 3H), 2.22-2.18 (m, 1H), 0.97 (d, J=6.0 Hz, 6H); ESI-MS m/z 461 [M+H]$^+$; HPLC purity: 97.53% (220 nm), 93.64% (254 nm).

Example 109. 4-(N,N-bis(methoxymethyl)sulfamoyl)benzyl (1-hydroxy-7-methyl-1,3-dihydrobenzo[c][1,2]oxaborole-6-carbonyl)-L-valinate (6-109)

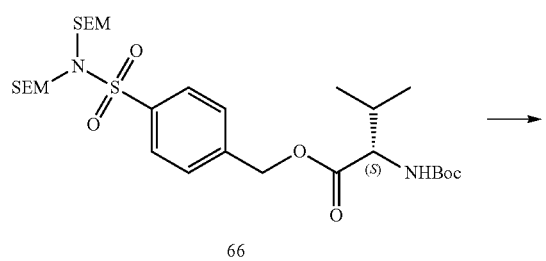

66

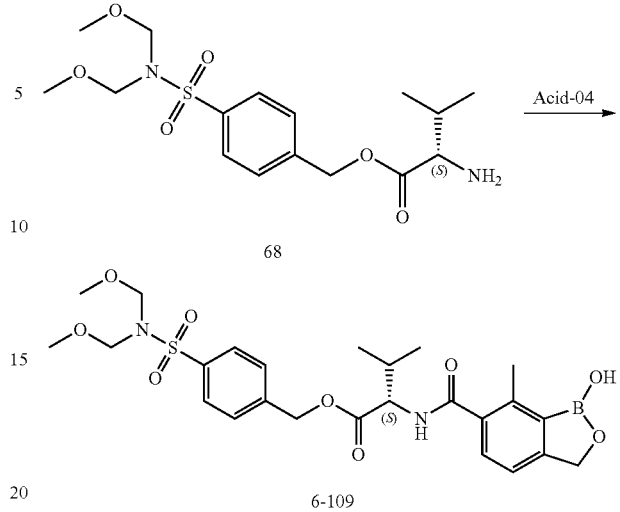

68

6-109

To a mixture of 66 (100 mg, 154 umol) in MeOH (10 mL) was added AcCl (24 mg, 0.31 mmol) dropwise, and then the mixture was stirred at 0° C. for 1 h under $N_2$ atmosphere. After quenched by addition H$_2$O (1 mL) at 10° C., the reaction mixture was concentrated under reduced pressure to give 68 (20 mg, 35%, colorless oil) which was used in the next step without further purification. $^1$H NMR (400 MHz, DMSO-$d_6$) δ 7.85 (d, J=8.0 Hz, 2H), 7.58 (d, J=8.0 Hz, 2H), 5.24-5.17 (m, 2H), 4.69 (s, 4H), 3.60 (t, J=6.0 Hz, 1H). 3.13 (s, 6H), 1.91-1.81 (m, 1H), 0.89-0.79 (m, 6H).

Compound 6-109 was prepared from 68 and Acid-04 in a similar manner to the last step of Example 1. $^1$H NMR (400 MHz, DMSO-$d_6$) δ 9.02 (s., 1H), 8.62 (d, J=7.2 Hz, 1H), 7.86 (d, J=8.4 Hz, 2H), 7.61 (d, J=8.0 Hz, 2H), 7.35 (d, J=8.0 Hz, 1H), 7.23 (d, J=7.6 Hz, 1H), 5.27 (s, 2H), 4.97 (s, 2H), 4.69 (s, 4H), 4.37 (t, J=7.2 Hz, 1H), 3.12 (s, 6H), 2.44 (s, 3H), 2.20-2.13 (m, 1H), 0.96-0.95 (m, 6H); ESI-MS m/z 547 [M+H]$^+$; HPLC purity: 83.51% (220 nm), 83.99% (254 nm).

Example 110. 3-((Dimethylamino)methyl)-4-(methylsulfonyl)benzyl (1-hydroxy-7-methyl-1,3-dihydrobenzo[c][1,2]oxaborole-6-carbonyl)-L-valinate (6-110)

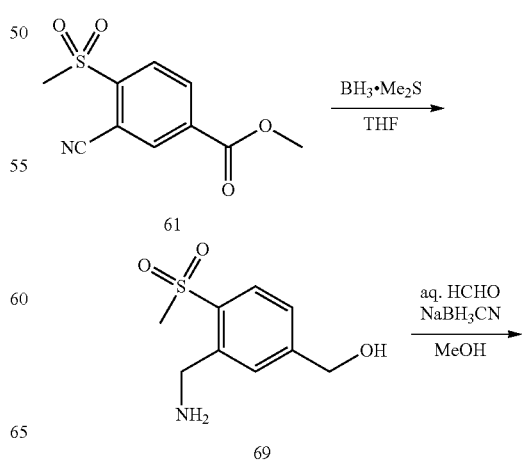

61

69

-continued

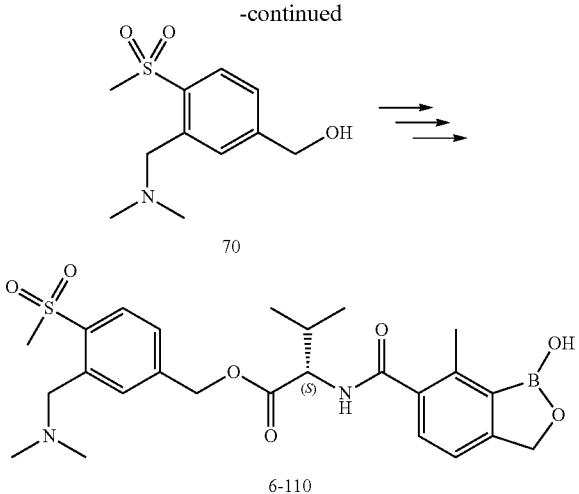

To a solution of 61 (2.39 g, 9.99 mmol) in THF (40 mL) was added BH$_3$-Me$_2$S (10 M, 5 mL) drop-wise at 0° C. under N$_2$. The mixture was stirred at 50° C. for 12 h. The reaction was quenched with water (30 mL) slowly at 0° C. Then the mixture was concentrated in vacuo to remove THF. The aqueous phase was washed with EtOAc (15 mL×2), DCM:i-PrOH=3:1 (20 mL×3) to remove impurities and the aqueous phase was concentrated in vacuo to give crude 69 (2.7 g) as a white solid. $^1$H NMR (400 MHz, DMSO-d$_6$) δ 8.42 (br s, 1H), 7.96 (d, J=8.0 Hz, 1H), 7.71 (s, 1H), 7.61 (d, J=8.0 Hz, 1H), 4.62 (s, 2H), 4.40 (d, J=5.6 Hz, 2H), 3.30 (s, 3H). To a solution of 69 (1.4 g, 6.5 mmol) in MeOH (20 mL) was added aq. 37% HCHO (4.8 mL). The mixture was stirred at 15° C. for 12 h. Then NaBH$_3$CN (1.23 g, 19.5 mmol) was added in portions at 0° C. The mixture was stirred at 15° C. for 12 h. The reaction was quenched by water (5 mL) slowly at 0° C., then dried with anhydrous Na$_2$SO$_4$, filtered and concentrated in vacuo to give 70 (2 g, crude) as a yellow oil. $^1$H NMR (400 MHz, MeOH-4) δ 8.02 (d, J=8.0 Hz, 1H), 7.53-7.51 (m, 2H), 4.67 (s, 2H), 3.85 (s, 2H), 3.36 (s, 3H), 2.25 (s, 6H).

Compound 6-110 was prepared from 70, N-BOC-(S)-valine and Acid-04 in a similar manner to Example 1. $^1$H NMR (400 MHz, DMSO-d$_6$) δ 9.28 (s, 1H), 8.66 (d, J=7.6 Hz, 1H), 8.09 (d, J=8.4 Hz, 1H), 7.86 (s, 1H), 7.81 (d, J=8.0 Hz, 1H), 7.36 (d, J=8.0 Hz, 1H), 7.24 (d, J=8.0 Hz, 1H), 5.39-5.29 (m, 2H), 4.98 (s, 2H), 4.61 (s, 2H), 4.40 (t, J=7.2 Hz 1H), 3.36 (s, 3H), 2.79 (s, 6H), 2.44 (s, 3H), 2.23-2.18 (m, 1H), 0.96 (d, J=6.0 Hz, 6H); ESI-MS m/z 517 [M+H]$^+$; HPLC purity: 95.11% (220 nm), 95.87% (254 nm).

Example 111. 4-((4-Methylpiperazin-1-yl)methyl) benzyl (1-hydroxy-7-methyl-1,3-dihydrobenzo[c][1,2]oxaborole-6-carbonyl)-L-valinate (6-111)

-continued

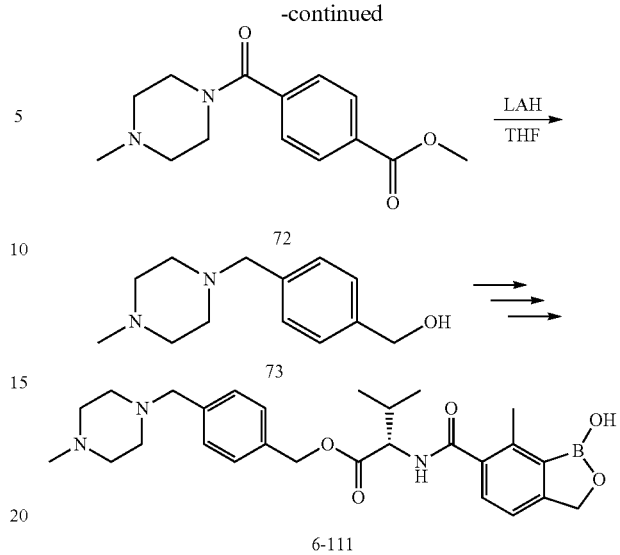

To a solution of 71 (1.8 g, 10 mmol) in DMF (15 mL) was added HATU (5.7 g, 15 mmol), TEA (3.04 g, 30 mmol) and 1-methylpiperazine (1.0 g, 10 mmol). The mixture was stirred at 15° C. for 2 h. The reaction mixture was partitioned between water (30 mL) and EtOAc (60 mL). The organic phase was separated, washed with brine (20 mL×2), dried over Na$_2$SO$_4$, filtered and concentrated under reduced pressure to give 72 (2.1 g, 80%) as a brown oil. $^1$H NMR (400 MHz, DMSO-d$_6$) δ 7.99 (d, J=8.0 Hz, 2H), 7.50 (d, J=8.4 Hz, 2H), 3.86 (s, 3H), 3.61 (s, 2H), 3.25 (s, 2H), 2.37 (s, 2H), 2.19 (s, 2H), 1.97 (s, 3H). To a mixture of 72 (1.54 g, 5.87 mmol) in THF (20 mL) was added LiAlH$_4$ (334 mg, 8.81 mmol) at 0° C., and then the mixture was stirred at 0° C. for 1 h under N$_2$ atmosphere. The reaction mixture was quenched by sat. sodium potassium tartrate (1.2 mL), filtered and concentrated under reduced pressure to give 73 (1.2 g, crude) as a pale yellow oil. $^1$H NMR (400 MHz, DMSO-d$_6$) δ 7.26-7.21 (m, 4H), 5.10 (t, J=6.0 Hz, 1H), 4.46 (d, J=5.6 Hz, 2H), 3.41 (s, 2H), 2.32 (s, 8H), 2.13 (s, 3H).

Compound 6-111 was prepared from 73, N-BOC-(S)-valine and Acid-04 in a similar manner to Example 1. $^1$H NMR (400 MHz, DMSO-d$_6$) δ 9.05 (s, 1H), 8.61 (d, J=7.2 Hz, 1H), 7.49 (s, 4H), 7.36 (d, J=7.6 Hz, 1H), 7.24 (d, J=7.6 Hz, 1H), 5.22 (s, 2H), 4.98 (s, 2H), 4.35 (s, 1H), 4.18 (s, 2H), 3.20 (s, 8H), 2.83 (s, 3H), 2.44 (s, 3H), 2.17 (d, J=6.0 Hz, 1H), 0.96 (s, 6H); ESI-MS m/z 517 [M+H]$^+$; HPLC purity: 95.11% (220 nm), 95.87% (254 nm).

Example 112. Isopropyl (1-hydroxy-7-methyl-1,3-dihydrobenzo[c][1,2]oxaborole-6-carbonyl)-L-valinate (6-112)

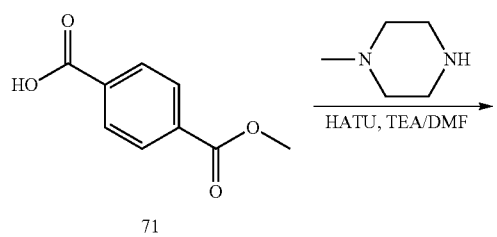

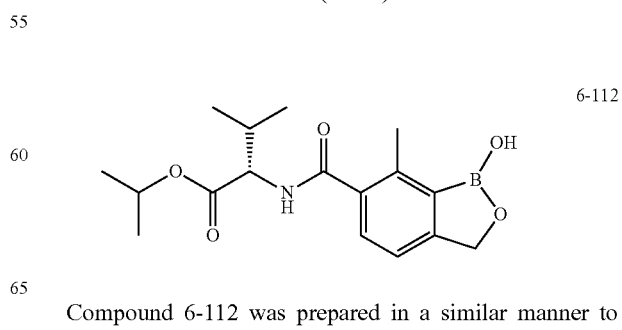

Compound 6-112 was prepared in a similar manner to Example 107 using 2-bromopropane instead of 2-chloroethyl methyl ether. $^1$H NMR (400 MHz, DMSO-d$_6$) δ 9.03 (s, 1H), 8.47 (d, J=7.6 Hz, 1H), 7.36 (d, J=8.0 Hz, 1H), 7.24 (d, J=8.0 Hz, 1H), 4.97-4.93 (m, 3H), 4.25 (t, J=7.2 Hz, 1H), 2.47 (s, 3H), 2.12-2.11 (m, 1H), 1.22 (t, J=5.6 Hz, 6H), 0.95 (d, J=6.4 Hz, 6H); ESI-MS m/z 334 [M+H]$^+$; HPLC purity: 95.58% (220 nm), 94.84% (254 nm).

Example 113. 3-(Pyrrolidin-1-ylmethyl)benzyl (1-hydroxy-7-methyl-1,3-dihydrobenzo[c][1,2]oxaborole-6-carbonyl)-L-valinate (6-113)

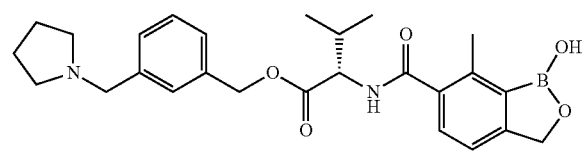

6-113

Compound 6-113 was prepared in a similar manner to Example 81 using pyrrolidine instead of dimethylamine. $^1$H NMR (400 MHz, DMSO-d$_6$) δ 9.05 (s, 1H), 8.60 (d, J=7.6 Hz, 1H), 7.55 (s, 1H), 7.50 (s, 3H), 7.34 (d, J=7.6 Hz, 1H), 7.24 (d, J=8.0 Hz, 1H), 5.22 (s, 2H), 4.97 (s, 2H), 4.38-4.32 (m, 3H), 3.33-3.23 (m, 2H), 3.09 (d, J=6.8 Hz, 2H), 2.43 (s, 3H), 2.22-2.12 (m, 1H), 1.99 (d, J=4.4 Hz, 2H), 1.88-1.77 (m, 2H), 0.95 (dd, J=6.4 Hz, 4.0 Hz, 6H); ESI-MS m/z 465 [M+H]$^+$; HPLC purity: 99.95% (220 nm), 99.05% (254 nm).

Example 114. (1-Methylpiperidin-4-yl)methyl (1-hydroxy-7-methyl-1,3-dihydrobenzo[c][1,2]oxaborole-6-carbonyl)-L-valinate (6-114)

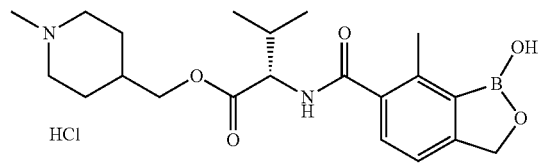

6-114

This compound was prepared from (1-methylpiperidin-4-yl)methanol, N-BOC-(S)-valine and Acid-04 in a similar manner to Example 1. $^1$H NMR (400 MHz, DMSO-d$_6$) δ 10.41 (s, 1H), 9.11 (s, 1H), 8.57 (d, J=7.6 Hz, 1H), 7.37 (d, J=7.6 Hz, 1H), 7.26 (d, J=8.0 Hz, 1H), 4.98 (s, 2H), 4.32 (t, J=7.2 Hz, 1H), 4.01-3.97 (m, 2H), 3.40 (d, J=11.6 Hz, 2H), 2.97-2.88 (m, 2H), 2.70 (d, J=4.4 Hz, 3H), 2.48 (s, 3H), 2.19-2.14 (m, 1H), 1.88 (d, J=11.6 Hz, 3H), 1.56-1.50 (m, 2H), 0.98 (d, J=4.8 Hz, 6H); ESI-MS m/z 416 [M+H]$^+$; HPLC purity: 99.67% (220 nm), 100% (254 nm).

Example 115. Cyclopentylmethyl (1-hydroxy-7-methyl-1,3-dihydrobenzo[c][1,2]oxaborole-6-carbonyl)-L-valinate (6-115)

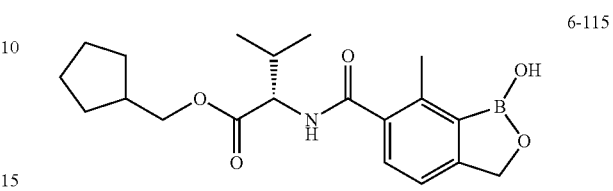

6-115

Compound 6-115 was prepared in a similar manner to Example 107 using bromomethylcyclopentane instead of 2-chloroethyl methyl ether. $^1$H NMR (400 MHz, DMSO-d$_6$) δ 9.04 (s, 1H), 8.51 (d, J=8.0 Hz, 1H), 7.37 (d, J=8.0 Hz, 1H), 7.24 (d, J=8.0 Hz, 1H), 4.97 (s, 2H), 4.30 (t, J=7.2 Hz 1H), 4.01-3.95 (m, 2H), 2.47 (s, 3H), 2.45-2.18 (m, 2H), 1.70-1.58 (m, 2H) 1.56-1.51 (m, 4H), 1.30-1.25 (m, 2H), 0.96 (d, J=8.0 Hz, 6H); ESI-MS m/z 374 [M+H]$^+$; HPLC purity: 99.95% (220 nm), 100% (254 nm).

Example 116. Isobutyl (1-hydroxy-7-methyl-1,3-dihydrobenzo[c][1,2]oxaborole-6-carbonyl)-L-valinate (6-116)

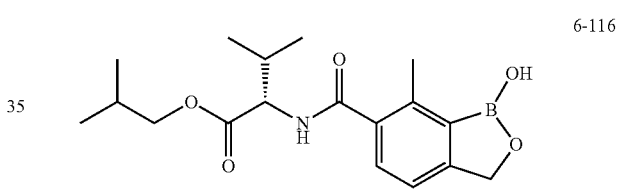

6-116

Compound 6-116 was prepared in a similar manner to Example 107 using isobutyl bromide instead of 2-chloroethyl methyl ether. $^1$H NMR (400 MHz, DMSO-d$_6$) δ 9.06 (s, 1H), 8.55 (d, J=7.6 Hz, 1H), 7.38 (d, J=8.0 Hz, 1H), 7.26 (d, J=7.6 Hz, 1H), 4.99 (s, 2H), 4.33 (d, J=7.6 Hz, 1H), 3.89 (q, J=3.6, 2.4 Hz, 2H), 2.50 (d, J=9.6 Hz, 3H), 2.19-2.14 (m, 1H), 1.95-1.88 (m, 1H), 0.97 (d, J=5.2 Hz, 6H), 0.92 (d, J=6.8 Hz, 6H); ESI-MS m/z 348 [M+H]$^+$; HPLC purity: 99.98% (220 nm), 100% (254 nm).

Example 117. 3-(Piperazin-1-ylmethyl)benzyl (1-hydroxy-7-methyl-1,3-dihydrobenzo[c][1,2]oxaborole-6-carbonyl)-L-valinate (6-117)

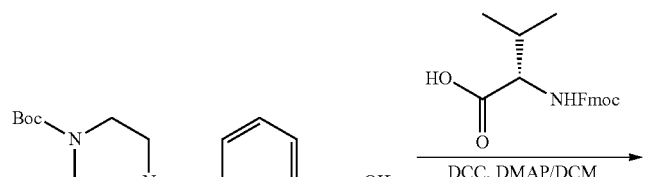

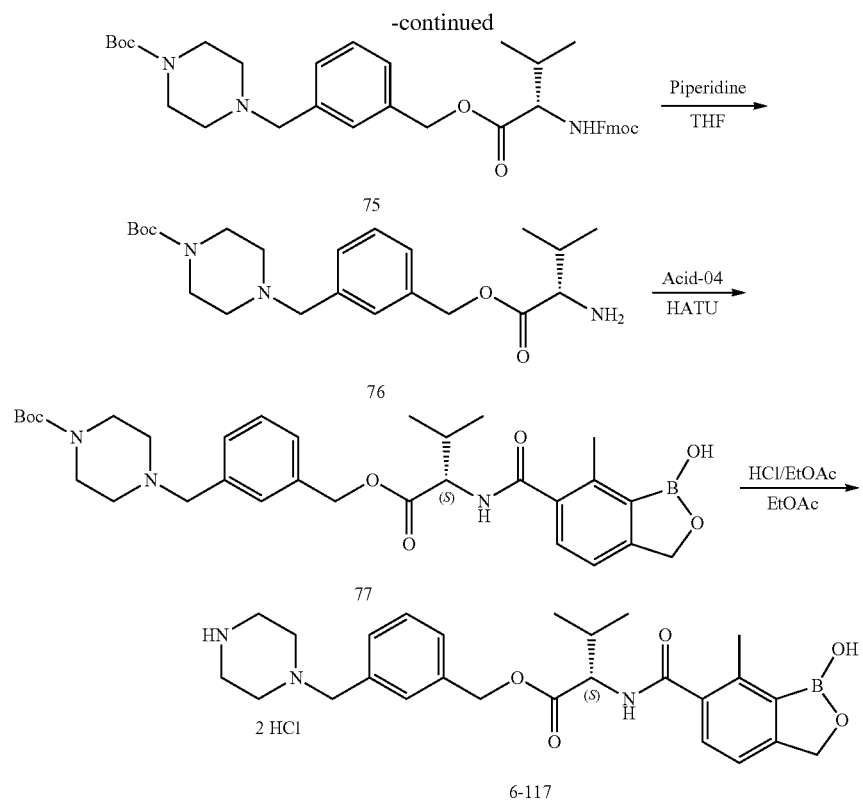

A mixture of 74 (1.50 g, 4.90 mmol), N-Fmoc-(S)-valine (1.83 g, 5.39 mmol), DCC (2.02 g, 9.79 mmol) and DMAP (60 mg, 0.49 mmol) in DCM (30 mL) was degassed and purged with $N_2$ for 3 times, and then the mixture was stirred at 15° C. for 12 h. After filtered and concentrated under reduced pressure, the mixture was purified by silica gel column chromatography (petroleum ether/EtOAc=2:1) to give 75 (1.0 g, 33%) as a white solid. $^1$H NMR (400 MHz, CDCl$_3$) δ 7.77 (d, J=7.6 Hz, 2H), 7.61 (d, J=7.2 Hz, 2H), 7.44-7.37 (m, 2H), 735-7.27 (m, 6H), 5.19 (q, J=12.4 Hz, 2H), 4.41 (d, J=7.2 Hz, 2H), 4.23 (d, J=4.8 Hz, 1H), 4.03 (s, 1H), 3.50 (s, 2H), 3.43 (s, 4H), 2.38 (s, 4H), 2.20 (d, J=6.0 Hz, 1H), 1.50-1.44 (m, 9H), 0.97-0.92 (m, 3H), 0.88 (d, J=6.4 Hz, 3H). To a solution of 75 (1.00 g, 1.59 mmol) in THF (10 mL) was added piperidine (1.36 g, 15.9 mmol). The mixture was stirred at 15° C. for 12 h. The reaction mixture was diluted with $H_2O$ (100 mL) and extracted with EtOAc (50 mL×2). The combined organic layers were washed with brine (50 mL×2), dried over $Na_2SO_4$, filtered and concentrated under reduced pressure. The residue was purified by silica gel column chromatography (DCM/MeOH=10/1) to give 76 (250 mg, 39%) as a pale yellow oil. $^1$H NMR (400 MHz, DMSO-d$_6$) δ 7.38-7.22 (m, 4H), 5.20-5.02 (m, 2H), 3.47 (s, 2H), 3.30 (br s, 4H), 3.19-3.13 (m, 1H), 2.29 (t, J=4.4 Hz, 4H), 1.88-1.80 (m, 1H), 1.38 (s, 9H), 0.86-0.78 (m, 6H). A mixture of Acid-04 (120 mg, 0.625 mmol), HATU (357 mg, 938 umol) and TEA (253 mg, 3.00 mmol) in DMF (2 mL) was stirred at 15° C. for 10 min, then 76 (253 mg, 0.625 mmol) was added to the mixture and stirred at 15° C. for 1 hour under $N_2$ atmosphere. The reaction mixture was diluted with $H_2O$ (10 mL) and extracted with EtOAc (10 mL×2). The combined organic layers were washed with brine (10 mL×2), dried over $Na_2SO_4$, filtered and concentrated under reduced pressure to give 77 (250 mg, crude, pale yellow oil) which was used in the next step without further purification. MS (ESI): mass calcd. for $C_{31}H_{42}BN_3O_7$ 579.31, m/z found 580.1 [M+H]$^+$. To a solution of 77 (250 mg, 0.431 mmol) in EtOAc (10 mL) was added HCl/EtOAc (6 M, 1 mL). The mixture was stirred at 15° C. for 2 h. Then some white solid precipitated. After filtration, the white solid was purified by prep. HPLC (column: Luna C18 100*30 5 u; liquid phase: [A-HCl/$H_2O$=0.040% v/v; B-ACN] B %: 5%-45%, 12 min]) to give 6-117 (93 mg, 45%) as a white solid. $^1$H NMR (400 MHz, DMSO-d$_6$) δ 9.07 (s, 1H), 8.59 (d, J=6.0 Hz, 1H), 7.67 (s, 2H), 7.49 (s, 2H), 7.33 (s, 1H), 7.24 (s, 1H), 5.19 (s, 2H), 4.97 (s, 2H), 4.38 (s, 3H), 3.42-3.01 (m, 8H), 2.43 (s, 3H), 2.19 (s, 1H), 0.95 (s, 6H); ESI-MS m/z 480 [M+H]$^+$; HPLC purity: 99.91% (220 nm), 100% (254 nm).

Example 118. 4-Fluorobenzyl N-(1-hydroxy-7-methyl-1,3-dihydrobenzo[c][1,2]oxaborole-6-carbonyl)-N-methyl-L-valinate (6-118)

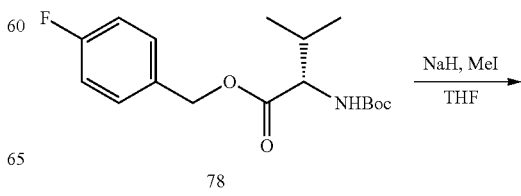

78

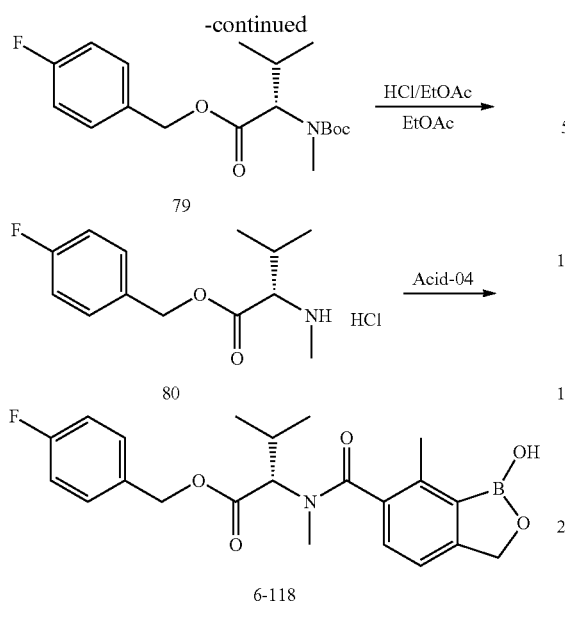

To a mixture of 78 (2.00 g, 6.15 mmol) and NaH (492 mg, 12.30 mmol) in THF (30 mL) was added MeI (1.75 g, 12.30 mmol), and then the mixture was stirred at 10° C. for 12 h under N$_2$ atmosphere. The reaction mixture was quenched by addition sat. NH$_4$Cl (60 mL) at 10° C., and extracted with EtOAc (40 mL×2). The combined organic layers were washed with brine (20 mL×2), dried over Na$_2$SO$_4$, filtered and concentrated under reduced pressure to give 79 (400 mg, 19%) as a pale yellow oil. $^1$H NMR (400 MHz, DMSO-d$_6$) δ 7.41 (br s, 2H), 7.20 (t, J=8.8 Hz, 2H), 5.18-5.08 (m, 2H), 4.28 (d, J=10.8 Hz, 1H), 2.73 (d, J=9.2 Hz, 3H), 2.15 (m, 1H), 1.38 (s, 9H), 0.91 (br s, 3H), 0.81 (br s, 3H). To a solution of 79 (400 mg, 1.18 mmol) in EtOAc (10 mL) was added HCl/EtOAc (6 M, 1.97 mL). The mixture was stirred at 15° C. for 2 hours. The reaction mixture was filtered and concentrated under reduced pressure to give 80 (300 mg, 92%) as a white solid. $^1$H NMR (400 MHz, CDCl$_3$) δ 9.63 (br s, 1H), 7.44 (dd, J=8.4, 5.6 Hz, 2H), 7.07 (t, J=8.4 Hz, 2H), 5.32-5.19 (m, 2H), 3.58 (d, J=4.0 Hz, 1H), 2.72 (s, 3H), 2.60 (m, 1H), 1.13-1.06 (m, 6H).

Compound 6-118 was prepared from 80 and Acid-04 in a similar manner to the last step of Example 1. $^1$H NMR (400 MHz, DMSO-d$_6$) δ 9.04 (s, 1H), 7.47 (dd, J=8.4, 5.6 Hz, 2H), 7.30-7.19 (m, 3H), 7.06 (br s, 1H), 5.26-5.12 (m, 2H), 4.97 (s, 2H) 4.86 (br s, 1H), 3.00 (d, J=8.4 Hz, 1H), 2.61 (s, 2H), 2.34-2.14 (m, 4H), 1.02 (d, J=6.0 Hz, 3H), 0.93 (d, J=6.4 Hz, 3H); ESI-MS m/z 414 [M+H]$^+$; HPLC purity: 99.60% (220 nm), 95.53% (254 nm).

Example 119. Cyclohexylmethyl (1-hydroxy-7-methyl-1,3-dihydrobenzo[c][1,2]oxaborole-6-carbonyl)-L-valinate (6-119)

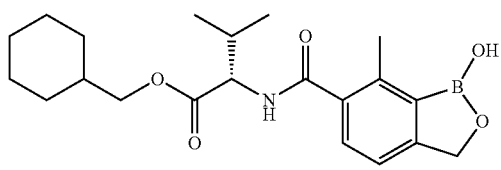

This compound was prepared from cyclohexylmethanol, N-BOC-(S)-valine and Acid-04 in a similar manner to Example 1. $^1$H NMR (400 MHz, DMSO-d$_6$) δ 9.04 (s, 1H), 8.52 (d, J=7.6 Hz, 1H), 7.36 (d, J=7.6 Hz, 1H), 7.24 (d, J=7.6 Hz, 1H), 4.97 (s, 2H), 4.31 (t, J=7.0 Hz, 1H), 3.90 (br s, 2H), 2.47 (s, 3H), 2.14 (dd, J=12.8, 6.0 Hz, 1H), 1.78-1.56 (m, 6H), 1.29-1.01 (m, 4H), 0.95 (d, J=5.2 Hz, 6H); ESI-MS m/z 388 [M+H]$^+$; HPLC purity: 99.38% (220 nm), 100% (254 nm).

Example 120. Thiazol-5-ylmethyl (1-hydroxy-7-methyl-1,3-dihydrobenzo[c][1,2]oxaborole-6-carbonyl)-L-valinate (6-120)

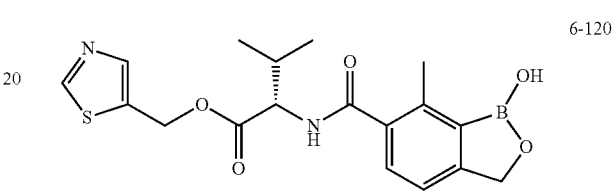

Compound 6-120 was prepared in a similar manner to Example 107 using 5-(chloromethyl)thiazole instead of 2-chloroethyl methyl ether. $^1$H NMR (400 MHz, DMSO-d$_6$) δ 9.13 (s, 1H), 9.02 (s, 1H), 8.57 (d, J=7.6 Hz, 1H), 8.00 (s, 1H), 7.35 (d, J=7.2 Hz, 1H), 7.24 (d, J=7.6 Hz, 1H), 5.45 (q, J=13.2, 16.0 Hz, 2H), 4.98 (s, 2H), 4.32 (t, J=7.2 Hz, 1H), 2.44 (s, 3H), 2.16-2.11 (m, 1H), 0.94-0.91 (m, 6H); ESI-MS m/z 389 [M+H]$^+$; HPLC purity: 95.91% (220 nm), 94.63% (254 nm).

Example 121. 4-Fluorophenethyl (1-hydroxy-7-methyl-1,3-dihydrobenzo[c][1,2]oxaborole-6-carbonyl)-L-valinate (6-121)

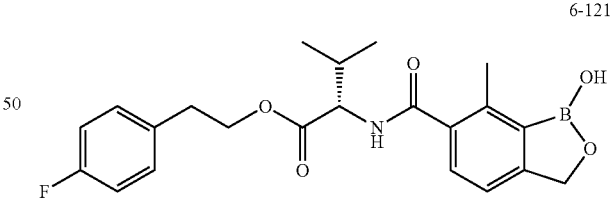

Compound 6-121 was prepared in a similar manner to Example 107 using 1-(2-bromoethyl)-4-fluorobenzene instead of 2-chloroethyl methyl ether. $^1$H NMR (400 MHz, DMSO-d$_6$) δ 9.03 (s, 1H), 8.48 (d, J=7.2 Hz, 1H), 7.35-7.33 (m, 3H), 7.25 (d, J=8.0 Hz, 1H), 7.11 (t, J=8.4 Hz, 2H), 4.99 (s, 2H), 4.37-4.28 (m, 3H), 2.95-2.92 (m, 2H), 2.47 (s, 3H), 2.11-2.06 (m, 1H), 0.89 (d, J=6.4 Hz, 6H); ESI-MS m/z 414 [M+H]$^+$; HPLC purity: 99.48% (220 nm), 99.10% (254 nm).

Example 122. 3-((Methylamino)methyl)benzyl (1-hydroxy-7-methyl-1,3-dihydrobenzo[c][1,2]oxa-borole-6-carbonyl)-L-valinate (6-122)

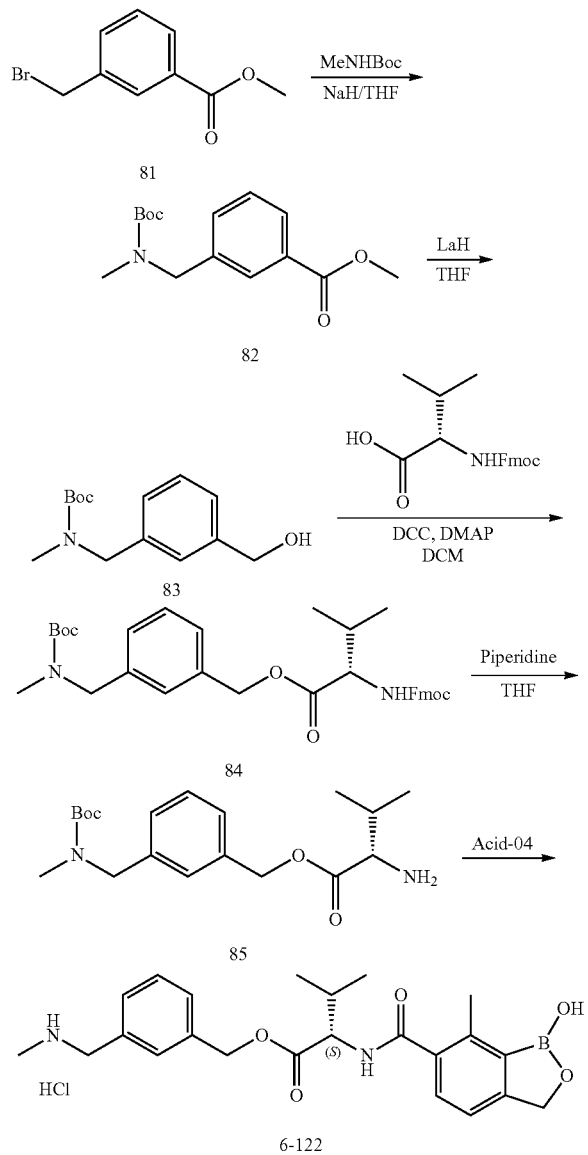

To a solution of tert-butyl-N-methylcarbamate (3.00 g, 22.9 mmol) in THF (50 mL) was added NaH (1.37 g, 34.3 mmol) in portions at 0° C. The reaction mixture was stirred at 15° C. for an hour. Then 81 (5.24 g, 22.9 mmol) in THF (20 mL) was added dropwise. The reaction mixture was stirred at 15° C. for 13 h. The reaction was quenched by ice water (10 mL) slowly and then extracted with EtOAc (20 mL×3). The combined organic phase was washed with brine (10 mL×2), dried over anhydrous $Na_2SO_4$, filtered and concentrated in vacuo. The residue was purified via silica gel column chromatography (petroleum ether/ethyl acetate=4:1) to give 82 (2.9 g, 45%) as a colorless oil. $^1$H NMR (400 MHz, $CDCl_3$) δ 7.95-7.91 (m, 2H), 7.42-7.38 (m, 2H), 4.45 (s, 2H), 3.91 (s, 3H), 2.85 (s, 3H), 1.48 (s, 9H). To a solution of 82 (2.8 g, 10 mmol) in THF (20 mL) was added $LiAlH_4$ (456 mg, 12.0 mmol) in portions at 0° C. The mixture was stirred at 15° C. for 2 hours. The mixture was cooled to 0° C. and quenched by saturated solution of potassium sodium tartrate (0.5 mL), the mixture was concentrated in vacuum (40° C.) to give 83 (1.8 g, 71%) as a colorless oil. $^1$H NMR (400 MHz, $CDCl_3$) δ 7.32-7.29 (m, 2H), 7.27-7.23 (m, 1H), 7.15-7.14 (m, 1H), 4.68 (s, 2H), 4.42 (s, 2H), 2.82 (s, 3H), 1.48 (s, 9H). To a solution of 83 (1.5 g, 6.0 mmol) in DCM (20 mL) was added N-Fmoc-(S)-valine (2.23 g, 6.57 mmol), DCC (1.6 g, 7.8 mmol) and DMAP (73 mg, 0.60 mmol). The mixture was stirred at 15° C. for 12 h. Then DCM (10 mL) was added and the organic layer was washed with brine (10 mL×3), dried over $Na_2SO_4$ and concentrated in vacuum. The residue was purified by column chromatography (petroleum ether/ethyl acetate=4:1) to give 84 (1.8 g, 53%) as a colorless oil. $^1$H NMR (400 MHz, $CDCl_3$) δ 7.70-7.80 (m, 2H), 7.54-7.62 (m, 2H), 7.35-7.42 (m, 2H), 7.23-7.33 (m, 4H), 7.19 (br s, 2H), 5.34-5.32 (m, 1H), 5.29-5.14 (m, 2H), 4.43-4.41 (m, 4H), 4.40-4.14 (m, 4H), 2.83 (s, 3H), 2.12-2.23 (m, 1H), 1.47 (s, 9H), 0.86 (dd, J=6.84, 2.87 Hz, 6H). To a solution of 84 (1.00 g, 1.75 mmol) in THF (6 mL) was added piperidine (298 mg, 3.50 mmol). The mixture was stirred at 15° C. for 12 h. The mixture was concentrated in reduced pressure at 40° C. The residue was purified by column chromatography (petroleum ether/ethyl acetate=1:4) to give 85 (400 mg, 65%) as a colorless oil. $^1$H NMR (400 MHz, DMSO-$d_6$) δ 7.37-7.35 (m, 1H), 7.34-7.29 (m, 1H), 7.27-7.22 (m, 1H), 7.18-7.17 (m, 1H), 5.16-5.06 (m, 2H), 4.37 (s, 2H), 3.15 (d, J=4.0 Hz, 1H), 2.74 (s, 3H), 1.99-1.84 (m, 1H), 1.42-1.39 (m, 9H), 0.85 (d, J=6.8 Hz, 3H), 0.79 (s, J=6.4 Hz, 3H). To a solution of Acid-04 (164 mg, 0.856 mmol) in DMF (3 mL) was added HATU (390 mg, 1.03 mmol) and TEA (260 mg, 2.57 mmol). The mixture was stirred at 20° C. for 1 h. Then 85 (300 mg, 0.856 mmol) was added in one portion. The mixture was stirred at 20° C. for 11 h. The reaction was quenched by water (10 mL) slowly at 0° C. and then extracted with EtOAc (10 mL×3). The combined organic phase was washed with brine (10 mL×1), dried over anhydrous $Na_2SO_4$, filtered and then HCl/EtOAc (4 M, 4 mL) was added. The mixture was stirred at 20° C. for 12 h. The mixture was concentrated in vacuo. The residue was purified by prep. HPLC (column: Luna C18 100×30 mm; liquid phase: 0.1% TFA-ACN; B %: 10%-40%, 12 min). After prep. HPLC, 3N HCl (2 mL) was added before freeze drying. 6-122 (137 mg, 33%) was obtained as an off white solid. $^1$H NMR (400 MHz, DMSO-$d_6$) δ 9.21 (br s, 2H), 9.03 (s, 1H), 8.59 (d, J=8.0 Hz, 1H), 7.55-7.51 (m, 2H), 7.46-7.45 (m, 2H), 7.35 (d, J=8.0 Hz, 1H), 7.24 (d, J=8.0 Hz, 1H), 5.19 (s, 2H), 4.97 (s, 2H), 4.37 (t, J=8.0 Hz 1H), 4.10 (s, 2H), 2.39 (s, 3H), 2.21-2.16 (m, 1H), 0.96 (d, J=6.0 Hz, 6H); ESI-MS m/z 425 [M+H]$^+$; HPLC purity: 94.93% (220 nm), 87.86% (254 nm).

Example 123. Quinoxalin-2-ylmethyl (1-hydroxy-7-methyl-1,3-dihydrobenzo[c][1,2]oxaborole-6-carbonyl)-L-valinate (6-123)

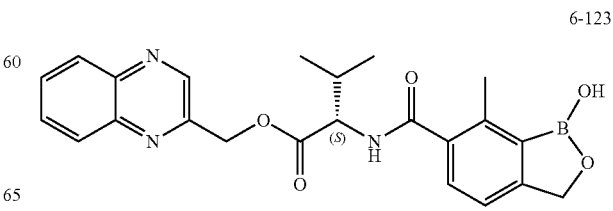

Compound 6-123 was prepared in a similar manner to Example 107 using 2-(bromomethyl)quinoxaline instead of 2-chloroethyl methyl ether. ¹H NMR (400 MHz, DMSO-d₆) δ 9.05 (s, 1H), 9.01 (s, 1H), 8.63 (d, J=8.0 Hz, 2H), 8.14-8.12 (m, 1H), 8.08-8.06 (m, 1H), 7.90-7.88 (m, 2H), 7.36 (d, J=8.0 Hz, 1H), 7.22 (d, J=8.0 Hz, 1H), 5.57-5.49 (m, 2H), 4.96 (s, 2H), 4.46 (t, J=4.5 Hz, 1H), 2.45 (s, 3H), 2.44-2.24 (m, 1H), 1.00 (d, J=6.0 Hz, 6H); ESI-MS m/z 434 [M+H]⁺; HPLC purity: 98.71% (220 nm), 96.67% (254 nm).

Example 124. Thiazol-2-ylmethyl (1-hydroxy-7-methyl-1,3-dihydrobenzo[c][1,2]oxaborole-6-carbonyl)-L-valinate (6-124)

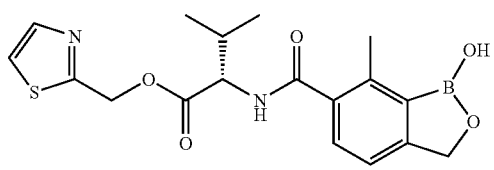

6-124

Compound 6-124 was prepared in a similar manner to Example 107 using 2-(chloromethyl)thiazole instead of 2-chloroethyl methyl ether. ¹H NMR (400 MHz, DMSO-d₆) δ 9.04 (s, 1H), 8.62 (d, J=8.0 Hz, 1H), 7.84 (d, J=4.0 Hz, 1H), 7.81 (d, J=4.0 Hz, 1H), 7.36 (d, J=8.0 Hz, 1H), 7.24 (d, J=8.0 Hz, 1H), 5.52-5.41 (m, 2H), 4.97 (s, 2H), 4.38 (t, J=8.0 Hz 1H), 2.44 (s, 3H), 2.32-2.15 (m, 1H), 0.96 (d, J=6.0 Hz, 6H); ESI-MS m/z 389 [M+H]⁺; HPLC purity: 99.65% (220 nm), 100% (254 nm).

Example 125. Quinolin-2-ylmethyl (1-hydroxy-7-methyl-1,3-dihydrobenzo[c][1,2]oxaborole-6-carbonyl)-L-valinate (6-125)

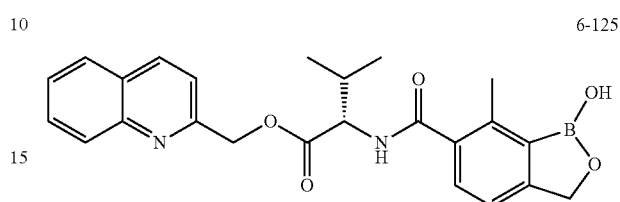

6-125

Compound 6-125 was prepared in a similar manner to Example 107 using 2-(chloromethyl)quinoline instead of 2-chloroethyl methyl ether. ¹H NMR (400 MHz, DMSO-d₆) δ 8.69 (d, J=8.0 Hz, 1H), 8.64 (d, J=8.4 Hz, 1H), 8.14-8.10 (m, 2H), 7.90 (t, J=8.0 Hz, 1H), 7.78-7.72 (m, 2H), 7.39 (d, J=7.6 Hz, 1H), 7.24 (d, J=7.6 Hz, 1H), 5.54 (s, 2H), 4.98 (s, 2H), 4.48 (t, J=7.2 Hz, 1H), 2.45 (s, 3H), 2.29-2.24 (m, 1H), 1.02 (d, J=6.8 Hz, 6H); ESI-MS m/z 433 [M+H]⁺; HPLC purity: 97.79% (220 nm), 97.66% (254 nm).

Example 126. 3-(Piperazin-1-yl)benzyl (1-hydroxy-7-methyl-1,3-dihydrobenzo[c][1,2]oxaborole-6-carbonyl)-L-valinate (6-126)

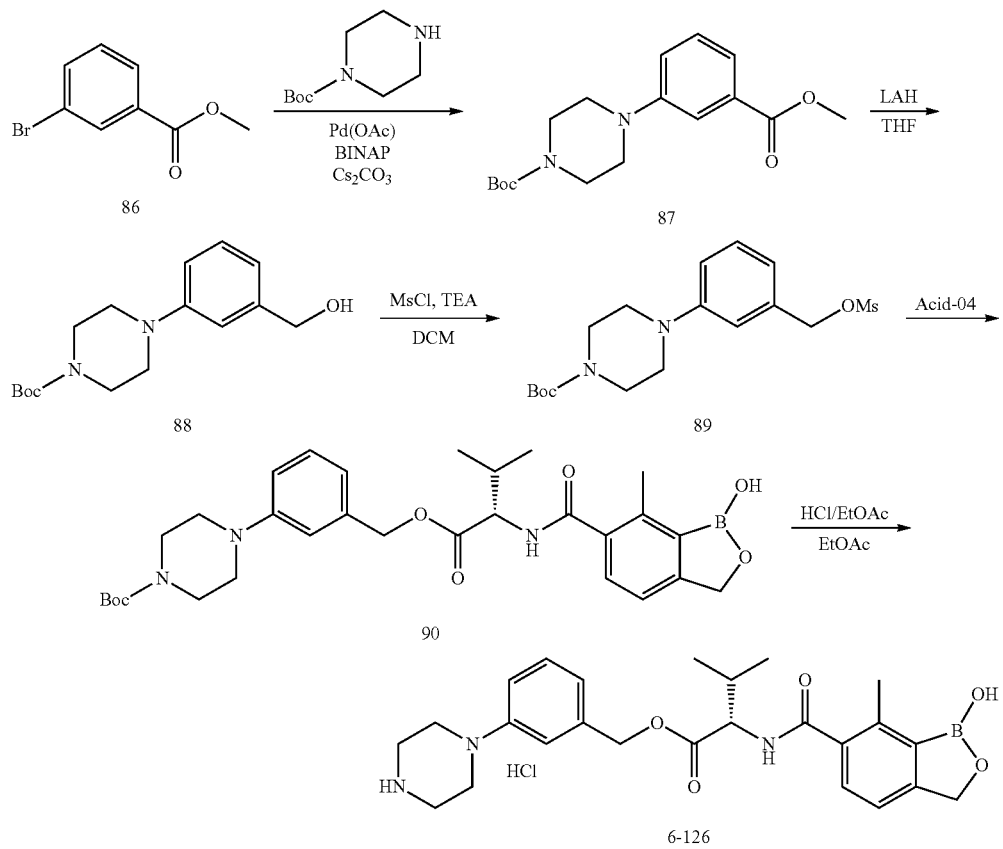

A mixture of 86 (3.00 g, 14.0 mmol), N-Boc-piperazine (2.73 g, 14.7 mmol), Pd(OAc)$_2$ (313 mg, 1.40 mmol), Cs$_2$CO$_3$ (9.09 g, 27.9 mmol) and BINAP (869 mg, 1.40 mmol) in toluene (20 mL) was degassed and purged with N$_2$ for 3 times, and then the mixture was stirred at 100° C. for 12 h under N$_2$ atmosphere. The reaction mixture was filtered and concentrated under reduced pressure to give 87 (3.80 g, 85%) as a pale yellow solid. $^1$H NMR (400 MHz, CDCl$_3$) δ 7.60 (s, 1H), 7.55 (d, J=7.6 Hz, 1H), 7.33 (t, J=8.0 Hz, 1H), 7.13 (d, J=2.4 Hz, 1H), 3.91 (s, 3H), 3.60 (t, J=4.4 Hz, 4H), 3.19 (t, J=4.8 Hz, 4H), 1.49 (s, 9H). To a solution of 87 (1.00 g, 3.12 mmol) in THF (20 mL) was added LiAlH$_4$ (118 mg, 3.12 mmol). The mixture was stirred at 0° C. for 1 h. The reaction mixture was quenched by sodium potassium tartrate (0.5 mL) at 15° C., and then filtered and concentrated under reduced pressure to give 88 (700 mg, 77%) as a pale yellow oil. $^1$H NMR (400 MHz, CDCl$_3$) δ 7.28-7.25 (m, 1H), 6.96 (s, 1H), 6.89-6.84 (m, 2H), 4.66 (s, 2H), 3.58 (t, J=4.8 Hz, 4H), 3.15 (t, J=4.8 Hz, 4H), 1.49 (s, 9H). To a solution of 88 (293 mg, 1.00 mmol) and Et$_3$N (304 mg, 3.00 mmol) in DCM (10 mL) was added MsCl (229 mg, 2.00 mmol). The mixture was stirred at 0° C. for 2 h. The reaction mixture was quenched by addition H$_2$O (20 mL) at 15° C., and then extracted with EtOAc (20 mL×2). The combined organic layers were washed with brine (10 mL×2), dried over Na$_2$SO$_4$, filtered and concentrated under reduced pressure to give crude 89 (200 mg, yellow solid) which was used in the next step without further purification. MS (ESI): mass calcd. for C$_{17}$H$_{26}$N$_2$O$_5$S 370.16, m/z found 371.2 [M+H]$^+$. A mixture of 89 (300 mg, 810 umol), 6-003 (236 mg, 0.810 mmol) and K$_2$CO$_3$ (336 mg, 2.43 mmol) in DMF (5 mL) was stirred at 60° C. for 1 h under N$_2$ atmosphere. The reaction mixture was quenched by H$_2$O (10 mL) at 15° C., and then extracted with EtOAc (20 mL×2). The combined organic layers were washed with brine (10 mL×2), dried over Na$_2$SO$_4$, filtered and concentrated under reduced pressure to give crude 90 (400 mg, pale yellow oil) which was used in the next step without further purification. MS (ESI): mass calcd. for C$_{30}$H$_{40}$BN$_3$O$_7$ 565.30, m/z found 566.3 [M+H]$^+$. To a solution of 90 (400 mg, 0.707 mmol) in EtOAc (10 mL) was added HCl/EtOAc (6 M, 1.18 mL). The mixture was stirred at 15° C. for 1 h. After concentrated under reduced pressure, the reaction mixture was purified by prep. HPLC (column: Luna C18 100×30 mm; liquid phase: [A-HCl/H$_2$O=0.040% v/v; B-ACN] B %: 13%-43%, 12 min]) to give 6-126 (102 mg, 28%) as a white solid. $^1$H NMR (400 MHz, DMSO-d$_6$) δ 9.17 (s, 2H), 8.58 (d, J=7.2 Hz, 1H), 7.34 (d, J=7.2 Hz, 1H), 7.28-7.22 (m, 2H), 7.01 (s, 1H), 6.95 (d, J=8.0 Hz, 1H), 6.88 (d, J=7.2 Hz, 1H), 5.13 (s, 2H), 4.97 (s, 2H), 4.34 (t, J=7.2 Hz, 1H), 3.36 (d, J=5.2 Hz, 4H), 3.17 (d, J=2.8 Hz, 4H), 2.44 (s, 3H), 2.20-2.11 (m, 6.8 Hz, 1H), 0.958-0.942 (m, 6H); ESI-MS m/z 466 [M+H]$^+$; HPLC purity: 97.27% (220 nm), 96.92% (254 nm).

Example 127. Quinolin-6-ylmethyl (1-hydroxy-7-methyl-1,3-dihydrobenzo[c][1,2]oxaborole-6-carbonyl)-L-valinate (6-127)

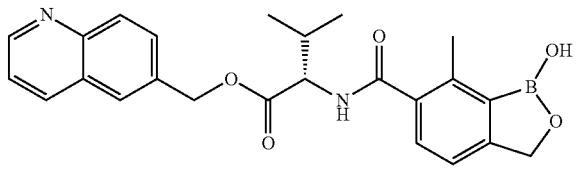

Compound 6-127 was prepared in a similar manner to Example 107 using 6-(chloromethyl)quinoline instead of 2-chloroethyl methyl ether. $^1$H NMR (400 MHz, DMSO-d$_6$) δ 9.00 (s, 1H), 8.88 (d, J=3.2 Hz, 1H), 8.58 (d, J=8.0 Hz, 1H), 8.32 (d, J=3.2 Hz, 1H), 8.02-8.00 (m, 2H), 7.55-7.52 (m, 1H), 7.33-7.31 (m, 1H), 7.26 (d, J=8.0 Hz, 1H), 7.18 (d, J=8.0 Hz, 1H), 5.37-5.36 (m, 2H), 4.94 (s, 2H), 4.38 (t, J=7.2 Hz, 1H), 2.41 (s, 3H), 2.18-2.14 (m, 1H), 0.93 (d, J=6.4 Hz, 6H); ESI-MS m/z 433 [M+H]$^+$; HPLC purity: 99.81% (220 nm), 100% (254 nm).

Example 128. Thiazol-4-ylmethyl (1-hydroxy-7-methyl-1,3-dihydrobenzo[c][1,2]oxaborole-6-carbonyl)-L-valinate (6-128)

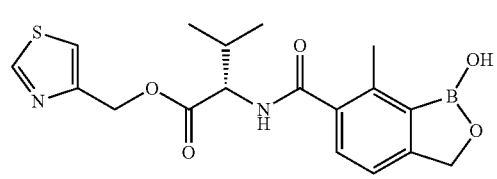

Compound 6-128 was prepared in a similar manner to Example 107 using 4-(chloromethyl)thiazole instead of 2-chloroethyl methyl ether. $^1$H NMR (400 MHz, DMSO-d$_6$) δ 9.09 (s, 1H), 9.02 (s, 1H), 8.55 (d, J=8.0 Hz, 1H), 7.75 (d, J=1.2 Hz, 1H), 7.32 (d, J=8.0 Hz, 1H), 7.21 (d, J=7.6 Hz, 1H), 5.30-5.21 (m, 2H), 4.94 (s, 2H), 4.32 (t, J=7.6 Hz, 1H), 2.41 (s, 3H), 2.14-2.09 (m, 1H), 0.91 (dd, J=4.0 Hz, 2.8 Hz, 6H); ESI-MS m/z 389 [M+H]$^+$; HPLC purity: 99.53% (220 nm), 100% (254 nm).

Example 129. 4-Fluorobenzyl (1-hydroxy-5-methyl-1,3-dihydrobenzo[c][1,2]oxaborole-6-carbonyl)-L-valinate (6-129)

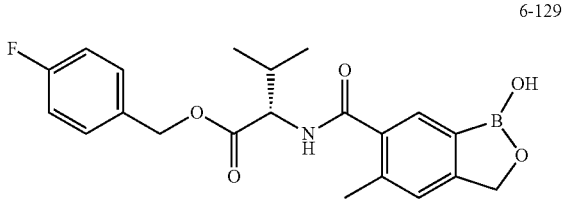

This compound was prepared from 4-fluorobenzylalcohol, N-BOC-(S)-valine and Acid-14 in a similar manner to Example 1. $^1$H NMR (400 MHz, DMSO-d$_6$) δ 9.19 (s, 1H), 8.60 (d, J=7.6 Hz, 1H), 7.66 (s, 1H), 7.46-7.42 (m, 2H), 7.24 (s, 1H), 7.19 (d, J=8.8 Hz, 1H), 5.14 (q, J=12.4, 5.6 Hz, 2H), 4.95 (s, 2H), 4.33 (t, J=6.8 Hz, 1H), 2.30 (s, 3H), 2.16-2.11 (m, 1H), 0.91 (d, J=6.4 Hz, 6H); ESI-MS m/z 400 [M+H]$^+$; HPLC purity: 99.53% (220 nm), 100% (254 nm).

Example 130. 4-(Morpholinomethyl)benzyl (1-hydroxy-7-methyl-1,3-dihydrobenzo[c][1,2]oxaborole-6-carbonyl)-L-valinate (6-130)

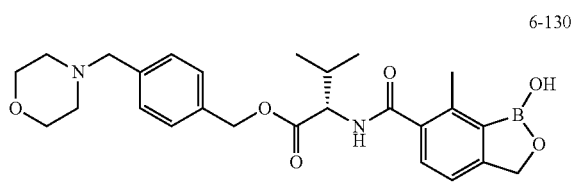

6-130

This compound was prepared from (4-(morpholinomethyl)phenyl)methanol, N-BOC-(S)-valine and Acid-14 in a similar manner to Example 1. $^1$H NMR (400 MHz, DMSO-$d_6$) δ 9.06 (br s, 1H), 8.62 (d, J=6.8 Hz, 1H), 7.61 (d, J=7.2 Hz, 2H), 7.50 (d, J=7.2 Hz, 2H), 7.36 (d, J=7.2 Hz, 1H), 7.25 (d, J=7.2 Hz, 1H), 5.23 (s, 2H), 4.98 (s, 2H), 4.35 (s, 3H), 3.94 (d, J=11.6 Hz, 2H), 3.75 (t, J=11.2 Hz, 2H), 3.21 (d, J=10.4 Hz, 2H), 3.10 (s, 2H), 2.44 (s, 3H), 2.18 (d, J=6.0 Hz, 1H), 0.97 (s, 6H); ESI-MS m/z 481 [M+H]$^+$; HPLC purity: 100% (220 nm), 100% (254 nm).

Example 131. 4-(Pyrrolidin-1-ylmethyl)benzyl (1-hydroxy-7-methyl-1,3-dihydrobenzo[c][1,2]oxaborole-6-carbonyl)-L-valinate (6-131)

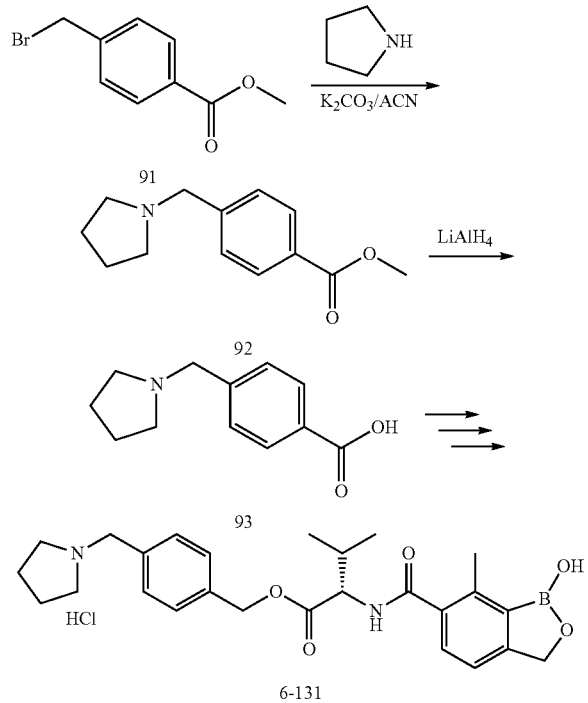

6-131

To a solution of 91 (3.0 g, 13 mmol) and pyrrolidine (1.21 g, 17.0 mmol) in CH$_3$CN (10 mL) was added K$_2$CO$_3$ (5.43 g, 39.0 mmol). The mixture was stirred at 80° C. for 12 h. After filtered, the residue was washed with CH$_3$CN (3 mL) and the combined filtrate was concentrated under reduced pressure to give 92 (2.5 g, 87%) as a colorless oil. $^1$H NMR (400 MHz, CDCl$_3$) δ 7.97 (d, J=7.6 Hz, 2H), 7.39 (d, J=8.0 Hz, 2H), 3.90 (s, 3H), 3.65 (s, 2H), 2.50 (s, 4H), 1.78 (s, 4H).

To a solution of 92 (0.80 g, 3.6 mmol) in THF (50 mL) was added LiAlH$_4$ (208 mg, 5.00 mmol) in portions at 0° C., and then the mixture was stirred at 20° C. for 12 h. The reaction mixture was quenched by saturated sodium potassium tartrate (1 mL) at 0° C., and then filtered. The filtrate was concentrated under reduced pressure to give 93 (0.51 g, crude) as a colorless oil. $^1$H NMR (400 MHz, CDCl$_3$) δ 7.39-7.32 (m, 4H), 4.70 (s, 2H), 3.63 (s, 2H), 2.52 (s, 4H), 1.82-1.79 (m, 4H).

Compound 6-131 was prepared from 93, N-BOC-(S)-valine and Acid-04 in a similar manner to Example 1. $^1$H NMR (400 MHz, DMSO-$d_6$) δ 10.05 (s, 1H), 9.07 (s, 1H), 8.62 (d, J=7.6 Hz, 1H), 7.56 (d, J=8.0 Hz, 2H), 7.49 (d, J=8.2 Hz, 2H), 7.36 (d, J=8.0 Hz, 1H), 7.25 (d, J=7.6 Hz, 1H), 5.23 (s, 2H), 4.98 (s, 2H), 4.38-4.35 (m, 3H), 3.35 (s, 2H), 3.18-3.06 (m, 2H), 2.44 (s, 3H), 2.21-2.15 (m, 1H), 2.04 (m, 2H), 1.89-1.86 (m, 2H), 0.98-0.95 (m, 6H); ESI-MS m/z 465 [M+H]$^+$; HPLC purity: 95.74% (220 nm), 92.57% (254 nm).

Example 132. Cyclopentyl (1-hydroxy-7-methyl-1,3-dihydrobenzo[c][1,2]oxaborole-6-carbonyl)-L-valinate (6-132)

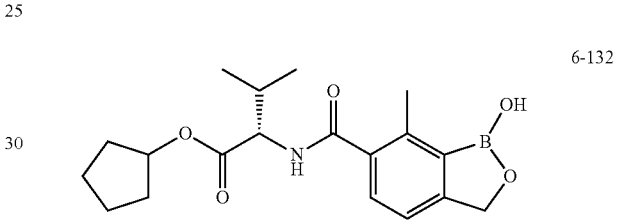

6-132

Compound 6-132 was prepared in a similar manner to Example 107 using bromocyclopentane instead of 2-chloroethyl methyl ether. $^1$H NMR (400 MHz, DMSO-$d_6$) δ 8.96 (s, 1H), 8.49 (d, J=7.2 Hz, 1H), 7.38 (d, J=7.6 Hz, 1H), 7.26 (d, J=7.6 Hz, 1H), 5.15 (s, 1H), 4.99 (s, 2H), 4.27 (t, J=7.2 Hz, 1H), 2.51 (s, 3H), 2.18-2.10 (m, 1H), 1.85 (d, J=4.8 Hz, 2H), 1.68-1.58 (m, 6H), 0.96 (d, J=6.4 Hz, 6H); ESI-MS m/z 360 [M+H]$^+$; HPLC purity: 99.59% (220 nm), 97.74% (254 nm).

Example 133. Cyclohexyl (1-hydroxy-7-methyl-1,3-dihydrobenzo[c][1,2]oxaborole-6-carbonyl)-L-valinate (6-133)

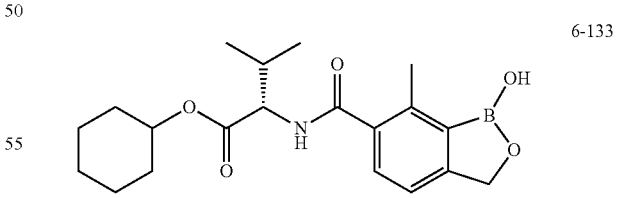

6-133

Compound 6-133 was prepared in a similar manner to Example 107 using bromocyclohexane instead of 2-chloroethyl methyl ether. $^1$H NMR (400 MHz, DMSO-$d_6$) δ 9.04 (s, 1H), 8.48 (d, J=8.0 Hz, 1H), 7.36 (d, J=8.0 Hz, 1H), 7.24 (d, J=8.0 Hz, 1H), 4.97 (s, 2H), 4.75 (s, 1H), 4.28 (t, J=6.0 Hz, 1H), 2.48 (s, 3H), 2.15-2.13 (m, 1H), 1.78 (s, 2H), 1.68 (s, 2H), 1.45-1.31 (m, 6H), 0.95 (d, J=4.0 Hz, 6H); ESI-MS m/z 374 [M+H]$^+$; HPLC purity: 99.57% (220 nm), 100% (254 nm).

Example 134. Tetrahydro-2H-pyran-4-yl (1-hydroxy-7-methyl-1,3-dihydrobenzo[c][1,2]oxaborole-6-carbonyl)-L-valinate (6-134)

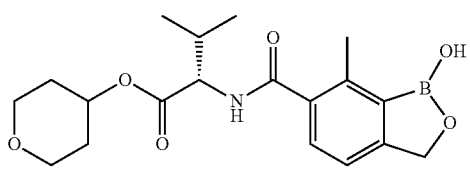

6-134

This compound was prepared from tetrahydro-2H-pyran-4-ol, N-BOC-(S)-valine and Acid-04 in a similar manner to Example 1. $^1$H NMR (400 MHz, DMSO-$d_6$) δ 9.04 (s, 1H), 8.53 (d, J=8.0 Hz, 1H), 7.36 (d, J=8.0 Hz, 1H), 7.24 (d, J=8.0 Hz, 1H), 4.97-4.94 (m, 3H), 4.29 (t, J=8.0 Hz 1H), 3.82-3.78 (m, 2H), 3.49-3.36 (m, 2H), 2.48 (s, 3H), 2.18-2.13 (m, 1H), 1.88-1.85 (m, 2H), 1.57-1.53 (m, 2H), 0.96 (d, J=4.0 Hz, 6H); ESI-MS m/z 376 [M+H]$^+$; HPLC purity: 98.56% (220 nm), 98.51% (254 nm).

Example 135. Oxetan-3-yl (1-hydroxy-7-methyl-1,3-dihydrobenzo[c][1,2]oxaborole-6-carbonyl)-L-valinate (6-135)

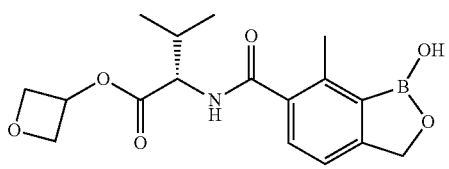

6-135

This compound was prepared from oxetan-3-ol, N-BOC-(S)-valine and Acid-04 in a similar manner to Example 1. $^1$H NMR (400 MHz, DMSO-$d_6$) δ 9.05 (s, 1H), 8.62 (d, J=8.0 Hz, 1H), 7.38 (d, J=8.0 Hz, 1H), 7.25 (d, J=8.0 Hz, 1H), 5.46-5.43 (m, 1H), 4.98 (s, 2H), 4.83 (t, J=8.0 Hz, 2H), 4.52-4.47 (m, 2H), 4.32 (t, J=4.0 Hz, 1H), 2.32 (s, 3H), 2.20-2.15 (m, 1H), 0.99 (dd, J=4.0 Hz, 8.0 Hz, 6H); ESI-MS m/z 348 [M+H]$^+$; HPLC purity: 95.11% (220 nm), 96.76% (254 nm).

Example 136. Cyclobutyl (1-hydroxy-7-methyl-1,3-dihydrobenzo[c][1,2]oxaborole-6-carbonyl)-L-valinate (6-136)

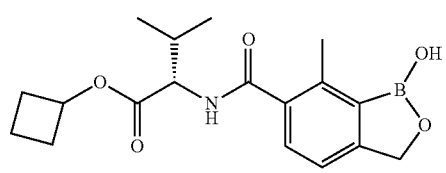

6-136

This compound was prepared from cyclobutanol, N-BOC-(S)-valine and Acid-04 in a similar manner to Example 1. $^1$H NMR (400 MHz, DMSO-$d_6$) δ 9.05 (br s, 1H), 8.51 (d, J=7.2 Hz, 1H), 7.36 (d, J=7.6 Hz, 1H), 7.24 (d, J=7.6 Hz, 1H), 4.97-4.92 (m, 3H), 4.25 (t, J=7.2 Hz, 1H), 2.48 (s, 3H), 2.30 (d, J=8.8 Hz, 2H), 2.14-2.12 (m, 1H), 2.07-2.00 (m, 2H), 1.76 (q, J=10.0 Hz, 1H), 1.63-1.58 (m, 1H), 0.95 (d, J=6.4 Hz, 6H); ESI-MS m/z 346 [M+H]$^+$; HPLC purity: 99.96% (220 nm), 100% (254 nm).

Example 137. Quinazolin-2-ylmethyl (1-hydroxy-7-methyl-1,3-dihydrobenzo[c][1,2]oxaborole-6-carbonyl)-L-valinate (6-137)

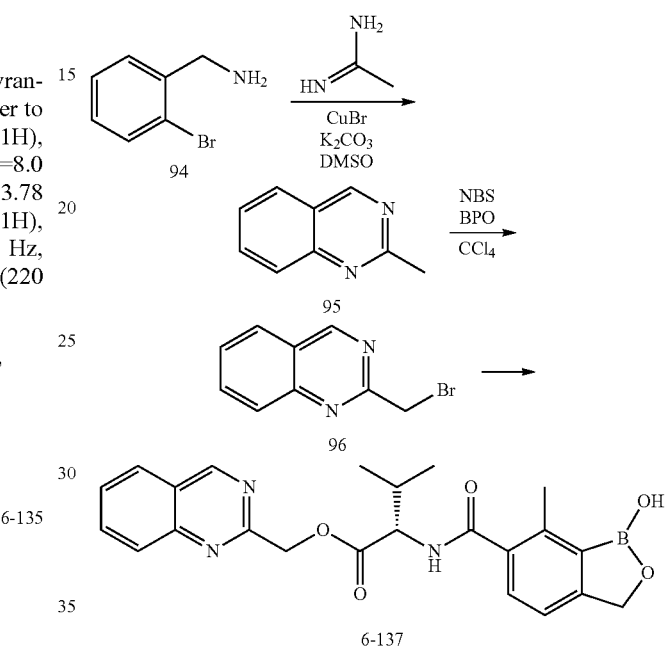

A mixture of 94 (5.00 g, 26.9 mmol), acetamidine (3.12 g, 53.8 mmol), CuBr (385 mg, 2.69 mmol) and K$_2$CO$_3$ (11.1 g, 80.6 mmol) in DMSO (50 mL) was degassed and purged with N$_2$ for 3 times, and then the mixture was stirred at 100° C. for 14 h under N$_2$ atmosphere and then under air for 2 h at 25° C. The reaction was quenched by water (50 mL) slowly and then extracted with EtOAc (40 mL×3). The combined organic phase was washed with brine (20 mL×2), dried over anhydrous Na$_2$SO$_4$, filtered and concentrated in vacuo. The residue was purified by silica gel column chromatography (petroleum ether/ethyl acetate=5:1) to give 95 (2.5 g, 65%) as a yellow oil. $^1$H NMR (400 MHz, CDCl$_3$) δ 9.33 (s, 1H), 7.96 (d, J=8.0 Hz, 1H), 7.90-7.86 (m, 2H) 7.60 (t, J=8.0 Hz, 1H), 2.91 (s, 3H). To a solution of 95 (1.40 g, 9.71 mmol) in CCl$_4$ (10 mL) was added NBS (1.56 g, 8.74 mmol) and BPO (470 mg, 1.94 mmol). The mixture was stirred at 80° C. for 2 h. The reaction was filtered and concentrated in vacuo. The residue was purified by prep. TLC (petroleum ether/ethyl acetate=4:1) to give 96 (150 mg, 6.9%) as a yellow solid. $^1$H NMR (400 MHz, CDCl$_3$) δ 9.46 (s, 1H), 8.05 (d, J=8.0 Hz, 1H), 7.98-7.95 (m, 2H) 7.70 (t, J=8.0 Hz, 1H), 4.80 (s, 2H).

Compound 6-137 was prepared in a similar manner to Example 107 using 96 instead of 2-chloroethyl methyl ether. $^1$H NMR (400 MHz, DMSO-$d_6$) δ 9.63 (s, 1H), 8.58 (d, J=8.0 Hz, 1H), 8.19 (d, J=8.0 Hz, 1H), 8.03 (t, J=4.0 Hz, 1H), 7.94 (d, J=8.0 Hz, 1H), 7.77 (t, J=8.0 Hz, 1H), 7.39 (d, J=8.0 Hz, 1H), 7.23 (d, J=8.0 Hz, 1H), 5.54 (d, J=16.0 Hz, 1H), 5.43 (d, J=16.0 Hz, 1H), 4.97 (s, 2H), 4.53 (t, J=8.0 Hz 1H), 2.47 (s, 3H), 2.38-2.33 (m, 1H), 1.08 (d, J=8.0 Hz, 6H); ESI-MS m/z 434 [M+H]⁺; HPLC purity: 97.45% (220 nm), 95.68% (254 nm).

Example 138. (1H-Imidazol-4-yl)methyl (1-hydroxy-7-methyl-1,3-dihydrobenzo[c][1,2]oxaborole-6-carbonyl)-L-valinate (6-138)

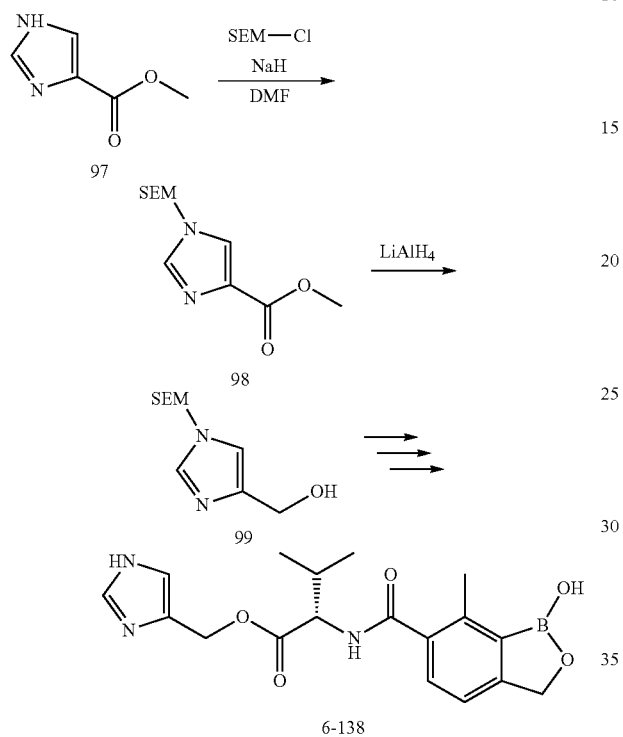

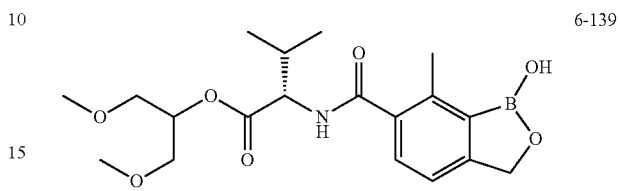

To a solution of 97 (3.00 g, 23.8 mmol) in DMF (5 mL) was added NaH (1.14 g, 28.6 mmol) in portions at 0° C. The mixture was stirred at 0° C. for 1 h. Then SEM-Cl (8.44 mL, 47.6 mmol) was added drop-wise at 0° C. The reaction mixture was stirred at 25° C. for 13 h. The reaction was quenched by sat. aq. NH₄Cl (10 mL) at 0° C. and then extracted with EtOAc (20 mL×3). The combined organic phase was washed with brine (20 mL), dried over anhydrous Na₂SO₄, filtered and concentrated in vacuo. The residue was purified by column chromatography (petroleum ether/ethyl acetate=1:2) to give 98 (2.00 g, yield 33%) as a yellow oil. ¹H NMR (400 MHz, CDCl₃) δ 7.73 (s, 1H), 7.62 (s, 1H), 5.31 (s, 2H), 3.91 (s, 3H), 3.50 (t, J=8.0 Hz, 2H), 0.92 (t, J=8.0 Hz, 2H), −0.01 (s, 9H). To a solution of 98 (2.00 g, 7.80 mmol) in THF (20 mL) was added LiAlH₄ (355 mg, 9.36 mmol) in portions at 0° C. The mixture was stirred at 25° C. for 3 h. The reaction was quenched by sat. aq. potassium sodium tartrate (1 mL) at 0° C., filtered and concentrated in vacuo to give 99 (1.4 g, yield 79%) as a colorless oil. ¹H NMR (400 MHz, CDCl₃) δ 7.56 (s, 1H), 6.99 (s, 1H), 5.23 (s, 2H), 4.61 (s, 2H), 3.48 (t, J=8.0 Hz, 2H), 0.91 (t, J=8.0 Hz, 2H), 0.01 (s, 9H).

Compound 6-138 was prepared from 99 and Acid-04 in a similar manner to Example 108. ¹H NMR (400 MHz, DMSO-d₆) δ 9.15 (s, 1H), 8.60 (d, J=8.0 Hz, 1H), 7.75 (s, 1H), 7.34 (d, J=8.0 Hz, 1H), 7.23 (d, J=8.0 Hz, 1H), 5.28 (d, J=12.0 Hz, 1H), 5.18 (d, J=12.0 Hz, 1H), 4.96 (s, 2H), 4.33 (t, J=8.0 Hz 1H), 2.47 (s, 3H), 2.18-2.13 (m, 1H), 0.92 (dd, J=4.0 Hz, 8.0 Hz, 6H); ESI-MS m/z 372 [M+H]⁺; HPLC purity: 96.31% (220 nm), 99.54% (254 nm).

Example 139. 1,3-Dimethoxypropan-2-yl (1-hydroxy-7-methyl-1,3-dihydrobenzo[c][1,2]oxaborole-6-carbonyl)-L-valinate (6-139)

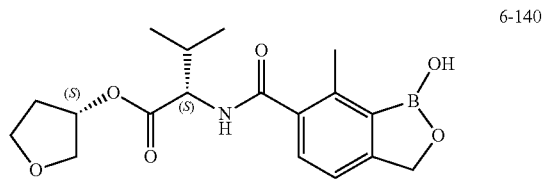

This compound was prepared from 1,3-dimethoxypropan-2-ol, N-BOC-(S)-valine and Acid-04 in a similar manner to Example 1. ¹H NMR (400 MHz, DMSO-d₆) δ 9.03 (s, 1H), 8.51 (d, J=8.0 Hz, 1H), 7.37 (d, J=7.6 Hz, 1H), 7.24 (d, J=7.6 Hz, 1H), 5.12-5.09 (m, 1H), 4.97 (s, 2H), 4.35-4.31 (m, 1H), 3.51-3.46 (m, 4H), 3.25 (d, J=10.0 Hz, 6H), 2.47 (s, 3H), 2.17-2.12 (m, 1H), 0.96 (d, J=6.4 Hz, 6H); ESI-MS m/z 394 [M+H]⁺; HPLC purity: 99.79% (220 nm), 100% (254 nm).

Example 140. (S)-Tetrahydrofuran-3-yl (1-hydroxy-7-methyl-1,3-dihydrobenzo[c][1,2]oxaborole-6-carbonyl)-L-valinate (6-140)

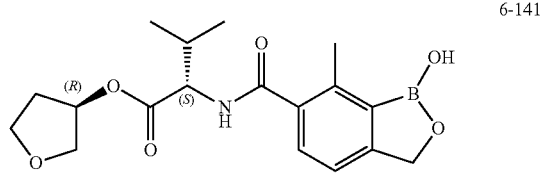

This compound was prepared from (S)-tetrahydrofuran-3-ol, N-BOC-(S)-valine and Acid-04 in a similar manner to Example 1. ¹H NMR (400 MHz, DMSO-d₆) δ 9.04 (br s, 1H), 8.54 (d, J=7.6 Hz, 1H), 7.37 (d, J=7.2 Hz, 1H) 7.25 (d, J=7.6 Hz, 1H), 5.29 (s, 1H), 4.98 (s, 2H), 4.26 (t, J=6.8 Hz, 1H), 3.84-3.67 (m, 4H), 2.48 (s, 3H) 2.21-2.13 (m, 2H), 1.94-1.92 (m, 1H), 0.96 (d, J=6.4 Hz, 6H); ESI-MS m/z 362 [M+H]⁺; HPLC purity: 99.71% (220 nm), 98.22% (254 nm).

Example 141. (R)-Tetrahydrofuran-3-yl (1-hydroxy-7-methyl-1,3-dihydrobenzo[c][1,2]oxaborole-6-carbonyl)-L-valinate (6-141)

This compound was prepared from (R)-tetrahydrofuran-3-ol, N-BOC-(S)-valine and Acid-04 in a similar manner to Example 1. ¹H NMR (400 MHz, DMSO-d₆) δ 9.05 (br s, 1H), 8.54 (d, J=7.6 Hz, 1H), 7.37 (d, J=8.0 Hz, 1H) 7.25 (d, J=8.0 Hz, 1H), 5.29 (t, J=5.2 Hz, 1H) 4.97 (s, 2H), 4.26 (t, J=7.2 Hz, 1H), 3.81-3.72 (m, 4H), 2.47 (s, 3H), 2.19-2.11 (m, 2H), 1.91-1.88 (m, 1H), 0.96 (d, J=6.4 Hz, 6H); ESI-MS m/z 362 [M+H]⁺; HPLC purity: 99.83% (220 nm), 100% (254 nm).

Example 142. 1-Methylpiperidin-4-yl (1-hydroxy-7-methyl-1,3-dihydrobenzo[c][1,2]oxaborole-6-carbonyl)-L-valinate (6-142)

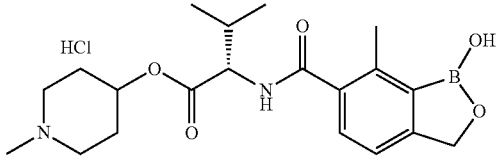

6-142

This compound was prepared from 1-methylpiperidin-4-ol, N-BOC-(S)-valine and Acid-04 in a similar manner to Example 1. ¹H NMR (400 MHz, DMSO-d₆) δ 10.85 (s, 1H), 9.10 (s, 1H), 8.59 (d, J=7.2 Hz, 1H), 7.38 (t, J=7.2 Hz, 1H), 7.49 (q, J=2.8 Hz, 4.8 Hz, 1H), 4.99 (s, 2H), 5.10-4.92 (m, 1H), 4.43-4.24 (m, 1H), 3.43 (d, J=12.4 Hz, 1H), 3.34 (s, 1H), 3.11-3.08 (m, 2H), 2.74-2.71 (m, 3H), 2.49 (s, 3H), 2.15-2.14 (m, 1H), 2.12-1.94 (m, 4H), 0.98 (t, J=6.0 Hz, 6H); ESI-MS m/z 389 [M+H]⁺; HPLC purity: 97.80% (220 nm), 96.87% (254 nm).

Example 143. (1H-Imidazol-2-yl)methyl (1-hydroxy-7-methyl-1,3-dihydrobenzo[c][1,2]oxaborole-6-carbonyl)-L-valinate (6-143)

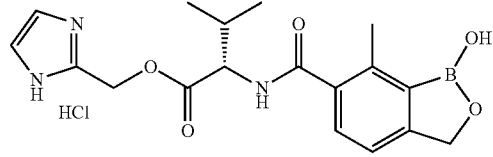

6-143

This compound was prepared from methyl 1H-imidazole-2-carboxylate and Acid-04 in a similar manner to Example 138. ¹H NMR (400 MHz, DMSO-d₆) δ 9.00 (br s, 1H), 8.67 (d, J 6.8 Hz, 1H), 7.73 (s, 2H), 7.36 (d, J=7.6 Hz, 1H), 7.24 (d, J=7.2 Hz, 1H), 5.42 (s, 2H), 4.97 (s, 2H), 4.41 (t, J=6.8 Hz, 1H), 2.42 (s, 3H), 2.23-2.18 (m, 1H), 0.94 (d, J=6.8 Hz, 6H); ESI-MS m/z 372 [M+H]⁺; HPLC purity: 93.06% (220 nm), 90.56% (254 nm).

Example 144. ((R)-2,2-Dimethyl-1,3-dioxolan-4-yl)methyl (1-hydroxy-7-methyl-1,3-dihydrobenzo[c][1,2]oxaborole-6-carbonyl)-L-valinate (6-144)

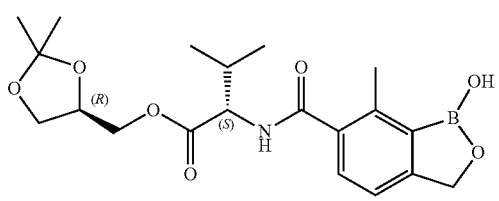

6-144

This compound was prepared from (S)-(2,2-dimethyl-1,3-dioxolan-4-yl)methanol, N-BOC-(S)-valine and Acid-04 in a similar manner to Example 1. ¹H NMR (400 MHz, DMSO-d₆) δ 9.03 (s, 1H), 8.54 (d, J=7.6 Hz, 1H), 7.39 (d, J=8.0 Hz, 1H), 7.25 (d, J=7.6 Hz, 1H), 4.99 (s, 2H), 4.34 (t, J=7.6 Hz, 1H), 4.30-4.27 (m, 1H), 4.26-4.20 (m, 1H), 4.11-4.02 (m, 2H), 3.71 (t, J=7.2 Hz, 1H), 2.49 (s, 3H), 2.19-2.13 (m, 1H), 1.35 (s, 3H), 1.29 (s, 3H), 0.98 (d, J=6.8 Hz, 6H); ESI-MS m/z 406 [M+H]⁺; HPLC purity: 98.83% (220 nm), 99.07% (254 nm).

Example 145. ((S)-2,2-Dimethyl-1,3-dioxolan-4-yl)methyl (1-hydroxy-7-methyl-1,3-dihydrobenzo[c][1,2]oxaborole-6-carbonyl)-L-valinate (6-145)

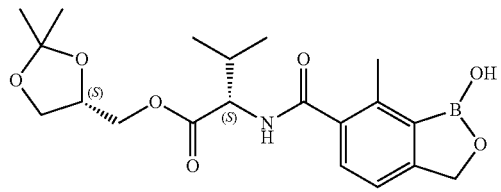

6-145

This compound was prepared from (R)-(2,2-dimethyl-1,3-dioxolan-4-yl)methanol, N-BOC-(S)-valine and Acid-04 in a similar manner to Example 1. ¹H NMR (400 MHz, DMSO-d₆) δ 9.03 (s, 1H), 8.54 (d, J=8.0 Hz, 1H), 7.38 (d, J=8.0 Hz, 1H), 7.24 (d, J=8.0 Hz, 1H), 4.98 (s, 2H), 4.32-4.29 (m, 2H), 4.15-4.12 (m, 2H), 4.10-4.02 (m, 1H), 3.71-3.69 (m, 1H), 2.47 (s, 3H), 2.18-2.13 (m, 1H), 1.34 (s, 3H), 1.28 (s, 3H), 0.96 (d, J=8.0 Hz, 6H); ESI-MS m/z 406 [M+H]⁺; HPLC purity: 98.83% (220 nm), 99.07% (254 nm).

Example 146. Piperidin-4-yl (1-hydroxy-7-methyl-1,3-dihydrobenzo[c][1,2]oxaborole-6-carbonyl)-L-valinate (6-146)

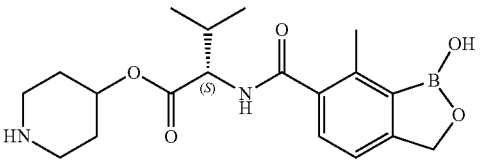

6-146

This compound was prepared from tert-butyl 4-hydroxypiperidine-1-carboxylate, N-Fmoc-(S)-valine and Acid-04 in a similar manner to Example 117. ¹H NMR (400 MHz, DMSO-d₆) δ 8.96 (s, 2H), 8.60 (d, J=8.0 Hz, 1H), 7.37 (d, J=8.0 Hz, 1H), 7.25 (d, J=8.0 Hz, 1H), 5.03-4.99 (m, 1H), 4.98 (s, 2H), 4.30 (t, J=8.0 Hz, 1H), 3.20-3.17 (m, 2H), 3.10-3.08 (m, 2H), 2.48 (s, 3H), 2.17-2.15 (m, 1H), 2.02-2.00 (m, 2H), 1.82-1.80 (m, 2H), 0.96 (d, J=8.0 Hz, 6H); ESI-MS m/z 375 [M+H]⁺; HPLC purity: 98.56% (220 nm), 96.69% (254 nm).

Example 147. (R)-2,3-dihydroxypropyl (1-hydroxy-7-methyl-1,3-dihydrobenzo[c][1,2]oxaborole-6-carbonyl)-L-valinate (6-147)

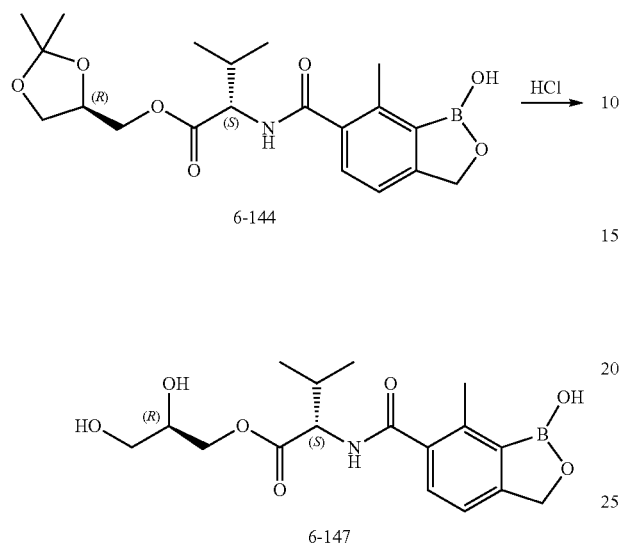

A mixture of 6-144 and 37% HCl (0.5 mL) in DMF (5 mL) was stirred at 25° C. for another 12 h. The mixture was filtered and concentrated in vacuum. The residue was purified by prep. HPLC (column: Luna C8 100×30 mm; liquid phase: water water (0.1% TFA)-ACN; B %: 10%-35%, 12 mins) to give 6-147 (206 mg, 3%) as a white solid. $^1$H NMR (400 MHz, DMSO-d$_6$) δ 9.01 (s, 1H), 8.45 (d, J=8.0 Hz, 1H), 7.34 (d, J=7.6 Hz, 1H), 7.20 (d, J=8.0 Hz, 1H), 4.94 (s, 2H), 4.83-4.75 (m, 1H), 4.64 (s, 1H), 4.34 (t, J=7.2 Hz, 1H), 4.14-4.10 (m, 1H), 3.95-3.92 (m, 1H), 3.65-3.63 (m, 1H), 3.47-3.34 (m, 2H), 2.44 (s, 3H), 2.17-2.09 (m, 1H), 0.92 (t, J=4.4 Hz, 6H); ESI-MS m/z 366 [M+H]$^+$; HPLC purity: 98.56% (220 nm), 96.69% (254 nm).

Example 148. (S)-2,3-dihydroxypropyl (1-hydroxy-7-methyl-1,3-dihydrobenzo[c][1,2]oxaborole-6-carbonyl)-L-valinate (6-148)

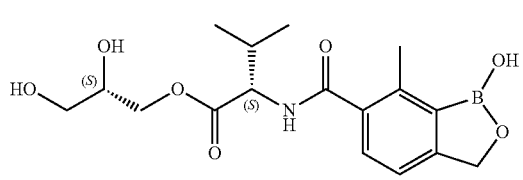

This compound was prepared from 6-145 in a similar manner to Example 147. $^1$H NMR (400 MHz, DMSO-d$_6$) δ 9.02 (s, 1H), 8.47 (d, J=8.0 Hz, 1H), 7.38 (d, J=8.0 Hz, 1H), 7.24 (d, J=8.0 Hz, 1H), 4.97 (s, 2H), 4.39-4.36 (m, 1H), 4.23-4.13 (m, 1H), 4.03-3.99 (m, 1H), 3.69-3.65 (m, 2H), 3.39-3.37 (m, 2H), 2.48 (s, 3H), 2.38-2.33 (m, 1H), 0.97-0.95 (m, 6H); ESI-MS m/z 366 [M+H]$^+$; HPLC purity: 99.66% (220 nm), 99.63% (254 nm).

Example 149. 3-hydroxy-2-(hydroxymethyl)propyl (1-hydroxy-7-methyl-1,3-dihydrobenzo[c][1,2]oxaborole-6-carbonyl)-L-valinate (6-149)

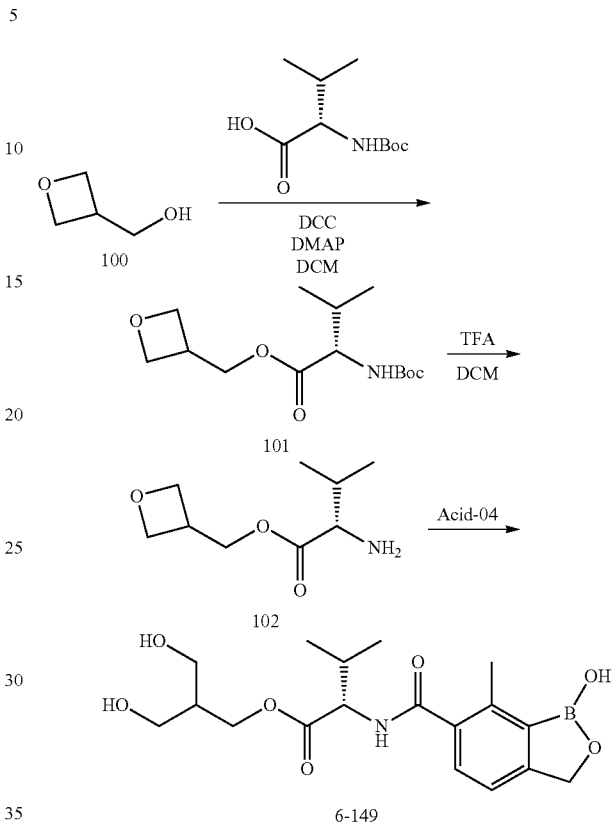

To a solution of 100 (1.06 g, 12.0 mmol) in DCM (20 mL) was added N-Boc-(S)-valine (2.17 g, 9.99 mmol), DCC (2.68 g, 13.0 mmol) and DMAP (122 mg, 0.999 mmol). The mixture was stirred at 25° C. for 14 h. The mixture was filtered and concentrated in vacuo. The residue was purified by column chromatography (petroleum ether/ethyl acetate=5:1) to give 101 (2.1 g, 73%) as a colorless oil. $^1$H NMR (400 MHz, CDCl$_3$) δ 4.99-4.83 (m, 1H), 4.81-4.80 (m, 2H), 4.48-4.46 (m, 2H), 4.40-4.37 (m, 2H), 4.14-4.12 (m, 1H), 3.36-3.29 (m, 1H), 2.14-2.11 (m, 1H), 1.45 (s, 9H), 0.97 (d, J=8.0 Hz, 3H), 0.90 (d, J=8.0 Hz, 3H). To a solution of 101 (1.00 g, 3.48 mmol) in DCM (15 mL) was added TFA (5 mL). The mixture was stirred at 25° C. for 2 h. The mixture was concentrated in vacuum to give 102 (800 mg, 76%) as a colorless oil.

$^1$H NMR (400 MHz, CDCl$_3$) δ 4.40-4.55 (m, 1H), 4.24-4.33 (m, 1H), 3.95-4.03 (m, 1H), 3.73-3.86 (m, 1H), 2.32-2.44 (m, 1H), 1.08 (t, J=7.5 Hz, 6H). To a solution of Acid-04 (200 mg, 1.04 mmol) in DMF (3 mL) was added HATU (474 mg, 1.25 mmol) and NMM (315 mg, 3.12 mmol). The mixture was stirred at 25° C. for 0.5 h. Then 102 (344 mg, 1.14 mmol) was added in one portion. The mixture was stirred at 25° C. for 12 h. The mixture was purified by prep. HPLC (column: Luna C8 100×30 mm; liquid phase: water (0.1% TFA)-ACN; B %: 18%-48%, 12 mins) to give 6-149 (101 mg, 26%) as a white solid. $^1$H NMR (400 MHz, DMSO-d$_6$) δ 9.04 (s, 1H), 8.51 (d, J=8.0 Hz, 1H), 7.37 (d, J=8.0 Hz, 1H), 7.24 (d, J=8.0 Hz, 1H), 4.97 (s, 2H), 4.51 (t, J=4.0 Hz, 2H), 4.32 (t, J=8.0 Hz 1H), 4.10-4.05 (m, 2H), 3.47-3.42 (m, 4H), 2.47 (s, 3H), 1.88-1.85 (m, 1H), 2.23-

2.21 (m, 1H), 0.95 (d, J=8.0 Hz, 6H); ESI-MS m/z 380 [M+H]⁺; HPLC purity: 99.75% (220 nm), 100% (254 nm).

Example 150. Oxetan-3-ylmethyl (1-hydroxy-7-methyl-1,3-dihydrobenzo[c][1,2]oxaborole-6-carbonyl)-L-valinate (6-150)

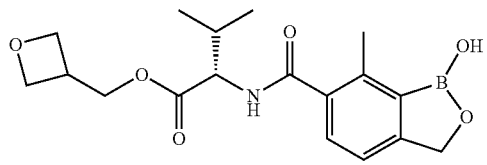

6-150

This compound was prepared from oxetan-3-ylmethanol, N-Fmoc-(S)-valine and Acid-04 in a similar manner to Example 117. ¹H NMR (400 MHz, DMSO-d₆) δ 9.05 (s, 1H), 8.55 (d, J=8.0 Hz, 1H), 7.37 (d, J=8.0 Hz, 1H), 7.25 (d, J=8.0 Hz, 1H), 4.98 (s, 2H), 4.64-4.38 (m, 2H), 4.37-4.30 (m, 5H), 3.30-3.27 (m, 1H), 2.47 (s, 3H), 2.17-2.12 (m, 1H), 0.96 (dd, J=4.0 Hz, 8.0 Hz, 6H); ESI-MS m/z 362 [M+H]⁺; HPLC purity: 96.41% (220 nm), 97.05% (254 nm).

Example 151. 2,2,2-Trifluoroethyl (1-hydroxy-7-methyl-1,3-dihydrobenzo[c][1,2]oxaborole-6-carbonyl)-L-valinate (6-151)

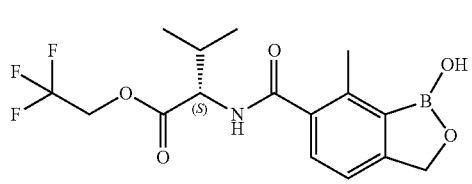

6-151

This compound was prepared from 2,2,2-trifluoroethan-1-ol, N-Fmoc-(S)-valine and Acid-04 in a similar manner to Example 117. ¹H NMR (400 MHz, DMSO-d₆) δ 9.05 (s, 1H), 8.55 (d, J=8.0 Hz, 1H), 7.37 (d, J=8.0 Hz, 1H), 7.25 (d, J=8.0 Hz, 1H), 4.98 (s, 2H), 4.64-4.38 (m, 2H), 4.37-4.30 (m, 5H), 3.30-3.27 (m, 1H), 2.47 (s, 3H), 2.17-2.12 (m, 1H), 0.96 (dd, J=4.0 Hz, 8.0 Hz, 6H); ESI-MS m/z 362 [M+H]⁺; HPLC purity: 96.41% (220 nm), 97.05% (254 nm).

Example 152. (4-(Methoxymethyl)tetrahydro-2H-pyran-4-yl)methyl (1-hydroxy-7-methyl-1,3-dihydrobenzo[c][1,2]oxaborole-6-carbonyl)-L-valinate (6-152)

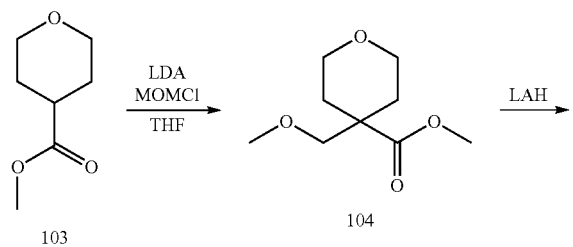

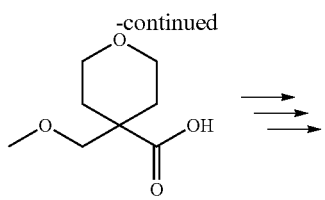

105

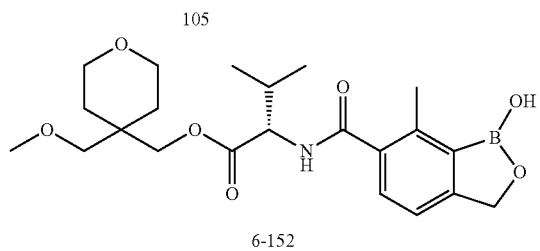

6-152

To a solution of 103 (5.00 g, 34.7 mmol) in THF (50 mL) was added LDA (2 M, 17.3 mL) at −78° C. The mixture was stirred at 0° C. for 0.5 h. Then MOMCl (4.19 g, 52.0 mmol) was added in one portion at −78° C. The mixture was stirred at 25° C. for 1 h. The reaction was quenched with water (20 mL) slowly and then extracted with EtOAc (20 mL×3). The combined organic phase was washed with brine (20 mL), dried over anhydrous Na₂SO₄, filtered and concentrated in vacuo to give 104 (5.6 g, crude) as a yellow oil. ¹H NMR (400 MHz, CDCl₃) δ 3.76-3.69 (m, 2H), 3.67 (s, 3H), 3.42-3.40 (m, 2H), 3.39 (s, 2H), 3.24 (s, 3H), 2.01-1.98 (m, 2H), 1.55-1.48 (m, 2H). To a solution of 104 (2.00 g, 10.6 mmol) in THF (20 mL) was added LiAlH₄ (807 mg, 21.3 mmol) in portions at 0° C. The mixture was stirred at 25° C. for 12 hours. The mixture was cooled to 0° C. and quenched by saturated solution of potassium sodium tartrate (3 mL), the precipitate formed was collected, filtered and concentrated in vacuo to give crude 105 (1.2 g) as a colorless oil and used in the next step without further purification. ¹H NMR (400 MHz, CDCl₃) δ 3.67-3.64 (m, 6H), 3.40 (s, 2H), 3.35 (s, 3H), 1.53-1.48 (m, 4H).

Compound 6-152 was prepared from 105, N-Fmoc-(S)-valine and Acid-04 in a similar manner to Example 117. ¹H NMR (400 MHz, DMSO-d₆) δ 9.04 (s, 1H), 8.54 (d, J=8.0 Hz, 1H), 7.37 (d, J=8.0 Hz, 1H), 7.25 (d, J=8.0 Hz, 1H), 4.97 (s, 2H), 4.34 (t, J=8.0 Hz, 1H), 4.04 (q, J=8.0 Hz, 2H), 3.56 (t, J=8.0 Hz, 4H), 3.30 (s, 2H), 3.24 (s, 2H), 2.47 (s, 3H), 2.16-2.13 (m, 1H), 1.45 (s, 4H), 0.96 (d, J=8.0 Hz, 6H); ESI-MS m/z 434 [M+H]⁺;

HPLC purity: 97.28% (220 nm), 97.90% (254 nm).

Example 153. 2,2,3,3,3-Pentafluoropropyl (1-hydroxy-7-methyl-1,3-dihydrobenzo[c][1,2]oxaborole-6-carbonyl)-L-valinate (6-153)

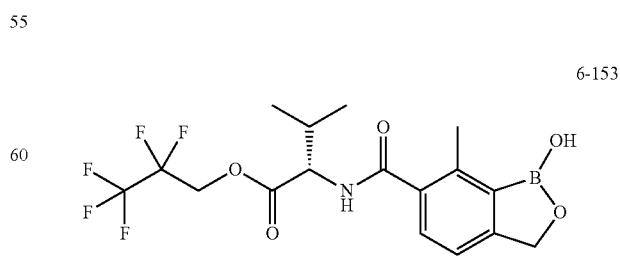

6-153

This compound was prepared from 2,2,3,3,3-pentafluoropropan-1-ol, N-Fmoc-(S)-valine and Acid-04 in a similar manner to Example 117. ¹H NMR (400 MHz, DMSO-d₆) δ 9.05 (s, 1H), 8.68 (d, J=7.2 Hz, 1H), 7.37 (d, J=8.0 Hz, 1H), 7.25 (d, J=8.0 Hz, 1H), 4.98 (s, 2H), 4.93-4.82 (m, 2H), 4.40 (t, J=7.2 Hz, 1H), 2.47 (s, 3H), 2.20-2.13 (m, 1H), 0.98 (dd, J=6.4 Hz 2.4 Hz, 6H); ESI-MS m/z 424 [M+H]⁺; HPLC purity: 99.71% (220 nm), 100% (254 nm).

Example 154. (4,4-Difluorocyclohexyl)methyl (1-hydroxy-7-methyl-1,3-dihydrobenzo[c][1,2]oxaborole-6-carbonyl)-L-valinate (6-154)

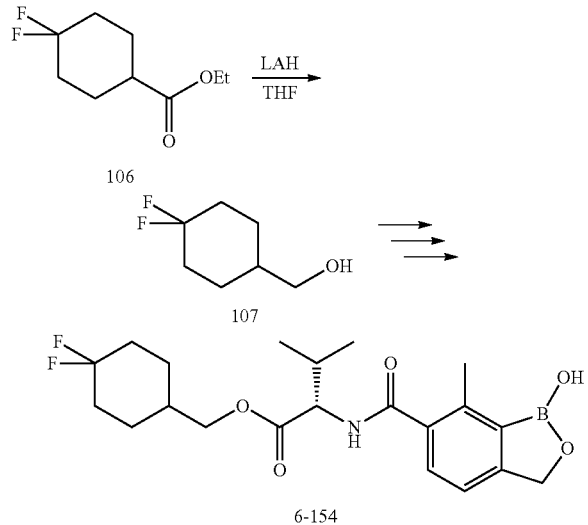

To a solution of 106 (4.00 g, 20.8 mmol) in THF (40 mL) was added LiAlH₄ (1.18 g, 31.2 mmol) in portions at 0° C. The mixture was stirred at 25° C. for 4 h. The mixture was cooled to 0° C. and quenched by saturated solution of potassium sodium tartrate (3 mL) the precipitate formed was collected, filtered and concentrated in vacuo to give 107 (2.6 g, 83%) as a colorless oil. ¹H NMR (400 MHz, CDCl₃) δ 3.45 (J=4.0 Hz, 2H), 2.07-2.03 (m, 2H), 2.01-1.83 (m, 2H), 1.82-1.79 (m, 2H), 1.72-1.64 (m, 1H), 1.28-1.24 (m, 2H).

Compound 6-154 was prepared from 107, N-Fmoc-(S)-valine and Acid-04 in a similar manner to Example 117. ¹H NMR (400 MHz, DMSO-d₆) δ 9.03 (s, 1H), 8.53 (d, J=8.0 Hz, 1H), 7.36 (d, J=8.0 Hz, 1H), 7.24 (d, J=8.0 Hz, 1H), 4.97 (s, 2H), 4.31 (t, J=8.0 Hz, 1H), 3.99 (d, J=8.0 Hz, 2H), 2.47 (s, 3H), 2.17-2.11 (m, 1H), 2.07-2.01 (m, 2H), 1.85-1.79 (m, 5H), 1.28-1.25 (m, 2H), 0.98 (d, J=4.0 Hz, 3H), 0.94 (d, J=4.0 Hz, 3H); ESI-MS m/z 424 [M+H]⁺; HPLC purity: 96.95% (220 nm).

Example 155. 4,4-Difluorocyclohexyl (1-hydroxy-7-methyl-1,3-dihydrobenzo[c][1,2]oxaborole-6-carbonyl)-L-valinate (6-155)

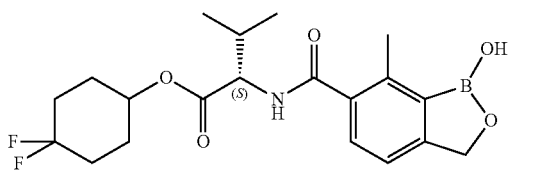

This compound was prepared from 4,4-difluorocyclohexan-1-ol, N-Fmoc-(S)-valine and Acid-04 in a similar manner to Example 117. ¹H NMR (400 MHz, DMSO-d₆) δ 9.04 (s, 1H), 8.56 (d, J=8.0 Hz, 1H), 7.36 (d, J=8.0 Hz, 1H), 7.25 (d, J=8.0 Hz, 1H), 4.97 (s, 3H), 4.30 (t, J=8.0 Hz, 1H), 2.47 (s, 3H), 2.16-2.13 (m, 1H), 2.07-1.99 (m, 4H), 1.85-1.76 (m, 4H), 0.96 (d, J=8.0 Hz, 6H); ESI-MS m/z 410 [M+H]⁺; HPLC purity: 99.28% (220 nm), 99.20% (254 nm).

Example 156. 1,1,1,3,3,3-Hexafluoropropan-2-yl (1-hydroxy-7-methyl-1,3-dihydrobenzo[c][1,2]oxaborole-6-carbonyl)-L-valinate (6-156)

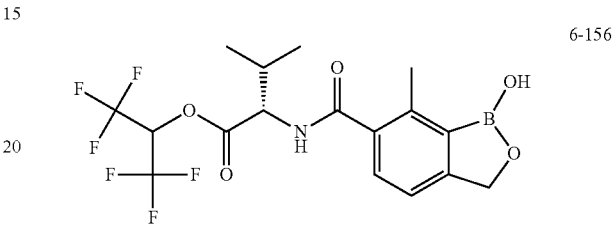

This compound was prepared from 1,1,1,3,3,3-hexafluoropropan-2-ol, N-Fmoc-(S)-valine and Acid-04 in a similar manner to Example 117. ¹H NMR (400 MHz, DMSO-d₆) δ 9.06 (s, 1H), 8.84 (d, J=8.0 Hz, 1H), 7.36 (d, J=8.0 Hz, 1H), 7.27 (d, J=8.0 Hz, 1H), 6.93-6.86 (m, 1H), 4.98 (s, 2H), 4.42 (t, J=8.0 Hz, 1H), 2.49 (s, 3H), 2.20-2.07 (m, 1H), 1.00 (q, J=8.0 Hz, 6H); ESI-MS m/z 442 [M+H]⁺; HPLC purity: 96.04% (220 nm), 93.40% (1,4-dioxepan-6-yl)methyl (1-hydroxy-7-methyl-1,3-dihydrobenzo[c][1,2]oxaborole-6-carbonyl)-L-valinate (254 nm).

Example 157. (1,4-Dioxepan-6-yl)methyl (1-hydroxy-7-methyl-1,3-dihydrobenzo[c][1,2]oxaborole-6-carbonyl)-L-valinate (6-157)

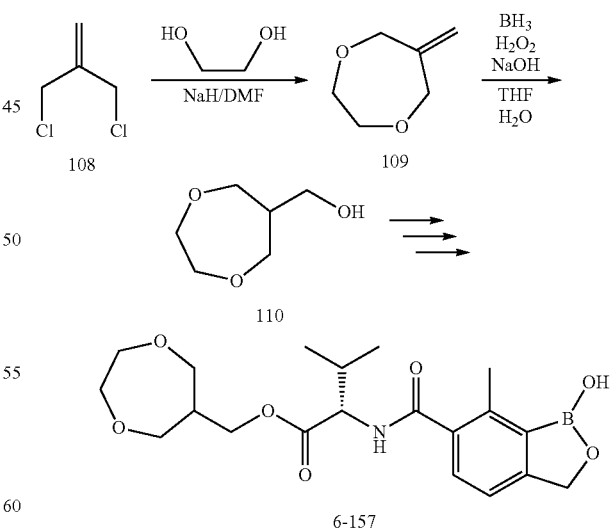

A mixture of ethylene glycol (6.46 g, 104 mmol) and NaH (10.4 g, 260 mmol, 60% purity) in DMF (50 mL) was stirred at 0° C. for 0.5 h. Then 108 (13.00 g, 104 mmol) was added to the mixture and stirred at 15° C. for 2.5 h. The reaction mixture was diluted with H₂O (100 mL) and extracted with MTBE (50 mL×2). The combined organic layers were washed with brine (30 mL×2), dried over Na$_2$SO$_4$, filtered and concentrated under reduced pressure to give 109 (8.0 g, crude, yellow oil) to be used in the next step without further purification.

To a solution of 109 (8.00 g, 70.1 mmol) in THF (50 mL) was added BH$_3$·Me$_2$S (10 M, 7.7 mL). The mixture was stirred at 0° C. for 1 h. Then H$_2$O$_2$ (23.8 g, 210 mmol, 30% purity) was added dropwise to the reaction mixture, an aqueous NaOH (1 M, 210 mL) were added under ice-cooling, and the mixture was stirred at 0° C. for 1 h. The mixture was extracted with DCM/isopropanol (6/1, 50 mL×2). The organic layer was washed with saturated brine (50 mL) and dried over Na$_2$SO$_4$, and the solvent was evaporated under reduced pressure to give 110 (1.20 g, crude) as a pale yellow oil.

Compound 6-157 was prepared from 110, N-Fmoc-(S)-valine and Acid-04 in a similar manner to Example 117. $^1$H NMR (400 MHz, DMSO-d$_6$) δ 8.53 (d, J=7.6 Hz, 1H), 7.37 (d, J=8.0 Hz, 1H), 7.25 (d, J=8.0 Hz, 1H), 4.97 (s, 2H), 4.30 (t, J=7.2 Hz, 1H), 4.05-4.03 (m, 2H), 3.82 (dd, J=12.4, 5.2 Hz, 2H), 3.64-3.61 (m, 6H), 2.47 (s, 3H), 2.31-2.28 (m, 1H), 2.18-2.11 (m, 1H), 0.95 (dd, J=6.8, 2.4 Hz, 6H); ESI-MS m/z 406 [M+H]$^+$; HPLC purity: 99.36% (220 nm), 99.47% (254 nm).

Example 158. (3-(Methoxymethyl)oxetan-3-yl) methyl (1-hydroxy-7-methyl-1,3-dihydrobenzo[c][1,2]oxaborole-6-carbonyl)-L-valinate (6-158)

Compound 6-158 was prepared from 113, N-Fmoc-(S)-valine and Acid-04 in a similar manner to Example 117. $^1$H NMR (400 MHz, DMSO-d$_6$) δ 9.04 (s, 1H), 8.56 (d, J=8.0 Hz, 1H), 7.37 (d, J=8.0 Hz, 1H), 7.25 (d, J=7.6 Hz, 1H), 4.97 (s, 2H), 4.39-4.33 (m, 5H), 4.28 (s, 2H), 3.56 (s, 2H), 3.30 (s, 3H), 2.47 (s, 3H), 2.20-2.12 (m, 1H), 0.96 (d, J=6.4 Hz, 6H); ESI-MS m/z 406 [M+H]$^+$; HPLC purity: 100% (220 nm), 100% (254 nm).

Example 159. (2-(Trifluoromethyl)pyrimidin-5-yl) methyl (1-hydroxy-7-methyl-1,3-dihydrobenzo[c][1,2]oxaborole-6-carbonyl)-L-valinate (6-159)

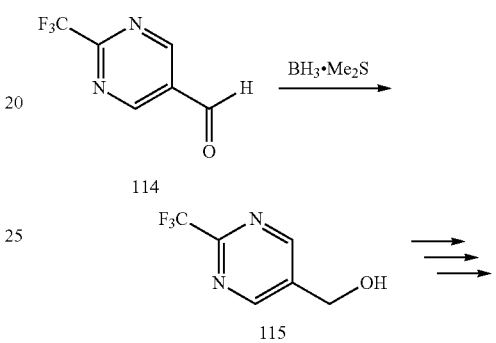

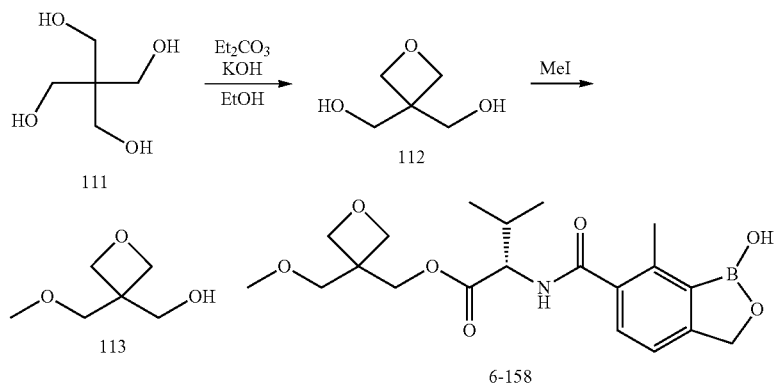

A mixture of 111 (100 g, 734 mmol), diethyl carbonate (104 g, 881 mmol) and KOH (412 mg, 7.34 mmol) in EtOH (25 mL) was degassed and purged with N$_2$ for 3 times, and then the mixture was stirred at 140° C. for 12 h under N$_2$ atmosphere. After EtOH and diethyl carbonate was removed by distillation, the mixture was purified by distillation under reduced pressure (0.019 mbar) to give 112 (20.0 g, 23%) as a white gum. $^1$H NMR (400 MHz, DMSO-d$_6$) δ 4.76 (br s, 1H), 4.27 (s, 4H), 3.54 (s, 4H). To a solution of 112 (5.00 g, 42.3 mmol) and NaOH (1.69 g, 42.3 mmol) in DMF (20 mL) was added MeI (5.41 g, 38.1 mmol) dropwise at 0° C. The mixture was stirred at 15° C. for 12 h. DMF was evaporated under reduced pressure, the reaction mixture was diluted with H$_2$O (50 mL) and extracted with EtOAc (30 mL×2). The combined organic layers were washed with brine (20 mL×2), dried over Na$_2$SO$_4$, filtered and concentrated under reduced pressure to give 113 (1.00 g, crude, brown oil) to be used in the next step without further purification.

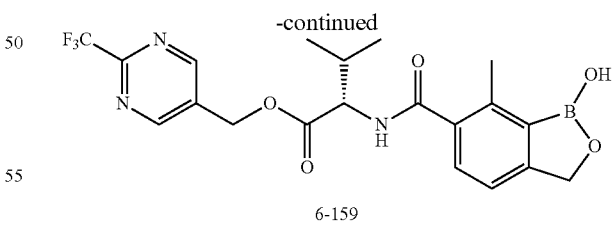

To a solution of 114 (500 mg, 2.84 mmol) in THF (10 mL) was added BH$_3$·Me$_2$S (10 M, 2.84 mL) at 0° C. The mixture was stirred at 0° C. for 5 h. The reaction mixture was quenched by addition MeOH (5 mL) at 0° C., and then concentrated under reduced pressure to give a residue. The crude 115 (500 mg, white solid) was used in the next step with further purification.

Compound 6-159 was prepared from 115, N-BOC-(S)-valine and Acid-04 in a similar manner to Example 1. $^1$H NMR (400 MHz, DMSO-d$_6$) δ 9.14 (s, 2H), 9.05 (br s, 1H), 8.66 (d, J=7.6 Hz, 1H), 7.36 (d, J=7.2 Hz, 1H), 7.25 (d, J=7.6 Hz, 1H), 5.42-5.36 (m, 2H), 4.98 (s, 2H), 4.39 (t, J=7.0 Hz, 1H), 2.41 (s, 3H), 2.22-2.17 (m, 1H), 0.98 (d, J=6.4 Hz, 6H); ESI-MS m/z 452 [M+H]$^+$; HPLC purity: 98.44% (220 nm), 97.67% (254 nm).

Example 160. (2-(Trifluoromethyl)pyrimidin-4-yl) methyl (1-hydroxy-7-methyl-1,3-dihydrobenzo[c][1,2]oxaborole-6-carbonyl)-L-valinate (6-160)

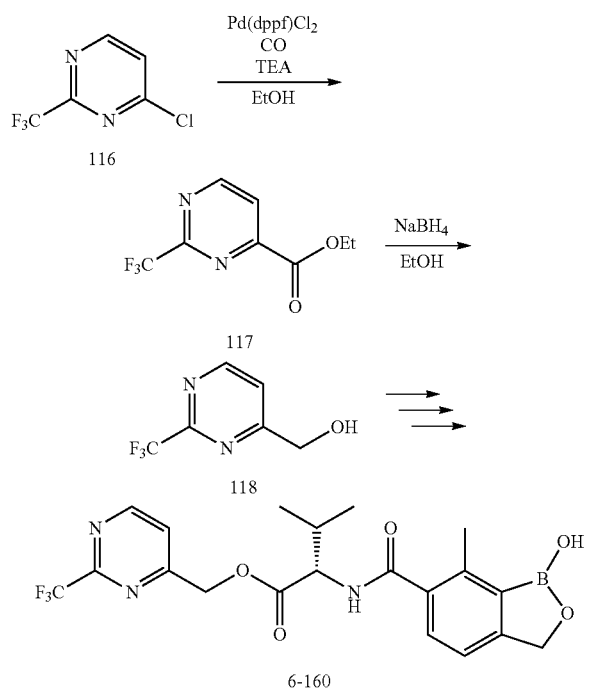

To a solution of 116 (2.00 g, 11.0 mmol) in EtOH (50 mL) was added TEA (4.56 mL, 32.9 mmol) and Pd(dppf)Cl$_2$ (802 mg, 1.10 mmol). The suspension was degassed under vacuum and purged with CO several times. The mixture was stirred under CO (50 psi) atmosphere at 60° C. for 16 h. The reaction mixture was filtered and the filtrate was concentrated. The residue was purified via silica gel column chromatography (petroleum ether/ethyl acetate=30:1) to give 117 (600 mg, 25%) as a white solid. $^1$H NMR (400 MHz, CDCl$_3$) δ 9.16 (d, J=4.0 Hz, 1H), 8.19 (d, J=4.0 Hz, 1H), 4.54 (q, J=8.0 Hz, 2H), 1.47 (t, J=8.0 Hz, 3H). To a solution of 117 (700 mg, 3.18 mmol) in THF (5 mL) and EtOH (0.5 mL) was added NaBH$_4$ (241 mg, 6.36 mmol) at 0° C. The mixture was stirred at 0° C. for 2 h. The reaction was quenched with water (2 mL) slowly at 0° C. and then extracted with EtOAc (5 mL×3). The combined organic phase was washed with brine (5 mL), dried over anhydrous Na$_2$SO$_4$, filtered and concentrated in vacuo to give 118 (500 mg, yield 88%) as a colorless oil. $^1$H NMR (400 MHz, CDCl$_3$) δ 8.90 (d, J=4.0 Hz, 1H), 7.63 (d, J=4.0 Hz, 1H), 4.90 (s, 2H).

Compound 6-160 was prepared from 117, N-BOC-(S)-valine and Acid-04 in a similar manner to Example 1. $^1$H NMR (400 MHz, DMSO-d$_6$) δ 9.10 (d, J=8.0 Hz, 1H), 9.04 (s, 1H), 8.69 (d, J=8.0 Hz, 1H), 7.93 (d, J=8.0 Hz, 1H), 7.38 (d, J=8.0 Hz, 1H), 7.25 (d, J=8.0 Hz, 1H), 5.40 (s, 2H), 4.97 (s, 2H), 4.44 (t, J=8.0 Hz, 1H), 2.45 (s, 3H), 2.26-2.07 (m, 1H), 1.01 (dd, J=8.0 Hz, 4.0 Hz, 6H); ESI-MS m/z 452 [M+H]$^+$; HPLC purity: 99.93% (220 nm), 99.54% (254 nm).

Example 161. (6-(trifluoromethyl)pyrimidin-4-yl) methyl (1-hydroxy-7-methyl-1,3-dihydrobenzo[c][1,2]oxaborole-6-carbonyl)-L-valinate (6-161)

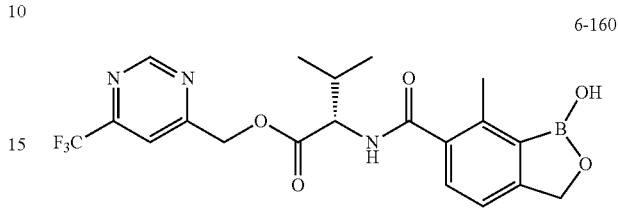

This compound was prepared in a similar manner to Example 160 using 4-chloro-6-(trifluoromethyl)pyrimidine instead of 116. $^1$H NMR (400 MHz, DMSO-d$_6$) δ 9.43 (s, 1H), 9.04 (s, 1H), 8.72 (d, J=7.2 Hz, 1H), 8.12 (s, 1H), 7.39 (d, J=8.0 Hz, 1H), 7.24 (d, J=7.6 Hz, 1H), 5.47-5.37 (m, 2H), 4.97 (s, 2H), 4.43 (t, J=7.2 Hz, 1H), 2.44 (s, 3H), 2.23-2.19 (m, 1H), 1.01 (dd, J=6.8, 3.2 Hz, 6H); ESI-MS m/z 452 [M+H]$^+$; HPLC purity: 99.09% (220 nm), 97.38% (254 nm).

Example 162. (6-(Trifluoromethyl)pyrimidin-4-yl) methyl (1-hydroxy-7-methyl-1,3-dihydrobenzo[c][1,2]oxaborole-6-carbonyl)-L-valinate (6-162)

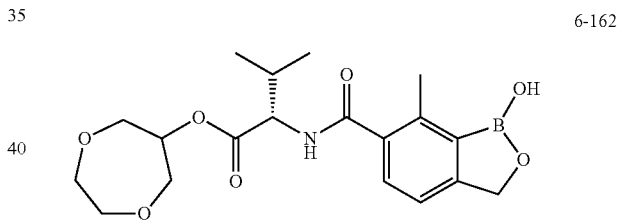

ESI-MS m/z 392 [M+H]$^+$; HPLC purity: 99.78% (220 nm), 100% (254 nm).

Example 163. 4-(2-(Pyrrolidin-1-yl)ethoxy)benzyl (1-hydroxy-7-methyl-1,3-dihydrobenzo[c][1,2]oxaborole-6-carbonyl)-L-valinate (6-163)

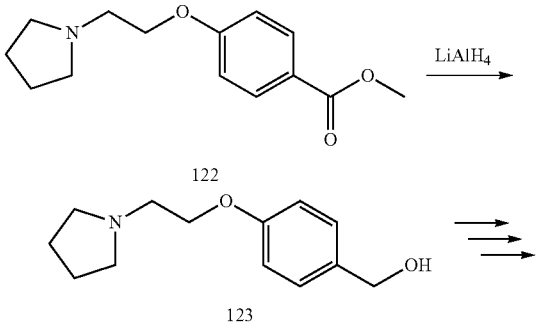

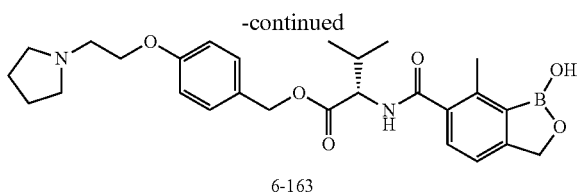

6-163

To a solution of 122 (*J. Med. Chem.* 1984, 27, 1057; 500 mg, 2.01 mmol) in THF (5.00 mL) was added LiAlH$_4$ (153 mg, 4.02 mmol) at 0° C. The mixture was stirred at 60° C. for 2 h. Then saturated solution of potassium sodium tartrate (2 mL) was added into the mixture at 0° C., filtered and concentrated under reduced pressure to give 123 (390 mg, 1.76 mmol, 88%) as a white solid. $^1$H NMR (400 MHz, CDCl$_3$) δ 7.32-7.18 (m, 2H), 6.88 (d, J=8.4 Hz, 2H), 4.60 (s, 2H), 4.08 (t, J=6.2 Hz, 2H), 2.88 (t, J=6.0 Hz, 2H), 2.61 (s., 4H), 1.80 (dt, J=6.8, 3.2 Hz, 4H).

Compound 6-163 was prepared from 123, N-BOC-(S)-valine and Acid-04 in a similar manner to Example 1. $^1$H NMR (400 MHz, DMSO-d$_6$) δ 9.03 (s, 1H), 8.52 (d, J=7.9 Hz, 1H), 7.37-7.28 (m, 3H), 7.22 (d, J=7.5 Hz, 1H), 6.92 (d, J=8.4 Hz, 2H), 5.17-5.01 (m, 2H), 4.96 (s, 2H), 4.31 (t, J=7.3 Hz, 1H), 4.05 (t, J=5.7 Hz, 2H), 2.76 (t, J=5.7 Hz, 2H), 2.43 (s, 3H), 2.18-2.05 (m, 1H), 1.67 (dt, J=6.5, 3.1 Hz, 4H), 0.92 (d, J=6.4 Hz, 3H), 0.90 (d, J=6.4 Hz, 3H); ESI-MS m/z 495 [M+H]$^+$; HPLC purity: 95.47% (220 nm), 90.82% (254 nm).

Example 164. (1-Hydroxy-1,3-dihydrobenzo[c][1,2]oxaborole-6-carbonyl)-L-alanine (6-164)

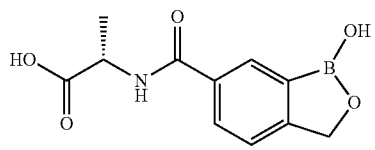

6-164

A solution of 6-002 (40 mg, 0.11 mmol) obtained in Example 2 in TFA (2 mL) and dichloromethane (2 mL) was stirred at room temperature for 1 h. The solvents were removed under reduced pressure to give 6-164 (27 mg, 100%). $^1$H NMR (400 MHz, DMSO-d$_6$) δ 12.53 (b, 1H), 9.32 (s, 1H), 8.63 (s, 1H), 8.22 (s, 1H), 7.94 (d, J=8.0 Hz, 1H), 7.47 (d, J=7.6 Hz, 1H), 5.01 (s, 2H), 4.37 (q, J=6.8 Hz, 2H), 1.36 (d, J=6.8 Hz, 3H); ESI-MS: m/z 248 [M−H]$^-$; HPLC purity: 100% (220 nm), 100% (254 nm).

Example 165. 4-Fluorobenzyl (1-hydroxy-7-methyl-1,3-dihydrobenzo[c][1,2]oxaborole-6-carbonyl)-L-valinate (6-165)

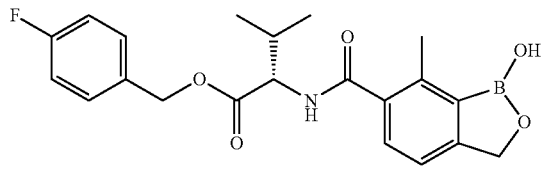

6-165

The mixture of Acid-04 (150 mg, 0.77 mmol), compound of Example B-1 (203 mg, 0.77 mmol) and DIEA (0.4 mL, 2.33 mmol) in DMF was added HATU (325 mg, 0.86 mmol). The mixture was stirred at rt for 3 hrs. The crude product was purified by pre-HPLC and pre-TLC to get 6-165 (125 mg, 40% yield). $^1$H NMR (400 MHz, DMSO-d$_6$) δ 9.03 (s, 1H), 8.57 (d, J=7.2 Hz, 1H), 7.47-7.43 (m, 2H), 7.33 (d, J=7.6 Hz, 1H), 7.23-7.18 (m, 3H), 5.21 (d, J=12.4 Hz, 1H), 5.11 (d, J=12.4 Hz, 1H)), 4.96 (s, 2H), 4.33 (t, J=7.2 Hz, 1H), 2.42 (s, 3H), 2.14-2.13 (m, 1H), 0.94 (d, J=6.8 Hz, 3H), 0.92 (d, J=6.8 Hz, 3H); ESI-MS m/z 400 [M+H]$^+$; HPLC purity: 100% (220 nm), 100% (254 nm).

Example 166. 3,4-Difluorobenzyl (1-hydroxy-7-methyl-1,3-dihydrobenzo[c][1,2]oxaborole-6-carbonyl)-L-valinate (6-166)

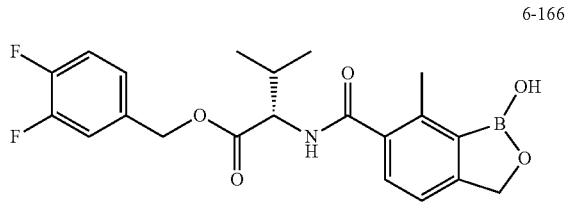 [SMILES: Cc1c(C(=O)N[C@H](C(=O)OCc2ccc(F)c(F)c2)C(C)C)ccc2c1B(O)OC2]

6-166

To a solution of N-BOC-(S)-valine (2.6 g, 12.15 mmol, 1.00 eq) and (3,4-difluorophenyl)methanol (2.8 g, 19.44 mmol) in dry DCM (65 ml) was added DCC (4.45 g, 21.56 mmol) and DMAP (0.219 g, 1.797 mmol). The reaction mixture was stirred at 25° C. for 18 hours. The mixture was filtered and washed with DCM (100 ml) and concentrated to give the crude product. The residue was purified via column chromatography (SiO$_2$, Petroleum ether/Ethyl acetate=50/1 to 10:1) to give 3,4-difluorobenzyl (tert-butoxycarbonyl)-L-valinate (3.7 g, 88% yield) as a yellow sticky solid. The reaction was repeated at the same scale to provide an additional quantity for use in the next step.

To a stirred solution of 3,4-difluorobenzyl (tert-butoxycarbonyl)-L-valinate (5 g, 14.57 mmol) in dioxane (25 ml) was added 3 N HCL-dioxane (25 ml). The reaction mixture was stirred at RT for 18 h. After workup, the crude compound was triturated in diethyl ether to get 3,4-difluorobenzyl L-valinate hydrochloride (2.65 g, 63% yield) as white solid.

To a solution of Acid-04 (0.7 g, 3.64 mmol) in DMF (20 ml) was added 3,4-difluorobenzyl L-valinate hydrochloride (1.06 g, 4.37 mmol), EDCI (1.04 g, 5.47 mmol), HOBt (738 mg, 5.47 mmol) and DIPEA (2.01 ml, 10.93 mmol). The reaction mixture was stirred at RT for 18 hours. The reaction mixture was purified by combi-flash (reverse phase) to get 6-166 (350 mg, 23% yield) as white solid. $^1$H NMR (400 MHz, DMSO-d$_6$) δ 9.02 (s, 1H), 8.58 (d, J=7.94 Hz, 1H), 7.54-7.39 (m, 2H), 7.35-7.17 (m, 3H), 5.15 (s, 2H), 4.95 (s, 2H), 4.33 (t, J=7.1 Hz, 1H), 2.41 (s, 3H), 2.20-2.08 (m, 1H), 0.94 (d, J=6.6 Hz, 3H), 0.92 (d, J=6.6 Hz, 3H); ESI-MS m/z 418 [M+H]$^+$; HPLC purity: 98.35% (220 nm), 98.15% (254 nm).

Example 167. 4-Chloro-3-(2-morpholinoethoxy) benzyl (1-hydroxy-7-methyl-1,3-dihydrobenzo[c][1,2]oxaborole-6-carbonyl)-L-valinate (6-167)

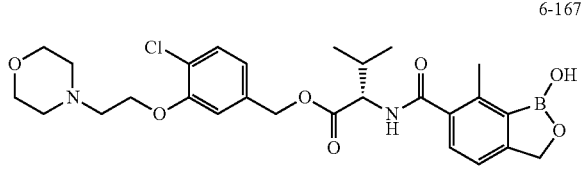 [SMILES: Cc1c(C(=O)N[C@H](C(=O)OCc2ccc(Cl)c(OCCN3CCOCC3)c2)C(C)C)ccc2c1B(O)OC2]

6-167

This compound was prepared in a similar manner to Example 163. ¹H NMR (400 MHz, DMSO-d$_6$) δ 9.43 (s, 1H), 9.04 (s, 1H), 8.72 (d, J=7.2 Hz, 1H), 8.12 (s, 1H), 7.39 (d, J=8.0 Hz, 1H), 7.24 (d, J=7.6 Hz, 1H), 5.47-5.37 (m, 2H), 4.97 (s, 2H), 4.43 (t, J=7.2 Hz, 1H), 2.44 (s, 3H), 2.23-2.19 (m, 1H), 1.00 (d, J=6.8 Hz, 3H), 0.99 (d, J=6.8 Hz, 3H); ESI-MS m/z 545 [M+H]⁺; HPLC purity: 96.16% (220 nm), 95.23% (254 nm).

Example 168. (6-(Trifluoromethyl)pyridin-3-yl) methyl (1-hydroxy-7-methyl-1,3-dihydrobenzo[c][1,2]oxaborole-6-carbonyl)-L-valinate (6-168)

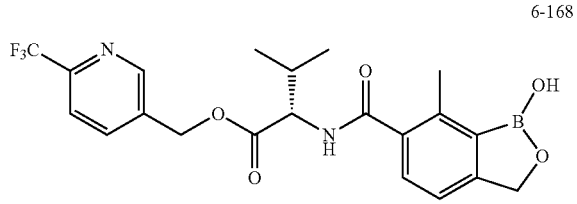 [SMILES: Cc1c(C(=O)N[C@H](C(=O)OCc2ccc(C(F)(F)F)nc2)C(C)C)ccc2c1B(O)OC2]

6-168

This compound was prepared from (6-(trifluoromethyl)pyridin-3-yl)methanol, N-BOC-(S)-valine and Acid-04 in a similar manner to Example 1. ¹H NMR (400 MHz, DMSO-d$_6$) δ 9.01 (s, 1H), 8.82 (s, 1H), 8.61 (d, J=7.5 Hz, 1H), 8.13 (d, J=7.9 Hz, 1H), 7.95 (d, J=7.9 Hz, 1H), 7.45-7.15 (m, 2H), 5.35 (s, 2H), 4.97 (s, 2H), 4.38 (t, J=7.3 Hz, 1H), 2.42 (s, 3H), 2.27-2.10 (m, 1H), 0.96 (d, J=6.6 Hz, 6H); ESI-MS m/z 451 [M+H]⁺; HPLC purity: 95.79% (220 nm), 92.56% (254 nm).

Example 169. 4-Fluorobenzyl (S)-3-hydroxy-2-(1-hydroxy-7-methyl-1,3-dihydrobenzo[c][1,2]oxaborole-6-carboxamido)-3-methylbutanoate (6-169)

6-169

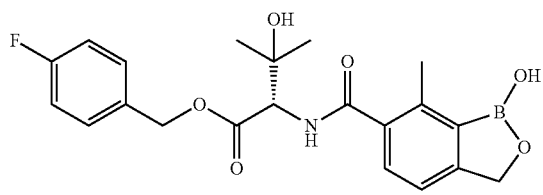

To a solution of (3,4-difluorophenyl)methanol (2.43 g, 19.31 mmol) and (S)-2-((tert-butoxycarbonyl)amino)-3-hydroxy-3-methylbutanoic acid (3 g, 12.87 mmol, 1.00 eq) and in dry DCM (35 ml) was added DCC (4.77 g, 23.16 mmol) and DMAP (0.471 g, 3.85 mmol). The reaction mixture was stirred at 25° C. for 16 hours. The mixture was filtered and washed with DCM (100 ml) and concentrated to give the crude product. The residue was purified by combi-flash (reverse phase) to give 4-fluorobenzyl (S)-2-((tert-butoxycarbonyl)amino)-3-hydroxy-3-methylbutanoate (2.8 g, 64% yield) as a yellow syrup.

To a stirred solution of 4-fluorobenzyl (S)-2-((tert-butoxycarbonyl)amino)-3-hydroxy-3-methylbutanoate (2.8 g, 5.27 mmol) in DCM (5 ml) at 0° C. was added TFA (2 ml). The reaction mixture was stirred at RT for 2 hours. Following removal of solvent and TFA by rotary evaporation, the residue was dissolved in DCM then adjusted pH to 7, dried over Na$_2$SO$_4$, concentrated to give crude 4-fluorobenzyl (S)-2-amino-3-hydroxy-3-methylbutanoate (2.77 g) as yellow syrup which was used in the next step without further purification.

To a solution of Acid-04 (67.7 mg, 0.352 mmol) in DMF (2 ml) was added 4-fluorobenzyl (S)-2-amino-3-hydroxy-3-methylbutanoate (85 mg, 0.352 mmol), EDCI (101 g, 0.529 mmol), HOBt (71.4 mg, 0.529 mmol) and DIPEA (0.25 ml, 1.41 mmol) at RT. The reaction mixture was stirred at RT for 18 hours. The reaction mixture was purified by combi-flash (reverse phase) to get 6-169 (52 mg, 35% yield) as white solid. ¹H NMR (400 MHz, DMSO-d$_6$) δ 9.06 (s, 1H), 8.23 (d, J=8.0 Hz, 1H), 7.53-7.44 (m, 2H), 7.37 (d, J=7.8 Hz, 1H), 7.29-7.18 (m, 3H), 5.17 (d, J=3.8 Hz, 2H), 4.98 (s, 2H), 4.82 (s, 1H), 4.47 (d, J=8.0 Hz, 1H), 2.46-2.44 (m, 3H), 1.24 (s, 6H); ESI-MS m/z 416 [M+H]⁺; HPLC purity: 96.10% (220 nm), 93.44% (254 nm).

Example 170. 2-Morpholinoethyl (1-hydroxy-7-methyl-1,3-dihydrobenzo[c][1,2]oxaborole-6-carbonyl)-L-valinate (6-170)

6-170

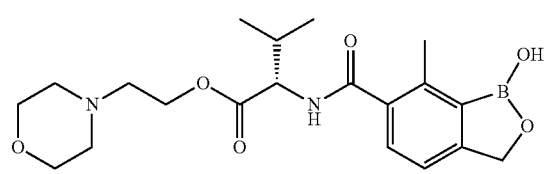

This compound was prepared from 2-morpholinoethan-1-ol, N-BOC-(S)-valine and Acid-04 in a similar manner to Example 1. ¹H NMR (400 MHz, DMSO-d$_6$) δ 8.63 (d, J=8.0 Hz, 1H), 7.39 (d, J=8.0 Hz, 1H), 7.23 (d, J=8.0 Hz, 1H), 4.96 (s, 2H), 4.57-4.54 (m, 1H), 4.47-4.44 (m, 1H), 4.40-4.36 (m, 1H), 3.89 (s, 2H), 3.80 (s, 2H), 3.43 (s, 4H), 3.15 (s, 2H), 2.43 (s, 3H), 2.21-2.16 (m, 1H), 0.95 (d, J=6.4 Hz, 6H); ESI-MS m/z 405 [M+H]⁺; HPLC purity: 99.93% (220 nm), 100% (254 nm).

Example 171. (5-(trifluoromethyl)pyridin-2-yl)methyl (1-hydroxy-7-methyl-1,3-dihydrobenzo[c][1,2]oxaborole-6-carbonyl)-L-valinate (6-171)

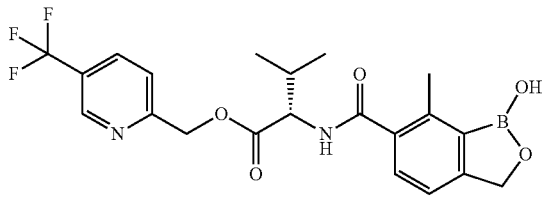

6-171

This compound was prepared from (5-(trifluoromethyl)pyridin-2-yl)methyl L-valinate and Acid-01 in a similar manner to the last step of Example 1. $^1$H NMR (300 MHz, DMSO-$d_6$): δ 9.03 (s, 1H), 8.96 (s, 1H), 8.64 (d, J=7.7 Hz, 1H), 8.27 (dd, J=8.20, 2.0 Hz, 1H), 7.73 (d, J=8.0 Hz, 1H), 7.37 (d, J=7.7 Hz, 1H), 7.24 (d, J=8.0 Hz, 1H), 5.35 (s, 2H), 4.97 (s, 2H), 4.43 (t, J=7.3 Hz, 1H), 2.44 (s, 3H), 2.28-2.13 (m, 1H), 0.99 (d, J=6.6 Hz, 6H); LC-MS: m/z 451.37 [M+H]$^+$. HPLC purity: 97.38% (220 nm) and chiral HPLC purity is 94.17% (210 nm).

Example 172. (tetrahydro-2H-pyran-4-yl)methyl (1-hydroxy-7-methyl-1,3-dihydrobenzo[c][1,2]oxaborole-6-carbonyl)-L-valinate (6-172)

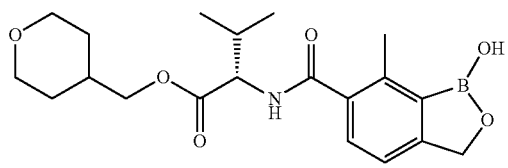

6-172

A mixture of (tert-butoxycarbonyl)-L-valine (3.64 g, 16.75 mmol), 4-(bromomethyl)tetrahydro-2H-pyran (3.00 g, 16.75 mmol) and NaHCO$_3$ (2.81 g, 33.50 mmol) in DMF (30 mL) was stirred at 70° C. for 12 hours under N$_2$ atmosphere. The reaction mixture was diluted with H$_2$O (100 mL) and extracted with MTBE (50 mL×2). The combined organic layers were washed with brine (20 mL×2), dried over Na$_2$SO$_4$, filtered and concentrated under reduced pressure to give (tetrahydro-2H-pyran-4-yl)methyl (tert-butoxycarbonyl)-L-valinate (5 g, yield 94.63%, pale yellow oil) which was used into the next step without further purification. $^1$H NMR (400 MHz, CDCl$_3$) δ 5.01 (d, J=8.4 Hz, 1H), 4.22 (dd, J=8.8 Hz, 4.8 Hz, 1H), 4.00-3.97 (m, 4H), 3.40 (t, J=11.2 Hz, 2H), 2.16-2.11 (m, 1H), 1.96-1.90 (m, 1H), 1.63 (d, J=13.2 Hz, 2H), 1.45 (s, 9H), 0.97 (d, J=6.4 Hz, 3H), 0.90 (d, J=7.2 Hz, 3H).

To a solution of (tetrahydro-2H-pyran-4-yl)methyl (tert-butoxycarbonyl)-L-valinate (5.00 g, 15.85 mmol) in EtOAc (50 mL) was added HCl/EtOAc (6 M, 26.42 mL). After stirred at 15° C. for 2 hours, the mixture was concentrated under reduced pressure to give (tetrahydro-2H-pyran-4-yl)methyl L-valinate hydrochloride (3.80 g, yield 95.23%) as a white solid. $^1$H NMR (400 MHz, DMSO-$d_6$) δ 8.53 (br. s., 2H), 4.04 (d, J=6.0 Hz, 2H), 3.88-3.84 (m, 3H), 3.29 (t, J=11.2 Hz, 2H), 2.21-2.17 (m, 1H), 1.91-1.86 (m, 1H), 1.59 (d, J=13.65 Hz, 2H), 1.29-1.34 (m, 2H), 0.97 (dd, J=16.4, 7.2 Hz, 6H).

A mixture of Acid-04 (2.00 g, 10.42 mmol), TEA (3.16 g, 31.26 mmol) and HATU (4.75 g, 12.50 mmol) in DMF (10 mL) was degassed and purged with N$_2$ for 3 times and stirred at 15° C. for 10 mins. Then (tetrahydro-2H-pyran-4-yl)methyl L-valinate hydrochloride (2.75 g, 10.94 mmol) was added to the reaction mixture and stirred at 15° C. for 20 mins under N$_2$ atmosphere. After filtered, the mixture was purified by prep-HPLC (column: Phenomenex Synergi Max-RP 250*80 10 u; liquid phase: [A-TFA/H$_2$O=0.075% v/v; B-ACN] B %: 10%-40%, 20 mins]) to give 6-172 (1.300 g, yield 24.98%) as a white solid. $^1$H NMR (400 MHz, DMSO-$d_6$) δ 9.04 (br s, 1H), 8.54 (d, J=7.6 Hz, 1H), 7.37 (d, J=7.6 Hz, 1H), 7.24 (d, J=7.6 Hz, 1H), 4.97 (s, 2H), 4.31 (t, J=7.0 Hz, 1H), 3.96 (d, J=6.0 Hz, 2H), 3.85 (d, J=9.2 Hz, 2H), 3.29 (t, J=11.6 Hz, 2H), 2.47 (s, 3H), 2.14 (dd, J=13.2, 6.4 Hz, 1H), 1.87 (br s, 1H), 1.59 (d, J=12.0 Hz, 2H), 1.31-1.23 (m, 2H), 0.96 (d, J=4.4 Hz, 6H); ESI-MS m/z 390 [M+H]$^+$; HPLC purity: 98.49% (220 nm), 89.53% (254 nm).

Example 173. 2-(Pyridin-2-yl)ethyl (1-hydroxy-7-methyl-1,3-dihydrobenzo[c][1,2]oxaborole-6-carbonyl)-L-valinate (6-173)

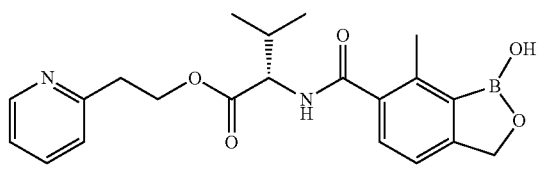

6-173

This compound was prepared from 2-(pyridin-2-yl)ethan-1-ol, N-BOC-(S)-valine and Acid-04 in a similar manner to Example 1. $^1$H NMR (400 MHz, DMSO-$d_6$) δ 8.79 (d, J=5.6 Hz, 1H), 8.52-8.47 (m, 2H), 8.05 (d, J=8.0 Hz, 1H). 7.91 (t, J=6.4 Hz, 1H), 7.30-7.28 (m, 1H), 7.24-7.22 (m, 1H), 4.97 (s, 2H), 4.61-4.51 (m, 2H), 4.24 (t, J=7.2 Hz, 1H), 3.46 (t, J=6.0 Hz, 2H), 2.41 (s, 3H), 2.08-1.99 (m, 1H), 0.83 (t, J=6.4 Hz, 6H); ESI-MS m/z 397 [M+H]$^+$; HPLC purity: 96.77% (220 nm), 98.73% (254 nm).

Example 174. Benzyl (1-hydroxy-1,3-dihydrobenzo[c][1,2]oxaborole-6-carbonyl)-L-alaninate (6-174)

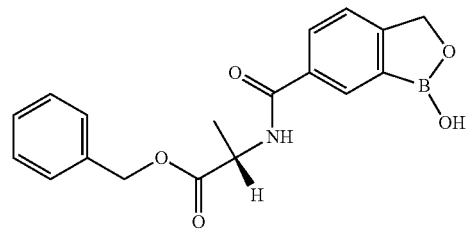

6-174

This compound was prepared from benzyl L-alaninate and Acid-01 in a similar manner to Example 1. ESI-MS m/z 340 [M+H]$^+$; HPLC purity: 94.51% (220 nm), 97.57% (254 nm).

Example 175. Benzyl (1-hydroxy-1,3-dihydrobenzo[c][1,2]oxaborole-6-carbonyl)-D-alaninate (6-175)

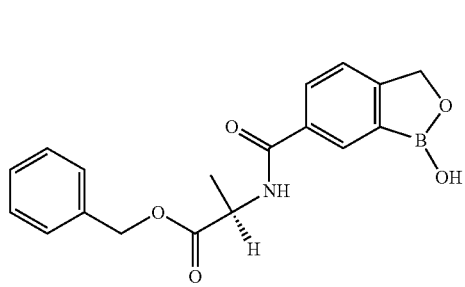

6-175

This compound was prepared from benzyl D-alaninate and Acid-01 in a similar manner to Example 1. ESI-MS m/z 340 [M+H]⁺; HPLC purity: 91.01% (220 nm), 100% (254 nm).

Example 176. Methyl (S)-2-(1-hydroxy-1,3-dihydrobenzo[c][1,2]oxaborole-6-carboxamido)-3-(pyridin-4-yl)propanoate (6-176)

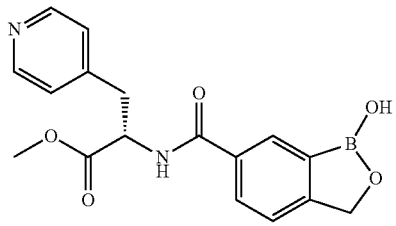

6-176

This compound was prepared from methyl (S)-2-amino-3-(pyridin-4-yl)propanoate and Acid-01 in a similar manner to the last step of Example 1. ESI-MS m/z 341 [M+H]⁺;

Example 177. Dimethyl (1-hydroxy-1,3-dihydrobenzo[c][1,2]oxaborole-6-carbonyl)-L-aspartate (6-177)

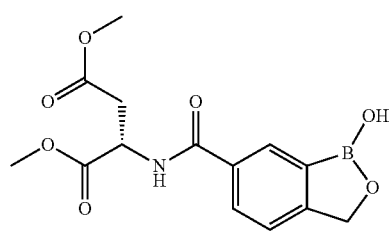

6-177

This compound was prepared from dimethyl L-aspartate and Acid-01 in a similar manner to the last step of Example 1. ESI-MS m/z 322 [M+H]⁺;

Example 178. Methyl (1-hydroxy-1,3-dihydrobenzo[c][1,2]oxaborole-6-carbonyl)-L-leucinate (6-178)

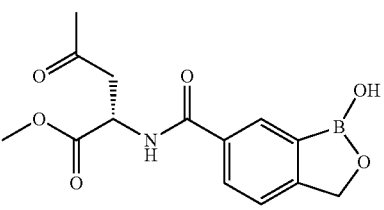

6-178

This compound was prepared from methyl L-leucinate and Acid-01 in a similar manner to the last step of Example 1. ESI-MS m/z 306 [M+H]⁺;

Example 179. Methyl (1-hydroxy-1,3-dihydrobenzo[c][1,2]oxaborole-6-carbonyl)-L-valinate (6-179)

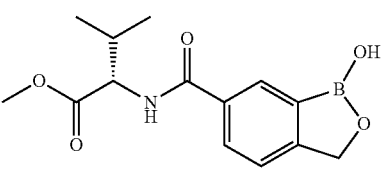

6-179

This compound was prepared from methyl L-valinate and Acid-01 in a similar manner to the last step of Example 1. ESI-MS m/z 292 [M+H]⁺;

Example 180. Methyl (1-hydroxy-1,3-dihydrobenzo[c][1,2]oxaborole-6-carbonyl)-L-alloisoleucinate (6-180)

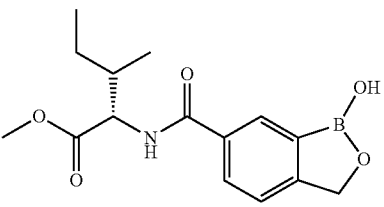

6-180

This compound was prepared from methyl L-alloisoleucinate and Acid-01 in a similar manner to the last step of Example 1. ESI-MS m/z 306 [M+H]⁺;

Example 181. Methyl (1-hydroxy-1,3-dihydrobenzo[c][1,2]oxaborole-6-carbonyl)-L-phenylalaninate (6-181)

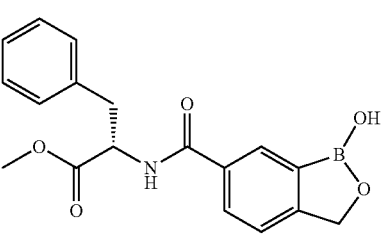

6-181

This compound was prepared from methyl L-phenylalaninate and Acid-01 in a similar manner to the last step of Example 1. ESI-MS m/z 340 [M+H]$^+$;

Example 182. Methyl (1-hydroxy-1,3-dihydrobenzo[c][1,2]oxaborole-6-carbonyl)-L-tyrosinate (6-182)

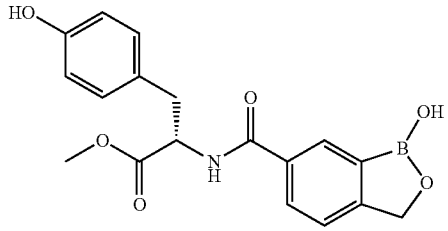

6-182

This compound was prepared from methyl L-tyrosinate and Acid-01 in a similar manner to the last step of Example 1. ESI-MS m/z 356 [M+H]$^+$;

Example 183. Methyl (1-hydroxy-1,3-dihydrobenzo[c][1,2]oxaborole-6-carbonyl)-L-tryptophanate (6-183)

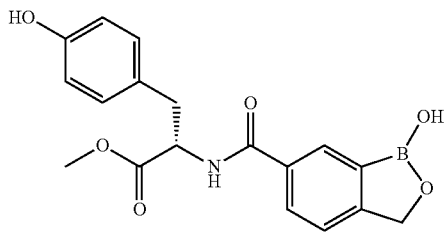

6-182

This compound was prepared from methyl L-tryptophanate and Acid-01 in a similar manner to the last step of Example 1. ESI-MS m/z 379 [M+H]$^+$;

Example 184. Methyl (S)-3-cyclopropyl-2-(1-hydroxy-1,3-dihydrobenzo[c][1,2]oxaborole-6-carboxamido)propanoate (6-184)

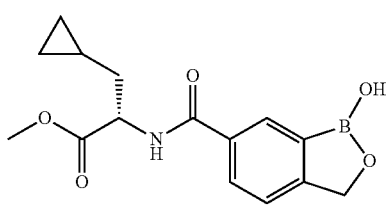

6-184

This compound was prepared from methyl (S)-2-amino-3-cyclopropylpropanoate and Acid-01 in a similar manner to the last step of Example 1. ESI-MS m/z 304 [M+H]$^+$;

Example 185. 3,4-difluorobenzyl (1-hydroxy-1,3-dihydrobenzo[c][1,2]oxaborole-6-carbonyl)-L-valinate (6-185)

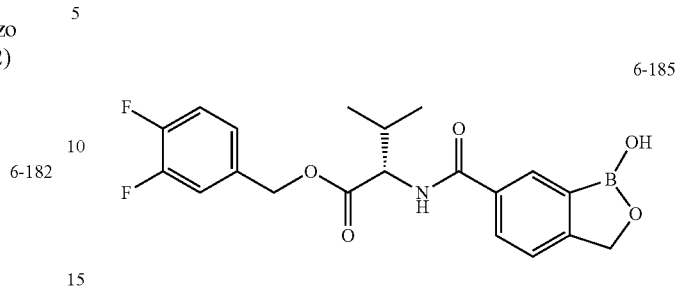

6-185

This compound was prepared from 3,4-difluorobenzyl L-valinate and Acid-01 in a similar manner to the last step of Example 1. $^1$H NMR (300 MHz, DMSO-d$_6$): δ 9.31 (s, 1H), 8.69 (d, J=7.7 Hz, 1H), 8.24 (s, 1H), 7.95 (dd, J=7.9, 1.7 Hz, 1H), 7.53-7.37 (m, 3H), 7.30-7.20 (m, 1H), 5.15 (s, 2H), 5.05 (s, 2H), 4.34 (t, J=7.5 Hz, 1H), 2.22 (qd, J=13.8 Hz, 1H), 0.98 (d, J=6.6 Hz, 3H), 0.96 (d, J=6.6 Hz, 3H); LC-MS: m/z 404.40 [M+H]$^+$ HPLC purity: 98.78% (220 nm), 97.43% (254 nm), chiral HPLC purity is 96.73% (232 nm).

Example 186. Pyrazin-2-ylmethyl (1-hydroxy-7-methyl-1,3-dihydrobenzo[c][1,2]oxaborole-6-carbonyl)-L-valinate (6-186)

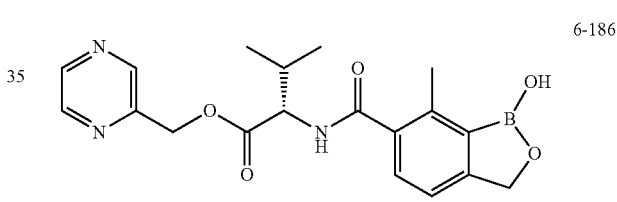

6-186

This compound was prepared from pyrazin-2-ylmethyl L-valinate and Acid-04 in a similar manner to the last step of Example 1. $^1$H NMR (400 MHz, DMSO-d$_6$): δ 9.03 (s, 1H), 8.77 (d, J=1.5 Hz, 1H), 8.69-8.52 (m, 3H), 7.36 (d, J=7.3 Hz, 1H), 7.24 (d, J=7.8 Hz, 1H), 5.41-5.24 (m, 2H), 4.97 (s, 2H), 4.47-4.30 (m, 1H), 2.43 (s, 3H), 2.19 (qd, J=13.3, 6.8, Hz, 1H), 0.97 (dd, J=6.8, 2.4 Hz, 6H); LC-MS: m/z 384.05 [M+H]$^+$. HPLC purity: 95.93% (220 nm), 95.25% (254 nm) and chiral HPLC purity is 97.38% (220 nm).

Example 187. Pyridin-3-ylmethyl (1-hydroxy-7-methyl-1,3-dihydrobenzo[c][1,2]oxaborole-6-carbonyl)-L-valinate (6-187)

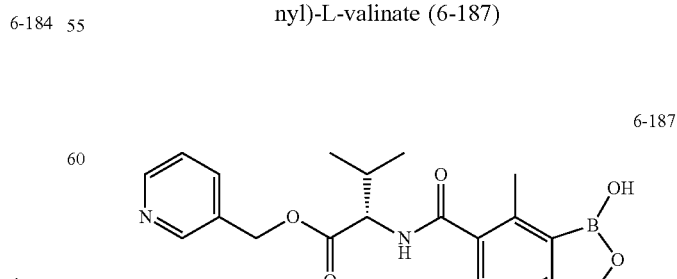

6-187

This compound was prepared from pyridin-3-ylmethyl L-valinate and Acid-04 in a similar manner to the last step of Example 1. $^1$H NMR (400 MHz, DMSO-$d_6$): δ 9.03 (s, 1H), 8.70-8.46 (m, 3H), 7.82 (br d, J=7.8 Hz, 1H), 7.42 (dd, J=7.8, 4.9 Hz, 1H), 7.33 (d, J=7.8 Hz, 1H), 7.23 (d, J=7.3 Hz, 1H), 5.31-5.16 (m, 2H), 4.97 (s, 2H), 4.35 (br t, J=7.3 Hz, 1H), 2.42 (s, 3H), 2.21-2.09 (m, 1H), 0.93 (dd, J=2.0, 6.8 Hz, 6H); LC-MS: m/z 383.35 [M+H]$^+$. HPLC purity: 98.95% (220 nm), 98.46% (254 nm) and chiral HPLC purity is 95.05% (215 nm).

Example 188. Tert-butyl (1-hydroxy-7-methyl-1,3-dihydrobenzo[c][1,2]oxaborole-6-carbonyl)-L-valinate (6-188)

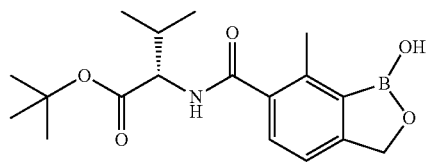

6-188

This compound was prepared from (s)-Valine t-butyl ester and Acid-04 in a similar manner to the last step of Example 1. $^1$H NMR (400 MHz, DMSO-$d_6$): δ 9.03 (s, 1H), 8.39 (d, J=7.8 Hz, 1H), 7.36 (d, J=7.8 Hz, 1H), 7.24 (d, J=7.8 Hz, 1H), 4.97 (s, 2H), 4.18 (dd, J=7.8, 6.8 Hz, 1H), 2.49-2.42 (m, 3H), 2.11 (qd, J=13.7, 6.8 Hz, 1H), 1.44 (s, 9H), 0.95 (d, J=5.9 Hz, 6H); LC-MS: m/z 348.19 [M+H]$^+$. HPLC purity: 98.79% (220 nm) and chiral HPLC purity is 96.91% (211 nm).

Example 189. (6-cyanopyridin-2-yl)methyl (1-hydroxy-7-methyl-1,3-dihydrobenzo[c][1,2]oxaborole-6-carbonyl)-L-valinate (6-189)

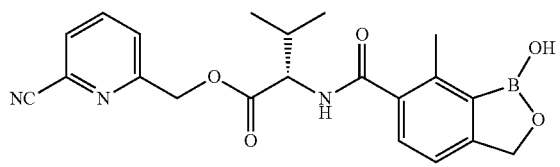

6-189

This compound was prepared from (6-cyanopyridin-2-yl)methyl L-valinate and Acid-04 in a similar manner to the last step of Example 1. $^1$H NMR (400 MHz, DMSO-$d_6$): δ 9.03 (s, 1H), 8.69-8.54 (m, 1H), 8.17-8.08 (m, 1H), 8.01 (d, J=7.3 Hz, 1H), 7.83 (d, J=7.8 Hz, 1H), 7.37 (d, J=7.8 Hz, 1H), 7.24 (d, J=7.8 Hz, 1H), 5.39-5.20 (m, 2H), 4.97 (s, 2H), 4.41 (t, J=7.1 Hz, 1H), 2.44 (s, 3H), 2.28-2.14 (m, 1H), 1.00 (d, J=6.8 Hz, 3H), 0.98 (d, J=6.8 Hz, 3H); LC-MS: m/z 408.46 [M+H]$^+$. HPLC purity: 98.89% (220 nm), 97.41% (254 nm) and chiral HPLC purity is 99.44% (210 nm).

Example 190. Pyridin-4-ylmethyl (1-hydroxy-7-methyl-1,3-dihydrobenzo[c][1,2]oxaborole-6-carbonyl)-L-valinate (6-190)

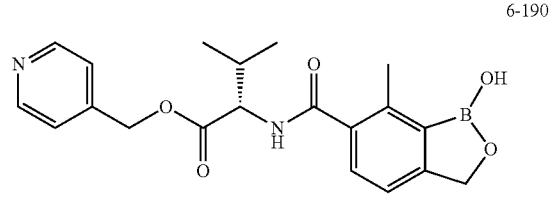 [SMILES: Cc1c(C(=O)N[C@H](C(=O)OCc2ccncc2)C(C)C)ccc2c1B(O)OC2]

6-190

This compound was prepared from pyridin-4-ylmethyl L-valinate and Acid-04 in a similar manner to the last step of Example 1. $^1$H NMR (300 MHz, DMSO-$d_6$): δ 9.04 (br s, 1H), 8.65 (br d, J=7.7 Hz, 1H), 8.57 (d, J=5.9 Hz, 2H), 7.46-7.33 (m, 3H), 7.24 (d, J=7.7 Hz, 1H), 5.24 (s, 2H), 4.97 (s, 2H), 4.40 (t, J=7.2 Hz, 1H), 2.44 (s, 3H), 2.20 (br dd, J=13.4, 6.8 Hz, 1H), 0.99 (d, J=6.6 Hz, 3H), 0.96 (d, J=6.6 Hz, 3H); LC-MS: m/z 383.32 [M+H]$^+$. HPLC purity: 97.2% (220 nm) and chiral HPLC purity is 95.08% (212 nm).

Example 191. Pyridin-2-ylmethyl (1-hydroxy-7-methyl-1,3-dihydrobenzo[c][1,2]oxaborole-6-carbonyl)-L-valinate (6-191)

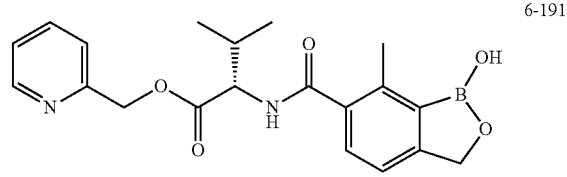 [SMILES: Cc1c(C(=O)N[C@H](C(=O)OCc2ccccn2)C(C)C)ccc2c1B(O)OC2]

6-191

This compound was prepared from pyridin-2-ylmethyl L-valinate and Acid-04 in a similar manner to the last step of Example 1. $^1$H NMR (400 MHz, DMSO-$d_6$): δ 9.03 (s, 1H), 8.61 (d, J=7.8 Hz, 1H), 8.56 (br d, J=3.9 Hz, 1H), 7.83 (dt, J=7.6, 1.5 Hz, 1H), 7.48 (d, J=7.8 Hz, 1H), 7.41-7.31 (m, 2H), 7.24 (d, J=7.8 Hz, 1H), 5.33-5.13 (m, 2H), 4.97 (s, 2H), 4.41 (t, J=7.3 Hz, 1H), 2.44 (s, 3H), 2.20 (qd, J=13.5, 6.8 Hz, 1H), 0.97 (dd, J=6.8, 1.5 Hz, 6H);

LC-MS: m/z 383.45 [M+H]$^+$. HPLC purity: 99.25% (220 nm), 98.10% (254 nm) and chiral HPLC purity is 98.92% (210 nm).

Example 192. Benzyl (7-ethoxy-1-hydroxy-1,3-dihydrobenzo[c][1,2]oxaborole-6-carbonyl)-L-valinate (6-192)

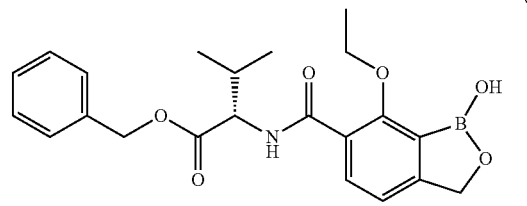

6-192

This compound was prepared from L-Valine benzyl ester and Acid-13 in a similar manner to the last step of Example 1. ¹H NMR (300 MHz, DMSO-d₆): δ9.36 (s, 1H), 8.71 (d, J=8.1 Hz, 1H), 7.97 (d, J=7.7 Hz, 1H), 7.53-7.27 (m, 5H), 7.16 (d, J=7.7 Hz, 1H), 5.30-5.10 (m, 2H), 5.01 (s, 2H), 4.62-4.30 (m, 3H), 2.31-2.03 (m, 1H), 1.32 (t, J=7.0 Hz, 3H), 0.93 (d, J=7.0 Hz, 6H); LC-MS: m/z 412.01 [M+H]⁺. HPLC purity: 99.77% (220 nm) and 99.36% (254 nm) and chiral HPLC purity is 99.73% (210 nm).

Example 193. (6-morpholinopyrazin-2-yl)methyl (1-hydroxy-7-methyl-1,3-dihydrobenzo[c][1,2]oxaborole-6-carbonyl)-L-valinate (6-193)

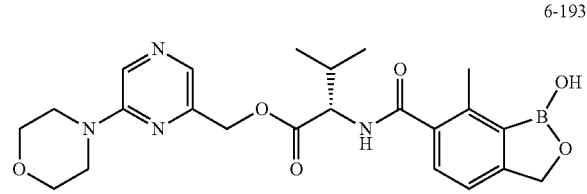 [SMILES: Cc1c(C(=O)N[C@H](C(=O)OCc2cncc(N3CCOCC3)n2)C(C)C)ccc2c1B(O)OC2]

6-193

This compound was prepared from (6-morpholinopyrazin-2-yl)methyl L-valinate and Acid-04 in a similar manner to the last step of Example 1. ¹H NMR (300 MHz, DMSO-d₆): δ 9.07 (s, 1H), 8.63 (br d, J=8.1 Hz, 1H), 8.28 (s, 1H), 7.96 (s, 1H), 7.35 (d, J=7.7 Hz, 1H), 7.24 (d, J=7.7 Hz, 1H), 5.19-5.03 (m, 2H), 4.97 (s, 2H), 4.39 (br t, J=7.2 Hz, 1H), 3.81-3.63 (m, 4H), 3.59-3.47 (m, 4H), 2.44 (s, 3H), 2.18 (br dd, J=13.4, 6.4 Hz, 1H), 0.97 (br d, J=6.6 Hz, 6H); LC-MS: m/z 468.99 [M+H]⁺. HPLC purity: 97.87% (220 nm), 97.59% (254 nm) and chiral HPLC purity is 98.56% (252 nm).

Example 194. Benzyl (1-hydroxy-7-methoxy-1,3-dihydrobenzo[c][1,2]oxaborole-6-carbonyl)-L-valinate (6-194)

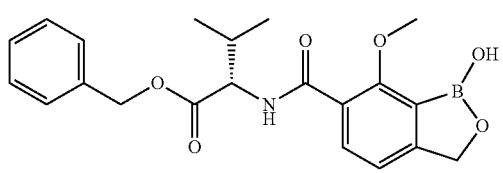

6-194

This compound was prepared from L-Valine benzyl ester and Acid-12 in a similar manner to the last step of Example 1. ¹H NMR (300 MHz, DMSO-d₆): δ 9.39 (s, 1H), 8.62 (d, J=8.1 Hz, 1H), 7.87 (d, J=7.7 Hz, 1H), 7.57-7.30 (m, 5H), 7.16 (d, J=7.7 Hz, 1H), 5.29-5.09 (m, 2H), 5.02 (s, 2H), 4.49 (dd, J=8.1, 5.5 Hz, 1H), 4.07 (s, 3H), 2.20 (dt, J=13.0, 6.6 Hz, 1H), 0.93 (dd, J=4.0, 6.6 Hz, 6H); LC-MS: m/z 398.40 [M+H]⁺. HPLC purity: 99.03% (220 nm), chiral HPLC purity is 99.71% (215 nm).

Example 195. 4-fluorobenzyl (1-hydroxy-7-methoxy-1,3-dihydrobenzo[c][1,2]oxaborole-6-carbonyl)-L-valinate (6-195)

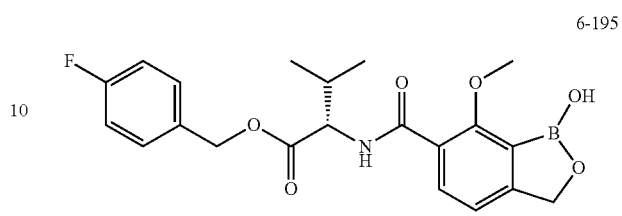

6-195

This compound was prepared from 4-fluorobenzyl L-valinate and Acid-12 in a similar manner to the last step of Example 1. ¹H NMR (300 MHz, DMSO-d₆): δ 9.39 (s, 1H), 8.62 (d, J=8.1 Hz, 1H), 7.87 (d, J=8.1 Hz, 1H), 7.46 (dd, J=8.6, 5.7 Hz, 2H), 7.30-7.02 (m, 3H), 5.27-5.09 (m, 2H), 5.02 (s, 2H), 4.48 (dd, J=7.7, 5.5 Hz, 1H), 4.07 (s, 3H), 2.30-2.07 (m, 1H), 0.93 (d, J=6.6 Hz, 3H), 0.91 (d, J=6.6 Hz, 3H); 0.92 (dd, J=4.0, 6.6 Hz, 6H); LC-MS: m/z 416.38 [M+H]⁺. HPLC purity: 99.3% (220 nm), chiral HPLC purity is 98.89% (217 nm).

Example 196. 4-Fluorobenzyl (7-ethoxy-1-hydroxy-1,3-dihydrobenzo[c][1,2]oxaborole-6-carbonyl)-L-valinate (6-196)

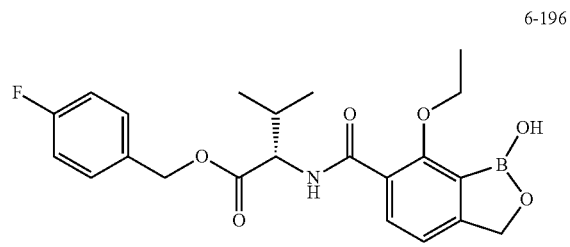

6-196

This compound was prepared from 4-fluorobenzyl L-valinate and Acid-13 in a similar manner to the last step of Example 1. ¹H NMR (400 MHz, DMSO-d₆): δ 9.35 (s, 1H), 8.70 (d, J=8.3 Hz, 1H), 7.96 (d, J=7.8 Hz, 1H), 7.54-7.41 (m, 2H), 7.30-7.07 (m, 3H), 5.27-5.12 (m, 2H), 5.01 (s, 2H), 4.61-4.33 (m, 3H), 2.23-2.08 (m, 1H), 1.32 (t, J=7.1 Hz, 3H), 0.92 (d, J=5.9 Hz, 6H); LC-MS: m/z 430.38 [M+H]⁺. HPLC purity: 99.23% (220 nm) and chiral HPLC purity is 97.74% (218 nm).

Example 197. (6-morpholinopyridin-2-yl)methyl (1-hydroxy-7-methyl-1,3-dihydrobenzo[c][1,2]oxaborole-6-carbonyl)-L-valinate (6-197)

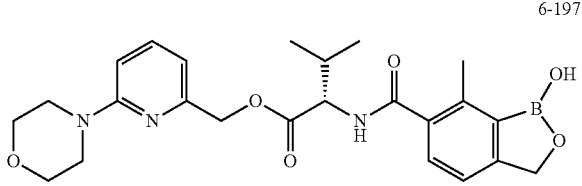 [SMILES: Cc1c(C(=O)N[C@H](C(=O)OCc2cccc(N3CCOCC3)n2)C(C)C)ccc2c1B(O)OC2]

6-197

This compound was prepared from (6-morpholinopyridin-2-yl)methyl L-valinate and Acid-04 in a similar manner to the last step of Example 1. ¹H NMR (300 MHz, DMSO-d₆): δ 9.04 (s, 1H), 8.59 (br d, J=7.7 Hz, 1H), 7.61-7.51 (m, 1H), 7.36 (d, J=7.7 Hz, 1H), 7.24 (d, J=7.7 Hz, 1H), 6.83-6.69 (m, 2H), 5.11-5.02 (m, 2H), 4.97 (s, 2H), 4.40 (t, J=7.3 Hz, 1H), 3.72-3.62 (m, 4H), 3.49-3.38 (m, 4H), 2.45 (s, 3H), 2.24-2.13 (m, 1H), 0.97 (d, J=6.6 Hz, 6H); LC-MS: m/z 468.43 [M+H]⁺. HPLC purity: 97.75% (220 nm) and 99.50% (254 nm); chiral HPLC purity is 98.07% (248 nm).

Example 198. (R)-1-phenylethyl (1-hydroxy-7-methyl-1,3-dihydrobenzo[c][1,2]oxaborole-6-carbonyl)-L-valinate (6-198)

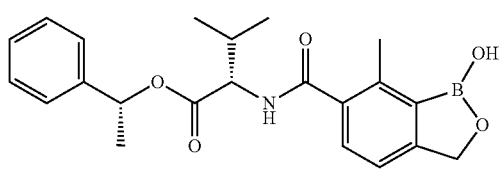

6-198

This compound was prepared from (R)-1-phenylethyl L-valinate and Acid-04 in a similar manner to the last step of Example 1. ¹H NMR (300 MHz, DMSO-d₆): δ 9.03 (s, 1H), 8.58 (d, J=8.1 Hz, 1H), 7.48-7.28 (m, 6H), 7.28-7.19 (m, 1H), 5.89 (q, J=6.6 Hz, 1H), 4.97 (s, 2H), 4.33 (t, J=7.5 Hz, 1H), 2.46 (s, 3H), 2.16 (qd, J=13.6, 6.7 Hz, 1H), 1.49 (d, J=6.6 Hz, 3H), 0.96 (d, J=6.8 Hz, 1H), 0.94 (d, J=6.8 Hz, 3H); LC-MS: m/z 396.45 [M+H]⁺. HPLC purity: 98.07% (220 nm) and 96.63% (254 nm); chiral HPLC purity is 97.84% (214 nm).

Example 199. (S)-1-phenylethyl (1-hydroxy-7-methyl-1,3-dihydrobenzo[c][1,2]oxaborole-6-carbonyl)-L-valinate (6-199)

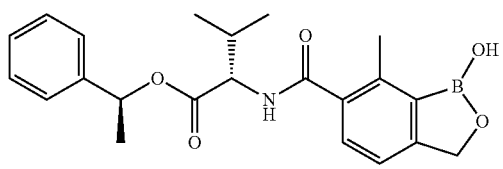

6-199

This compound was prepared from (S)-1-phenylethyl L-valinate and Acid-04 in a similar manner to the last step of Example 1. ¹H NMR (300 MHz, DMSO-d₆): δ 9.03 (s, 1H), 8.51 (d, J=8.1 Hz, 1H), 7.52-7.30 (m, 6H), 7.28-7.17 (m, 1H), 5.87 (q, J=6.6 Hz, 1H), 4.97 (s, 2H), 4.36 (dd, J=7.9, 6.4 Hz, 1H), 2.44 (s, 3H), 2.17 (qd, J=6.7, 13.4 Hz, 1H), 1.51 (d, J=6.6 Hz, 3H), 0.89 (dd, J=13.8, 6.8 Hz, 6H); LC-MS: m/z 396 [M+H]t HPLC purity: 99.08% (220 nm) and chiral HPLC purity is 98.31% (210 nm).

Example 200. (5-cyanopyridin-2-yl)methyl (1-hydroxy-7-methyl-1,3-dihydrobenzo[c][1,2]oxaborole-6-carbonyl)-L-valinate (6-200)

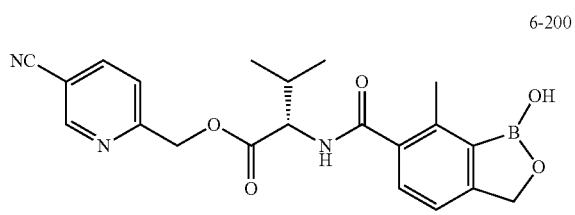 [SMILES: Cc1c(C(=O)N[C@H](C(=O)OCc2ccc(C#N)cn2)C(C)C)ccc2c1B(O)OC2]

6-200

This compound was prepared from (5-cyanopyridin-2-yl)methyl L-valinate and Acid-04 in a similar manner to the last step of Example 1. ¹H NMR (300 MHz, DMSO-d6): δ 9.08-8.94 (m, 2H), 8.66 (d, J=7.3 Hz, 1H), 8.38 (dd, J=2.2, 8.4 Hz, 1H), 7.70 (d, J=8.1 Hz, 1H), 7.37 (d, J=7.7 Hz, 1H), 7.25 (d, J=7.7 Hz, 1H), 5.50-5.21 (m, 2H), 4.97 (s, 2H), 4.42 (t, J=7.2 Hz, 1H), 2.47 (d, J=13.2 Hz, 3H), 2.21 (qd, J=13.7, 7.0 Hz, 1H), 0.99 (dd, J=6.8, 1.3 Hz, 6H); LC-MS: m/z 408.36 [M+H]⁺. HPLC purity: 97.57% (220 nm) and chiral HPLC purity is 98.17% (215 nm).

Example 201. (6-(4-methylpiperazin-1-yl)pyridin-2-yl)methyl (1-hydroxy-7-methyl-1,3-dihydrobenzo[c][1,2]oxaborole-6-carbonyl)-L-valinate (6-201)

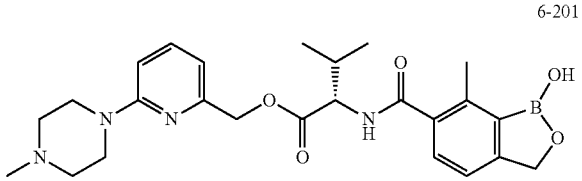 [SMILES: Cc1c(C(=O)N[C@H](C(=O)OCc2cccc(N3CCN(C)CC3)n2)C(C)C)ccc2c1B(O)OC2]

6-201

This compound was prepared from (6-(4-methylpiperazin-1-yl)pyridin-2-yl)methyl L-valinate and Acid-04 in a similar manner to the last step of Example 1. ¹H NMR (300 MHz, DMSO-d₆): δ 9.05 (br s, 1H), 8.61 (br d, J=7.7 Hz, 1H), 7.75-7.57 (m, 1H), 7.36 (d, J=7.7 Hz, 1H), 7.29-7.19 (m, 1H), 6.98-6.74 (m, 2H), 5.09 (s, 2H), 4.98 (s, 2H), 4.56-4.29 (m, 3H), 3.50 (br d, J=8.8 Hz, 2H), 3.08 (br d, J=10.6 Hz, 4H), 2.90-2.69 (m, 3H), 2.45 (s, 3H), 2.27-2.10 (m, 1H), 0.98 (d, J=6.6 Hz, 6H); LC-MS: m/z 481.46 [M+H]⁺ HPLC purity: 98.11% (220 nm), 98.54% (254 nm) and chiral HPLC purity is 98.33% (245 nm).

Example 202. (5-fluoropyrimidin-2-yl)methyl (1-hydroxy-7-methyl-1,3-dihydrobenzo[c][1,2]oxaborole-6-carbonyl)-L-valinate (6-202)

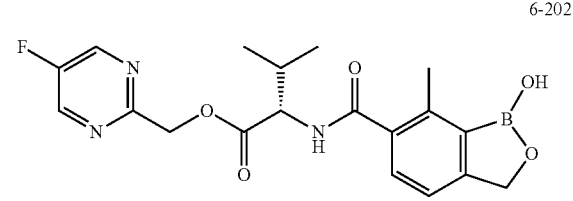 [SMILES: Cc1c(C(=O)N[C@H](C(=O)OCc2ncc(F)cn2)C(C)C)ccc2c1B(O)OC2]

6-202

This compound was prepared from (5-fluoropyrimidin-2-yl)methyl L-valinate and Acid-04 in a similar manner to the last step of Example 1. ¹H NMR (300 MHz, DMSO-d₆): δ 9.04 (s, 1H), 8.92 (d, J=0.7 Hz, 2H), 8.58 (d, J=8.1 Hz, 1H), 7.38 (d, J=7.7 Hz, 1H), 7.24 (d, J=7.7 Hz, 1H), 5.33 (m, 2H), 4.97 (s, 2H), 4.47 (dd, J=6.4, 7.9 Hz, 1H), 2.45 (s, 3H), 2.25 (qd, J=6.7, 13.3 Hz, 1H), 1.00 (dd, J=6.6, 2.2 Hz, 6H); LC-MS: m/z 402.39 [M+H]⁺. HPLC purity: 98.58% (220 nm) and chiral HPLC purity is 98.47% (210 nm).

Example 203. (4-(trifluoromethyl)pyrimidin-2-yl)methyl (1-hydroxy-7-methyl-1,3-dihydrobenzo[c][1,2]oxaborole-6-carbonyl)-L-valinate (6-203)

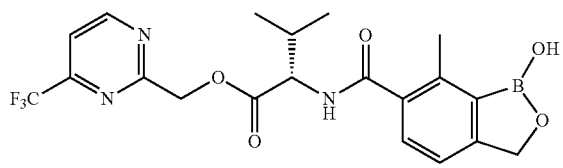

6-203

This compound was prepared from (4-(trifluoromethyl)pyrimidin-2-yl)methyl L-valinate and Acid-04 in a similar manner to the last step of Example 1. ¹H NMR (300 MHz, DMSO-d₆): δ 9.20 (d, J=5.1 Hz, 1H), 9.03 (s, 1H), 8.58 (d, J=8.1 Hz, 1H), 7.99 (d, J=5.1 Hz, 1H), 7.38 (d, J=7.7 Hz, 1H), 7.23 (d, J=7.7 Hz, 1H), 5.57-5.28 (m, 2H), 4.97 (s, 2H), 4.62-4.38 (m, 1H), 2.46 (s, 3H), 2.27 (qd, J=6.7, 13.3 Hz, 1H), 1.03 (dd, J=2.8, 6.8 Hz, 6H); LC-MS: m/z 452.36 [M+H]⁺. HPLC purity: 96.72% (220 nm) and chiral HPLC purity is 95.23% (215 nm).

Example 204. (6-(4-methylpiperazin-1-yl)pyrazin-2-yl)methyl (1-hydroxy-7-methyl-1,3-dihydrobenzo[c][1,2]oxaborole-6-carbonyl)-L-valinate (6-204)

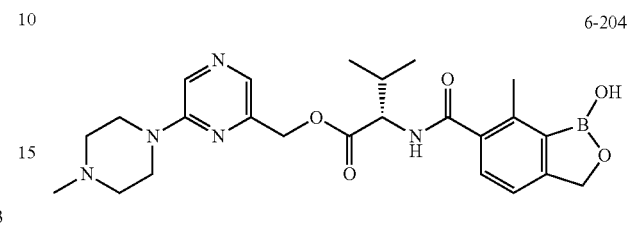

6-204

This compound was prepared from (6-(4-methylpiperazin-1-yl)pyrazin-2-yl)methyl L-valinate and Acid-04 in a similar manner to the last step of Example 1. ¹H NMR (300 MHz, DMSO-d₆): δ 9.06 (s, 1H), 8.62 (br d, J=7.7 Hz, 1H), 8.27 (s, 1H), 7.91 (s, 1H), 7.35 (d, J=7.7 Hz, 1H), 7.23 (d, J=7.7 Hz, 1H), 5.22-5.03 (m, 2H), 4.97 (s, 2H), 4.46-4.31 (m, 1H), 3.56 (br s, 4H), 2.50-2.33 (m, 7H), 2.30-1.97 (m, 4H), 0.96 (d, J=6.6 Hz, 6H). LC-MS: m/z 482 [M+H]⁺. HPLC purity: 98.14% (220 nm), 99.12% (254 nm) and chiral HPLC purity is 99.11% (210 nm).

Example 205. (6-(piperazin-1-yl)pyrazin-2-yl)methyl (1-hydroxy-7-methyl-1,3-dihydrobenzo[c][1,2]oxaborole-6-carbonyl)-L-valinate (6-205)

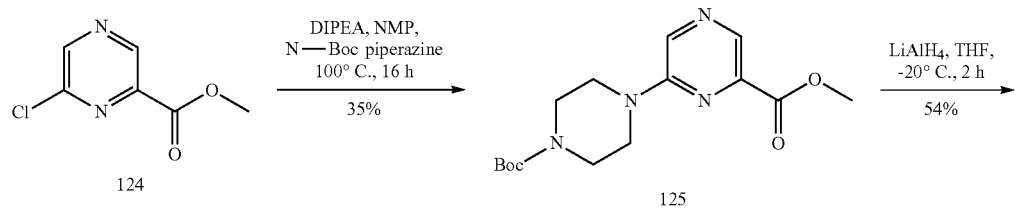

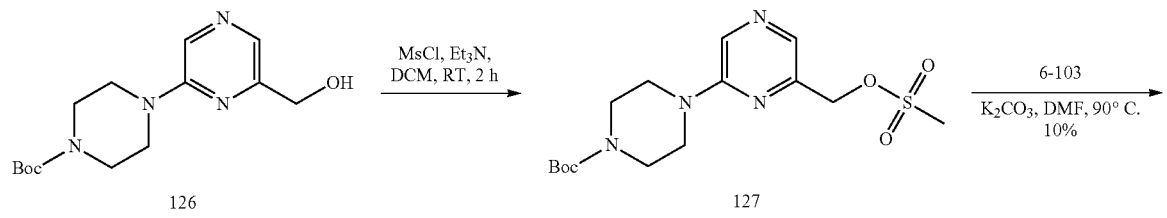

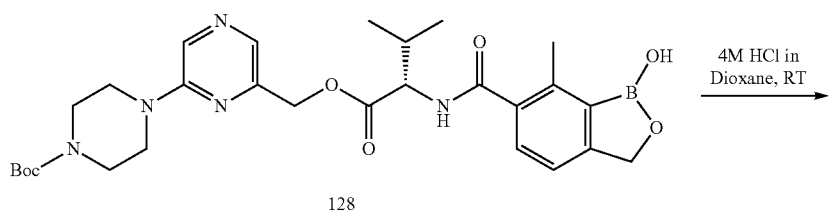

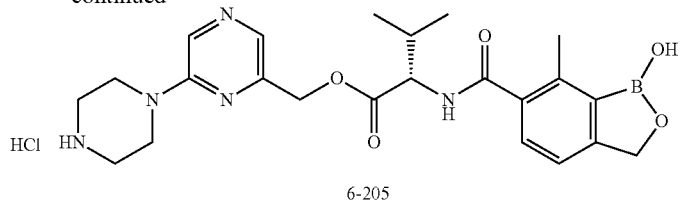

6-205

To a stirred solution of 124 (1.5 g, 8.72 mmol) in NMP (10 vol) was added DIPEA (7.6 ml, 43.60 mmol) and N-Boc-piperazine (3.24 g, 17.44 mmol) at RT. The reaction mixture was stirred at 100° C. for 16 h. The progress of the reaction was monitored by TLC. The reaction mixture was quenched with water and was extracted with ethyl acetate (3×100 ml). The combined organic layer was concentrated under reduced pressure to get the crude material. The crude compound was purified via column chromatography on silica-gel (100-200 mesh, 15-20% EtOAc:Pet ether) to afford 125 (1 g, 35%) as a colorless liquid. To a stirred solution of 125 (1 g, 3.10 mmol) in dry THF (10 mL) was added LiAlH$_4$ solution (2 M in THF, 0.776 ml, 1.55 mmol) drop wise at −20° C. and stirred at the same temperature for 2 h. The progress of the reaction was monitored by TLC. TLC showed formation of a polar spot with complete consumption of starting material. The reaction was quenched with saturated sodium sulphate and filtered the reaction mixture through a pad of celite. The filtrate was evaporated under reduced pressure to get the crude residue. The crude compound was purified via column chromatography on silica gel (100-200 mesh, 25-28% EtOAc:Pet ether) to afford 126 (500 mg, 54%) as a pale yellow solid. To a stirred solution of 126 (500 mg, 1.70 mmol) in DCM (10 vol) was added TEA (0.715 mL, 5.10 mmol) and methane sulfonyl chloride (0.197 mL, 2.55 mmol) drop wise at 0° C. The reaction mass was stirred at RT for 2 h. TLC showed formation of a non-polar spot with complete consumption of starting material. The reaction mixture was concentrated under reduced pressure to get 400 mg of crude 127 as a yellow syrup. The crude compound was as such used in the next step without any further purification. To a stirred solution of 6-103 (375.4 mg, 1.29 mmol) in DMF (20 ml) was added K$_2$CO$_3$ (355.6 mg, 2.57 mmol) at RT and was stirred at RT for 10 min. Then 127 (400 mg, crude, 1.075 mmol) in DMF was added drop wise at RT. The reaction mass was heated to 90° C. for 16 h. The reaction mixture was quenched with ice cold water and was extracted into EtOAc (2×100 ml). The combined organic layers were washed with water, brine and dried over Na$_2$SO$_4$. The solvent was removed under reduced pressure to get the crude material. The crude compound was purified by C-18 column with 0.01% HCOOH in water and acetonitrile] and to afford 128 (95 mg, 10%) as a white solid. To a stirred solution of 128 (90 mg, 0.158 mmol) in 1,4-dioxane (10 vol) was added 4 M HCl-dioxane (10 mL) at 0° C. The reaction mixture was stirred at RT for 2 h. The solvent was removed under reduced pressure to get the residue, which was triturated with ether to get 85 mg of 6-205 as HCl salt. $^1$H NMR (400 MHz, DMSO-d$_6$): δ 9.14 (br s, 3H), 8.61 (br d, J=7.8 Hz, 1H), 8.36 (s, 1H), 8.02 (s, 1H), 7.40-7.31 (m, 1H), 7.24 (d, J=7.8 Hz, 1H), 5.24-5.06 (m, 2H), 4.97 (s, 2H), 4.47-4.35 (m, 1H), 3.90-3.76 (m, 4H), 3.17 (br s, 4H), 2.49-2.37 (m, 3H), 2.22-2.11 (m, 1H), 0.97 (br d, J=6.8 Hz, 6H). LC-MS: m/z 468.34 [M+H]$^+$. HPLC purity: 95.10% (220 nm), 96.29% (254 nm) and chiral HPLC purity is 95.97% (247 nm).

Example 206. 2-(2,6-dimethylmorpholino)ethyl (1-hydroxy-7-methyl-1,3-dihydrobenzo[c][1,2]oxaborole-6-carbonyl)-L-valinate (6-206)

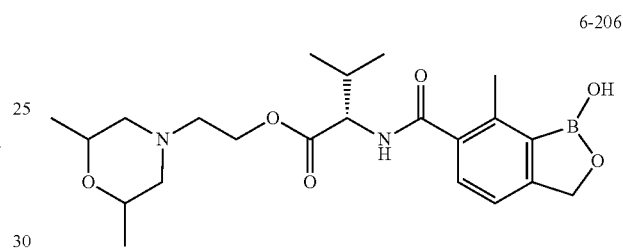

6-206

This compound was prepared from 2-(2,6-dimethylmorpholino)ethyl L-valinate and Acid-04 in a similar manner to the last step of Example 1. $^1$H NMR (400 MHz, DMSO-d$_6$): δ 9.03 (s, 1H), 8.49 (d, J=7.8 Hz, 1H), 7.38 (d, J=7.8 Hz, 1H), 7.25-7.16 (m, 1H), 4.97 (s, 2H), 4.33-4.22 (m, 2H), 4.15 (td, J=11.5, 5.5 Hz, 1H), 3.51 (br dd, J=3.7, 6.1 Hz, 2H), 2.76 (br d, J=10.3 Hz, 2H), 2.51 (br s, 2H), 2.47 (s, 3H), 2.14 (qd, J=13.7, 6.8 Hz, 1H), 1.67 (br d, J=8.3 Hz, 2H), 1.07-0.90 (m, 12H). LC-MS: m/z 433.38 [M+H]$^+$. HPLC purity: 95.98% (220 nm) and chiral HPLC purity is 95.04% (211 nm).

Example 207. 2-morpholinopropyl (1-hydroxy-7-methyl-1,3-dihydrobenzo[c][1,2]oxaborole-6-carbonyl)-L-valinate (6-207)

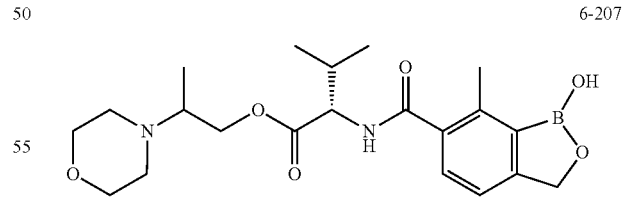

6-207

This compound was prepared from 2-(3-methylmorpholino)ethyl L-valinate and Acid-04 in a similar manner to the last step of Example 1. $^1$H NMR (300 MHz, DMSO-d$_6$): δ 9.04 (br s, 1H), 8.50 (br d, J=7.7 Hz, 1H), 7.38 (d, J=7.7 Hz, 1H), 7.24 (d, J=8.1 Hz, 1H), 4.97 (s, 2H), 4.42-4.13 (m, 2H), 4.06-3.85 (m, 4H), 3.67-3.44 (m, 4H), 2.89-2.69 (m, 1H), 2.48-2.36 (m, 7H), 2.23-2.06 (m, 1H), 0.96-0.94 (m, overlapping, 9H); LC-MS: m/z 419.32 [M+H]$^+$ HPLC purity is 99.11% (220 nm).

Example 208. 3-morpholinopropyl (1-hydroxy-7-methyl-1,3-dihydrobenzo[c][1,2]oxaborole-6-carbonyl)-L-valinate (6-208)

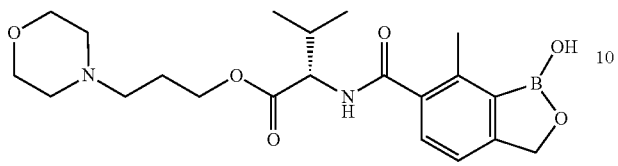

6-208

This compound was prepared from 3-morpholinopropyl L-valinate and Acid-04 in a similar manner to the last step of Example 1. $^1$H NMR (300 MHz, DMSO-d$_6$): δ 9.04 (br s, 1H), 8.51 (br d, J=7.7 Hz, 1H), 7.37 (d, J=7.7 Hz, 1H), 7.28-7.16 (m, 1H), 4.97 (s, 2H), 4.35-4.25 (m, 1H), 4.19-4.04 (m, 2H), 3.72-3.49 (m, 4H), 2.48 (d, J=5.5 Hz, 3H), 2.42-2.27 (m, 6H), 2.21-2.05 (m, 1H), 1.76 (q, J=6.7 Hz, 2H), 0.96 (d, J=6.6 Hz, 6H). LC-MS: m/z: 419.29 [M+H]$^+$ HPLC purity: 97.20% (220 nm) and chiral HPLC purity is 95.25% (218 nm).

Example 209. 3-hydroxy-3-methylbutyl (1-hydroxy-7-methyl-1,3-dihydrobenzo[c][1,2]oxaborole-6-carbonyl)-L-valinate (6-209)

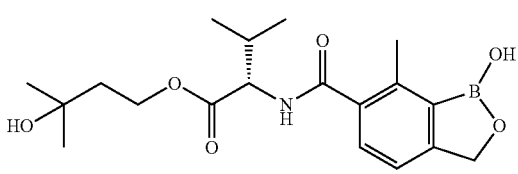

6-209

This compound was prepared from 3-hydroxy-3-methylbutyl L-valinate and Acid-04 in a similar manner to the last step of Example 1. $^1$H NMR (300 MHz, DMSO-d$_6$): δ 9.04 (s, 1H), 8.50 (d, J=8.1 Hz, 1H), 7.37 (d, J=7.7 Hz, 1H), 7.24 (d, J=7.7 Hz, 1H), 4.97 (s, 2H), 4.38 (s, 1H), 4.32-4.25 (m, 1H), 4.22-4.14 (m, 2H), 2.50-2.42 (m, 3H), 2.23-2.02 (m, 1H), 1.72 (t, J=7.5 Hz, 2H), 1.12 (s, 6H), 0.95 (d, J=7.0 Hz, 6H). LC-MS: m/z 378.29[M+H]$^+$. HPLC purity: 97% (220 nm) and chiral HPLC purity is 97.9% (219 nm).

Example 210. (tetrahydrofuran-2-yl)methyl (1-hydroxy-7-methyl-1,3-dihydrobenzo[c][1,2]oxaborole-6-carbonyl)-L-valinate (6-210)

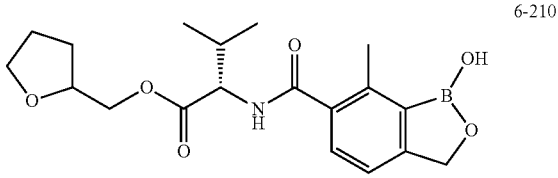 [SMILES: Cc1c(C(=O)N[C@H](C(=O)OCC2CCCO2)C(C)C)ccc2c1B(O)OC2]

6-210

This compound was prepared from cyclopentylmethyl L-valinate and Acid-04 in a similar manner to the last step of Example 1. $^1$H NMR (300 MHz, DMSO-d$_6$): δ 9.03 (s, 1H), 8.61-8.45 (m, 1H), 7.38 (d, J=7.7 Hz, 1H), 7.24 (d, J=8.1 Hz, 1H), 4.97 (s, 2H), 4.32 (t, J=7.2 Hz, 1H), 4.17-3.95 (m, 3H), 3.83-3.54 (m, 2H), 2.47 (s, 3H), 2.14 (qd, J=13.5, 6.9 Hz, 1H), 2.00-1.73 (m, 3H), 1.60 (br dd, J=9.0, 6.1 Hz, 1H), 0.96 (d, J=6.6 Hz, 6H); LC-MS: m/z 376.24 [M+H]$^+$ HPLC purity: 96.93% (220 nm).

Example 211. 2-hydroxy-2-methylpropyl (1-hydroxy-7-methyl-1,3-dihydrobenzo[c][1,2]oxaborole-6-carbonyl)-L-valinate (6-211)

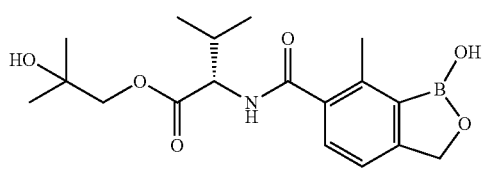

6-211

This compound was prepared from 2-hydroxy-2-methylpropyl L-valinate and Acid-04 in a similar manner to the last step of Example 1. $^1$H NMR (300 MHz, DMSO-d$_6$): δ 9.04 (s, 1H), 8.51 (d, J=8.1 Hz, 1H), 7.38 (d, J=7.7 Hz, 1H), 7.25 (d, J=7.7 Hz, 1H), 4.98 (s, 2H), 4.58 (br s, 1H), 4.40 (dd, J=6.4, 7.9 Hz, 1H), 3.86 (s, 2H), 2.47 (s, 3H), 2.18 (qd, J=6.7, 13.5 Hz, 1H), 1.13 (s, 6H), 0.99 (d, J=7.0 Hz, 3H), 0.98 (d, J=7.0 Hz, 3H); LC-MS: m/z 364.28 [M+H]$^+$. HPLC purity: 99.4% (220 nm) and chiral HPLC purity is 97.03% (212 nm).

Example 212. 2-(2-oxopyrrolidin-1-yl)ethyl (1-hydroxy-7-methyl-1,3-dihydrobenzo[c][1,2]oxaborole-6-carbonyl)-L-valinate (6-212)

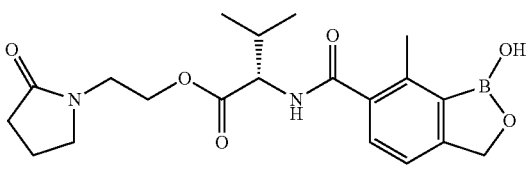

6-212

This compound was prepared from 2-(2-oxopyrrolidin-1-yl)ethyl L-valinate and Acid-04 in a similar manner to the last step of Example 1. $^1$H NMR (300 MHz, DMSO-d$_6$) δ 9.04 (br s, 1H), 8.50 (d, J=8.1 Hz, 1H), 7.38 (d, J=7.7 Hz, 1H), 7.24 (d, J=7.7 Hz, 1H), 4.97 (s, 2H), 4.36-4.27 (m, 1H), 4.20 (t, J=5.5 Hz, 2H), 3.50-3.33 (m, 4H), 2.48 (d, J=5.5 Hz, 3H), 2.29-2.06 (m, 3H), 1.89 (quin, J=7.4 Hz, 2H), 0.94 (d, J=6.6 Hz, 6H); LC-MS: m/z 403.28 [M+H]$^+$. HPLC purity: 96.7% (220 nm) and chiral HPLC purity is 98.12% (215 nm).

Example 213. (6-(piperazin-1-yl)pyridin-2-yl)
methyl (1-hydroxy-7-methyl-1,3-dihydrobenzo[c][1,
2]oxaborole-6-carbonyl)-L-valinate (6-213)

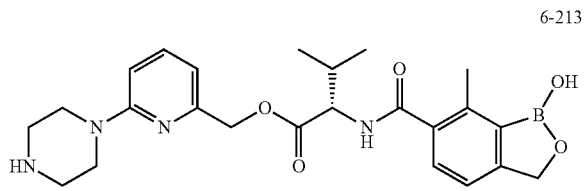 [SMILES: Cc1c(C(=O)N[C@H](C(=O)OCc2cccc(N3CCNCC3)n2)C(C)C)ccc2c1B(O)OC2]

6-213

This compound was prepared from methyl 6-chloropicolinate in a similar manner to Example 205. $^1$H NMR (400 MHz, DMSO-d$_6$): δ 9.10 (br s, 2H), 8.60 (br d, J=7.8 Hz, 1H), 7.72-7.60 (m, 1H), 7.36 (d, J=7.8 Hz, 1H), 7.24 (d, J=7.8 Hz, 1H), 6.87 (d, J=8.3 Hz, 1H), 6.81 (d, J=7.3 Hz, 1H), 5.09 (s, 2H), 4.97 (s, 2H), 4.57-4.29 (m, 1H), 3.79-3.66 (m, 4H), 3.15 (br s, 4H), 2.49-2.39 (m, 3H), 2.20 (qd, J=13.6, Hz, 1H), 0.98 (d, J=6.8 Hz, 6H). LC-MS: m/z 467.35 [M+Na]$^+$. HPLC purity: 97.48% (220 nm) and chiral HPLC purity is 96.58% (246 nm).

Example 214. 2-(1,4-oxazepane-4-yl)ethyl (1-hydroxy-7-methyl-1,3-dihydrobenzo[c][1,2]oxaborole-6-carbonyl)-L-valinate (6-214)

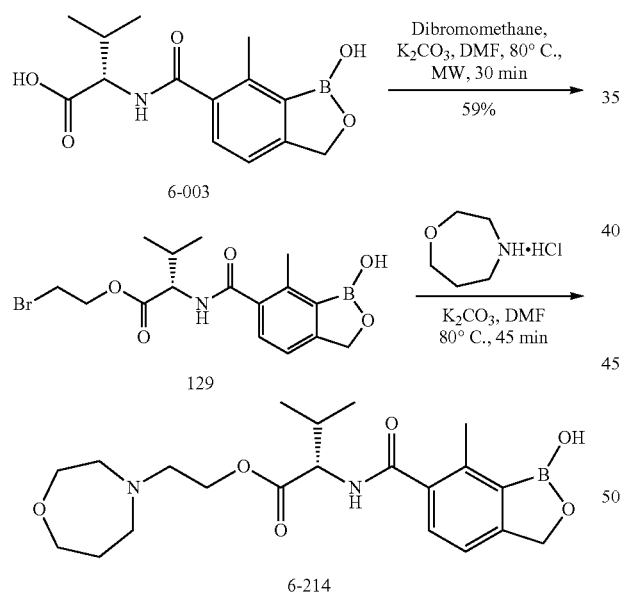

6-214

To a stirred solution of 6-003 (1.00 g, 3.43 mmol) in DMF (10 mL) was added K$_2$CO$_3$ (948 mg, 6.87 mmol) at RT. The reaction mixture was stirred at RT for 10 min. Then 1,2-dibromoethane (2.9 mL, 34.36 mmol) was added at RT. The reaction mixture was irradiated under microwave at 80° C. for 30 min. The progress of the reaction was monitored by TLC. The reaction mixture was quenched with ice cold water and was extracted into EtOAc (2×100 ml). The combined organic layers were washed with water, brine and dried over Na$_2$SO$_4$. The solvent was removed under reduced pressure to get 129 (800 mg, 59%) as an off-white solid. To a stirred solution of 1,4-oxazepane hydrochloride (200 mg, 1.98 mmol) in DMF (10 vol) was added 129 (786 mg, 1.98 mmol), and potassium carbonate (819 mg, 5.94 mmol) at room temperature. The reaction mixture was stirred at 80° C. for 1 h. The progress of the reaction was monitored by TLC. TLC showed formation of a non-polar spot with complete consumption of both the starting materials. The solvent was removed under reduced pressure to get the crude material. The crude compound was purified via [C-18 column with 0.1% HCOOH in water and acetonitrile] to afford 6-214 (181 mg, 22%) as an off-white gummy solid. $^1$H NMR (400 MHz, DMSO-d$_6$): δ 9.03 (s, 1H), 8.52 (br d, J=7.3 Hz, 1H), 7.38 (d, J=7.8 Hz, 1H), 7.24 (d, J=7.8 Hz, 1H), 4.97 (s, 2H), 4.38-4.07 (m, 3H), 3.71-3.47 (m, 4H), 2.97-2.63 (m, 6H), 2.47 (s, 3H), 2.15 (qd, J=13.3, 6.8 Hz, 1H), 1.86-1.76 (m, 2H), 0.97 (d, J=6.8 Hz, 6H); LC-MS: m/z 419.35 [M+H]$^+$. HPLC purity: 97.02% (220 nm) and chiral HPLC purity is 97.7% (215 nm).

Example 215. ((R)-tetrahydrofuran-2-yl)methyl (1-hydroxy-7-methyl-1,3-dihydrobenzo[c][1,2]oxaborole-6-carbonyl)-L-valinate (6-215)

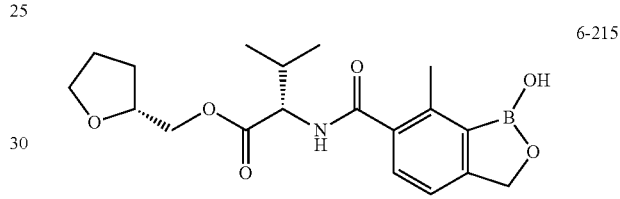

6-215

This compound was prepared from ((R)-tetrahydrofuran-2-yl)methyl L-valinate and Acid-04 in a similar manner to the last step of Example 1. $^1$H NMR (400 MHz, DMSO-d$_6$): δ 9.03 (s, 1H), 8.52 (d, J=7.8 Hz, 1H), 7.38 (d, J=7.8 Hz, 1H), 7.24 (d, J=7.8 Hz, 1H), 4.97 (s, 2H), 4.36-4.27 (m, 1H), 4.20-4.09 (m, 1H), 4.06-3.95 (m, 2H), 3.80-3.72 (m, 1H), 3.70-3.60 (m, 1H), 2.47 (s, 3H), 2.21-2.08 (m, 1H), 2.01-1.74 (m, 3H), 1.61 (ddd, J=11.9, 8.4, 6.6 Hz, 1H), 0.98 (d, J=6.8 Hz, 3H), 0.94 (d, J=6.8 Hz, 3H) LC-MS: m/z 376.28 [M+H]$^+$. HPLC purity: 97.39% (220 nm) and chiral HPLC purity is 96.76% (225 nm).

Example 216. 2-(2-oxooxazolidin-3-yl)ethyl (1-hydroxy-7-methyl-1,3-dihydrobenzo[c][1,2]oxaborole-6-carbonyl)-L-valinate (6-216)

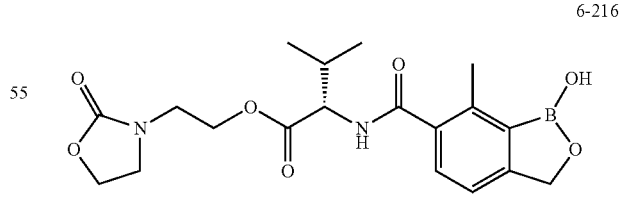

6-216

This compound was prepared from 2-(2-oxooxazolidin-3-yl)ethyl L-valinate and Acid-04 in a similar manner to the last step of Example 1. $^1$H NMR (400 MHz, DMSO-d$_6$): δ 9.03 (s, 1H), 8.52 (d, J=7.8 Hz, 1H), 7.38 (d, J=7.8 Hz, 1H), 7.24 (d, J=7.8 Hz, 1H), 4.97 (s, 2H), 4.34-4.29 (m, 1H), 4.28-4.17 (m, 4H), 3.60 (t, J=8.1 Hz, 2H), 3.50-3.39 (m, 2H), 2.47 (s, 3H), 2.14 (dd, J=13.5, 6.6 Hz, 1H), 0.95 (d, J=6.8 Hz, 6H); LC-MS: m/z 405.26 [M+H]⁺. HPLC purity: 99.25% (220 nm) and Chiral HPLC purity is 98.99% (211 nm)

Example 217. 2-(2-oxa-7-azaspiro[3.5]nonan-7-yl) ethyl (1-hydroxy-7-methyl-1,3-dihydrobenzo[c][1,2]oxaborole-6-carbonyl)-L-valinate (6-217)

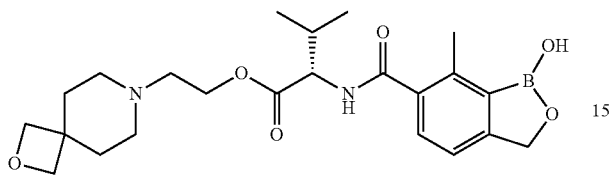

6-217

This compound was prepared from 2-oxa-7-azaspiro[3.5]nonane in a similar manner to the last step of Example 214. ¹H NMR (300 MHz, DMSO-d₆): δ 9.04 (s, 1H), 8.53 (br d, J=7.3 Hz, 1H), 7.38 (d, J=7.7 Hz, 1H), 7.25 (br d, J=7.7 Hz, 1H), 4.98 (s, 2H), 4.40-4.08 (m, 7H), 2.95-2.51 (m, 6H), 2.47 (br s, 3H), 2.14 (br dd, J=13.8, 6.8 Hz, 1H), 1.79 (br s, 4H), 0.96 (d, J=6.6 Hz, 6H). LC-MS: m/z 445.4 [(M+H)⁺]. HPLC purity: 93.46% (220 nm) and chiral HPLC purity is 96.16% (211 nm).

Example 218. 2-(2-oxa-6-azaspiro[3.3]heptan-6-yl) ethyl (1-hydroxy-7-methyl-1,3-dihydrobenzo[c][1,2]oxaborole-6-carbonyl)-L-valinate (6-218)

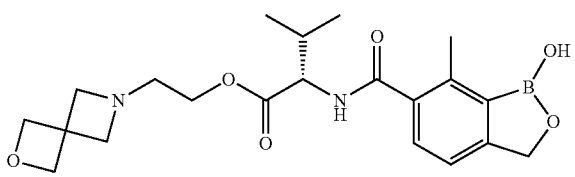

6-218

This compound was prepared from 2-oxa-6-azaspiro[3.3]heptane in a similar manner to the last step of Example 214. ¹H NMR (300 MHz, DMSO-d₆): δ 9.04 (br s, 1H), 8.52 (br d, J=8.1 Hz, 1H), 7.39 (d, J=7.7 Hz, 1H), 7.25 (d, J=7.7 Hz, 1H), 4.98 (s, 2H), 4.58 (s, 4H), 4.32 (t, J=7.2 Hz, 1H), 4.06 (br t, J=5.3 Hz, 2H), 3.50 (br s, 4H), 2.73 (br s, 2H), 2.48 (br s, 3H), 2.24-2.04 (m, 1H), 0.96 (d, J=7.0 Hz, 6H). LC-MS: 417.31 [M+H]⁺. HPLC purity: 97.53% and chiral HPLC purity is 99.04% (212 nm).

Example 219. 2-(3-methylmorpholino)ethyl (1-hydroxy-7-methyl-1,3-dihydrobenzo[c][1,2]oxaborole-6-carbonyl)-L-valinate (6-219)

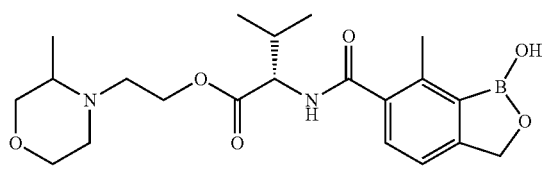

6-219

This compound was prepared from 2-(3-methylmorpholino)ethyl L-valinate and Acid-04 in a similar manner to the last step of Example 1. ¹H NMR (400 MHz, DMSO-d₆): δ 9.04 (br s, 1H), 8.69-8.41 (m, 1H), 7.38 (d, J=7.3 Hz, 1H), 7.25 (br d, J=7.8 Hz, 1H), 4.98 (s, 2H), 4.53-3.96 (m, 4H), 3.77-3.34 (m, 4H), 3.12-2.86 (m, 2H), 2.75 (br s, 1H), 2.48 (s, 3H), 2.41-2.24 (m, 2H), 2.15 (br s, 1H), 1.32-1.11 (m, 1H), 1.03-0.84 (m, 7H); LC-MS: m/z 419.35[M+H]⁺. HPLC purity: 99.61% (220 nm).

Example 220. (1-hydroxycyclopentyl)methyl (1-hydroxy-7-methyl-1,3-dihydrobenzo[c][1,2]oxaborole-6-carbonyl)-L-valinate (6-220)

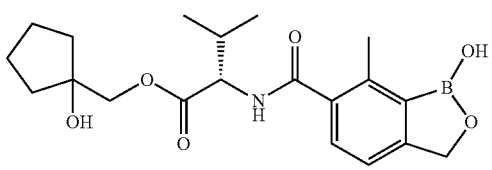

6-220

This compound was prepared from (1-hydroxycyclopentyl)methyl L-valinate and Acid-04 in a similar manner to the last step of Example 1. ¹H NMR (400 MHz, DMSO-d₆): δ 9.03 (s, 1H), 8.49 (d, J=8.2 Hz, 1H), 7.38 (d, J=7.6 Hz, 1H), 7.25 (d, J=7.9 Hz, 1H), 4.97 (s, 2H), 4.49 (s, 1H), 4.39 (dd, J=7.9, 6.4 Hz, 1H), 4.09-3.94 (m, 2H), 2.47 (s, 3H), 2.18 (qd, J=13.4, 6.7 Hz, 1H), 1.71 (br d, J=4.0 Hz, 2H), 1.55 (br s, 6H), 0.98 (d, J=7.0 Hz, 3H); 0.94 (d, J=7.0 Hz, 3H); LC-MS: m/z 387.82[M+H]⁺. HPLC purity: 97.94% (220 nm) and chiral HPLC purity is 97.86% (213 nm).

Example 221. 4-fluorobenzyl 3-(1-hydroxy-7-methyl-1,3-dihydrobenzo[c][1,2]oxaborole-6-carboxamido)oxetane-3-carboxylate (6-221)

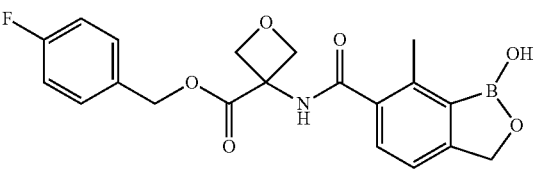

6-221

This compound was prepared from 4-fluorobenzyl 3-aminooxetane-3-carboxylate and Acid-04 in a similar manner to the last step of Example 1. ¹H NMR (300 MHz, DMSO-d₆): δ 9.48 (s, 1H), 9.07 (br s, 1H), 7.57-7.35 (m, 3H), 7.32-7.02 (m, 3H), 5.22 (s, 2H), 5.04-4.84 (m, 4H), 4.67 (d, J=6.6 Hz, 2H), 2.42 (s, 3H); LCMS: m/z 400.27[M+H]⁺. HPLC purity: 95.08% (220 nm).

Example 222. 2-morpholinoethyl 3-(1-hydroxy-7-methyl-1,3-dihydrobenzo[c][1,2]oxaborole-6-carboxamido)oxetane-3-carboxylate (6-222)

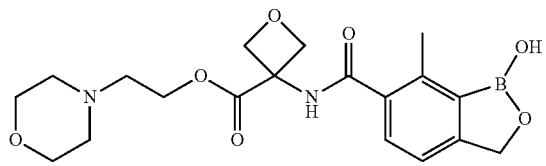

6-222

This compound was prepared from 2-morpholinoethyl 3-aminooxetane-3-carboxylate and Acid-04 in a similar manner to the last step of Example 1. $^1$H NMR (300 MHz, DMSO-d$_6$): δ 9.47 (s, 1H), 9.08 (s, 1H), 7.51 (d, J=7.7 Hz, 1H), 7.29 (br d, J=7.7 Hz, 1H), 5.09-4.87 (m, 4H), 4.67 (br d, J=6.6 Hz, 2H), 4.31 (br s, 2H), 3.54 (br s, 4H), 2.52 (br s, 6H), 2.47-2.17 (m, 3H); LC-MS: m/z 404.8 [M+H]$^+$ HPLC purity: 97.2% (220 nm).

Example 223. Pyridin-2-ylmethyl 3-(1-hydroxy-7-methyl-1,3-dihydrobenzo[c][1,2]oxaborole-6-carboxamido)oxetane-3-carboxylate (6-223)

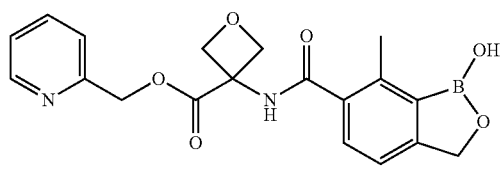

6-223

This compound was prepared from pyridin-2-ylmethyl 3-aminooxetane-3-carboxylate and Acid-04 in a similar manner to the last step of Example 1. $^1$H NMR (300 MHz, DMSO-d$_6$): δ 9.54 (s, 1H), 9.07 (s, 1H), 8.56 (d, J=4.0 Hz, 1H), 7.92-7.77 (m, 1H), 7.49-7.42 (m, 2H), 7.35 (dd, J=7.2, 5.3 Hz, 1H), 7.26 (d, J=7.7 Hz, 1H), 5.31 (s, 2H), 5.04-4.93 (m, 4H), 4.71 (d, J=6.6 Hz, 2H), 2.44 (s, 3H): LC-MS: m/z 383.24 [M+H]t HPLC purity: 99.27% (220 nm).

Example 224. Cyclopentylmethyl 3-(1-hydroxy-7-methyl-1,3-dihydrobenzo[c][1,2]oxaborole-6-carboxamido)oxetane-3-carboxylate (6-224)

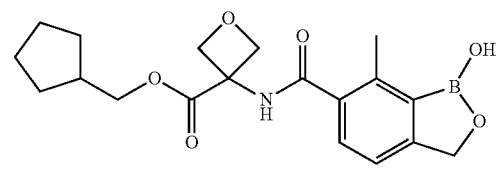

6-224

This compound was prepared from cyclopentylmethyl 3-aminooxetane-3-carboxylate and Acid-04 in a similar manner to the last step of Example 1. $^1$H NMR (400 MHz, DMSO-d$_6$): δ 9.44 (s, 1H), 9.08 (s, 1H), 7.48 (d, J=7.7 Hz, 1H), 7.29 (d, J=7.7 Hz, 1H), 4.99 (s, 2H), 4.91 (d, J=6.6 Hz, 2H), 4.66 (d, J=6.6 Hz, 2H), 4.06 (d, J=7.0 Hz, 2H), 2.47 (br s, 3H), 2.26-2.11 (m, 1H), 1.77-1.61 (m, 2H), 1.60-1.40 (m, 4H), 1.25 (br dd, J=6.8, 11.9 Hz, 2H); LC-MS: m/z 374.3 [M+H]$^+$. HPLC purity: 97.32% (220 nm).

Example 225. (2-aminopyrimidin-5-yl)methyl (1-hydroxy-7-methyl-1,3-dihydrobenzo[c][1,2]oxaborole-6-carbonyl)-L-valinate (6-225)

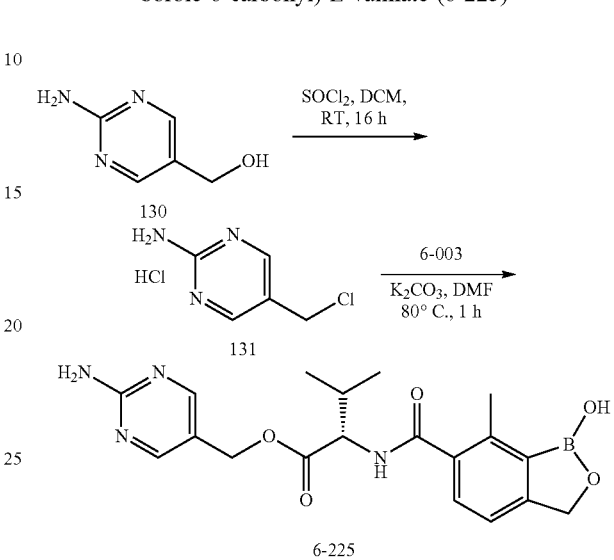

To a stirred suspension of 130 (500 mg, 4 mmol) in DCM (10 mL) was added SOCl$_2$ (1 mL) drop wise at 0° C. After completion of the addition, the reaction mixture was allowed to RT for 16 h. The reaction mixture was concentrated under reduced pressure to get 290 mg of crude 131 as HCl salt. The crude compound was as such taken for next step without any further purification. To a stirred solution of 6-003 (582 mg, 2 mmol) in DMF (10 mL) was added 131 (290 mg, crude, 2 mmol) and K$_2$CO$_3$ (828 mg, 6 mmol) at RT. The reaction mixture was irradiated under microwave at 80° C. for 1 h. The progress of the reaction was monitored by TLC. The solvent was removed under reduced pressure to get the crude material. The crude compound was purified by Grace Purification system [C-18 column with 0.01% HCOOH in water and acetonitrile] to afford 500 mg of crude 6-225. The crude compound was purified by prep. HPLC purification to get 6-225 (60 mg, 4% two steps) as a white solid. $^1$H NMR (400 MHz, DMSO-d$_6$): δ 9.03 (br s, 1H), 8.53 (br d, J=7.8 Hz, 1H), 8.31 (s, 2H), 7.35-7.30 (d, J=7.3 Hz, 1H), 7.23 (d, J=7.3 Hz, 1H), 7.09-6.84 (m, 2H), 5.13-4.85 (m, 4H), 4.37-4.22 (m, 1H), 2.43 (s, 3H), 2.11 (qd, J=13.3, 6.3 Hz, 1H), 0.92 (d, J=6.8 Hz, 3H), 0.90 (d, J=6.8 Hz, 3HLC-MS: m/z 399.22 [M+H]$^+$. HPLC purity: 94.03% (220 nm) and chiral HPLC purity is 98.99% (229 nm).

Example 226. (4-fluorotetrahydro-2H-pyran-4-yl)methyl (1-hydroxy-7-methyl-1,3-dihydrobenzo[c][1,2]oxaborole-6-carbonyl)-L-valinate (6-226)

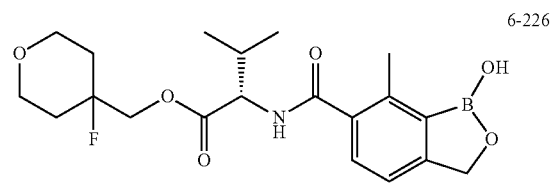 [SMILES: Cc1c(C(=O)N[C@H](C(=O)OCC2(F)CCOCC2)C(C)C)ccc2c1B(O)OC2]

6-226

This compound was prepared from (4-fluorotetrahydro-2H-pyran-4-yl)methyl L-valinate and Acid-04 in a similar manner to the last step of Example 1. $^1$H NMR (400 MHz, DMSO-d$_6$): δ 9.03 (s, 1H), 8.58 (d, J=7.3 Hz, 1H), 7.37 (d, J=7.8 Hz, 1H), 7.25 (d, J=7.3 Hz, 1H), 4.97 (s, 2H), 4.35 (t, J=7.3 Hz, 1H), 4.29-4.14 (m, 2H), 3.73 (td, J=11.5, 3.8 Hz, 2H), 3.56 (dt, J=3.9, 10.8 Hz, 2H), 2.47 (s, 3H), 2.16 (qd, J=13.6, 6.7 Hz, 1H), 1.91-1.69 (m, 4H), 0.97 (dd, J=6.8, 3.4 Hz, 6H); LC-MS: m/z 408.23 [M+H]$^+$ HPLC purity: 99.40% (220 nm) and chiral HPLC purity is 98.37% (210 nm).

Example 227. (1,4-dioxan-2-yl)methyl (1-hydroxy-7-methyl-1,3-dihydrobenzo[c][1,2]oxaborole-6-carbonyl)-L-valinate (6-227)

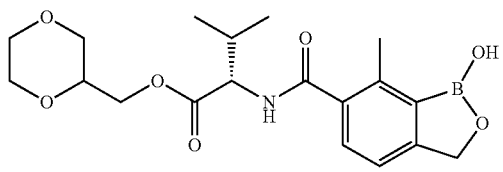

6-227

This compound was prepared from (1,4-dioxan-2-yl)methyl L-valinate and Acid-04 in a similar manner to the last step of Example 1. $^1$H NMR (400 MHz, DMSO-d$_6$): δ 9.03 (s, 1H), 8.54 (d, J=7.8 Hz, 1H), 7.38 (d, J=7.3 Hz, 1H), 7.25 (d, J=7.8 Hz, 1H), 4.98 (s, 2H), 4.36-4.27 (m, 1H), 4.17-3.98 (m, 2H), 3.78-3.69 (m, 3H), 3.66-3.52 (m, 2H), 3.51-3.40 (m, 1H), 3.38-3.33 (m, 1H), 2.47 (s, 3H), 2.21-2.08 (m, 1H), 0.97 (d, J=6.6 Hz, 3H), 0.95 (d, J=6.6 Hz, 3H); LC-MS: m/z 392.22 [M+H]$^+$. HPLC purity: 99.17% (220 nm).

Example 228. Cyclopentylmethyl (S)-3-hydroxy-2-(1-hydroxy-7-methyl-1,3-dihydrobenzo[c][1,2]oxaborole-6-carboxamido)-3-methylbutanoate (228)

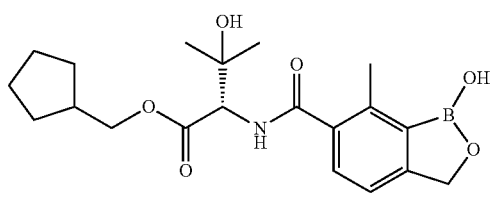

6-228

This compound was prepared from cyclopentylmethyl (S)-2-amino-3-hydroxy-3-methylbutanoate and Acid-04 in a similar manner to the last step of Example 1. $^1$H NMR (400 MHz, DMSO-d$_6$): δ 9.05 (s, 1H), 8.12 (d, J=8.3 Hz, 1H), 7.41 (d, J=7.8 Hz, 1H), 7.26 (d, J=7.8 Hz, 1H), 4.98 (s, 2H), 4.74 (s, 1H), 4.40 (d, J=7.8 Hz, 1H), 4.06-3.77 (m, 2H), 2.49 (d, J=5.4 Hz, 3H), 2.24-2.02 (m, 1H), 1.78-1.65 (m, 2H), 1.62-1.45 (m, 4H), 1.25 (d, J=2.9 Hz, 8H); LC-MS: m/z 390.24 [M+H]$^+$. HPLC purity is 98.87% (220 nm) and chiral HPLC purity is 99.5% (227 nm).

Example 229. (1-hydroxycyclohexyl)methyl (1-hydroxy-7-methyl-1,3-dihydrobenzo[c][1,2]oxaborole-6-carbonyl)-L-valinate (6-229)

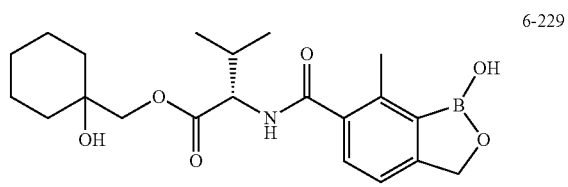 [SMILES: Cc1c(C(=O)N[C@H](C(=O)OCC2(O)CCCCC2)C(C)C)ccc2c1B(O)OC2]

6-229

This compound was prepared from (1-hydroxycyclohexyl)methyl L-valinate and Acid-04 in a similar manner to the last step of Example 1. $^1$H NMR (300 MHz, DMSO-d$_6$): δ 9.04 (s, 1H), 8.50 (d, J=8.1 Hz, 1H), 7.38 (d, J=7.7 Hz, 1H), 7.25 (d, J=8.1 Hz, 1H), 4.97 (s, 2H), 4.40 (dd, J=6.6, 8.1 Hz, 1H), 4.32 (s, 1H), 3.87 (s, 2H), 2.47 (s, 3H), 2.18 (br dd, J=13.4, 6.8, Hz, 1H), 1.67-1.32 (m, 9H), 1.17 (br d, J=11.0 Hz, 1H), 0.97 (d, J=7.0 Hz, 3H), 0.96 (d, J=7.0 Hz, 3H); LC-MS: m/z 404.27 [M+H]$^+$ HPLC purity: 99.19% (220 nm) and chiral HPLC purity is 96.91% (210 nm).

Example 230. Pyridin-2-ylmethyl (S)-3-hydroxy-2-(1-hydroxy-7-methyl-1,3-dihydrobenzo[c][1,2]oxaborole-6-carboxamido)-3-methylbutanoate (6-230)

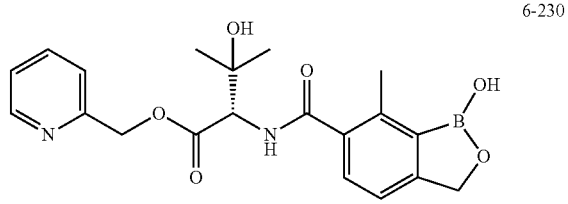 [SMILES: Cc1c(C(=O)N[C@H](C(=O)OCc2ccccn2)C(C)(C)O)ccc2c1B(O)OC2]

6-230

This compound was prepared from pyridin-2-ylmethyl (S)-2-amino-3-hydroxy-3-methylbutanoate and Acid-04 in a similar manner to the last step of Example 1. $^1$H NMR (300 MHz, DMSO-d$_6$): δ 9.05 (br s, 1H), 8.55 (br d, J=4.4 Hz, 1H), 8.29 (d, J=8.1 Hz, 1H), 7.82 (dt, J=7.7, 1.8 Hz, 1H), 7.60-7.47 (m, 1H), 7.45-7.32 (m, 2H), 7.25 (d, J=7.7 Hz, 1H), 5.37-5.16 (m, 2H), 5.04-4.82 (m, 3H), 4.53 (d, J=8.1 Hz, 1H), 2.45 (s, 3H), 1.27 (d, J=4.4 Hz, 6H)

LC-MS: m/z 399.25 [M+H]$^+$. HPLC purity: 93.98% (220 nm) and chiral HPLC purity is 96.7% (210 nm).

Example 231. 2-(6-oxa-3-azabicyclo[3.1.1]heptan-3-yl)ethyl (1-hydroxy-7-methyl-1,3-dihydrobenzo[c][1,2]oxaborole-6-carbonyl)-L-valinate (6-231)

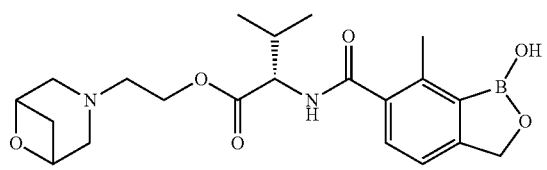

6-231

This compound was prepared from 6-oxa-3-azabicyclo[3.1.1]heptane in a similar manner to the last step of Example 214. ¹H NMR (300 MHz, DMSO-d₆): δ 9.03 (br s, 1H), 8.51 (d, J=7.7 Hz, 1H), 7.37 (d, J=8.1 Hz, 1H), 7.24 (d, J=7.7 Hz, 1H), 4.97 (s, 2H), 4.40 (d, J=5.9 Hz, 2H), 4.35-4.28 (m, 2H), 4.25-4.15 (m, 1H), 3.06 (br d, J=11.0 Hz, 2H), 2.87-2.76 (m, 3H), 2.74-2.61 (m, 2H), 2.47 (s, 3H), 2.24-2.02 (m, 2H), 0.96 (d, J=6.6 Hz, 6H); LC-MS: m/z 417.31 [M+H]⁺. HPLC purity: 95.6% (220 nm) and chiral HPLC purity is 95.17% (215 nm).

Example 232. (6-(dimethylamino)pyrazin-2-yl)methyl (1-hydroxy-7-methyl-1,3-dihydrobenzo[c][1,2]oxaborole-6-carbonyl)-L-valinate (6-232)

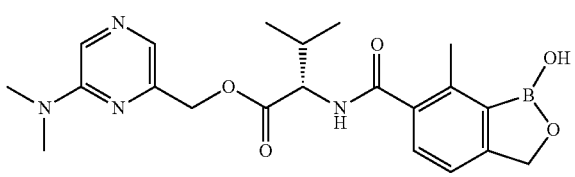

6-232

This compound was prepared from (6-(dimethylamino)pyrazin-2-yl)methyl L-valinate and Acid-04 in a similar manner to the last step of Example 1. ¹H NMR (300 MHz, DMSO-d₆): δ 9.04 (s, 1H), 8.64 (br d, J=7.7 Hz, 1H), 8.33 (d, J=4.8 Hz, 1H), 7.37 (d, J=7.7 Hz, 1H), 7.24 (d, J=7.7 Hz, 1H), 6.63 (d, J=4.8 Hz, 1H), 5.04 (s, 2H), 4.97 (s, 2H), 4.44 (t, J=7.3 Hz, 1H), 3.10 (s, 6H), 2.46 (s, 3H), 2.22 (br dd, J=6.8, 13.4 Hz, 1H), 0.99 (d, J=6.6 Hz, 6H); LC-MS: m/z 427.27 [M+H]⁺. HPLC purity: 98.46% (220 nm), 98.32% (254 nm) and chiral HPLC purity is 99.61% (244 nm).

Example 233. (3-methyltetrahydrofuran-3-yl)methyl (1-hydroxy-7-methyl-1,3-dihydrobenzo[c][1,2]oxaborole-6-carbonyl)-L-valinate (6-233)

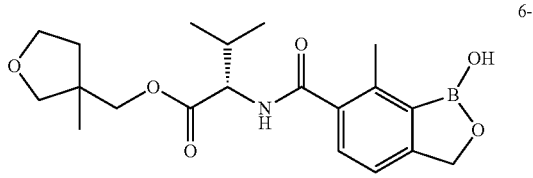

6-233

This compound was prepared from (3-methyltetrahydrofuran-3-yl)methyl L-valinate and Acid-04 in a similar manner to the last step of Example 1. ¹H NMR (300 MHz, DMSO-d₆): δ 9.04 (s, 1H), 8.55 (br d, J=7.7 Hz, 1H), 7.37 (d, J=7.7 Hz, 1H), 7.25 (d, J=7.7 Hz, 1H), 4.97 (s, 2H), 4.37-4.27 (m, 1H), 4.05-3.92 (m, 2H), 3.75 (t, J=7.2 Hz, 2H), 3.57 (dd, J=8.4, 5.1 Hz, 1H), 3.29-3.22 (m, 1H), 2.48 (s, 3H), 2.22-2.06 (m, 1H), 1.89-1.71 (m, 1H), 1.66-1.50 (m, 1H), 1.10 (s, 3H), 1.01-0.84 (m, 6H); LC-MS: m/z 390.3 [M+H]⁺. HPLC purity: 96.4% (220 nm).

Example 234. ((R)-tetrahydrofuran-3-yl)methyl (1-hydroxy-7-methyl-1,3-dihydrobenzo[c][1,2]oxaborole-6-carbonyl)-L-valinate (6-234)

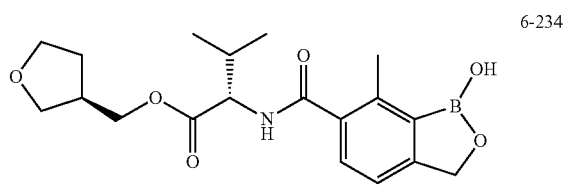 [SMILES: Cc1c(C(=O)N[C@H](C(=O)OC[C@@H]2CCOC2)C(C)C)ccc2c1B(O)OC2]

6-234

This compound was prepared from ((S)-tetrahydrofuran-2-yl)methyl L-valinate and Acid-04 in a similar manner to the last step of Example 1. ¹H NMR (300 MHz, DMSO-d₆): δ 9.04 (s, 1H), 8.54 (d, J=7.7 Hz, 1H), 7.37 (d, J=7.7 Hz, 1H), 7.25 (d, J=7.7 Hz, 1H), 4.98 (s, 2H), 4.30 (t, J=7.2 Hz, 1H), 4.15-3.91 (m, 2H), 3.82-3.54 (m, 3H), 3.45 (dd, J=8.6, 5.7 Hz, 1H), 2.57-2.51 (m, 1H), 2.47 (s, 3H), 2.14 (qd, J=13.5, 6.6 Hz, 1H), 2.01-1.85 (m, 1H), 1.58 (dt, J=13.1, 6.8 Hz, 1H), 0.96 (dd, J=6.8, 1.7 Hz, 6H); LC-MS: m/z 376.24 [M+H]⁺. HPLC purity: 96.3% (220 nm) and chiral HPLC purity is 97.66% (210 nm).

Example 235. ((S)-tetrahydrofuran-3-yl)methyl (1-hydroxy-7-methyl-1,3-dihydrobenzo[c][1,2]oxaborole-6-carbonyl)-L-valinate (6-235)

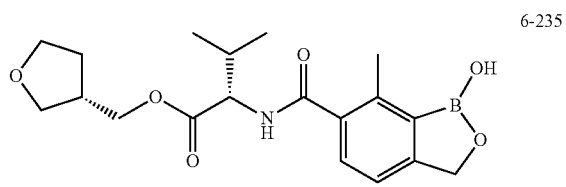 [SMILES: Cc1c(C(=O)N[C@H](C(=O)OC[C@H]2CCOC2)C(C)C)ccc2c1B(O)OC2]

6-235

This compound was prepared from ((R)-tetrahydrofuran-2-yl)methyl L-valinate and Acid-04 in a similar manner to the last step of Example 1. ¹H NMR (400 MHz, DMSO-d₆): δ 9.04 (s, 1H), 8.53 (d, J=7.3 Hz, 1H), 7.37 (d, J=7.3 Hz, 1H), 7.25 (d, J=7.8 Hz, 1H), 4.97 (s, 2H), 4.34-4.27 (m, 1H), 4.11-3.95 (m, 2H), 3.79-3.69 (m, 2H), 3.65-3.58 (m, 1H), 3.44 (dd, J=8.8, 5.9 Hz, 1H), 2.57-2.51 (m, 1H), 2.47 (s, 3H), 2.14 (qd, J=13.3, 6.8 Hz, 1H), 2.02-1.90 (m, 1H), 1.64-1.53 (m, 1H), 0.98 (d, J=6.8 Hz, 3H), 0.94 (d, J=6.8 Hz, 3H); LC-MS: m/z 376.24 [M+H]⁺; HPLC purity: 99.29% (220 nm) and chiral HPLC purity is 97.79% (215 nm).

Example 236. (5-(trifluoromethyl)pyrimidin-2-yl)methyl (1-hydroxy-7-methyl-1,3-dihydrobenzo[c][1,2]oxaborole-6-carbonyl)-L-valinate (6-236)

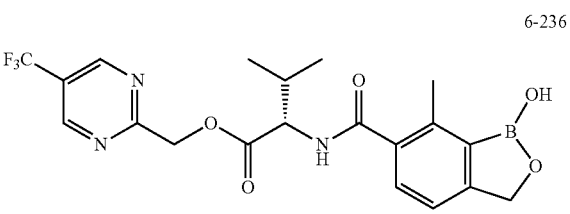 [SMILES: Cc1c(C(=O)N[C@H](C(=O)OCc2ncc(C(F)(F)F)cn2)C(C)C)ccc2c1B(O)OC2]

6-236

This compound was prepared from (5-(trifluoromethyl)pyrimidin-2-yl)methyl L-valinate and Acid-04 in a similar manner to the last step of Example 1. ¹H NMR (300 MHz, DMSO-d₆): δ 9.29 (s, 2H), 9.02 (s, 1H), 8.58 (d, J=7.8 Hz, 1H), 7.39 (d, J=7.8 Hz, 1H), 7.24 (d, J=7.3 Hz, 1H), 5.44 (q, J=15.2 Hz, 2H), 4.97 (s, 2H), 4.51 (dd, J=7.8, 6.4 Hz, 1H), 2.46 (s, 3H), 2.28 (qd, J=13.5, 6.8 Hz, 1H), 1.03 (dd, J=6.6, 4.6 Hz, 6H); LC-MS: m/z 452.16 [M+H]⁺. HPLC purity: 98.97% (220 nm) and chiral HPLC purity is 99.74% (215 nm).

Example 237. (2-aminopyrimidin-4-yl)methyl (1-hydroxy-7-methyl-1,3-dihydrobenzo[c][1,2]oxaborole-6-carbonyl)-L-valinate (6-237)

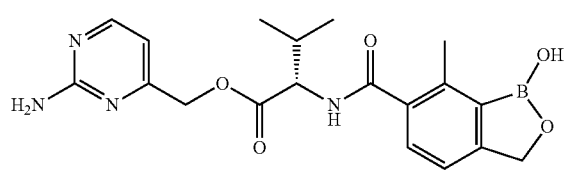

6-237

This compound was prepared from (2-aminopyrimidin-4-yl)methyl L-valinate and Acid-04 in a similar manner to the last step of Example 1. ¹H NMR (400 MHz, DMSO-d₆): δ 9.03 (s, 1H), 8.64 (br d, J=7.8 Hz, 1H), 8.23 (d, J=5.4 Hz, 1H), 7.38 (d, J=7.3 Hz, 1H), 7.25 (br d, J=7.3 Hz, 1H), 6.76-6.57 (m, 3H), 5.11-4.91 (m, 4H), 4.42 (br t, J=7.1 Hz, 1H), 2.46 (s, 3H), 2.29-2.15 (m, 1H), 0.99 (br d, J=6.4 Hz, 6H); LC-MS: m/z 399.22 [M+H]⁺. HPLC purity: 97.35% (220 nm) and chiral HPLC purity is 99.97% (222 nm).

Example 238. 2-morpholinoethyl (S)-3-hydroxy-2-(1-hydroxy-7-methyl-1,3-dihydrobenzo[c][1,2]oxaborole-6-carboxamido)-3-methylbutanoate (6-238)

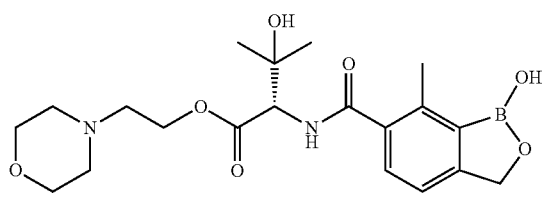

6-238

This compound was prepared from 2-morpholinoethyl (S)-2-amino-3-hydroxy-3-methylbutanoate and Acid-04 in a similar manner to the last step of Example 1. ¹H NMR (400 MHz, DMSO-d₆): δ 9.05 (s, 1H), 8.13 (s, 1H), 7.41 (d, J=7.8 Hz, 1H), 7.26 (d, J=7.8 Hz, 1H), 4.98 (s, 2H), 4.42 (m, 2H), 4.20 (br s, 1H), 4.18 (br s, 1H), 3.54 (s, 4H), 2.60-2.32 (m, 9H), 1.26 (d, J=6.4 Hz, 6H); LC-MS: m/z 421.27 [M+H]⁺. HPLC purity: 96.83% (220 nm) and chiral HPLC purity is 98.10% (210 nm).

Example 239. ((R)-tetrahydrofuran-2-yl)methyl (S)-3-hydroxy-2-(1-hydroxy-7-methyl-1,3-dihydrobenzo[c][1,2]oxaborole-6-carboxamido)-3-methylbutanoate (6-239)

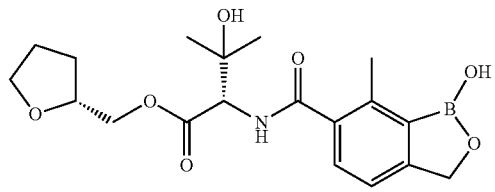

6-239

This compound was prepared from ((R)-tetrahydrofuran-2-yl)methyl (S)-2-amino-3-hydroxy-3-methylbutanoate and Acid-04 in a similar manner to the last step of Example 1. ¹H NMR (400 MHz, DMSO-d₆): δ 9.05 (s, 1H), 8.13 (d, J=7.6 Hz, 1H), 7.41 (d, J=7.6 Hz, 1H), 7.26 (d, J=8 Hz, 1H), 4.98 (s, 2H), 4.74 (s, 1H), 4.42 (d, J=8.4 Hz, 1H), 4.12 (m, 1H), 4.08-3.98 (m, 2H), 3.76 (m, 1H), 3.65 (m, 1H), 2.50 (m, 3H), 1.95-1.75 (m, 3H), 1.61 (m, 1H), 1.20 (m, 6H); LC-MS: m/z 392.22 [M+H]⁺. HPLC purity: 98.71% (220 nm) and chiral HPLC purity is 94.97% (210 nm).

Example 240. (2-(methylamino)pyrimidin-4-yl)methyl (1-hydroxy-7-methyl-1,3-dihydrobenzo[c][1,2]oxaborole-6-carbonyl)-L-valinate (6-240)

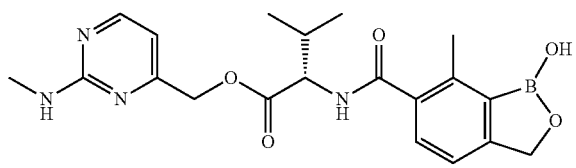

6-240

This compound was prepared from (2-(methylamino)pyrimidin-4-yl)methyl L-valinate and Acid-04 in a similar manner to the last step of Example 1. ¹H NMR (300 MHz, DMSO-d₆): δ 9.04 (s, 1H), 8.64 (d, J=7.8 Hz, 1H), 8.27 (br d, J=4.2 Hz, 1H), 7.38 (d, J=7.8 Hz, 1H), 7.25 (d, J=7.8 Hz, 1H), 7.11 (m, 1H), 6.61 (d, J=4.8 Hz, 1H), 5.01 (s, 2H), 4.97 (s, 2H), 4.42 (t, J=7.2 Hz, 1H), 2.78 (d, J=4.8 Hz, 3H), 2.46 (s, 3H), 2.22 (m, 1H), 0.98 (d, J=6.6 Hz, 6H); LC-MS: m/z 413.18 [M+H]⁺. HPLC purity: 98.37% (220 nm) and chiral HPLC purity is 96.6% (210 nm).

Example 241. (tetrahydro-2H-pyran-4-yl)methyl (S)-3-hydroxy-2-(1-hydroxy-7-methyl-1,3-dihydrobenzo[c][1,2]oxaborole-6-carboxamido)-3-methylbutanoate (6-241)

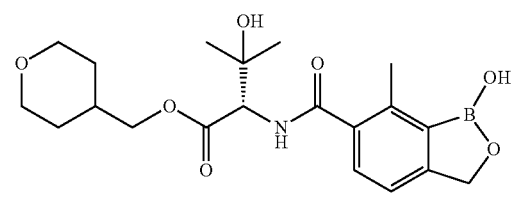

6-241

This compound was prepared from (tetrahydro-2H-pyran-4-yl)methyl (S)-2-amino-3-hydroxy-3-methylbutanoate and Acid-04 in a similar manner to the last step of Example 1. $^1$H NMR (300 MHz, DMSO-d$_6$): δ 9.05 (s, 1H), 8.17 (d, J=8.7 Hz, 1H), 7.41 (d, J=7.8 Hz, 1H), 7.26 (d, J=7.8 Hz, 1H), 4.98 (s, 2H), 4.75 (s, 1H), 4.42 (d, J=8.7 Hz, 1H), 3.96 (d, J=6.6 Hz, 2H), 3.84 (m, 2H), 3.26 (d, J=10.5 Hz, 2H), 2.45 (m, 3H), 1.87 (m, 1H), 1.62-1.58 (m, 2H), 1.33-1.20 (m, 8H); LC-MS: m/z 406.22 [M+H]$^+$. HPLC purity: 98.28% (220 nm) and chiral HPLC purity is 99.48% (210 nm)

Example 242. 3-Fluoro-4-(2-(pyrrolidin-1-yl)ethoxy)benzyl (1-hydroxy-7-methyl-1,3-dihydrobenzo[c][1,2]oxaborole-6-carbonyl)-L-valinate (6-242)

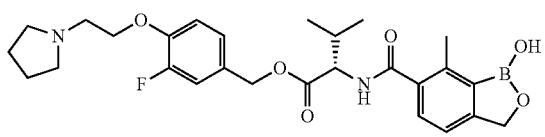

6-242

This compound was prepared from methyl 3-fluoro-4-hydroxybanzoate, N-Boc-(S)-valine and Acid-04 in a similar manner to Example 163. $^1$H NMR (400 MHz, DMSO-d$_6$): δ 9.03 (s, 1H), 8.56 (d, J 8.0 Hz, 1H), 7.33 (d, J 8.0 Hz, 1H), 7.27-7.18 (m, 2H), 7.17-7.16 (m, 2H), 5.10 (dd, J=12.0 Hz, 20.0 Hz, 2H), 4.97 (s, 2H), 4.33 (t, J=8.0 Hz, 1H), 4.14 (t, J=4.0 Hz, 2H), 2.79 (t, J=8.0 Hz, 2H), 2.50 (s, 3H), 2.49-2.13 (m, 1H), 1.69-1.66 (m, 4H), 0.95 (d, J=8.0 Hz, 3H), 0.91 (d, J=8.0 Hz, 3H); ESI-MS m/z 513 [M+H]$^+$; HPLC purity: 98.20% (220 nm), 94.25% (254 nm).

Example 243. 3-Chloro-4-(2-(pyrrolidin-1-yl)ethoxy)benzyl (1-hydroxy-7-methyl-1,3-dihydrobenzo[c][1,2]oxaborole-6-carbonyl)-L-valinate (6-243)

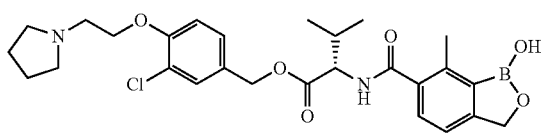

6-243

This compound was prepared from methyl 3-chloro-4-hydroxybanzoate, N-Boc-(S)-valine and Acid-04 in a similar manner to Example 163. $^1$H NMR (400 MHz, DMSO-d$_6$): δ 9.03 (s, 1H), 8.56 (d, J=7.6 Hz, 1H), 7.47 (d, J=1.6 Hz, 1H), 7.35-7.33 (m, 1H), 7.33-7.31 (m, 1H), 7.23 (d, J=7.6 Hz, 1H), 7.16 (d, J=8.4 Hz, 1H), 5.14-5.06 (m, 2H), 4.97 (s, 2H), 4.33 (t, J=7.2 Hz, 1H), 4.15 (t, J=6.0 Hz, 2H), 2.81 (t, J=5.6 Hz, 2H), 2.56-2.52 (m, 4H), 2.44 (s, 3H), 2.14 (q, J=6.8, 13.6 Hz, 1H), 1.72-1.64 (m, 4H), 0.93 (dd, J=1.2 Hz, 7.2 Hz, 6H); ESI-MS m/z 529 [M+H]$^+$; HPLC purity: 98.38% (220 nm), 94.90% (254 nm).

Example 244. 4-Chloro-3-(2-(pyrrolidin-1-yl)ethoxy)benzyl (1-hydroxy-7-methyl-1,3-dihydrobenzo[c][1,2]oxaborole-6-carbonyl)-L-valinate (6-244)

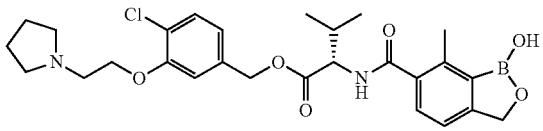

6-244

This compound was prepared from methyl 4-chloro-3-hydroxybanzoate, N-Boc-(S)-valine and Acid-04 in a similar manner to Example 163. $^1$H NMR (400 MHz, DMSO-d$_6$): δ 9.05 (s, 1H), 8.61 (d, J=7.6 Hz, 1H), 7.42 (d, J=8.0 Hz, 1H), 7.35 (d, J=8.0 Hz, 1H), 7.24 (d, J=8.0 Hz, 1H), 7.19 (s, 1H), 7.00-6.98 (m, 1H), 5.18 (s, 2H), 4.98 (s, 2H), 4.35 (t, J=7.2 Hz, 1H), 4.12 (t, J=4.2 Hz, 2H), 2.79 (t, J=5.6 Hz, 2H), 2.54-2.53 (m, 4H), 2.45 (s, 3H), 2.20-2.14 (m, 1H), 1.68-1.65 (m, 4H), 0.96 (dd, J=3.6, 3.2 Hz, 6H); ESI-MS m/z 529 [M+H]$^+$; HPLC purity: 96.52% (220 nm), 95.91% (254 nm).

Example 245. 4-Fluoro-3-(2-(pyrrolidin-1-yl)ethoxy)benzyl (1-hydroxy-7-methyl-1,3-dihydrobenzo[c][1,2]oxaborole-6-carbonyl)-L-valinate (6-245)

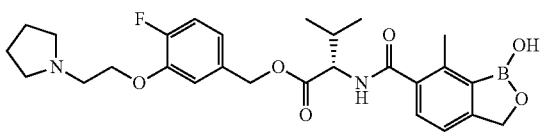

6-245

This compound was prepared from methyl 4-fluoro-3-hydroxybanzoate, N-Boc-(S)-valine and Acid-04 in a similar manner to Example 163. $^1$H NMR (400 MHz, DMSO-d$_6$): δ 9.03 (s, 1H), 8.58 (d, J=7.6 Hz, 1H), 7.34 (d, J=8.0 Hz, 1H), 7.24-7.17 (m, 3H), 6.97-6.96 (m, 1H), 5.14 (d, J=2.0 Hz, 2H), 4.97 (s, 2H), 4.35-4.31 (m, 1H), 4.09 (t, J=6.0 Hz, 2H), 2.76 (t, J=6.0 Hz, 2H), 2.49-2.46 (m, 4H), 2.43 (s, 3H), 2.19-2.10 (m, 1H), 1.66-1.64 (m, 4H), 0.95 (dd, J=3.2, 6.4 Hz, 6H); ESI-MS m/z 513 [M+H]$^+$; HPLC purity: 98.72% (220 nm), 100% (254 nm).

Example 246. 3-Fluoro-4-(3-(pyrrolidin-1-yl)propoxy)benzyl (1-hydroxy-7-methyl-1,3-dihydrobenzo[c][1,2]oxaborole-6-carbonyl)-L-valinate (6-246)

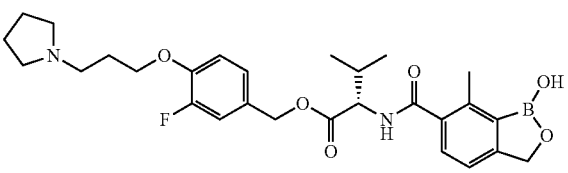

6-246

This compound was prepared from methyl 4-fluoro-3-hydroxybanzoate, N-Boc-(S)-valine and Acid-04 in a similar manner to Example 163. ¹H NMR (400 MHz, DMSO-d₆): δ 9.05 (s, 1H), 8.56 (d, J=8.0 Hz, 1H), 7.33 (d, J=8.0 Hz, 1H), 7.27-7.21 (m, 2H), 7.16-7.15 (m, 2H), 5.00 (q, J=12.0 Hz, 2H), 4.97 (s, 2H), 4.33 (t, J=8.0 Hz, 1H), 4.09 (t, J=8.0 Hz, 2H), 2.43 (s, 3H), 2.16-2.11 (m, 1H), 1.90 (t, J=4.0 Hz, 2H), 1.68 (s, 4H), 0.93 (dd, J=8.0, 4.0 Hz, 6H); ESI-MS m/z 527 [M+H]⁺; HPLC purity: 96.19% (220 nm), 91.57% (254 nm).

Example 247. 3-Fluoro-4-(3-(pyrrolidin-1-yl)propoxy)benzyl (1-hydroxy-7-methyl-1,3-dihydrobenzo[c][1,2]oxaborole-6-carbonyl)-L-valinate (6-247)

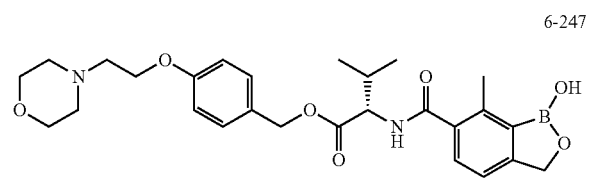 [SMILES: Cc1c(C(=O)N[C@H](C(=O)OCc2ccc(OCCN3CCOCC3)cc2)C(C)C)ccc2c1B(O)OC2]

6-247

This compound was prepared from methyl 4-(2-morpholinoethoxy)benzoate, N-Boc-(S)-valine and Acid-04 in a similar manner to Example 163. ¹H NMR (400 MHz, DMSO-d₆): δ 9.03 (s, 1H), 8.53 (d, J=8.0 Hz, 1H), 7.34-7.31 (m, 3H), 7.23 (d, J=8.0 Hz, 1H), 6.94 (d, J=8.4 Hz, 2H), 5.14-5.04 (m, 2H), 4.97 (s, 2H), 4.32 (t, J=7.2 Hz, 1H), 4.08 (t, J=6.0 Hz, 2H), 3.57 (t, J=4.0 Hz, 4H), 2.68 (t, J=5.6 Hz, 2H), 2.45 (d, J=4.4 Hz, 4H), 2.43 (s, 3H), 2.15-2.07 (m, 1H), 0.92-0.91 (m, 6H); ESI-MS m/z 511 [M+H]⁺; HPLC purity: 95.94% (220 nm), 97.37% (254 nm).

Example 248. (4,4-difluorocyclohexyl)methyl (S)-3-hydroxy-2-(1-hydroxy-7-methyl-1,3-dihydrobenzo[c][1,2]oxaborole-6-carboxamido)-3-methylbutanoate (6-248)

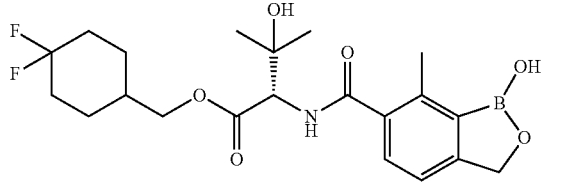

6-248

This compound was prepared from (4,4-difluorocyclohexyl)methyl (S)-2-amino-3-hydroxy-3-methylbutanoate and Acid-04 in a similar manner to the last step of Example 1. ¹H NMR (300 MHz, DMSO-d₆): δ 7.41 (d, J=8 Hz, 1H), 7.27 (d, J=8 Hz, 1H), 4.98 (s, 2H), 4.41 (s, 1H), 3.99 (d, J=5.6 Hz, 2H), 2.48 (s, 3H), 2.1-1.95 (m, 3H), 1.90-1.70 (m, 6H), 1.32-1.23 (m, 8H); LC-MS: m/z 440.35 [M+H]⁺. HPLC purity: 99.59% (220 nm) and chiral HPLC purity is 99.54% (210 nm).

Example 249. 3-Fluoro-4-(3-(pyrrolidin-1-yl)propoxy)benzyl (1-hydroxy-7-methyl-1,3-dihydrobenzo[c][1,2]oxaborole-6-carbonyl)-L-valinate (6-249)

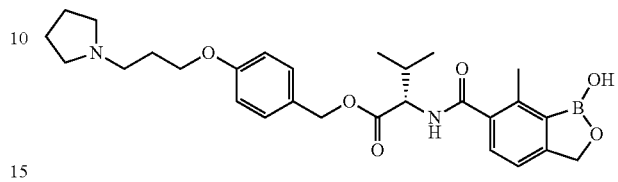

6-249

This compound was prepared from methyl 4-(3-(pyrrolidin-1-yl)propoxy)benzoate, N-Boc-(S)-valine and Acid-04 in a similar manner to Example 163. ¹H NMR (400 MHz, DMSO-d₆): δ 9.04 (s, 1H), 8.52 (d, J=7.6 Hz, 1H), 7.34-7.30 (m, 3H), 7.22 (d, J=8.0 Hz, 1H), 6.91 (d, J=8.8 Hz, 2H), 5.13-5.04 (m, 2H), 4.97 (s, 2H), 4.33-4.30 (m, 1H), 4.02-3.99 (m, 2H), 2.53-2.52 (m, 2H), 2.43-2.41 (m, 7H), 2.15-2.10 (m, 1H), 1.90-1.85 (m, 2H), 1.69-1.65 (m, 4H), 0.92 (d, J=6.8 Hz, 6H); ESI-MS m/z 509 [M+H]⁺; HPLC purity: 96.08% (220 nm), 96.68% (254 nm).

Example 250. (3-hydroxytetrahydrofuran-3-yl)methyl (1-hydroxy-7-methyl-1,3-dihydrobenzo[c][1,2]oxaborole-6-carbonyl)-L-valinate (6-250)

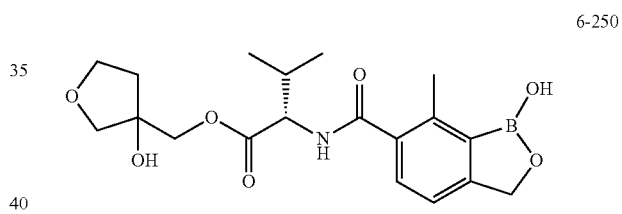

6-250

This compound was prepared from (3-hydroxytetrahydrofuran-3-yl)methyl L-valinate and Acid-04 in a similar manner to the last step of Example 1. ¹H NMR (400 MHz, DMSO-d₆): δ 9.05 (s, 1H), 8.51 (d, J=7.8 Hz, 1H), 7.38 (d, J=8.0 Hz, 1H), 7.24 (d, J=8.0 Hz, 1H), 5.07 (s, 1H), 4.98 (s, 2H), 4.39 (m, 1H), 4.12 (m, 2H), 3.90-3.70 (m, 2H), 3.63 (dd, J=8.8 Hz, 1H), 3.5 (d, J=8.0 Hz, 1H), 2.50 (m, 3H), 2.23-2.1 (m, 1H), 1.97-1.87 (m, 1H), 1.84-1.75 (m, 1H), 0.96 (m, 6H); LC-MS: m/z 392.25 [M+H]⁺. HPLC purity: 98.1% (220 nm).

Example 251. (5-Fluoro-6-(trifluoromethyl)pyridin-3-yl)methyl (1-hydroxy-7-methyl-1,3-dihydrobenzo[c][1,2]oxaborole-6-carbonyl)-L-valinate (6-251)

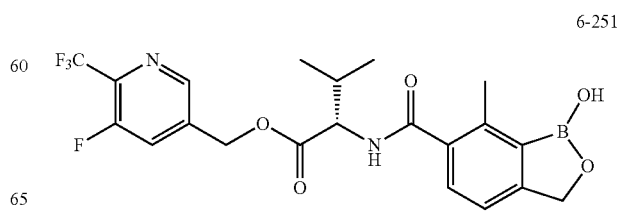

6-251

To a solution of 5-bromo-2-chloro-3-fluoropyridine (17.0 g, 65.3 mmol) in THF (200 mL) was added i-PrMgCl.LiCl (1.3 M, 60 mL) dropwise at 0° C. over a period of 30 minutes under $N_2$. The mixture was stirred at 15° C. for 2 h. Then methyl chloroformate (15.4 g, 163 mmol) was added drop-wise at 0° C. over a period of 30 minutes. The mixture was stirred at 15° C. for 11 h. The reaction was quenched by water (100 mL) slowly and then extracted with EtOAc (100 mL×3). The combined organic phase was washed with brine (100 mL×2), dried over anhydrous $Na_2SO_4$, filtered, and concentrated in vacuo. The residue was purified via column chromatography ($SiO_2$, petroleum ether/ethyl acetate=100:1 to 50:1) to give methyl 6-chloro-5-fluoronicotinate (5.00 g, 32%) as a white solid.

To a solution of 6-chloro-5-fluoronicotinate (5.00 g, 26.4 mmol) in acetonitrile (100 mL) was added TMSCl (5.73 g, 52.8 mmol). The mixture was stirred at 50° C. for 55 minutes. Then the mixture was cooled to 15° C., and poured into a solution of NaI (39.54 g, 263.8 mmol) in acetonitrile (100 mL) in one portion. The mixture was stirred at 15° C. for 5 minutes. The mixture was filtered and quenched by sat. $Na_2S_2O_3$ (100 mL), and then extracted with EtOAc (100 mL×3). The combined organic phase was washed with brine (100 mL), dried over anhydrous $Na_2SO_4$, filtered, and concentrated in vacuo. The residue was purified by recrystallization from MTBE (30 mL) to give 5-fluoro-6-iodonicotinate (3.00 g, 40%) as a yellow solid.

A mixture of 5-fluoro-6-iodonicotinate (1.50 g, 5.34 mmol), methyl 2,2-difluoro-2-fluorosulfonyl-acetate (5.13 g, 26.7 mmol), HMPA (2.87 g, 16.0 mmol) and CuI (3.05 g, 16.0 mmol) in DMF (15 mL) was stirred at 80° C. for 12 h under $N_2$ atmosphere. The reaction was quenched by water (30 mL) slowly and then extracted with EtOAc (50 mL×3). The combined organic phase was washed with brine (50 mL), dried over anhydrous $Na_2SO_4$, filtered, and concentrated in vacuo. The residue was purified via column chromatography ($SiO_2$, petroleum ether/ethyl acetate=50:1 to 2011) to give 5-fluoro-6-trifluoromethylnicotinate (470 mg, 35%) as an off white solid.

To a solution of methyl 5-fluoro-6-trifluoromethylnicotinate (440 mg, 1.97 mmol) in THF (2 mL) was added LAH (75 mg, 1.97 mmol) at −20° C. The mixture was stirred at −20° C. for 5 min. The reaction was quenched by sat. potassium sodium tartrate (1 mL), filtered, and concentrated in vacuum to give (5-fluoro-6-(trifluoromethyl)pyridin-3-yl) methanol (280 mg, 73%) a colorless oil.

(5-Fluoro-6-(trifluoromethyl)pyridin-3-yl)methyl (1-hydroxy-7-methyl-1,3-dihydrobenzo[c][1,2]oxaborole-6-carbonyl)-L-valinate was prepared from (5-fluoro-6-(trifluoromethyl)pyridin-3-yl)methanol, N-Boc-(S)-valine and Acid-04 in a similar manner to Example 1. $^1H$ NMR (400 MHz, DMSO-$d_6$) δ 9.03 (s, 1H), 8.67-8.65 (m, 2H), 8.15 (d, J=8.0 Hz, 1H), 7.35 (d, J=8.0 Hz, 1H), 7.24 (d, J=8.0 Hz, 1H), 5.38 (q, J=8.0 Hz, 2H), 4.97 (s, 2H), 4.39 (t, J=8.0 Hz, 1H), 2.42 (s, 3H), 2.22-2.17 (m, 1H), 0.97 (d, J=8.0 Hz, 6H); ESI-MS m/z 469 [M+H]$^+$; HPLC purity: 99.10% (220 nm), 97.74% (254 nm).

Example 252. In Vitro Alamar Blue 72 h Drug Sensitivity Assay for T. congolense Compounds were tested in vitro for chemotherapeutic potency against the IL3000 T. congolense (drug sensitive) strain, using the Alamar Blue assay with several modifications. Test compounds were prepared as 10 mg/mL DMSO stocks for each assay run. Compounds were assayed in at least three separate, independent test runs and an 11-point dilution curve was used to determine the $IC_{50}$ values. Bloodstream form trypanosomes were supported in HMI media containing 20% bovine serum and were incubated with test compounds for 69 h at 34° C. in a humidified atmosphere containing 5% $CO_2$. Thereafter, 10 μL of Resazurin dye (12.5 mg in 100 mL of phosphate buffered saline, Sigma-Aldrich, Buchs, Switzerland) were added for an additional 3 h. Plates were then read using a fluorescent plate reader (Spectramax, Gemini XS, Bucher Biotec, Basel, Switzerland) using an excitation wavelength of 536 nm and an emission wavelength of 588 nm. Data points were averaged to generate sigmoidal dose-response curves and $IC_{50}$ values were determined using Softmax Pro 5.2 software.

Results are shown in Table 1. Compounds have an activity designated as "A" provided an $IC_{50}$≤0.5 nM; compounds having an activity designated as "B" provided an $IC_{50}$ of 0.51-9.99 nM; and compounds having an activity designated as "C" provided an $IC_{50}$ of 10-5,000 nM.

Example 253. Ex Vivo Alamar Blue 48 h Drug Sensitivity Assay for T. vivax

Compounds were tested ex vivo for chemotherapeutic potency against the STIB719/ILRAD560 T. vivax (drug sensitive) strain, using the Alamar Blue assay with several modifications. Test compounds were prepared as 10 mg/mL DMSO stocks for each assay run. Compounds were assayed in at least three separate, independent test runs and an 11-point dilution curve was used to determine the $IC_{50}$ values. Bloodstream form trypanosomes were propagated and harvested from a highly parasitemic mouse (via cardiac puncture) and were incubated with test compounds for 45 hrs at 37° C. in a humidified atmosphere containing 5% $CO_2$, supported in HMI media containing 20% bovine serum. Thereafter, 10 μL of Resazurin dye (12.5 mg in 100 mL of phosphate buffered saline, Sigma-Aldrich, Buchs, Switzerland) were added for an additional 3 hrs. Plates were then read using a fluorescent plate reader (Spectramax, Gemini XS, Bucher Biotec, Basel, Switzerland) using an excitation wavelength of 536 nm and an emission wavelength of 588 nm. Data points were averaged to generate sigmoidal dose-response curves and $IC_{50}$ values were determined using Softmax Pro 5.2 software.

Results are shown in Table 1. Compounds have an activity designated as "A" provided an $IC_{50}$≤0.5 nM; compounds having an activity designated as "B" provided an $IC_{50}$ of 0.51-49.9 nM; compounds having an activity designated as "C" provided an $IC_{50}$ of 50-2,000 nM; and compounds having an activity designated as "D" provided an $IC_{50}$>2,000 nM.

Example 254. In Vitro $IC_{50}$ Measurement of T. cruzi Amastigote Killing Using TdTomato-Modified T. cruzi The T. cruzi parasites used in this assay were genetically modified to express Td Tomato fluorescent protein. Vero cells (African green monkey kidney epithelial cells) were harvested from continuous cultures using trypsin and added to the inner 60 wells of 96-well Greiner Bio One plates (plate catalog #655090) at 200 ul/well of 2.5×10$^6$ cells/mL. Cells were allowed to adhere for 1 h before infection with T. cruzi. T. cruzi for infection were harvested from previously-infected Vero cells, washed, pelleted and resuspended at 5×10$^6$/mL. 50 uL of parasites were added to each well containing Vero cells. Compounds were prepared from 5 mM stock concentrations in DMSO to final concentrations in wells ranging from 5 uM to 5 nM. Wells were provided for negative controls, lacking compounds. Plates were placed into a 37° C. incubator for 20 min, then a "Day 0" reading was taken on a Synergy H4 plate reader to record initial fluorescence levels, at 544 (excitation) and 612 nm (emission). 96-well plates were placed in Tupperware containers with wet paper towels and incubated at 37° C. incubator for 72 h. After 72 h plates were reread (Day 3 reading) and data analyzed using Excel and/or Graphpad software. Day 0 fluorescence was subtracted from Day 3 to remove input parasite fluorescence. Growth curves are generated and 50% and 90% inhibitory concentrations are determined by nonlinear regression analysis.

Results are shown in Table 1. Compounds have an activity designated as "A" provided an $IC_{50} \leq 20$ nM; compounds having an activity designated as "B" provided an $IC_{50}$ of 21-999 nM; and compounds having an activity designated as "C" provided an $IC_{50} \geq 1,000$ nM.

Table 1 shows the activity of selected compounds of this invention in the assays discussed in Examples 252-254, wherein each compound number corresponds to the compound numbering set forth in Examples 1-251 herein, supra.

TABLE 1

| Cpd# | IC50: I Org. Growth T. congolense 3 d [uM] | IC50: I Hypoxanthine Incorporation T. vivax 2 d [uM] | IC50: I Org. amastigote Growth T. cruzi 3 d [uM] |
|---|---|---|---|
| 6-001 | C | | |
| 6-002 | | | |
| 6-003 | C | | |
| 6-004 | C | | |
| 6-005 | B | B | B |
| 6-006 | B | B | |
| 6-007 | C | | C |
| 6-008 | B | B | B |
| 6-009 | B | C | C |
| 6-010 | C | | C |
| 6-011 | C | | |
| 6-012 | C | | |
| 6-013 | C | | |
| 6-014 | C | | |
| 6-015 | C | | |
| 6-016 | C | D | |
| 6-017 | C | B | C |
| 6-018 | C | C | |
| 6-019 | B | C | |
| 6-020 | C | C | C |
| 6-021 | B | B | |
| 6-022 | C | C | |
| 6-023 | C | C | C |
| 6-024 | B | C | |
| 6-025 | C | D | |
| 6-026 | B | C | |
| 6-027 | C | C | |
| 6-028 | C | | |
| 6-029 | C | | |
| 6-030 | B | B | B |
| 6-031 | B | B | |
| 6-032 | C | D | |
| 6-033 | C | | C |
| 6-034 | C | | |
| 6-035 | C | B | C |
| 6-036 | C | | B |
| 6-037 | C | | |
| 6-038 | A | A | A |
| 6-039 | B | A | |
| 6-040 | A | B | A |
| 6-041 | A | B | A |
| 6-042 | B | A | |
| 6-043 | A | C | A |
| 6-044 | A | | A |
| 6-045 | A | A | |
| 6-046 | A | B | A |
| 6-047 | A | A | A |
| 6-048 | A | A | |
| 6-049 | A | A | A |
| 6-050 | A | A | B |
| 6-051 | A | A | |
| 6-052 | A | A | |
| 6-053 | A | A | B |
| 6-054 | A | A | A |
| 6-055 | A | B | A |
| 6-056 | B | A | B |
| 6-057 | B | A | |
| 6-058 | A | B | C |
| 6-059 | B | A | B |
| 6-060 | B | B | B |
| 6-061 | B | B | B |
| 6-062 | B | A | |
| 6-063 | B | B | C |
| 6-064 | B | B | |
| 6-065 | B | B | B |
| 6-066 | A | B | A |
| 6-067 | A | A | A |
| 6-068 | | B | B |
| 6-069 | B | B | B |
| 6-070 | C | C | |
| 6-071 | C | C | B |
| 6-072 | A | A | A |
| 6-073 | B | A | A |
| 6-074 | A | B | B |
| 6-075 | C | C | C |
| 6-076 | B | A | B |
| 6-077 | B | B | A |
| 6-078 | C | B | |
| 6-079 | | B | B |
| 6-080 | B | A | B |
| 6-081 | A | A | B |
| 6-082 | B | A | B |
| 6-083 | A | A | A |
| 6-084 | C | B | |
| 6-085 | B | A | B |
| 6-086 | A | A | B |
| 6-087 | C | C | C |
| 6-088 | B | B | |
| 6-089 | | A | B |
| 6-090 | B | B | B |
| 6-091 | A | A | A |
| 6-092 | A | A | B |
| 6-093 | B | A | B |
| 6-094 | B | A | B |
| 6-095 | B | B | C |
| 6-096 | | B | C |
| 6-097 | B | B | B |
| 6-098 | A | A | A |
| 6-099 | A | A | B |
| 6-100 | A | A | A |
| 6-101 | A | A | A |
| 6-102 | C | B | C |
| 6-103 | C | B | C |
| 6-104 | C | B | |
| 6-105 | | B | B |
| 6-106 | | B | C |
| 6-107 | A | A | A |
| 6-108 | | B | C |
| 6-109 | B | A | B |
| 6-110 | B | A | B |
| 6-111 | B | A | A |
| 6-112 | B | B | A |
| 6-113 | A | A | A |
| 6-114 | B | B | B |
| 6-115 | | A | A |
| 6-116 | | A | A |
| 6-117 | C | B | C |
| 6-118 | C | C | C |
| 6-119 | A | A | A |
| 6-120 | B | A | B |
| 6-121 | A | A | A |

TABLE 1-continued

| Cpd# | IC50: I Org. Growth T. congolense 3 d [uM] | IC50: I Hypoxanthine Incorporation T. vivax 2 d [uM] | IC50: I Org. amastigote Growth T. cruzi 3 d [uM] |
|---|---|---|---|
| 6-122 | C | B | C |
| 6-123 | A | A | A |
| 6-124 | A | A | B |
| 6-125 | A | A | B |
| 6-126 | B | B | C |
| 6-127 |   | A | B |
| 6-128 | A |   | B |
| 6-129 |   | A | B |
| 6-130 | A | A | B |
| 6-131 | A | A | B |
| 6-132 | A | A | A |
| 6-133 | A | A | A |
| 6-134 | A | B | A |
| 6-135 | A | B | B |
| 6-136 | A | A | A |
| 6-137 | A | A | A |
| 6-138 | C | C | C |
| 6-139 | C | C | B |
| 6-140 | B | B | B |
| 6-141 | A | B | B |
| 6-142 | A | B | B |
| 6-143 | C | C | C |
| 6-144 | B | A | A |
| 6-145 | B | A | A |
| 6-146 | C | C | C |
| 6-147 | C | C | C |
| 6-148 | C | C | C |
| 6-149 | C | C | C |
| 6-150 | B | B | B |
| 6-151 | A | A | A |
| 6-152 | A | A | B |
| 6-153 | A | A | A |
| 6-154 | A | A | A |
| 6-155 | A |   | A |
| 6-156 | C | B | C |
| 6-157 | A |   | B |
| 6-158 |   | A | B |
| 6-159 | A | A |   |
| 6-160 | A |   | B |
| 6-161 | A |   | A |
| 6-162 | B |   |   |
| 6-163 | A |   |   |
| 6-164 | C | D | C |
| 6-165 | A | B | A |
| 6-166 | A | A | A |
| 6-167 | A | C | A |
| 6-168 | A | B | A |
| 6-169 | A | C | A |
| 6-170 | B | B | B |
| 6-171 | A | A | A |
| 6-172 | A | A | A |
| 6-173 | A | A | A |
| 6-174 | B | C |   |
| 6-175 | C |   |   |
| 6-176 |   |   |   |
| 6-177 |   |   |   |
| 6-178 |   |   |   |
| 6-179 | C |   |   |
| 6-180 |   |   |   |
| 6-181 | C |   |   |
| 6-182 |   |   |   |
| 6-183 | C |   |   |
| 6-184 | C |   |   |
| 6-185 |   |   | B |
| 6-186 | B | A | B |
| 6-187 |   | A | A |
| 6-188 | C | C | C |
| 6-189 | A | A | A |
| 6-190 | B | A | B |
| 6-191 |   | A | A |
| 6-192 | B | B | C |
| 6-193 | A | A | A |
| 6-194 |   | B | B |
| 6-195 |   | B | B |
| 6-196 | B | B | C |
| 6-197 | A | A | A |
| 6-198 |   |   | A |
| 6-199 |   |   | B |
| 6-200 | A | A | A |
| 6-201 | A | A | B |
| 6-202 | A | A | A |
| 6-203 | A | A | A |
| 6-204 | A | A | A |
| 6-205 |   |   | C |
| 6-206 | A | A | B |
| 6-207 | B | B | B |
| 6-208 | B | B | B |
| 6-209 | B | B | B |
| 6-210 | A | B | A |
| 6-211 | B | B | B |
| 6-212 | C | B | B |
| 6-213 |   |   | C |
| 6-214 | B | A | C |
| 6-215 | A | A | A |
| 6-216 | C | C | C |
| 6-217 |   | B | C |
| 6-218 | C | C | C |
| 6-219 | A | A | B |
| 6-220 | B |   | A |
| 6-221 | B |   | B |
| 6-222 | C | C | C |
| 6-223 | C | C | B |
| 6-224 | B | B | A |
| 6-225 | C |   | B |
| 6-226 | A |   | A |
| 6-227 |   |   | A |
| 6-228 | A |   | B |
| 6-229 | A | A | A |
| 6-230 |   | B | B |
| 6-231 |   |   | B |
| 6-232 |   |   | A |
| 6-233 |   |   | A |
| 6-234 |   |   | A |
| 6-235 |   |   | A |
| 6-236 |   |   |   |
| 6-237 |   |   |   |
| 6-238 |   |   |   |
| 6-239 |   |   |   |
| 6-240 |   |   |   |
| 6-241 |   |   |   |
| 6-242 | B |   | A |
| 6-243 | B |   | B |
| 6-245 | B |   | B |
| 6-246 | B | A |   |
| 6-247 | B | B | A |
| 6-248 |   |   | B |
| 6-249 | B | B | B |
| 6-250 |   |   | C |
| 6-251 |   |   |   |

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula 1:

or a pharmaceutically acceptable salt thereof, wherein:

$R^1$ is hydrogen or $C_{1-6}$ aliphatic;

$R^{1a}$ is hydrogen or $C_{1-6}$ aliphatic; or $R^1$ and $R^{1a}$ are taken together with the carbon atom to which they are attached to form an optionally substituted 3- to 6-membered spiro carbocyclic ring;

each $R^2$ is independently hydrogen, -halogen, —OR, —NO$_2$, —CN, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, or an optionally substituted group selected from the group consisting of $C_{1-6}$ aliphatic and 3- to 6-membered saturated or partially unsaturated monocyclic carbocyclyl;

$R^3$ is hydrogen or optionally substituted $C_{1-6}$ aliphatic;

$R^4$ is hydrogen, a natural or unnatural amino acid side-chain group, or an optionally substituted group selected from the group consisting of $C_{1-6}$ aliphatic, 3- to 7-membered saturated or partially unsaturated monocyclic carbocyclyl, and phenyl; or $R^3$ and $R^4$ are taken together with the carbon atom attached to $R^4$ and the nitrogen atom attached to $R^3$ to form an optionally substituted 3- to 6-membered heterocyclyl ring having 0-1 additional heteroatoms selected from oxygen, nitrogen, or sulfur;

$R^5$ is hydrogen or optionally substituted $C_{1-6}$ aliphatic; or

R4 and R5 are taken together with the carbon atom to which they are attached to form an optionally substituted 3- to 6- membered spiro heterocyclic ring having 1-2 heteroatoms selected from oxygen, nitrogen, or sulfur;

each R is independently hydrogen or optionally substituted $C_{1-6}$ aliphatic;

and L is selected from:

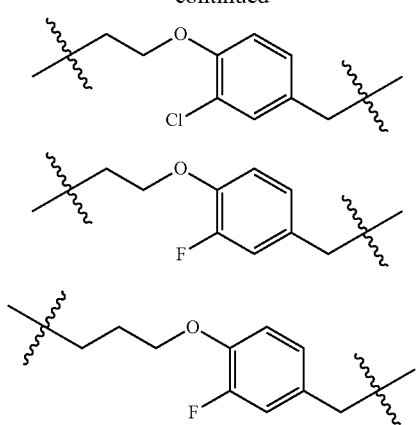

2. The compound of claim 1, wherein $R^6$ is an optionally substituted group selected from:

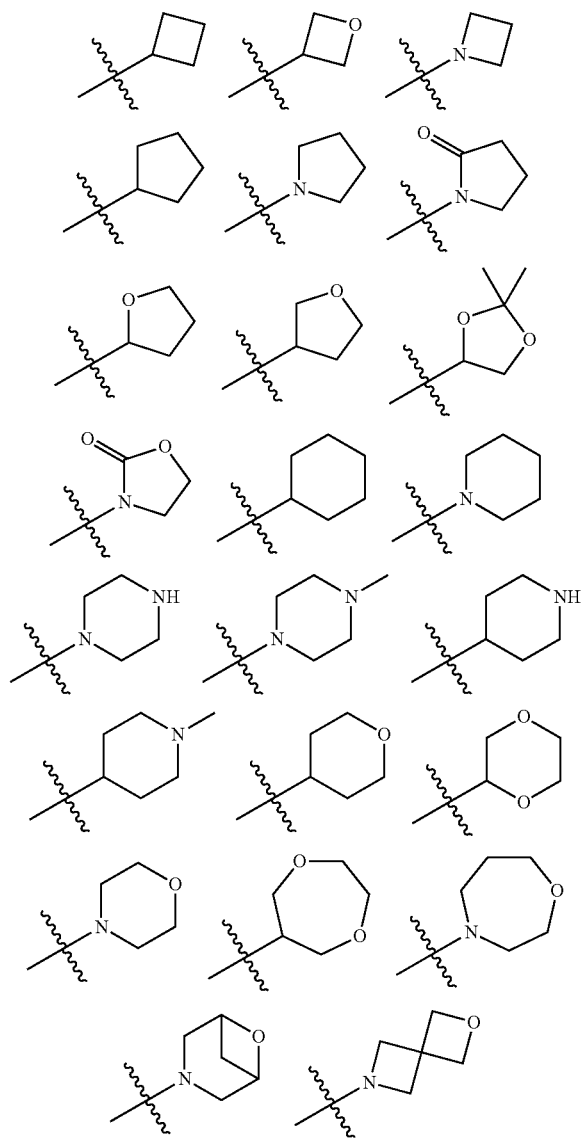

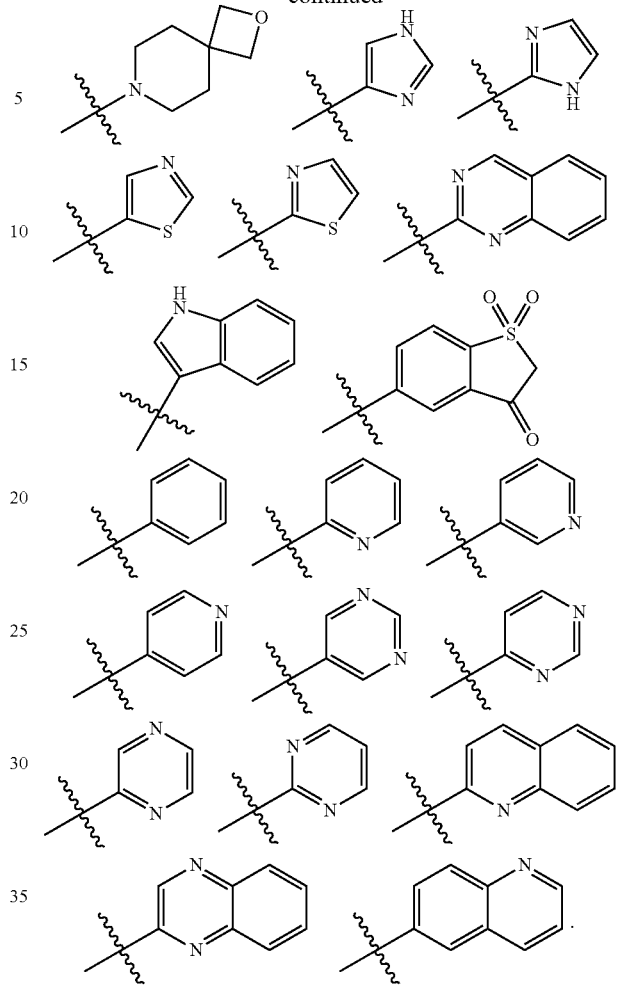

3. The compound of claim 1, wherein the compound is of formula II:

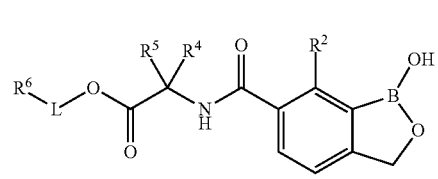

or a pharmaceutically acceptable salt thereof.

4. The compound of claim 1, wherein the compound is of formula III:

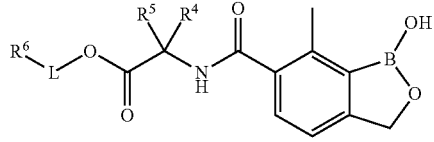

or a pharmaceutically acceptable salt thereof.

5. The compound of claim 4, wherein the compound is of formula III-a:

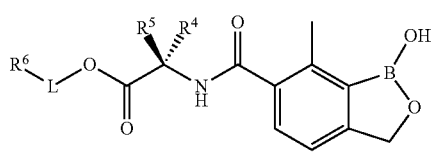

III-a or a pharmaceutically acceptable salt thereof.
6. A compound of formula IV:

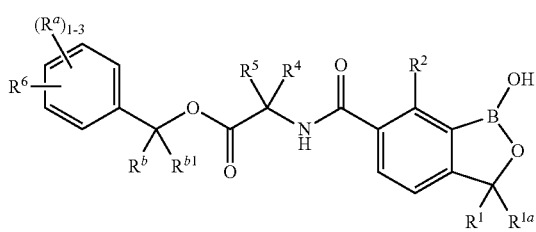

IV or a pharmaceutically acceptable salt thereof, wherein:
$R^1$ is hydrogen or $C_{1-6}$ aliphatic;
$R^{1a}$ is hydrogen or $C_{1-6}$ aliphatic; or
$R^1$ and $R^{1a}$ are taken together with the carbon atom to which they are attached to form an optionally substituted 3- to 6-membered spiro carbocyclic ring;
each $R^2$ is independently hydrogen, -halogen, —OR, —NO$_2$, —CN, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, or an optionally substituted group selected from the group consisting of $C_{1-6}$ aliphatic and 3- to 6-membered saturated or partially unsaturated monocyclic carbocyclyl;
$R^4$ is hydrogen, a natural or unnatural amino acid side-chain group, or an optionally substituted group selected from the group consisting of $C_{1-6}$ aliphatic, 3- to 7-membered saturated or partially unsaturated monocyclic carbocyclyl, and phenyl; or
$R^3$ and $R^4$ are taken together with the carbon atom attached to $R^4$ and the nitrogen atom attached to $R^3$ to form an optionally substituted 3- to 6-membered heterocyclyl ring having 0-1 additional heteroatoms selected from oxygen, nitrogen, or sulfur;
$R^5$ is hydrogen or optionally substituted $C_{1-6}$ aliphatic; or
R4 and R5 are taken together with the carbon atom to which they are attached to form an optionally substituted 3- to 6- membered spiro heterocyclic ring having 1-2 heteroatoms selected from oxygen, nitrogen, or sulfur;
$R^6$ is hydrogen, -halogen, —OR, —NO$_2$, —CN, —SR, —N(R)$_2$, —C(O)R, —C(O)OR, —S(O)R, —S(O)$_2$R, —C(O)N(R)$_2$, —SO$_2$N(R), —OC(O)R, —N(R)C(O)R, —N(R)C(O)OR, —N(R)SO$_2$R, —OC(O)N(R), an optionally substituted group selected from the group consisting of $C_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 3- to 6-membered heteroaryl having 1-4 heteroatoms selected from oxygen, nitrogen, or sulfur, 7- to 10-membered saturated or partially unsaturated bicyclic carbocyclyl, 8- to 10-membered bicyclic aryl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, and bridged bicyclic;
each $R^a$ is independently R, -halogen, —OR, —NO$_2$, —CN, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, or —OC(O)N(R)$_2$;
$R^b$ is hydrogen or methyl; and
$R^{b1}$ is hydrogen or methyl; and, each R is independently hydrogen or optionally substituted $C_{1-6}$ aliphatic.

7. The compound of claim 6, wherein the compound is of formula V:

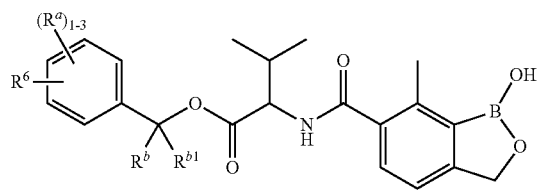

V or a pharmaceutically acceptable salt thereof, wherein
each $R^a$ is independently R, -halogen, —OR, —NO$_2$, —CN, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, or —OC(O)N(R)$_2$;
$R^b$ is hydrogen or methyl; and
$R^{b1}$ is hydrogen or methyl.

8. The compound of claim 6, wherein the compound is of formula V-a or V-b:

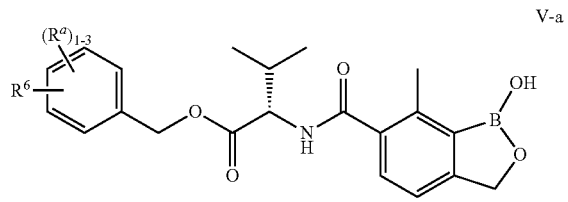

V-a

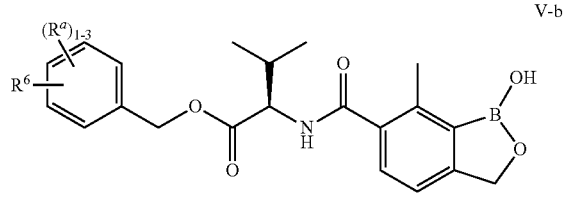

V-b or a pharmaceutically acceptable salt thereof, wherein
each $R^a$ is independently R, -halogen, —OR, —NO$_2$, —CN, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, or —OC(O)N(R)$_2$.

9. The compound of formula VI-a, VI-b, VI-c, VI-d, VI-e, or VI-f:

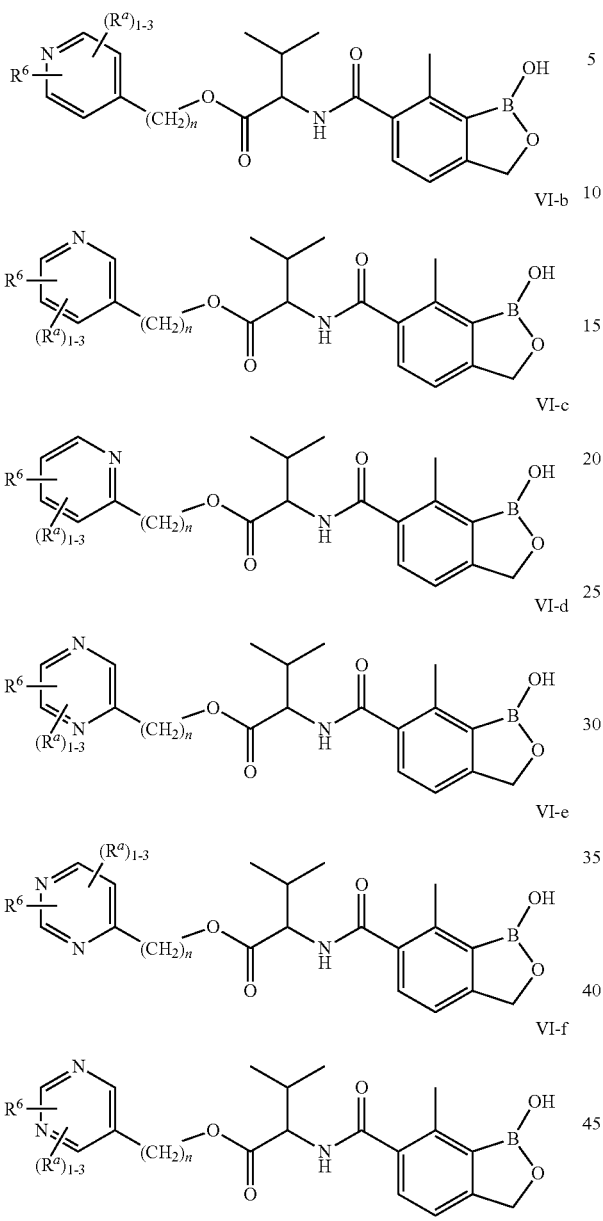

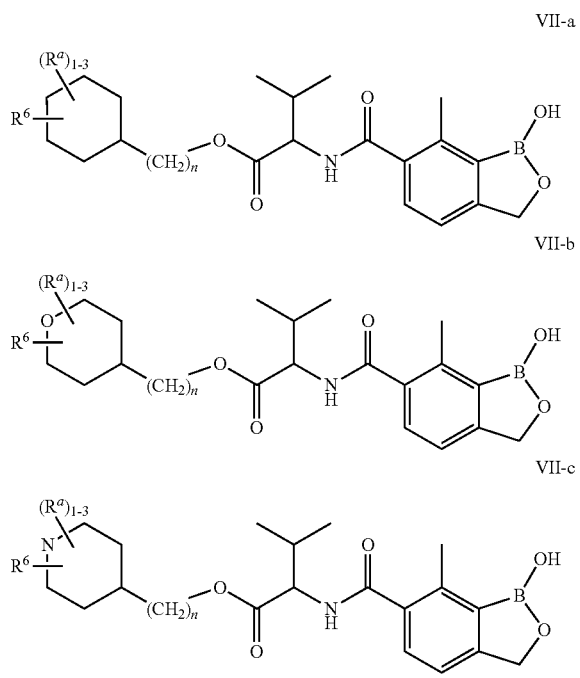

or a pharmaceutically acceptable salt thereof, wherein $R^6$ is hydrogen, -halogen, —OR, —NO$_2$, —CN, —SR, —N(R)$_2$, —C(O)R, —C(O)OR, —S(O)R, —S(O)$_2$R, —C(O)N(R), —SO$_2$N(R), —OC(O)R, —N(R)C(O)R, —N(R)C(O)OR, —N(R)SO$_2$R, —OC(O)N(R), an optionally substituted group selected from the group consisting of C$_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 3- to 6-membered heteroaryl having 1-4 heteroatoms selected from oxygen, nitrogen, or sulfur, 7- to 10-membered saturated or partially unsaturated bicyclic carbocyclyl, 8- to 10-membered bicyclic aryl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, and bridged bicyclic;

each R is independently hydrogen or optionally substituted C$_{1-6}$ aliphatic;

each $R^a$ is independently R, -halogen, —OR, —NO$_2$, —CN, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, or —OC(O)N(R)$_2$; and n is 0, 1, 2 or 3.

10. The compound of claim 1, wherein the compound is of formula VII-a, VII-b or VII-c:

or a pharmaceutically acceptable salt thereof, wherein:

$R^6$ is hydrogen, -halogen, —OR, —NO$_2$, —CN, —SR, —N(R), —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, —OC(O)N(R)$_2$, an optionally substituted group selected from the group consisting of C$_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 8- to 10-membered bicyclic aryl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, and bridged bicyclic;

each R is independently hydrogen or optionally substituted C$_{1-6}$ aliphatic;

each R$^a$ is independently R, -halogen, —OR, —NO$_2$, —CN, —SR, —N(R)$_2$, —C(O)R, —C(O)OR, —S(O)R, —S(O)$_2$R, —C(O)N(R)$_2$, —SO$_2$N(R)$_2$, —OC(O)R, —N(R)C(O)R, —N(R)C(O)OR, —N(R)SO$_2$R, or —OC(O)N(R)$_2$; and
n is 0, 1, 2 or 3.

11. The compound of claim 1, wherein the compound is of formula IX-a or IX-b:

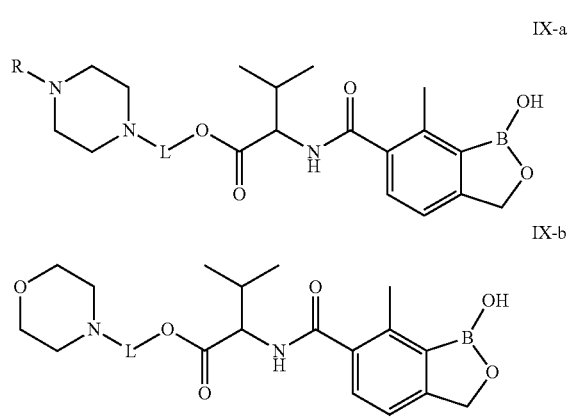

IX-a

IX-b or a pharmaceutically acceptable salt thereof, wherein R is hydrogen or methyl.

12. The compound of claim 11, where L is selected from:

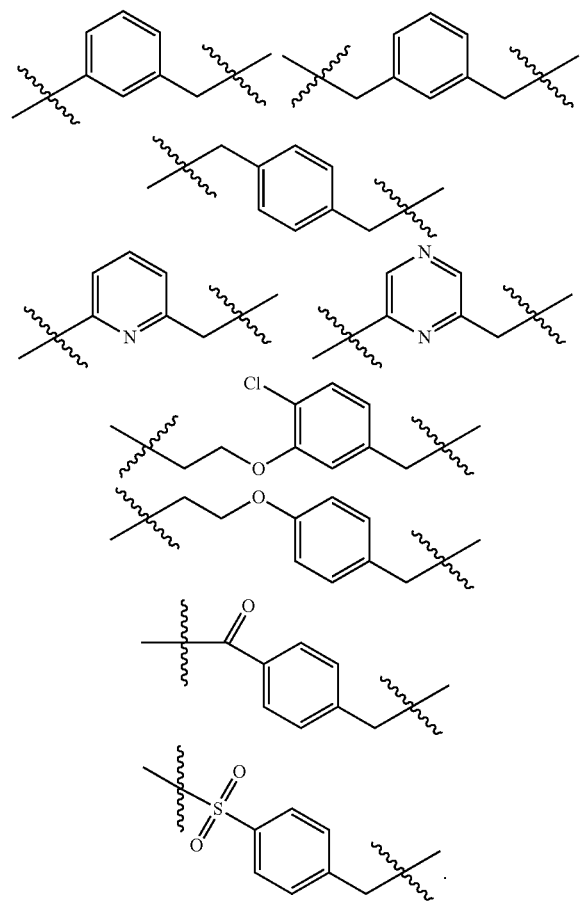

13. A compound selected from the compounds
3,4-Difluorobenzyl (1-hydroxy-7-methyl-1,3-dihydrobenzo[c][1,2]oxaborole-6-carbonyl)-L-valinate
4-Fluorobenzyl (S)-3-hydroxy-2-(1-hydroxy-7-methyl-1,3-dihydrobenzo[c][1,2]oxaborole-6-carboxamido)-3-methylbutanoate
(tetrahydro-2H-pyran-4-yl)methyl (1-hydroxy-7-methyl-1,3-dihydrobenzo[c][1,2]oxaborole-6-carbonyl)-L-valinate
((S)-tetrahydrofuran-3-yl)methyl (1-hydroxy-7-methyl-1,3-dihydrobenzo[c][1,2]oxaborole-6-carbonyl)-L-valinate, or
a pharmaceutically acceptable salt thereof.

14. The compound of claim 13, wherein the compound is:
(Tetrahydro-2H-pyran-4-yl)methyl (1-hydroxy-7-methyl-1,3-dihydrobenzo[c][1,2]oxaborole-6-carbonyl)-L-valinate; or, a pharmaceutically acceptable salt thereof.

15. The compound of claim 13, wherein the compound is:
3,4-Difluorobenzyl (1-hydroxy-7-methyl-1,3-dihydrobenzo[c][1,2]oxaborole-6-carbonyl)-L-valinate; or, a pharmaceutically acceptable salt thereof.

16. The compound of claim 13, wherein the compound is:
4-Fluorobenzyl (S)-3-hydroxy-2-(1-hydroxy-7-methyl-1,3-dihydrobenzo[c][1,2]oxaborole-6-carboxamido)-3-methylbutanoate; or, a pharmaceutically acceptable salt thereof.

17. The compound of claim 13, wherein the compound is:
((S)-tetrahydrofuran-3-yl)methyl (1-hydroxy-7-methyl-1,3-dihydrobenzo[c][1,2]oxaborole-6-carbonyl)-L-valinate; or, a pharmaceutically acceptable salt thereof.

18. A method of treating Chagas disease in a subject comprising administering to a subject a compound selected from the group consisting of:
(Tetrahydro-2H-pyran-4-yl)methyl (1-hydroxy-7-methyl-1,3-dihydrobenzo[c][1,2]oxaborole-6-carbonyl)-L-valinate;
3,4-Difluorobenzyl (1-hydroxy-7-methyl-1,3-dihydrobenzo[c][1,2]oxaborole-6-carbonyl)-L-valinate;
4-Fluorobenzyl (S)-3-hydroxy-2-(1-hydroxy-7-methyl-1,3-dihydrobenzo[c][1,2]oxaborole-6-carboxamido)-3-methylbutanoate; and,
((S)-tetrahydrofuran-3-yl)methyl (1-hydroxy-7-methyl-1,3-dihydrobenzo[c][1,2]oxaborole-6-carbonyl)-L-valinate; or, a pharmaceutically acceptable salt thereof, in an amount sufficient to treat the disease.

19. The method of claim 18, wherein the compound is:
(Tetrahydro-2H-pyran-4-yl)methyl (1-hydroxy-7-methyl-1,3-dihydrobenzo[c][1,2]oxaborole-6-carbonyl)-L-valinate; or, a pharmaceutically acceptable salt thereof.

20. The method of claim 18, wherein the compound is:
3,4-Difluorobenzyl (1-hydroxy-7-methyl-1,3-dihydrobenzo[c][1,2]oxaborole-6-carbonyl)-L-valinate; or, a pharmaceutically acceptable salt thereof.

21. The method of claim 18, wherein the compound is:
4-Fluorobenzyl (S)-3-hydroxy-2-(1-hydroxy-7-methyl-1,3-dihydrobenzo[c][1,2]oxaborole-6-carboxamido)-3-methylbutanoate; or, a pharmaceutically acceptable salt thereof.

22. The method of claim 18, wherein the compound is:
((S)-tetrahydrofuran-3-yl)methyl (1-hydroxy-7-methyl-1,3-dihydrobenzo[c][1,2]oxaborole-6-carbonyl)-L-valinate; or, a pharmaceutically acceptable salt thereof.

* * * * *

UNITED STATES PATENT AND TRADEMARK OFFICE
CERTIFICATE OF CORRECTION

PATENT NO. : 10,562,921 B2
APPLICATION NO. : 15/590159
DATED : February 18, 2020
INVENTOR(S) : Tsutomu Akama et al.

Page 1 of 1

It is certified that error appears in the above-identified patent and that said Letters Patent is hereby corrected as shown below:

In the Claims

Column 189, Claim 1:
Line 42, replace R4 and R5 with $R^4$ and $R^5$

Column 193, Claim 6:
Line 58, replace -OC(O)N(R) with -OC(O)N(R)$_2$
Line 64, replace 3- to 6- with 5- to 6-

Column 195, Claim 9:
Line 54, replace -C(O)N(R), -SO$_2$N(R) with -C(O)N(R)$_2$, -SO$_2$N(R)$_2$
Line 56, replace -OC(O)N(R) with -OC(O)N(R)$_2$
Line 62, replace 3- to 6- with 5- to 6-

Column 196, Claim 10:
Line 46, replace -N(R) with -N(R)$_2$

Signed and Sealed this
Twelfth Day of May, 2020

Andrei Iancu
*Director of the United States Patent and Trademark Office*